United States Patent [19]
Arthur et al.

[11] Patent Number: 6,013,508
[45] Date of Patent: Jan. 11, 2000

[54] POLYPEPTIDES IMPLICATED IN THE EXPRESSION OF RESISTANCE TO GLYCOPEPTIDES, IN PARTICULAR IN GRAM-POSITIVE BACTERIA, NUCLEOTIDE SEQUENCE CODING FOR THESE POLYPEPTIDES AND USE FOR DIAGNOSIS

[75] Inventors: Michel Arthur, Paris; Sylvie Dukta-Malen, Fresnes; Catherine Molinas; Patrice Courvalin, both of Paris, all of France

[73] Assignee: Institut Pasteur, Paris Cedex, France

[21] Appl. No.: 08/980,357

[22] Filed: Nov. 28, 1997

Related U.S. Application Data

[62] Division of application No. 08/286,819, Aug. 5, 1994, Pat. No. 5,871,910, which is a continuation of application No. 08/174,682, Dec. 28, 1993, abandoned, which is a continuation of application No. 07/917,146, filed as application No. PCT/FR91/00855, Oct. 29, 1991, abandoned.

[30] Foreign Application Priority Data

Oct. 31, 1990 [FR] France .................................. 90 13579

[51] Int. Cl.[7] .............................. C12N 1/21; C07H 21/04; C07H 21/02
[52] U.S. Cl. .................................... 435/252.3; 435/320.1; 435/325; 536/23.7
[58] Field of Search ................................ 435/320.1, 325, 435/252.3; 536/23.7

[56] References Cited

U.S. PATENT DOCUMENTS 5,770,361   6/1998   Arthur et al. ................................ 435/6

OTHER PUBLICATIONS

T. I. Nicas et al., "Activity of Glycopeptides Against Vancomycin–Resistant Gram–Positive Bacteria", Antimicrob Agents and Chemotherapy, vol. 33, No. 9, pp. 1477–1481, Sep. 1989.

Thalia I. Nicas et al., "Characterization of Vancomycin Resistance in *Enterococcus faecium* and *Enterococcus faecalis*", Antimicrobial Agents and Chemotherapy, vol. 33, No. 7, pp. 1121–1124, Jul. 1989.

A. Brisson–Noel et al., "Cloning and Heterospecific Expression of the Resistance Determinant vanA Encoding High Level Resistance to Glycopeptides in *Enterococcus faecium* BM4147", Antimicrobian Agents and Chemotherapy, vol. 34, No. 5, pp. 924–927, May 1990.

S. Dutka–Malen et al., "Phenotypic and Genotypic Heterogeneity of Glycopeptide Resistance Determinants in Gram–Positive Bacteria", Antimicrobian Agents and Chemotherapy, vol. 34, No. 10, pp. 1875–1879, Oct. 1990.

R. Leclercq et al., "Transferable Vancomycin and Teicoplanin Resistance in *Enterococcus faecium*", Antimicrobian Agents and Chemotherapy, vol. 33, No. 2, pp. 10–15, Jan. 1989.

(List continued on next page.)

*Primary Examiner*—Kenneth R. Horlick
*Attorney, Agent, or Firm*—Oblon, Spivak, McClelland, Maier & Neustadt, P.C.

[57] ABSTRACT

The invention relates to compositions and nucleic acids encoding polypeptides involved in the expression of resistance to glycopeptides, in particular to vancomycin and/or teicoplanin. The invention also relates to vectors containing said nucleic acids, transformed host cells and their use for the diagnosis of resistance to glycopeptides.

14 Claims, 94 Drawing Sheets

OTHER PUBLICATIONS

S. Dutka–Malen et al., "The Vana Glycopeptide Resistance Protein is Related to D–Alanyl–D–Alanine Ligase Cell Wall Biosynthesis Enzymes", Mol. Gen. Genet., vol. 224, No. 3, pp. 364–372, Dec. 1990.

T.D.H. Bugg et al., "Identification of Vancomycin Resistance Protein Vana as a D–Alanine: D–Alanine Ligase of Altered Substrate Specificity", Biochemistry, vol. 30, No. 8, pp. 2017–2021, Feb. 26, 1991.

Arthur C. Robinson et al., "Further Evidence for Overlapping Transcriptional Units in an *Escherichia coli* Cell Envelope–Cell Division Gene Cluster: DNA Sequence and Transcriptional Organization of the ddl ftsQ Region", Journal of Bacteriology, vol. 167, No. 3, pp. 809–817, Sep. 1986.

Elisabeth Daub et al., "Isolation, Cloning, and Sequencing of the *Salmonella typhimurium* ddlA Gene with Purification and Characterization of its Product, D–Alanine:D–Alinine Ligase (ADP Forming)", Biochemistry, Vo. 27, pp. 3701–3708, 1988.

Umesh Varshney et al., "Sequence Analysis, Expression, and Conservation Of *Escherichia coli* Uracil DNA Glycosylase and its Gene (UNG)", The Journal of Biological Chemistry, vol. 263, No. 16, pp. 7776–7784, 1988.

Michel Arthur et al., "Structural Relationship Between the Vancomycin Resistance Protein VanH and 2–Hydroxycarboxylic Acid Dehydrogenases", Gene, vol. 103, pp. 133–134, 1991.

```
AAGCTTTCTTTTGCTCTCATTTGTTAGAGATTTACTAACCGTATTAAATAGCTTCTTTTC
AGCCATTGCCCTTGCTTCCCACACCATTCTTCAAGTGTAGTGATAGCAGGCAGTATAAT
TTTGTTTTTCTTAGAAAATCTATGCATTCATGCAGTAGATGAATGCACTCAGGCATTTC
CAAAGCTAATTGATGAAGGTACTTAAATGTCATTCGATATTCACTCAGGTAAAGTTAC
AAAGTCGTATTCACTTCGAATTTTCAAATGATCCCAAAGTGTATTTCCTTTGAGG
ATAATGATCAAGCGAGGATGGACTAACACCAATCTGTTTCGATATATATTGTATGACCGA
ATCTGGGATGCTTTGATGAGTGGCCAACCGGGATACCGAAGAACAGCTAATTG
AACAGCAAATCCTAAACGGTTTTCTTCCCTCGCTTATTAACTATTTCTAAATCCCG
TTTGGAAAAGTGAAGTAGGTCCCCAGTATCATCTTCAGGATTTGCATAAAAGC
CTGTCTCTGTATTTCAATTTATTAGTTCAATTATATCAATAGAGTGTACTTGTCTCAAAA
CATTTCTGTATTTCAATTTATTAGTCAATTATATCAATAGAGCGTCTCATAAGACTTGTCTCAAAA
ACAAATGTAGTAGACTGATAAAATCATCGGTTATATTCGTGTCAGTTCGACTAACCAGAATCC
ATGAGGTGATATTTGCGGAAAAATCGGTTATATTCGTGTCAGTTCGACTAACCAGAATCC
TTCAAGACAATTCAGCAGTTGAACGAGATCGGAATGGATATTATAAAGAGAAAGTTT
CAGGAGCAACAAAGGATCGCGAGCAACTTAACTCGAATGTTAGACGATTACAGGAAGATG
ACATCATTTATGTTACAGACTTAACTCGAATCACTCGTAGTACAACAAGATCTATTGAAT
TAATCGATAACATACGAGATAAAAGGCCAATTACTGTAATGGCTGGTGTTAACC
ATTTATCAGAAGATAATCCATAAGTGAGACAACGTGAAGGGATTGAATTGGCTAAGAAAG
AATTAGAGCGAGATCTTATTCGGATGAGACAACGTGAAGGGATTGAATTGGCTAAGAAAG
AAGGAAAGTTAAAGGTCGATTAAAGAAGGAAATATGACTGTAAATCAAATTGTGAATTACTAAT
CGGXXAAAGCTATATAAAGAAGGAAATATGACTGTAAATCAAATTGTGAATTACTAAT
GTATCTAGGGCTTCATTATAAGTCTGATTAAAGAAGGAAATTATCAGAAGTGAATAATTTACTAAT
CCGCTAATGGCCGAAAGCCCTTTGATAAAAAAGGAAACTATAAATATTAACAGCTCCT
AGCGATGCCGAAAGCCCTTTGATAAAAAAGAAGAATCATCTCTTAAGAAATTCTTAGTCA
TTTATTATGTAAATGCTTATAATTCGGCCCTATAATCTGATAAATTATTAAGGGCAAAC
```

FIG. 4A

```
TTATGTGAAAGGGTGATAACTATGAGCGATAAAATACTTATTGTGGATGATGAACATGAA
ATTGCCGATTGGTTGAATTATACTTAAAAACGAGAATTATACGGTTTCAAATACTAT
ACCGCCAAAGAAGCATTGGAATGTATAGACAAGTCTGAGATTGACCTTGCCATTGGAC
ATCATGCTTCCGGCACAAGCGGCCTTACTATCTGTCAAAAATAAGGACAAGCACACC
TATCCGATTATCATGCTGATTATATACAGAGGTAGATAAAATTACAGGGTTAACA
ATCGGCGGGATGATTGCGCCGGCCTTTCGCCGGGAAAGAAGAAGCCCTTTCGGAGTTAATTGTCGGTA
AAGGCCCAGTTGCGCCGATACAAAAAATTCAGTGGTAAAGGAGCAGAACGAAAATGTT
ATCGTCACTCCCTTACTCCCACCGAGTTTCAATGTTAACACCATGAGTGTTATCTGAACGAGAAG
CAGTTATCCGGATGCTGCTATTCATGAGATATGGGGGCGACGAATATTTCAGCAAG
AATGTGGTTAGCTCCGAGCTGCTATTCATGAGATATGCGCGAAAAATGAACGACACATT
AGCAACAACACCATCACCGTGCATATCCGGCATTGGGGGTTGGTTATAAATGAATAAAA
GATAATCGAAATATCCAAACTAGAACGAACGAAACTTTACATGTATATCGTTGCAATTGTTGGT
AAACGACTATTCGTGTTGTATATTCGTTCAATGATCGAGGGAAACTTGGGATTGGAT
AGCAATTGTATTCGTGTTGTATATTCGTTCAATGATCGAGGGAAACTTGGGATTGGAT
CTTAAGTATTTGGAAAACAAATATGACTTAAATCACCTGGACGCGATGAATTATATCA
ATATTCCATACGGAACGTCGCTTTCAAATTCGCAAAATCAAATTGAGCTTTCTGCGAAGAGCAGGATGTGT
TATTCTATGTCGCGTCATGCTTTCAAATTCGCAAAATCAAATTGAGCTTTCTGCGAAGAGCAGGATGTGT
CATTGATGTACTTATTCAGAACGAAGATAAAACGGACTCGGAAGCAGGACTCTGGAAAATGGATGT
TATGGAACAAAAGCTCAACACATTAAGAAAAATGACGTTGTTATGTACTTGGCCACGATATTAAAACGCC
GCTGGCCGAACAAAGAAAAGAAGAATGACGTTGTTATGTACTTGGCCACGATATTAAAACGCC
CCTTACATCCATTATCGGTTATGTGCATATACGTTGGACAAAGCGTATCGACTCCAGACATGCCGGTAGA
TCAAAAGGCAAAGTGCATATACGTTGGACAAAGCGTATCGACTCCAGACATGCCGGTAGA
CGACGAGTTTTTGAGATTACTATGCTGGTGCAGATGACCGATGAATTTATCCTCAGCTTTCGC
CATAGACCTATACTATATGCTGGTGCAGATGACCGATGAATTTATCCTCAGCTTTCGC
ACATGGAAAACAGGCGGGTTATTCACGCCCCGAGGATCTGACCGTGTCCGGCGACCCTGA
```

```
GCTCTCATCATGCGGGCAAATGGAATATCATGCAATGAAGCGCAAAATCGCAGACGTTTGC
GCTCCATCATGGAAAACAGTGGGTTTGAAGCATATAGCCCTCGAATGGTGGCACTATGTAT
TAAGAGACGAACCATACCCCAATAGCTATTTGATTTCCCCGTTAAATAAACTTTAACC
GTTGCACGGACAAACTATATAAGCTAACTCTTTCGGCAGGAAAACCGACGTATGTAACTG
GTTCTTAGGGAATTATATATAGTAGATATTGAAGATGTAAGGCAGAGCGATATTGC
GGTCATTATCTGCGTGCGCCCATTGTCAACAGGCAGTTCAGCCTCGTTAAATTCAGCATGG
GTATCACTTATGAAAATTCATCTACATTGGTGATAATAGTAAATCCAGTAGGGCGAAATA
ATTGACTGTAATTTACGGGCAAAACGGCACAATCTCAAACGAGATTGTGCCGTTAAGG
GGAAGATTCTAGAAATATTTCATACTTCCAACTATAGTTAAGGAGGAGACTGAAAATG
AAGAAGTTGTTTTTTTATTGTTATTCTTAATATACTTAGGTTATGACTACGTT
AATGAAGCACTGTTTCTCAGGAAAAAGTCGAATTCAAAATTCAAATTATGATCAAAATCCCAAA
GAACATTTAGAAAATAGTGGGACTTCTGAAAATACCCAAGAGAAAACAATTACAGAAGAA
CAGGTTTATCAAGGAAATCTGCTATTAATCAATAGTAAATCATAATATCCTGTTCGCCAAGAAGTG
TGAAGTCAGATATCGTGTGAATTTATCTAAACATGACGAATTAATAACATTTCAGAGATCGGGTTGC
TTGATAGTAATATTTATATGTCAAAGAATTTTATTATTAATAGTGGCTATCGAGACTTTGATG
ATGCTGTAAAGGGTGGCGTTAGTCATTTCACTAGATGTAGGGGCTGAGTATCAAGCTTATTAGTG
AGCAAAGTGTGCTTTACCAAGGAAATCCAATAGCTGAGTATGCGAGTCAAGCTTGAGATGGAACGAGCCC
CTGAAGGAAAGTGGATAGAAGAAAATGCTTGGAAATACGGGTCATTTTACGTTATCCAG
AGGACAAAACAGAGAGTTAACAGGAATTC
```

LysLeuPhePheLeuLeuIleCys*ArgPheThrAsnArgIleLys*LeuLeuPhe
SerPheSerPheCysSerPheValArgAspLeuLeuThrValLeuAsnSerPheSer
AlaPheLeuPheAlaHisLeuLeuGluIleTyr*ProTyr*IleAlaSerPheGln
AAGCTTTCTTTTGCTCATTGTCTAGAGATTACTAACCGTATTAAATAGCTTCTTTTC

SerHisCysPheProHisSerPheLysCysSerAspSerArgGlnTyrAsn
AlaIleAlaLeuAlaSerHisThrIleLeuSerSerValValIleAlaGlySerIleIle
ProLeuProLeuProThrProPhePheGlnVal****GlnAlaVal*Phe
AGCCATTGCCCTTGCTTCCCACACCATTCTTTCAAGTGTAGTGATAGCAGGCAGTATAAT
                              100

PheValPheSer*LysIleTyrAlaPheMetGln*MetAsnGlyIleThrIlePhe
LeuPhePheLeuArgLysSerMetHisSerCysSerArg***MetAlaSerProPheSer
CysPhePheLeuGluAsnLeuCysIleHisAlaValAspGluTrpHisHisPhePro
TTTGTTTTTTCTTAGAAAATCTATGCATTCATGCAGTAGATGAATGGCATCACCATTTC

```
GlnSer***LeuMetLysValLeuLysCysHisSerIlePheThrGlnGlyLysSerTyr
LysAlaAsn*****ArgTyrLeuAsnValIleArgTyrSerLeuArgValLysValThr
LysLeuIleAspGluGlyThr***MetSerPheAspIleHisSerGly***LysLeuGln
CAAAGCTAATTGATGAAGGTACTTAAATGTCATTCGATATTCACTCAGGGTAAAAGTTAC
                              200
LysValValPheThrSerAsnPhePheGlnMetIleProLysCysIlePheProLeuArg
LysSerTyrSerLeuArgIleSerPheLys***SerGlnSerValPheSerLeu***Gly
SerArgIleHisPheGluPheLeuSerAsnAspProLysValTyrPheProPheGluAsp
AAAGTCGTATTCACTTCGAATTTCTTTCAAATGATCCCAAAGTGTATTTCCCTTTGAGG
                                                        300
```

```
IleMetIleLysArgGlyTrpThrAsnThrAsnLeuPheArgTyrIleLeuTyrAspArg
*****SerSerGluAspGlyLeuThrProIleCysPheAspIleCysMetThrGlu
AsnAspGlnAlaArgMetAsp***HisGlnSerValSerIleTyrIleVal***ProAsn
ATAATGATCAAGCGAGGATGGACTAACACCAATCTGTTTCGATATATATTGTATGACCGA

IleTrpAspAlaPheAspMetSerValTrpProThrGlyIleProLysAsnSer***Leu
SerGlyMetLeuLeuIle***ValTyrGlyGlnProTyrArgArgThrAlaAsn***
LeuGlyCysPhe***TyrGluCysMetAlaAsnArgAspThrGluGlnLeuIleGlu
ATCTGGGATGCTTTTGATATGAGTGTATGGCCAACCGGGATACCGAAGAACAGCTAATTG
                                          400

AsnSerLysSer***ThrValPhePheProProSerLeuIleAsnTyrPhe***IlePro
ThrAlaAsnProLysArgPheSerSerLeuLeuArgLeuLeuThrIleSerLysSerArg
GlnGlnIleLeuAsnGlyPheLeuProSerPheAlaTyr***LeuPheLeuAsnProVal
AACAGCAAATCCTAAACGGTTTCTTCCCTCCTTCGCTTATTAACTATTTCTAAATCCG
```

PheGlyLysSerGluValGlyProGlnTyrProPheIlePheArgAspLeuHisLysSer
LeuGluLysValLys***ValProSerIleHisSerSerSerGlyIleCysIleLysAla
TrpLysLys*SerArgSerProValSerIleHisLeuGlnGlyPheAla*LysPro
TTTGGAAAAGTGAAGTAGGTCCCCAGTATCCATTCATCTTCAGGATTTGCATAAAAGC
                            500
LeuSerLeuPheArgCysLysGlnPheSerThrSerArgAsnPheHisSerValSerPhe
CysLeuCysSerGlyValSerAsnSerLeuProLeuAlaIlePheIleGlnTyrHisSer
ValSerValProVal***AlaIleLeuTyrLeuSerGlnPheSerPheSerIleIlePro
CTGTCTCTGTTCCGGTGTAAGCAATTCTCTACCTCTCGCAATTTCATTCAGTATCATTC
                                                           600

HisPheCysIlePheAsnLeuLeuValGlnLeuTyrIleAsnArgValTyrSerIleAsp
IleSerValPheSerIleTyr***PheAsnTyrIleSerIleGluCysThrLeuLeuIle
PheLeuTyrPheGlnPheIleSerIleIleTyrGln*SerValLeuTyr*Tyr
CATTTCTGTATTTTCAATTATTAGTTCAATTATATCAATAGAGTGTACTCTATTGAT

ThrAsnValValAsp***AsnHisSer*GluArgLeuIleArgLeuValSerLys
GlnMet****ThrAspLysIleIleValLysSerValSer*AspLeuSerGlnLys
LysCysSerArgLeuIleLysSer***LeuArgAlaSerHisLysThrCysLeuLysAsn
ACAAATGTAGTAGACTGATAAAATCATAGTTAAGAGCGTCTCATAAGACTTGTCTCAAAA

700

MetArg*TyrPheAlaGluAsnArgLeuTyrSerCysGlnPheAsp*ProGluSer
***GlyAspIleLeuArgLysIleGlyTyrIleArgValSerSerThrAsnGlnAsnPro
GluValIlePheCysGlyLysSerValIlePheValSerValArgLeuThrArgIleLeu
ATGAGGTGATATTTTGCGGAAAATCGGTTATATTCGTGTCAGTTCGACTAACCAGAATCC

```
PheLysThrIleSerAlaValGluArgAspArgAsnGlyTyrTyrIleLysArgLysPhe
SerArgGlnPheGlnGlnLeuAsnGluIleGlyMetAspIleIle***ArgGluSerPhe
GlnAspAsnPheSerSer***ThrArgSerGluTrpIleLeuTyrLysGluLysValSer
TTCAAGACAATTTCAGCAGTTGAACGAGATCGGAATGGATATTATATAAAGAGAAAGTTT
                              .                              
                             800                             
GlnGluGlnGlnArgIleAlaSerAsnPheLysLysCys***ThrIleTyrArgLysMet
ArgSerAsnLysGlySerArgArgAlaThrSerLysSerValArgArgPheThrGlyArg**
GlyAlaThrLysAspArgGluGlnLeuLysValLeuAspAspLeuGlnGluAspAsp
CAGGAGCAACAAAGGATCGCGAGCAACTTCAAAAGTGTTAGACGATTTACAGGAAGATG
                              .                              
                             900                             
```

```
ThrSerPheMetLeuGlnThr***LeuGluSerLeuValValHisLysIleTyrLeuAsn

HisHisLeuCysTyrArgLeuAsnSerAsnHisSer***TyrThrArgSerIle***Ile

IleIleTyrValThrAspLeuThrAspIleThrArgSerThrArgGlnAspLeuPheGluLeu
ACATCATTTATGTTACAGACTTAACTGAATCACTCGTAGTACACAGATCTATTGAAT

*SerIleThrTyrGluIleLysArgGlnVal*LysIleHisGlyLeu

AsnArg***HisThrArg***LysGlyLysPheLysIleThrLysArgTyrMetAla***

IleAspAsnIleArgAspLysLysAlaSerLeuLysSerLeuLysAspThrTrpLeuAsp
TAATCGATAACATACGAGATAAAAAGGCAAGTTTAAAATCACTAAAGATACATGGCTTG
                                    1000

IleTyrGlnLysIleIleHisThrAlaAsnSer***LeuLeu***TrpLeuValLeuThr

PheIleArgArg***SerIleGlnProIleLeuAsnTyrCysAsnGlyTrpCys***Pro

LeuSerGluAspAsnProTyrSerGlnPheLeuIleThrValMetAlaGlyValAsnGln
ATTTATCAGAAGATAATCCATACAGCCAATTCTTAATTACTGTAATGGCTGGTGTTAACC
```

Asn*SerGluIleLeuPheGly*AspAsnValLysGlyLeuAsnTrpLeuArgLys
IleArgAlaArgSerTyrSerAspGluThrThr*ArgAsp*IleGly***GluArg
LeuGluArgAspLeuIleArgMetArgGlnArgGluGlyIleGluLeuAlaLysLysGlu
AATTAGAGCCGAGATCTTATTCGGATGAGACAACGTGAAGGATTGAATTGGCTAAGAAAG
                              .                              
                            1100                             
LysGluSerLeuLysValAsp*ArgSerIleIleLysIleThrGlnGlu*IleMet
ArgLysVal*ArgSerIleLysGluValSer*LysSerArgArgAsnGluLeuCys
GlyLysPheLysGlyArgLeuLysLysTyrHisLysAsnHisAlaGlyMetAsnTyrAla
AAGGAAAGTTTAAAGGTCGATTAAAGAAGTATCATAAAAATCACGCAGGAATGAATTATG
                              .                              
                            1200

FIG. 5H

ArgArgLysLeuTyrLysGluGlyAsnMetThrValAsnGlnIleCysGluIleThrAsn
GlyGluSerTyrIleLysLysGluIle*Leu*IleLysPheValLysLeuLeuMet
AlaLysAlaIle*ArgArgLysTyrAspCysLysSerAsnLeu*AsnTyr***Cys
CGGXXAAAGCTATATAAAGAAGGAAATGACTGTAAATCAAATTTGTGAAATTACTAAT

ValSerArgAlaSerLeuTyrArgLysLeuSerGluValAsnAsn***ProPheCysIle
TyrLeuGlyLeuHisTyrThrGlyAsnTyrGlnLys***IleIleSerHisSerValPhe
Ile*GlyPheIleIleGlnGluIleIleArgSerGlu*LeuAlaIleLeuTyrSer
GTATCTAGGGCTTCATTATACAGGAAATTATCAGAAGTGAATAATTAGCCATTCTGTATT
                                    1300
ProLeuMetGlyAsnIlePheLysGluGluLysGluThrIleLysTyr***GlnProPro
Arg*TrpAlaIlePheLeuLysLysLysArgLysLeu*AsnIleAsnSerLeuLeu
AlaAsnGlyGlnTyrPhe*ArgArgLysGlyAsnTyrLysIleLeuThrAlaSer*
CCGCTAATGGGCAATATTTTTAAAGAAGAAAAGGAAACTATAAATATTAACAGCCTCCT

FIG. 5I

```
SerAspAlaGluLysProPheAspLysLysArgIleIleIleLeuArgAsnSer***Ser
AlaMetProLysSerProLeuIleLeuIleLysLysGluSerSerSer***GluIleLeuSerHis
ArgCysArgLysAlaLeu*****LysLysAsnHisHisLeuLysLysPheLeuValIle
AGGGATGCCGAAAAGCCCTTGATAAAAAAGAATCATCTTAAGAATTCTTAGTCA
                              1400
PheIleMet***MetLeuIleAsnSerAlaLeu***SerAspLysLeuLeuArgAlaAsn
LeuLeuCysLysCysLeu***IleArgProTyrAsnLeuIleAsnTyr****GlyGlnThr
TyrTyrValAsnAlaTyrLysPheGlyProIleIle****IleIleLysGlyLysLeu
TTTATTATGTAAATGCTTATAAATTCGGCCCTATAATCTGATAATTATTAAGGCAAAC
                                                         1500
```

FIG. 5J

LeuCysGluArgValIleThrMetSerAspLysIleLeuIleValAspAspGluHisGlu
TyrValLysGly*Leu*AlaIleLysTyrLeuLeuTrpMetMetAsnMetLys
Met*LysGlyAspAsnTyrGluArg*AsnThrTyrCysGly***Thr*Asn
TTATGTGAAAGGGTGATAACTATGAGCGATAAATACTTATTGTGGATGATGAACATGAA

IleAlaAspLeuValGluLeuTyrLeuLysAsnGluAsnTyrThrValPheLysTyrTyr
LeuProIleTrpLeuAsnTyrThr***LysThrArgIleIleArgPheSerAsnThrIle
CysArgPheGly***IleIleLeuLysLysArgGluLeuTyrGlyPheGlnIleLeuTyr
ATTGCCGATTTGGTTGAATTATACTTAAAAAACGAGAATTATACGGTTTTCAAATACTAT
                                1600

ThrAlaLysGluAlaLeuGluCysIleAspLysSerGluIleAspLeuAlaIleLeuAsp
ProProLysHisTrpAsnVal***ThrSerLeuArgLeuThrLeuProTyrTrpThr
ArgGlnArgSerIleGlyMetTyrArgGlnVal*Asp*ProCysHisIleGlyHis
ACCGCCAAGAAGCATTGGAATGTATAGACAAGTCTGAGATTGACCTTGCCATATTGGAC

FIG. 5K

```
IleMetLeuProGlyThrSerGlyLeuThrIleCysGlnLysIleArgAspLysHisThr
SerCysPheProAlaGlnAlaAlaLeuLeuSerValLysLys***GlyThrSerThrPro
HisAlaSerArgHisLysArgProTyrTyrLeuSerLysAsnLysGlyGlnAlaHisLeu
ATCATGCTTCCCGGCACAAGCGGCCTTACTATCTGTCAAAAATAAGGGACAAGCACACC
                              1700
TyrProIleIleMetLeuThrGlyLysAspThrGluValAspLysIleThrGlyLeuThr
IleArgLeuSerCys***ProGlyLysIleGlnArg***IleLysLeuGlnGly***Gln
SerAspTyrHisAlaAspArgGluArgTyrArgGlyArg***AsnTyrArgValAsnAsn
TATCCGATTATCATGCTGACCGGGAAAGATACAGAGGTAGATAAAATTACAGGGTTAACA
                                                    1800
```

FIG. 5L

```
IleGlyAlaAspAspTyrIleThrLysProPheArgProLeuGluLeuIleAlaArgVal
SerAlaArgMetIleIle***ArgSerProPheAlaHisTrpSer***LeuLeuGly***
ArgArgGly***LeuTyrAsnGluAlaAlaLeuSerProThrGlyValAsnCysSerGlyLys
ATCGGCGGGATGATTATATAACGAAGCCCTTTCGCCCACTGGAGTTAATTGCTCGGGTA

LysAlaGlnLeuArgArgTyrLysLysPheSerGlyValValLysGluGlnAsnGluAsnVal
ArgProSerCysAlaAspThrLysAsnSerValGlu***ArgSerArgThrLysMetLeu
GlyProValAlaProIleGlnLysIleGlnTrpSerLysGlyAlaGluArgLysCysTyr
AAGGCCCAGTTGCGCCGATACAAAAAATTCAGTGGAGTAAAGGAGCAGAACGAAAATGTT
                                                    1900

IleValHisSerGlyLeuValIleAsnValAsnThrHisGluCysTyrLeuAsnGluLys
SerSerThrProAlaLeuSerLeuMetLeuThrProMetSerValIle***ThrArgSer
ArgProLeuArgProCysHis***Cys***HisPro***ValLeuSerGluArgGluAla
ATCGTCCACTCCGGCCTTGTCATTAATGTTAACACCCATGAGTGTTATCTGAACGAGAAG
```

FIG. 5M

```
GlnLeuSerLeuThrProThrGluPheSerIleLeuArgIleLeuCysGluAsnLysGly
SerTyrProLeuProProSerPheGlnTyrCysGluSerSerValLysThrArgGly
ValIleTyrSerHisArgValPheAsnThrAlaAsnProLeu***LysGlnGlyGlu
CAGTTATCCCTTACTCCCCACCGAGTTTTCAATACTGGCGAATCCCTCTGAAAACAAGGGG
                              .
                            2000

AsnValValSerSerGluLeuLeuPheHisGluIleTrpGlyAspGluTyrPheSerLys
MetTrpLeuAlaProSerCysTyrPheMetArgTyrGlyAlaThrAsnIleSerAlaArg
CysGly***LeuArgAlaAlaIleSer***AspMetGlyArgArgIlePheGlnGlnGlu
AATGTGGTTAGCTCCGAGCTGCTATTTCATGAGATATGGGGCGACGAATATTTCAGCAAG
                              .
                            2100
```

FIG. 5N

SerAsnAsnThrIleThrValHisIleArgHisLeuArgGluLysMetAsnAspThrIle
AlaThrThrProSerProCysIleSerGlyIleCysAlaLysLys***ThrThrProLeu
GlnGlnHisHisArgAlaTyrProAlaPheAlaArgLysAsnGluArgHisHis***
AGCAACAACACCATCACCGTGCATATCCGGCATTGCGCGAAAAATGAACGACACCATT

AspAsnProLysTyrIleLysThrValTrpGlyValGlyTyrLysIleGluLys***Lys
IleIleArgAsnIle***LysArgTyrGlyGlyLeuValIleLeuLysLeuLysAsnLysLys
*SerGluIleTyrLysAsnGlyMetGlyGlyTrpLeu*Asn***LysIleLysLys
GATAATCCGAAATATATAAAAACGGTATGGGGGGTTGGTTATAAAATGAAAAATAAAA
                                          2200

LysArgLeuPheGlnThrArgThrLysThrLeuHisValTyrArgCysAsnCysCysGly
AsnAspTyrSerLysLeuGluArgLysLeuTyrMetTyrIleValAlaIleValValVal
ThrThrIleProAsn*AsnGluAsnPheThrCysIleSerLeuGlnLeuLeuTrp*
AAACGACTATTCCAAACTAGAACGAAAACTTTACATGTATATCGTTGCAATTGTTGTGGT

FIG. 50

SerAsnCysIleArgValValTyrSerPheAsnAspProArgGluThrTrpGlyLeuAsp
AlaIleValPheValLeuTyrIleArgSerMetIleArgGlyLysLeuGlyAspTrpIle
GlnLeuTyrSerCysCysIlePheValGln***SerGluGlyAsnLeuGlyIleGlySer
AGCAATTGTATTCGTGTTGTATATTCGTTCAATGATCCGAGGGAAACTTGGGGATTGGAT
                                    .
                                  2300
LeuLysTyrPheGlyLysGlnIle***LeuLysSerProGlyArgAspGluIleIleSer
LeuSerIleLeuGluAsnLysTyrAspLeuAsnHisLeuAspAlaMetLysLeuTyrGln
*ValPheTrpLysThrAsnMetThr*IleThrTrpThrArg***AsnTyrIleAsn
CTTAAGTATTTTGGAAAACAAATATGACTTAAATCACCTGGACGGCGATGAAATTATATCA
                                    .
                                  2400

```
IlePheHisThrGluGlnTyrArgTyrLeuTyrCysGlyAspCysHis***TyrSer
TyrSerIleArgAsnAsnIleAspIlePheIleTyrValAlaIleValIleSerIleLeu
IleProTyrGlyThrIle***IleSerLeuPheMetTrpArgLeuSerLeuValPheLeu
ATATTCCATACGGAACAATATAGATATCTTTATTTATGTGGGATTGTCATTAGTATTCT

TyrSerMetSerArgHisAlaPheLysIleArgLysIleLeu***ArgAspLysTyrArg
IleLeuCysArgValMetLeuSerLysPheAlaLysTyrPheAspGluIleAsnThrGly
PheTyrValAlaSerCysPheGlnAsnSerGlnAsnThrLeuThrArg***IleProAla
TATTCTATGTCGCGTCATGCTTTCAAAATTCGCAAAATACTTTGACGAGATAAATACCGG
                                         2500

His***CysThrTyrSerGluArgArg***ThrAsn***AlaPheCysGlyAsnGlyCys
IleAspValLeuIleGlnAsnGluAspLysGlnIleGluLeuSerAlaGluMetAspVal
LeuMetTyrLeuPheArgThrLysIleAsnLysLeuSerPheLeuArgLysTrpMetLeu
CATTGATGTACTTATTCAGAACGAAGATAAACAAATTGAGCTTTCGCGAAATGGATGT
```

```
TyrGlyThrLysAlaGlnHisIleLysThrAspSerGlyLysAlaArgAlaGlyCysLys
MetGluGlnLysLeuAsnThrLeuLysArgThrLeuGluLysArgGluGlnAspAlaLys
TrpAsnLysSerSerThrHis***AsnGlyLeuTrpLysSerGluSerArgMetGlnSer
TATGGAACAAAAGCTCAACACATTAAAACGGACTCTGGAAAGCGAGAGCAGGATGCAAA
                           2600
AlaGlyArgThrLysLysLys***ArgCysTyrValLeuGlyAlaArgTyr***AsnAla
LeuAlaGluGlnArgLysAsnAspValValMetTyrLeuAlaHisAspIleLysThrPro
TrpProAsnLysGluLysMetThrLeuLeuCysThrTrpArgThrIleLeuLysArgPro
GCTGGCCGAACAAAGAAAAAATGACGTTGTTATGTACTTGGCGCACGATATTAAAACGCC
                                               2700
```

FIG. 5R

ProTyrIleHisTyrArgLeuPheGluProAla***ArgGlySerArgHisAlaGlyArg

LeuThrSerIleIleGlyTyrLeuSerLeuLeuAspGluAlaProAspMetProValAsp

LeuHisProLeuSerValIle*AlaCysLeuThrArgLeuGlnThrCysArg*Ile

CCTTACATCCATTATCGGTTATTGAGCCTGCTTGACGAGGCTCCAGACATGCCGGTAGA

SerLysGlyLysValCysAlaTyrHisIleThrLeuAspLysAlaTyrArgLeuGluGlnLeuIle

GlnLysAlaLysTyrValHisIleThrLeuAspLysAlaTyrArgLeuGluGlnLeuIle

LysArgGlnSerMetCysIleSerArgTrpThrLysArgIleAspSerAsnSer***Ser

TCAAAGGCAAAGTATGTGCATATCACGTTGGACAAAGCTATCGACTCGAACAGCTAAT
                                    2800

ArgArgValPhe*AspTyrThrVal*ProThrAsnAspAsnAlaAsnLysAsnAla

AspGluPhePheGluIleThrArgTyrAsnLeuGlnThrIleThrLeuThrLysThrHis

ThrSerPheLeuArgLeuHisGlyIleThrTyrLysArg*Arg*GlnLysArgThr

CGACGAGTTTTTGAGATTACACGGTATAACCTACAAACGATAACGCTAACAAAAACGCA

FIG. 5S

```
HisArgProIleLeuTyrAlaGlyAlaAspAspArg***IleLeuSerSerAlaPheArg
IleAspLeuTyrTyrMetLeuValGlnMetThrAspGluPheTyrProGlnLeuSerAla
*ThrTyrThrIleCysTrpCysArg*ProMetAsnPheIleLeuSerPheProHis
CATAGACCTATACTATATGCTGGTGCAGATGACCGATGAATTTATCCTCAGCTTTCCGC
                              2900                              
ThrTrpLysThrGlyGlyTyrSerArgProArgGlySerAspArgValArgArgPro***
HisGlyLysGlnAlaValIleHisAlaProGluAspLeuThrValSerGlyAspProAsp
MetGluAsnArgArgArgLeuPheThrProProArgIle***ProCysProAlaThrLeuIle
ACATGGAAAACAGGGCGGTTATTCACGCCCCCGAGGATCTGACCGTCCGGCGACCCTGA
                              3000
```

FIG. 5T

```
*ThrArgGluSerLeu*GlnHisPheGluLysArgArgCysIleGln*Gly*
LysLeuAlaArgValPheAsnAsnIleLeuLysAsnAlaAlaAlaTyrSerGluAspAsn
AsnSerArgGluSerLeuThrThrPhe***LysThrProLeuHisThrValArgIleThr
TAAACTCGGGAGAGTCTTAACAACATTTGAAAAACGCCGTGCATACAGTGAGGATAA

GlnHisHis***HisTyrArgGlyProLeuArgGlyCysGlyValAsnArgIleGlnGlu
SerIleIleAspIleThrAlaGlyLeuSerGlyLeuLysAspValValSerIleGluPheLysAsn
AlaSerLeuThrLeuProArgAlaSerProGlyMetTrpCysGlnSerAsnSerArgThr
CAGCATCATTGACATTACCGGGCCCTCTCCGGGGATGTGGTGTCAATCGAATTCAAGAA
                                    3100
HisTrpLysHisProLysArg***AlaSerCysHisIle***LysValLeu***AlaGly
ThrGlySerIleProLysAspLysLeuAlaAlaIlePheGluLysPheTyrArgLeuAsp
LeuGluAlaSerGlnLysIleSer***LeuProTyrLeuLysSerIleGlyTrpThr
CACTGGAAGCATCCCAAAAGATAAGCTAGCTGCCATATTTGAAAAGTTCTATAGGCTGGA
```

FIG. 5U

```
GlnPheSerPheArgTyrGlyTyrGlyThrTrpIleGlyAspCysLysArgAsn
AsnSerArgSerAspThrGlyGlyAlaGlyLeuGlyLeuAlaIleAlaLysGluIle
IleLeuValLeuProIleArgValAlaAlaArgAspLeuAspTrpArgLeuGlnLysLysLeu
CAATTCTCGTTCTTCCGATACGGGTGGCGCGGGACTTGGATTGGCGATTGCAAAAGAAAT
                            .                         .                         .
                           3200
TyrCysSerAlaTrpArgArgAlaAspLeuArgGlyLyLysLeu*****LeuTyrArgVal***
IleValGlnHisGlyGlyGlnIleTyrAlaGluSerTyrAspAsnTyrThrThrPheArg
LeuPheSerMetGluGlyArgPheThrArgLysAlaMetIleThrIleArgArgLeuGly
TATTGTTCAGCATGGAGGGCAGATTTACGCGAAAGCTATGATAACTATACGACGTTTAG
                            .                         .                         .
                                                                                3300
```

```
GlyArgAlaSerSerAspAlaArgLeuGly******LysGluValLeuArgAspValTyr
ValGluLeuProAlaMetProAspLeuValAspLysArgArgSer***GluMetTyrIle
*SerPheGlnArgCysGlnThrTrpLeuIleLysGlyGlyProLysArgCysIle*
GGTAGAGCTTCCAGGCGATGCCAGACTTGGTTGATAAAGGAGTCCTAAGAGATGTATAT

AsnPheLeuGlyLysSerGlnGlyTyrLeuTyrPhePheLeuGlyAsn***GlnPheAsn
IlePhe***GluAsnLeuLysValIlePheThrPheSer***GluIleAsnAsnLeuIle
PhePheArgLysIleSerArgLeuSerLeuLeuPheLeuArgLysLeuThrIle***Tyr
AATTTTTAGGAAAATCTCAAGGTTATCTTTACTTTTTCTTAGGAAATTAACAATTAAT
                           3400

IleLysLysArgLeuValLeuThrArg***Thr***TyrArgLysAsnGluProPheSer
LeuArgAsnGlySerPheLeuHisGlyArgLeuAsnThrValArgThrSerArgPheArg
*GluThrAlaArgSerTyrThrValAspLeuIlePro*GluArgAlaValPheVal
ATTAAGAAACGGCTCGTTCTTACACGGTAGACTTAATACCGTAGAGAACGAGCCGTTTCG
```

PhePheArgGluArgPheAspLysIleThrIleGlyIleProValLeuPheGlyAlaPhe
SerSerGluLysAspLeuThrArgLeuProLeuAlaSerProPheTyrLeuValProPhe
LeuGlnArgLysIle***GlnAspTyrHisTrpHisProArgPheIleTrpCysLeuSer
TTCTTCAGAGAAGATTTGACAAGATTACCATGGCATCCCGTTTATTTGGTGCCTTT
                            3500
HisArgLysGlyTrpSer*Leu*IleThrSerAlaLeuLeuPheMetAspValSer
ThrGluArgValGlyLeuAsnTyrGlu*HisArgHisTyrCysLeuTrpMet*Ala
GlnLysGlyLeuValLeuIleMetAsnAsnIleGlyIleThrValTyrGlyCysGluGln
CACAGAAAGGGTTGGTCTTAATTATGAATAACATCGGCATTACTGTTTATGGATGTGAGC
                                                        3600

```
ArgMetArgGlnMetHisSerMetLeuPheArgLeuAlaAlaLeuAlaLeuTrpGlnArg***
Gly***GlyArgCysIleProCysSerPheAlaSerLeuTrpArgTyrGlyAsnAspAsn
AspGluAlaAspAlaPheHisAlaAlaLeuSerProArgPheGlyValMetAlaThrIleIle
AGGATGAGGCAGATGCATTCCATGCTCTTTCGCCTCGCTTTGGCGTTATGGCAACGATAA

LeuThrProThrCysArgAsnProThrProArgLeuSerIleAsnValSerVal
***ArgGlnArgValGlyIleGlnArgAlaPheGlnSerMetTyrGlnCys
AsnAlaAsnValSerGluSerAlaLysSerAlaProPheAsnGlnCysIleSerVal
TTAACGCCAACGTGTCGGAATCCAACGCCAAATCCGGCCTTTCAATCAATGTATCAGTG
                            .      3700                .

TrpAspIleAsnGlnArgPheProProLeuPhePheLeuArg***ArgGluProVal***
GlyThr***IleArgAspPheArgLeuTyrSerSerCysAlaGluSerArgCysGlu
GlyHisLysSerGluIleSerAlaSerIleLeuLeuAlaLeuLysArgAlaGlyValLys
TGGGACATAAATCAGAGATTTCCGCCTCTATTCTTCTTCTTGGCTGAAGAGAGCCGGTGTGA
```

```
AsnIlePheLeuProGluAlaSerAlaAlaAlaIleIle***IleGlnLeuLeuLeuArgGlu
IleTyrPheTyrProLysHisArgLeuGlnSerTyrArgTyrArgTyrAsnCysCys***GluAsn
TyrIleSerThrArgSerIleGlyCysAsnHisIleAspThrThrAlaAlaLysArgMet
AATATATTTCTACCCGAAGCATCGGCTGCAATCATATAGATACAACTGCTAAGAGAA
                            3800
TrpAlaSerLeuSerThrMetTrpArgThrArgArgIleAlaLeuProIleIleLeu***
GlyHisHisCysArgGlnCysGlyValLeuAlaGly***ArgCysArgLeuTyrTyrAsp
GlyIleThrValAspAsnValAlaTyrSerProAspSerValAlaAspTyrThrMetMet
TGGGCATCACTGTCGACAATGTGGCGTACTCGCCCGGATAGCGTTGCCGATTATACTATGA
                                                              3900
```

FIG. 5Z

```
Cys***PheLeuTrpGlnTyrAlaThr***AsnArgLeuCysAlaAlaLeuTrpLysAsnMet
AlaAsnSerTyrGlySerThrGlnArgLysIleAspCysAlaLeuCysGlyLysThr***
LeuIleLeuMetAlaValArgAsnValLysSerIleValArgSerValGluLysHisAsp.
TGCTAATTCTTATGGCAGTACGCAACGTAAAATCGATTGTGCGCTCTGTGGAAAAACATG
                       .                       .
IleSerGlyTrpThrAlaThrValAlaArgTyrSerAlaThr***GlnLeuValTrpTrp
PheGlnValGlyGlnArgProTrpGlnArgHisAspSerTrpCysGlyGly
PheArgLeuAspSerAspArgGlyLysValLeuSerAspMetThrValGlyValValGly
ATTTCAGGTTGGACAGCGACCGTGGCAAGGTACTCAGCGACATGACAGTTGGTGTGGGTGG
                       .     4000              .
GluArgAlaArg***AlaLysArgLeuLeuSerGlyCysGluAspLeuAspValLysCys
AsnGlyProAspArgGlnSerGlyTyr***AlaAlaAlaArgIleTrpMet***SerVal
ThrGlyGlnIleGlyLysValAlaValIleGluArgLeuArgGlyPheGlyCysLysValLeu
GAACGGGCCAGATAGGCAAAGGCGGTTATTGAGCGGCTGCGAGGATTTGGATGTAAAGTGT
```

FIG. 5AA

```
TrpLeuIleValAlaAlaGluVal***Arg***ThrMetTyrArgLeuMetSerCysCys
GlyLeu***SerGlnProLysTyrArgGlyLysCysLeuThrVal****ValAlaAla
AlaTyrSerArgSerArgSerIleGluValAlaAsnTyrValProPheAspGluLeuGln
TGGCTTATAGTCGCAGCCGAAGTATAGAGGTAAACTATGTACCGTTTGATGAGTTGCTGC
                              .
                            4100
LysIleAlaIleSerLeuArgPheMetCysArgSerIleArgIleArgThrIleLeuSer
Lys***ArgTyrArgTyrAlaSerCysAlaAlaGlnTyrGlyTyrAlaLeuTyrTyrGln
AsnSerAspIleValThrLeuHisValProLeuAsnThrAspThrHisTyrIleIleSer
AAAATAGGCGATATCGTTACGCTTCATGTGCCGCTCAATACGGATACGCACTATATTATCA
                              .
                            4200
```

```
AlaThrAsnLysTyrArgGlu***SerLysGluHisPheLeuSerIleLeuGlyAlaVal
ProArgThrAsnThrGluAsnGlyAlaAlaArgSerIleSerTyrGlnTyrTrpAlaArgSer
HisGluGlnIleGlnArgMetLysGlnGlyAlaPheLeuIleAsnThrGlyArgGlyPro
GCCACGAACAAATACAGAGAATGAAGCAAGGAGCATTCTATCAATACTGGGCGCGGTC

HisLeu***IleProMetSerTrpLeuLysHis***LysThrGlyAsnTrpAlaValPro
ThrCysArgTyrLeu***ValGly***SerIleArgLysArgGluThrGlyArgCysArg
LeuValAspThrTyrGluLeuValLysAlaLeuGluAsnGlyLysLeuGlyAlaAla
CACTTGTAGATACCTATGAGTTGGTTAAAGCATTAGAAAACGGGAAACTGGGCGGGTGCCG
                                            4300

HisTrpMetTyrTrpLysGluArgLysSerPheSerThrLeuIleAlaProLysAsnGln
IleGlyCysIleGlyArgArgGlyArgGlyGluGluPheTyrSerAspCysThrGlnLysProIle
LeuAspValLeuGluGluGluGluPheTyrSerAspCysThrGlnLysProIle
CATTGGATGTATTGGAAGGAGAGGAAGAGTTTTCTACTCTGATTGCACCCAAAAACCAA
```

LeuIleIleAsnPheTyrLeuAsnPheLysGluCysLeuThr***** SerHisArgIle
***SerIlePheThr*ThrSerLysAsnAla***ArgAspAsnHisThrAlaTyr
AspAsnGlnPheLeuLeuLysLeuGlnArgMetProAsnValIleIleThrProHisThr
TTGATAATCAATTTTTACTTAAACTTCAAAGAATGCCTAACGTGATAATCACACCGCATA
                    .                    .                    .
                   4400

ArgProIleIleProSerLysArgCysValIleProLeuLysLysProLeuLysThrVal
GlyLeuLeuTyrArgAlaSerValAla*TyrArg*LysAsnHis***LysLeuPhe
AlaTyrTyrThrGluGlnAlaLeuArgAspThrValGluLysThrIleLysAsnCysLeu
CGGCCTATTATACCGAGCAAGCGTTGCGTGATACCGTTGAAAAACCATTAAAAACTGTT
                    .                    .                    .
                                                              4500

FIG. 5DD

TrpIleLeuLysGlyAspArgSerMetAsnArgIleLysValAlaAlaIleLeuPheGlyGly
GlyPhe*LysGluThrGlyAla*IleGlu***LysLeuGlnTyrCysLeuGlyVal
AspPheGluArgArgGlnGluHisGlu***AsnLysSerCysAsnThrValTrpGlyLeu
TGGATTTTGAAAGGAGACAGGAGCATGAATAGAATAAAAGTTGCAATACTGTTTGGGGGT

CysSerGluHisAspValSerValLysSerAlaIleGluIleAlaAlaAsnIleAsn
AlaGlnArgSerMetThrTyrArg*AsnLeuGln*Arg***ProLeuThrLeuIle
LeuArgGlyAla*ArgIleGlyLysIleCysAsnArgAspSerArg*His******
TGCTCAGAGGAGCATGACGTATCGGTAAAATCTGCAATAGAGATAGCCGCTAACATTAAT
            4600

LysGluLysTyrGluProLeuTyrIleGlyIleThrLysSerGlyValTrpLysMetCys
LysLysAsnThrSerArgTyrThrLeuGluLeuArgAsnLeuValTyrGlyLysCysAla
ArgLysIleArgAlaValIleHisTrpAsnTyrGluIleTrpCysMetGluAsnValArg
AAGAAAAAATACGAGCCGTTATACATTGGAATTACGAAATCTGGTGTATGGAAAATGTGC

FIG. 5EE

```
GluLysProCysAlaGluTrpGluAsnAspAsnCysTyrSerAlaValLeuSerProAsp
LysAsnLeuAlaArgAsnGlyLysThrThrIleAlaIleGlnLeuTyrSerArgArgIle
LysThrLeuArgGlyMetGlyLysArgGlnLeuLeuPheSerCysThrLeuAlaGly***
GAAAACCTTGCGCGGAATGGGAAAACGACAATTGCTATTCAGCTGTACTCTCGCCGGAT
                          4700
LysLysMetHisGlyLeuLeuValLysLysAsnHisGluTyrGluIleLysValAsp
LysLysCysThrAspTyrLeuLeuLysArgThrMetAsnMetLysSerThrMetLeuMet
LysAsnAlaArgIleThrCys***LysGluPro***Ile***AsnGlnProCys***Cys
AAAAAAATGCACGGATTACTTGTTAAAAGAACCATGAATATGAAATCAACCATGTTGAT
                                                        4800
```

```
ValAlaPheSerAlaLeuHisGlyLysSerGlyGluAspGlySerIleGlnGlyLeuPhe
***HisPheGlnLeuCysMetAlaSerGlnValLysMetAspProTyrLysValCysLeu
SerIlePheSerPheAlaTrpGlnValArg***ArgTrpIleHisThrArgSerVal***
GTAGCATTTCAGCTTTGCATGGCAAGTCAGGTGAAGATGGATCCATACAAGGTCTGTTT
                    .                    .                    .

GluLeuSerGlyIleProPheValGlyCysAspIleGlnSerSerAlaIleCysMetAsp
AsnCysProValSerLeuLeu***AlaAlaIlePheLysAlaGlnPheValTrpThr
IleValArgTyrProPheCysArgLeuArgTyrSerLysLeuSerAsnLeuTyrGlyGln
GAATTGTCCGGTATCCCTTTTGTAGGCTGCGATATTCAAAGCTCAGCAATTGTATGGAC
                    .            4900            .

LysSerLeuThrThrTyrIleValAlaAlaLysAsnAlaGlyIleAlaThrProAlaPheTrpVal
AsnArg***HisThrSerLeuArgLysMetLeuGly***LeuLeuProProPheGlyLeu
IleValAspIleHisArgCysGluLysCysTrpAspSerTyrSerArgLeuLeuGlyTyr
AAATCGTTGACATACATCGTTGCGAAAAATGCTGGGATAGCTACTCCCGCCTTTTGGGTT
                    .                    .                    .
```

IleAsnLysAspAspArgProValAlaAlaThrPheThrTyrProValPheValLysPro
LeuIleLysMetIleGlyArgTrpGlnLeuArgLeuProIleLeuPheLeuLeuSerArg
****Arg**AlaGlyGlySerTyrValTyrLeuSerCysPheCys*AlaGly
ATTAATAAAGATGATAGGCCGGTGGCAGCTACGTTTACCTATCCTGTTTTTGTTAAGCCG
                             .                            .
                           5000
AlaArgGlySerSerPheGlyValLysLysValAsnSerAlaAspGluLeuAspTyr
ArgValGlnAlaHisProSerVal***LysLysSerIleAlaArgThrAsnTrpThrThr
AlaPheArgLeuIleLeuArgCysGluLysSerGln***ArgGlyArgIleGlyLeuArg
GCGCGTTCAGGCTCATCCTTCGGTGTGAAAAAGTCAATAGCGGGACGAATTGGACTAC
                         .                            .
                                                    5100

FIG. 5HH

```
AlaIleGluSerAlaArgGlnTyrAspSerLysIleLeuIleGluGlnAlaValSerGly
GlnLeuAsnArgGlnAspAsnMetThrAlaLysSer***LeuSerArgLeuPheArgAla
Asn***IleGlyLysThrIle***GlnGlnAsnLeuAsn***AlaGlyCysPheGlyLeu
GCAATTGAATCGGCAAGACAATATGACAGCAAAATCTTAATTGAGCAGGCTGTTTCGGGC
                                    .
                                  5200

CysGluValGlyCysAlaValLeuGlyAsnSerAlaAlaLeuValValGlyGluValAsp
ValArgSerValValArgTyrTrpGluThrValProArg***LeuLeuAlaArgTrpThr
***GlyArgLeuCysGlyIleGlyLysGlnCysArgValSerCysTrpArgGlyGlyPro
TGTGAGGTCGGTTGTGCGGTTATTGGGAAACAGTGCCGCGTTAGTGTTGGCGAGGTGGAC

GlnIleArgLeuGlnTyrGlyIlePheArgIleHisGlnValGluProGluLysGly
LysSerGlyCysSerThrGluSerPheValPheIleArgLysSerSerArgLysLysAla
AsnGlnAlaAlaValAlaArgAsnLeuSerTyrSerSerGlySerArgAlaGlyLysArgLeu
CAAATCAGGCTGCAGTACGGAATCTTTCGTATTCATCAGGAAGTCGAGCCGGAAAAAGGC
```

FIG. 5II

```
SerGluAsnAlaValIleThrValProAlaAspLeuSerAlaAlaGluArgGlyArgIle
LeuLysThrGlnLeu***ProPheProGlnThrPheGlnArgSerGluAspGlyTyr
***LysArgSerTyrAsnArgSerArgArgProPheSerArgArgGlyAlaArgThrAspThr
TCTGAAAACGCAGTTATAACCGTTCCCGCAGACCTTTCAGCAGAGGAGCGAGGACGGATA
                      5300
GlnGluThrAlaAlaLysIleTyrLysAlaLeuGlyCysArgGlyLeuAlaArgValAsp
ArgLysArgGlnLysLysTyrIleLysArgSerAlaValGluVal***ProValTrpIle
GlyAsnGlyLyLysLysAsnIle***SerAlaArgLeu***ArgSerSerProCysGlyTyr
CAGGAAACGGCAAAAATATATAAAGCGCTCGGCTGTAGAGGTCTAGCCCGTGTGGAT
                                                      5400
```

MetPheLeuGlnAspAsnGlyArgIleValLeuAsnGluValLysAsnThrLeuProGlyPhe
CysPheTyrLysIleThrAlaAlaLeuTyr***ThrLysSerIleLeuCysProValSer
ValPheThrArg***ArgProHisCysThrGluArgSerGlnTyrSerAlaArgPheHis
ATGTTTTTACAAGATAACGGGCCGCATTGTACTGAACGAAGTCAATACTCTGCCCGGTTTC

ThrSerTyrSerArgTyrProArgMetMetAlaAlaAlaGlyIleAlaLeuProGluLeu
ArgHisThrValValIleProVal*TrpProLeuGlnValLeuHisPheProAsn*
ValIleGlnSerLeuSerProTyrAspGlyArgCysArgTyrCysThrSerArgThrAsp
ACGTCATACAGTCGTTATCCCGTATGATGGCCGCTGCAGGTATTGCACTTCCCGAACTG
                                    5500

IleAspArgLeuIleValLeuAlaLeuLysGly***AlaTrpLys*AspLeuLeu
LeuThrAla*SerTyr*Arg***ArgGlyAspLysHisGlyAsnArgIleTyrPhe
***ProLeuAspArgIleSerValLysGlyValIleSerMetGluIleGlyPheThrPhe
ATTGACCGCTTGATCGTATTAGCGTTAAAGGGGTGATAAGCATGAAATAGGATTACTT

```
Phe***MetLys***TyrThrValPheValGlyThrLeuAsnMetProLeuGlyIleIle

PheArg***AsnSerThrArgCysSerLeuGlyArg***IleCysHisLeuGly***Phe

LeuAspGluIleValHisGlyValArgTrpAspAlaLysTyrAlaThrTrpAspAsnPhe

TTTAGATGAAATAGTACACGGTGTTCGTTGGGACGCTAAATATGCCACTTGGGATAATT
         .                  .         .         .         .
                          5600

SerProGluAsnArgLeuThrValMetLys***IleAlaLeu***GlyHisThrSerTrp

HisArgLysThrGly***ArgLeu***SerLysSerHisCysArgAspIleArgValGly

ThrGlyLysProValAspGlyTyrGluValAsnArgIleValGlyThrTyrGluLeuAla

TCACCGGAAACCGGTTGACGGTTATGAAGTAAATCGCATTGTAGGACATACGAGTTGG
         .         .         .         .         .
                                              5700
```

```
LeuAsnArgPhe***ArgGlnLysAsnTrpLeuLeuProLysGlyThrAspCysPheTyr
***IleAlaPheGluGlyLysArgThrGlyCysTyrProArgValArgIleAlaSerMet
GluSerLeuLeuLysAlaLysGluLeuAlaAlaThrGlnGlyTyrGlyLeuLeuLeuTrp
CTGAATCGCTTTGAAGGCAAAGAACTGGCTGCTACCCAAGGTACGGGATTGCTTCTAT

GlyThrValThrValLeuSerValLeu***ThrValLeuCysAsnGlyLeuHisSerArg
GlyArgLeuProSer***AlaCysCysLysLeuPheTyrAlaMetGlyCysThrAlaGly
AspGlyTyrArgProLysArgAlaValAsnCysPheMetGlnTrpAlaAlaGlnProGlu
GGGACGGGTTACCGTCCTAAGCGTGCTGTAAACTGTTTATGCAATGGGCTGCACAGCCGG
                                    5800

LysIleThr***GlnArgLysValIleIleProIleLeuThrGluLeuArg***PheGln
Lys***ProAspLysGlyLysLeuLeuSerTyrGlnTyr***ProAsn***AspAspPheLys
AsnAsnLeuThrLysGluSerTyrTyrProAsnIleAspArgThrGluMetIleSerLys
AAAATAACCTGACAAAGGAAAGTTATTATCCCAATATTGACGAACTGAGATGATTTCAA
```

```
LysAspThrTrpLeuGlnAsnGlnAlaIleAlaAlaAlaValProLeuIleLeuArgPhe
ArgIleArgGlyPheLysIleLysPro***ProArgGlnCysHis***SerTyrAlaLeu
GlyTyrValAlaSerLysSerHisSerSerArgGlySerAlaIleAspLeuThrLeuTyr
AAGGATACGTGGCTTCAAAATCAAGCCAGTGCCATTGATCTTACGCTTT
                    .                   .                   .
                    5900
IleAsp***ThrArgValSerLeuTyrGlnTrpGlyAlaAspLeuIleLeuTrpMetAsn
SerIleArgHisGly***AlaCysThrAsnGlyGluProIle***PheTyrGly***Thr
ArgLeuAspThrGlyGluLeuValProMetGlySerArgPheAspPheMetAspGluArg
ATCGATTAGACACGGGTGAGCTTGTACCAATGGGAGCCGATTGATTTATGGATGAAC
                    .                   .                   .
                                                            6000
```

FIG. 5NN

AlaLeuIleMetArgGlnMetGluTyrHisAlaMetLysArgLysIleAlaAspValCys

LeuSerSerCysGlyLysTrpAsnIleMetGln***SerAlaLysSerGlnThrPheAla

SerHisHisAlaAlaAsnGlyIleSerCysAsnGluAlaGlnAsnArgArgArgLeuArg

GCTCTCATCATGCGGCAAATGGAATATCATGCAATGAAGCCAAAATCGCAGACGTTGC

AlaProSerTrpLysThrValGlyLeuLysHisIleAlaSerAsnGlyGlyThrMetTyr

LeuHisHisGlyLysGlnTrpVal*SerIle*ProArgMetValAlaLeuCysIle

SerIleMetGluAsnSerGlyPheGluAlaTyrSerLeuGluTrpTrpHisTyrValLeu

GCTCCATCATGGAAAACAGTGGGTTTGAAGCATATAGCCTCGAATGGTGGCACTATGTAT

6100

***GluThrAsnHisThrProIleAlaIleLeuIleSerProLeuAsnLysLeuLeuThr

LysArgArgThrIleProGln*LeuPhe*PheProArg*IleAsnPhe*Pro

ArgAspGluProTyrProAsnSerTyrPheAspPheProValLys***ThrPheAsnArg

TAAGAGACGAACCATACCCCAATAGCTATTTGATTCCCGTTAAATAAACTTTTAACC

FIG. 500

```
ValAlaArgThrAsnTyrIleSer***LeuPheArgArgGlnGluThrArgArgMet***Leu
LeuHisGlyGlnThrIle***AlaAsnSerPheGlyArgLysProAspValCysAsnTrp
CysThrAspLysLeuTyrLysLeuThrLeuSerAlaGlyAsnProThrTyrValThrGly
GTTGCACGGACAAACTATATAAGCTAACTCTTTCGGCAGGAAACCCGACGTATGTAACTG
                    .         6200         .                    .
ValLeuArgGluPheIleTyrSerArg***Tyr***ArgCysLysAlaGluArgTyrCys
PheLeuGlyAsnLeuTyrIleValAspSerIleGluAspValArgGlnSerAspIleAla
Ser***GlyIleTyrIle*****IleValLeuLysMet***GlyArgAlaIleLeuArg
GTTCTTAGGGAATTATATATAGTAGATATTGAAGATGTAAGGCAGAGAGGATATTGC
                    .         6300         .                    .
```

```
GlyHisTyrLeuArgAlaLeuAlaArgGlnAspSerLeuIleIleArgLeuIleAla***Arg
ValIleIleCysValArgCysGlyLysIleAla********Asp******SerHisArgGly
SerLeuSerAlaCysAlaAlaAlaAlaArg***ProAspAsnLysThrAspArgIleGluGly
GGTCATTATCTGCGTGCGCTGCCGCTGGGCAAGATAGCCTGATAATAGACTGATCGCATAGAGG

GlyGlyIleSerHisArgProLeuSerThrGlySerSerAlaSerLeuAsnSerAlaTrp
ValValPheHisThrAlaHisCysGlnAlaValGlnProArg***IleGlnHisGly
TrpTyrPheThrProProIleValAsnArgGlnPheSerLeuValLysPheSerMetGly
GGTGGTATTCACACGGCCCATTGTCAACAGGCAGTTCAGCCTCGTTAAATTCAGCATGG
                                6400

ValSerLeuMetLysIleHisLeuHisTrp********IleGln***GlyGluIle
TyrHisLeu***LysPheIleTyrIleGlyAspAsnSerLysSerArgAlaLys***
IleThrTyrGluAsnSerSerThrLeuValIleIleValAlaAsnProValGlyArgAsnAsn
GTATCACTTATGAAAATTCATCTCTACATTGGTGATAATAGTAAATCCAGTAGGGCGAAATA
```

IleAspCysAsnLeuArgGlyLysThrAlaGlnSerGlnThrArgLeuCysArgLeuArg
LeuThrValIleTyrGlyAlaLysArgHisAsnLeuLysArgAspCysAlaVal***Gly
*Leu*PheThrGlyGlnAsnGlyThrIleSerAsnGluIleValProPheLysGly
ATTGACTGTAATTTACGGGGCAAAACGGCACAATCTCAAACGGATTGTGCCGTTTAAGG
                              .         .         .
                                      6500

GlyArgPhe*LysTyrPheIleLeuProThrIle*LeuArgArgArgLeuLysMet
GluAspSerArgAsnIleSerTyrPheGlnLeuTyrSer*GlyGlyAsp*Lys***
LysIleLeuGluIlePheHisThrSerAsnTyrIleValLysGluThrGluAsnGlu
GGAAGATTCTAGAAATATTTCATACTTCCAACTATATAGTTAAGGAGGAGACTGAAAATG
                              .         .         .
                                      6600

```
LysLysLeuPhePheLeuLeuLeuPheLeuIleTyrLeuGlyTyrAspTyrVal
ArgSerCysPhePheTyrCysTyrCysTyrSer***TyrThr***ValMetThrThrLeu
GluValValPheIleValPheIleVaIIleValIleLeuAsnIleLeuArgLeu***LeuArg***
AAGAAGTTGTTTTTTTATTGTTATTCTTAATATACTTAGGTTATGACTACGTT

AsnGluAlaLeuPheSerGlnGluLysValGluPheGlnAsnTyrAspGlnAsnProLys
MetLysHisCysPheLeuArgLysLysSerAsnPheLysIleMetIleLysIleProLys
*SerThrValPheSerGlyLysSerArgIleSerLysLeu*SerLysSerGlnArg
AATGAAGCACTGTTTCTCAGGAAAAAGTCGAATTCAAATTATGATCAAAATCCAAA
                            6700

GluHisLeuGluAsnSerGlyThrSerGluAsnThrGlnGluLysThrIleThrGluGlu
AsnIle***LysIleValGlyLeuLeuLysIleProLysArgLysGlnLeuGlnLysAsn
ThrPheArgLys***TrpAspPhe***LysTyrProArgGluAsnAsnTyrArgArgThr
GAACATTAGAAATAGTGGGACTTCTGAAAATACCCAAGAGAAAACAATTACAGAAGAA
```

GlnValTyrGlnGlyAsnLeuLeuIleAsnSerLysTyrProValArgGlnGluVal
ArgPheIleLysGluIleCysTyr***SerIleValAsnIleLeuPheAlaLysLysCys
GlyLeuSerArgLysSerAlaIleAsnGln*****IleSerCysSerProArgSerVal
CAGGTTTATCAAGGAAATCTGCTATTAATCAATAGTAAATATCCTGTTCGCCAAGAAGTG
                              6800
*SerGlnIleSer*IleTyrLeuAsnMetThrAsn*****MetAspThrGlyCys
GluValArgTyrArgGluPheIle*Thr*ArgIleAsnLysTrpIleArgValAla
LysSerAspIleValAsnLeuSerLysHisAspGluLeuIleAsnGlyTyrGlyLeuLeu
TGAAGTCAGATATCGTGAATTTATCTAAACATGACGAATTAATAAATGGATACGGGTTGC
                                                        6900

FIG. 5TT

```
LeuIleValIlePheIleCysGlnLysLys***HisLysAsnPheGlnArgTrpSerMet
*******TyrLeuTyrValLysArgAsnSerThrLysIlePheArgAspGlyGln***
AspSerAsnIleTyrMetSerLysGluIleAlaGlnLysPheSerGluMetValAsnAsp
TTGATAGTAATATTTATATGTCAAAGAATAGCACAAAAATTTCAGAGATGGTCAATG

MetLeu***ArgValAlaLeuValIleLeuLeuIleValAlaIleGluThrLeuMet
CysCysLysGlyTrpArg***SerPheTyrTyr*****TrpLeuSerArgLeu*****
AlaValLysGlyGlyValSerHisPheIleIleAsnSerGlyTyrArgAspPheAspGlu
ATGCTGTAAAGGGTGGCGTTAGTCATTTATTATTAATAGTGGCTATCGAGACTTTGATG
                                7000

SerLysValCysPheThrLysLysTrpGlyLeuSerMetProTyrGlnGlnValIleVal
AlaLysCysAlaAlaLeuProArgAsnGlyGly***ValCysLeuThrSerArgLeu*****
GlnSerValLeuTyrGlnGluMetGlyAlaGluTyrAlaLeuProAlaGlyTyrSerGlu
AGCAAAGTGTGCTTACCAAGAAATGGGGGCTGAGTATGCCTTACCAGCAGGTTATAGTG
```

FIG. 5UU

SerIleIleGlnValTyrHis*Met*AspGlnAla****ArgLysTrpAsnGluPro
Ala***PheArgPheIleThrArgCysArgIleLysLeuAspGluAsnGlyThrSerPro
HisAsnSerGlyLeuSerLeuAspValGlySerSerLeuThrLysMetGluArgAlaPro
AGCATAATTCAGGTTTATCACTAGATGTAGGATCAAGCTTGACGAAAATGGAACGAGCCC
                            7100
LeuLysGluSerGly***LysLysMetLeuGlyAsnThrGlySerPheTyrValIleGln
***ArgLysValAspArgArgLysCysLeuGluIleArgValHisPheThrLeuSerArg
GluGlyLysTrpIleGluGluAsnAlaTrpLysTyrGlyPheIleLeuArgTyrProGlu
CTGAAGGAAAGTGGATAGAAGAAAATGCTTGGAAATACGGGTTCATTTTACGTTATCCAG
                                                     7200

FIG. 5VV

ArgThrLysGlnSer***GlnGluPhe
GlyGlnAsnArgValAsnArgAsnSer
AspLysThrGlyLeuThrGlyIleGln
AGGACAAAACAGAGTTAACAGGAATTC
7227

FIG. 5WW

EcoRV

GATATCGTTACGCTTCATGTGCCGCTCAATACGGATACGCCACTATATTATCAGCCACGAACAAA 64

TACAGAGAATGAAGCAAGGAGCATTTCTTATCAATACTCGGGCGCGGTCCACTTGTAGATACCTATGAGTTGGTTAAAGCATTAGAAAACGG 155

GAAACTGGGCGGTGCCGCATTGGATGTATTGGAAGGAGAGGAAGAGTTTTCTACTCTGATTGCACCCAAAAACCAATTGATAATCAATTT 246

TTACTTAAACTTCAAAGAATGCCTAACGTGATAATCACACCGCTATTATACCGAGCAAGCGTTGCGTGATACCGTTGAAAAAA 337

HaeIII
                      RBS      ▼MET ASN ARG ILE LYS VAL ALA ILE LEU PHE GLY GLY CYS
CCATTAAAAACTGTTTGGATTTGAAAGGAGAGAGGAGC ATG AAT AGA ATA AAA GTT GCA ATA CTG TTT GGG GGT TGC 415
                             NlaIII

SER GLU GLU HIS ASP VAL SER LYS SER ALA ILE GLU ILE ALA ALA ASN ILE ASN LYS PRO CYS ALA GLU TRP
TCA GAG GAG CAT GAC GTA TCG AAA TCT GCA ATA GAG ATA GCC GCT AAC ATT AAT AAA GAA CCT TGC GCG GAA TGG 484

GLU PRO LEU TYR ILE GLY ILE THR LYS SER ALA VAL LEU SER PRO ASP LYS LYS MET HIS GLY LEU VAL LYS LYS
GAG CCG TTA TAC ATT GGA ATT ACG AAA TCT GCA GTT CTC TCG CCG GAT AAA AAA ATG CAC GGA TTA CTT GTT AAA AAG 553

GLU ASN ASP ASN CYS TYR SER ALA VAL LEU ASN HIS VAL ALA PHE SER GLY ILE PRO PHE VAL GLY CYS ASP ILE GLN SER SER ALA
GAA AAC GAC AAT TGC TAT TCA GCT GTT CTT AAT CAT GTT GCA TTT TCA GCT GTA GCA TTT GTA GGC TGC GAT ATT CAA AGC TCA GCA 622

ASN HIS GLU TYR GLU ILE LEU PHE GLU LEU THR TYR ILE VAL ALA LYS ASN ALA GLY ILE ALA THR PRO ALA PHE TRP
AAC CAT GAA TAT GAA ATC AAC CAT GTT GAA TTG ACA TAC ATC GTT GCG AAA AAT GCT GGG ATA GCT ACT CCC GCC TTT TGG 691

GLY SER ILE GLN GLY LEU PHE GLU LEU THR TYR ILE VAL ALA LYS ASN ALA GLY ILE ALA THR PRO ALA PHE TRP
GGA TCC ATA CAA GGT CTG TTT GAA TTG ACA TAC ATC GTT GCG AAA AAT GCT GGG ATA GCT ACT CCC GCC TTT TGG 760

ILE CYS MET ASP LYS SER LEU THR TYR ILE VAL ALA LYS ASN ALA GLY ILE ALA THR PRO ALA PHE TRP
ATT TGT ATG GAC AAA TCG TTG ACA TAC ATC GTT GCG AAA AAT GCT GGG ATA GCT ACT CCC GCC TTT TGG 829

VAL ILE ASN LYS ASP ASP ARG PRO VAL ALA ALA THR PHE THR TYR PRO VAL PHE VAL LYS PRO ALA ARG
GTT ATT AAT AAA GAT GAT AGG CCG GTG GCA GCT ACG TTT ACC TAT CCT GTT TTT GTT AAG CCG GCG CGT 898

FIG.6A

```
SER GLY SER SER PHE GLY VAL LYS LYS VAL ASN SER ALA ASP CLU LEU ASP TYR ALA ILE GLU SER ALA
TCA GGC TCA TCC TTC GGT GTG AAA AAA GTC AAT AGC GCG GAC GAA TTG GAC TAC GCA ATT GAA TCG GCA    967

ARG GLN TYR ASP SER LYS SER ILE LEU GLU ILE GLN ALA VAL SER GLY CYS GLU VAL GLY CYS ALA VAL LEU
AGA CAA TAT GAC AGC AAA ATC TTA ATT GAG CAG GCT GTT TCG GGC TGT GAG GTC GGT TGT GCG GTA TTG   1036

GLY ASN SER ALA ALA LEU VAL VAL GLY GLU VAL ASP GLN ILE ARG LEU GLN TYR GLY ILE PHE ARG ILE
GGA AAC AGT GCC GCG TTA GTT GTT GGC GAG GTG GAC CAA ATC AGG CTG CAG TAC GGA ATC TTT CGT ATT   1105

HIS GLN VAL GLU PRO GLU LYS PRO GLU ASN ALA VAL ILE THR VAL PRO ALA ASP LEU SER ALA
CAT CAG GTC GAA CCG GAG AAA GGC TCT GAA AAC GCA GTT ATA ACC GTT CCC GCA GAC CTT TCA GCA       1174

GLU GLU ARG GLY ARG ILE GLN THR GLU ALA LYS ILE TYR LYS ALA LEU GLY CYS ARG GLY LEU ALA
GAG GAG CGA CGA GGA ATA CAG ACG GAA ACG GCA AAA ATA TAT AAA GCG CTC GGC TGT AGA GGT CTA GCC   1243

ARG VAL ASP MET PHL LEU GLN ASP ASN GLY ARG ILE VAL LEU ASN GLU VAL ASN THR LEU PRO GLY PHE
CGT GTG GAT ATG TTT TTA CAA GAT AAC GGC CGC ATT GTA CTG AAC GAA GTC AAT ACT CTG CCC GGT TTC   1312

THR SER TYR SER ARG TYR PRO ARG MET MET ALA MET PRO GLU LEU ILE ASP ARG
ACG TCA TAC AGT CGT TAT CCC CGT ATG ATG GCC GCT GCA GGT ATT GCA CTT CCC GAA CTG ATT GAC CGC  1381

LEU ILE VAL LEU ALA LEU LYS GLY *** *** ***
TTG ATC GTA TTA GCG TTA AAG GGG TGA TAA GCATGGAAATAGGATTTACTTTTTTAGATGAAATAGTACACGGTGTTCGTT   1462
                                            ▲
                                            NlaIII
GGGACGCTAAATATGCCACTTGGGATAATTTCACCGGAAAACCGGTTGACGGTTATGAAGTAAATCGCATTGTAGGGACATACGAGTTGGC   1553
TGAATCGCTTTTGAAGGCAAAAGAACTGGCTGCTACCCAAGGGTACGGATTGCTTCTATGGGACGGTTACGTCCTAAGCGTGCTGTAAAC   1644
TGTTTATGCAATGGGCTGCACAGCCGGAAAATAACCTGACAAAGGAAAGTTATTATCCCAATATTGACCGAACTGAGATGATTTCAAAAG   1735
        sacII
GGATACGTGGcTTCAAAAATCAAGCCATAGCCGCG                                                          1769
```

FIG.6B

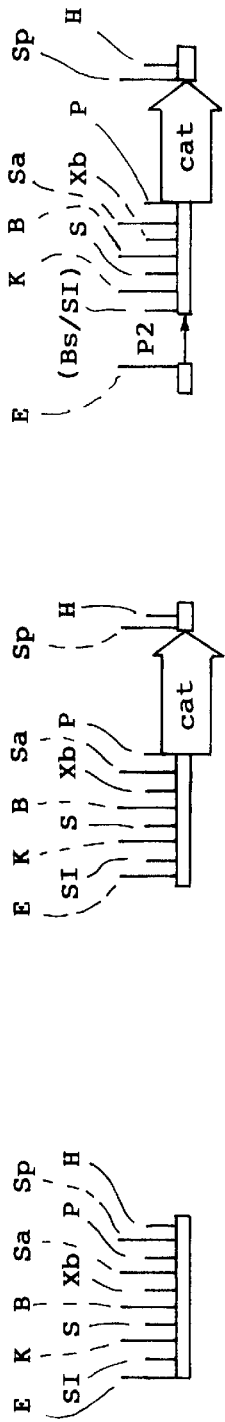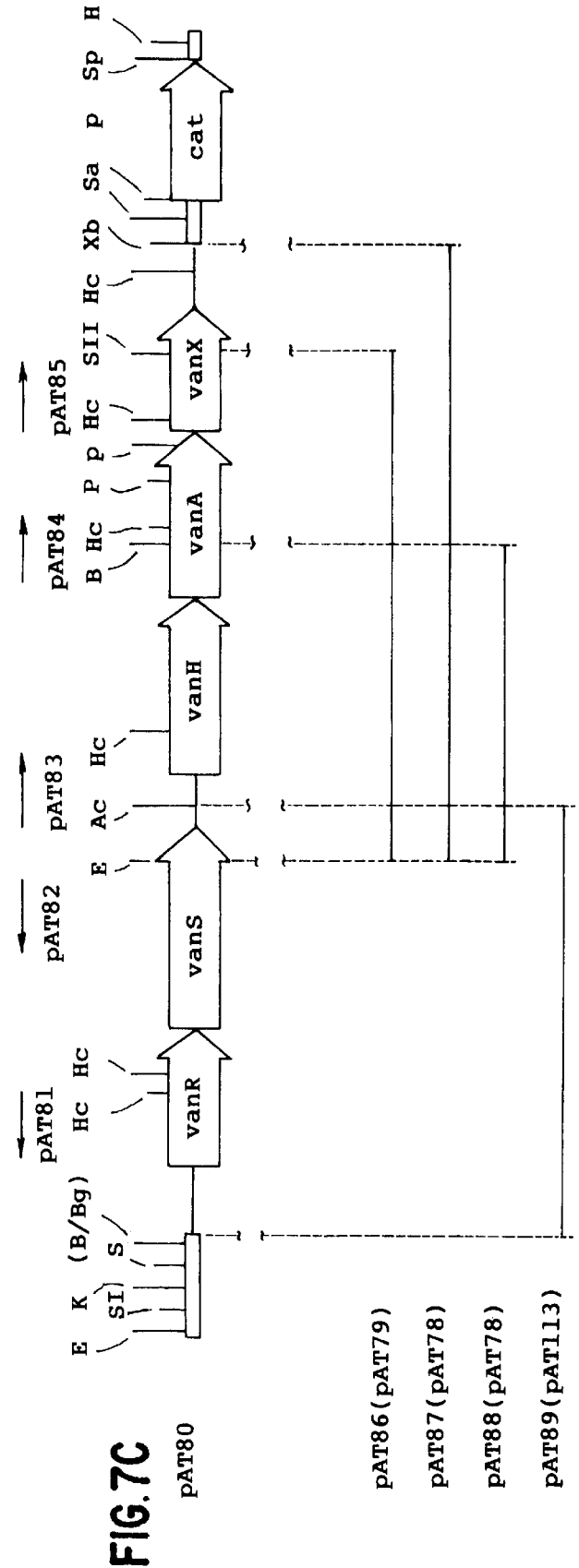
FIG. 7B
FIG. 7C
FIG. 7D

Ia. brin "+"

```
1
GGG GTA GCG TCA GGA AAA TGC GGA TTT ACA ACG CTA AGC CTA TTT TCC TGA CGA ATC CCT
61
CGT TTT TAA CAA CGT TAA GAA AGT TTT AGT GGT CTT AAA GAA TTT AAT GAG ACT ACT TTC
121
TCT GAG TTA AAA TGG TAT TCT CCT AGT AAA TTA ATA TGT TCC CAA CCT TCA ACT GGC GAC ATA
181
TGG TGT AAC AAA TCT TCA TTA AAG CTA CCT GTC CGT TTT TTA TAT TCA ACT GCT GTT GTT
241
AGG TGG AGA GTA TTC CAA ATA CTT ATA GCA TTG ATA ATT ATG TTT AAA GCA CTG GCT CTT
301
TGC AAT TGA TGC TGT ATG GCT TCT CTA AGC TCA CCT TGT TTT CCG AAG AAA ATA GCT
361
CTT GCC AAT CCA TTC ATG ATA TAA TTC AAA ATA AAG ATC GTT TTT TCT ATT CGG CCC ATC TCA CGT
421
GAT TCA TCC GAT ATA TAA TTC AAG CTG TTT TGT CTT GAA TAG GAA CCT AGC TTC CCC ATA ATA AGG GAT
481
AAG GCT GTA GCT AAG CTG TTT TGT CTT GAA TAG GAA CCT AGC TTC CCC ATA ATA AGG GAT
541
GCT GAA ACT GTT CCC TCC CTT ATA GAA TGA GCT AAT CGC AAA ACA TCC TCA TAA TTT TCT
601
TTA ATG ACC TTT GTA TTT ATT TGT CCA CGT AAA ATG GCT TCT AGT TTT GGA TAC TCA CTT
```

FIG. 8A

```
 661                                                                GCA AAT TTA
 GCT TTA TCT ATC GTA AAT AAT TTT GAG TCC GAT AAA TCC CTT ATT CTT GGG GCA AAT TTA
 721
 AAT CCT AAT AAA TGA GTC AGT CCG AAT ATT TGG TCA GTG TAA CCG GCA GTG TCT GTA TAA
 781
 TGT TCC TCT ATG TTT AGA TCC GTC TCA TGA TGT AAC AAA CCA TCC AAA ACA TGA ATC GCA
 841
 TCT CTT GAA TTA GTA TGA ATA ATC TTT GTG TAG TAA GAA GAG AAT TGA TCA CTT GTA AAT
 901
 CGG TAG ATG GTG GCT CCT TTT CCA GTT CCA TAA TGT GGA TTT GCA TCT GCA TGT AGT GAT
 961
 GAA ACA CCT AGC TGC ATT CTC ATA CCA TCT GAC GAA GAT GTT GTA CCG TCG CCC CAA TAG
1021
 AAA GGC AAT TGT AAT TTA TGA TGA AAG TTT ACT AAT ATG GCT TGG GCT TTA TTC ATG GCA
1081
 TCT TCA TAC ATG CGC CAT TGA GAT ACA TTG GCT AGT TGC TTA TAT GTA AGT CCG GGT GTG
1141
 GCT TCG GCC ATC TTG CTC AAG CCA ATA TTC ATT CCC ATT CCT AAA AGG GCA GCC ATG ATA
1201
 ATG ATT GTT TCT TCC TTA TCT GGT TTT CGA TTA TTG GAA GCA TGA GTG AAT TTT ATT CTT GGT AGC ATC
1261
 AAT CCT GTT ATA TGG GCC ACA TCC ATG AGT TTT TTT GCT TCT TTT TCT AAG CGT GCA
1321
 TGA TAA AGG CTT GCA CTA AAT TTT TCA AGA GAA ACC CCA TCT AAC TTA TTG GAA GCT GCA AAC
1381
 AGT GAT AGC TTT CCT GTT TCA TTA AAG CTG GTT CTC TCC GTT ATA TAA TCT TCG AAT GAT AAA
1441
 CAC TTT AAC CTT TCA TTA AAG
```

FIG. 8B

```
1501
     CTA ACT GAT AAT CTC GTA TTC CCC TTC GAT TGA TTC CAT GTA TCT TCC GAA AAC AAA TAT
1561
     TCC TCA AAA TCC CTA TAT TGT CTG CTG CCA ACA ATG GAA ACA TCT CCT GCC CGA ACA TGC
1621
     TCC CGA AGT TCT GTT AAA ACA GCC ATT TCA TAG TAA TGA CGA TTA ATT GTT GTA CCA TCA
1681
     TCC TCG TAT AAA TGT CTT TTC CAT CGT TTT GAA ATA AAA TCC ACA GGT GAG TCA TCA GGC
1741
     ACT TTT CGC TTT CCA GAT TCG TTC ATT CCT CGG ATA ATC TCA ACA GCT TGT AAA AGT GGC
1801
     TCA TTT GCC TTT GTA GAA TGA AAC CGT TTT TGC AGT AAG TCT AAA TAA TCA TAG TCG GCA GGA CGT GCA AGT
1861
     AGT GAA TAA AAC CGT TTT TGC AGT AAG TCT AAA TAA TCA TAG TCG GCA GGA CGT GCA AGT
1921
     TCC TGA GCC TCT TCT ACT GAA GAG ACA AAG GTA TTC CAT TCA ATA ACC GAT TCT AAA ACC
1981
     TTA AAA ACG TCT TCT AAT TTT TCC TCT CTT GCT TTA ATT AAT GCT TGT CCG ATG TTC GTA AAG
2041
     TGT ATA ACT TTC TCA TTT AGC TTT TGT TTC TGG ATT TCC TCT TGA GCC TTA
2101
     CGA CCT TTT GAT AAC AAA CTA AGT ATT TGC CTA TCA TGA ATT TCA AAC GCT TTA TCC GTT
2161
     AGC TCC TGA GTA AGT TGT AAT AAA TAG ATG GTT CTT GAG CCT AAG CGA GAC AGC TGT TGA
2221
     AAG TCA CGG AAT GCA TAC GGC TCG TAT CTT GAG CCT AAG CGA GAC AGC TGT TGA
2281
     TTA CGG TGC AAA TGA CTA ATT TGC ACT GTT TCT AAA TCC ATT CCT CGT ATG TAT TCG AGT
2341
```

FIG. 8C

```
CGT TCT ATT ATT TTT AGA AAA GTT TCG GGT GAA GGA TGA CCC GGT GGC TCT TTT AAC CAA
2401
CCC AAT ATC GTT TTA TTG GAT TCG GAT GGA TGC TGC GAG GTA ATA ATC CCT TCA AGC TTT
2461
TCT TTT TGC TCA TTT GTT AGA GAT TTA CTA ACC GTA TTA AAT AGC TTC TTT TCA GCC ATT
2521
GCC CTT GCT TCC CAC ACC ATT CTT TCA AGT GTA GTG ATA GCA GGC AGT ATA ATT TTG TTT
2581
TTT CTT AGA AAA TCT ATG CAT TCA AAT GTC ATT CGA TAT TCA CTC AGG GCA TCA CCA TTT TCC AAA GCT
2641
AAT TGA TGA AGG TAC TTA AAT GTC ATT CGA TAT TCA CAA AGT TTT TCC CTT TGA GGA TAA TGA
2701
TAT TCA CTT CGA ATT TCT TTC AAA TGA TCC ATC TGT TTC GAT ATA TAT TGT ATG ACC GAA TCT GGG
2761
TCA AGC GAG GAT GGA CTA ACA CCA ATC TGT TTC CAA CCG GAA TAC CGA AGA ACA GCT AAT TGA ACA GCA
2821
ATG CTT TTG ATA TGA GTG TAT TCT TCC CTC CGC TTA TTA ACT ATT TCT AAA TCC CGT TTG GAA
2881
AAT CCT AAA CGG TTT TCT CGA ATT GGA CTA TGA GTG TAT TCT TCC CTC GCA ATT TTC ATT CAG TAT CAT TCC ATT TCT
2941
AAA GTG AAG TAG GTC CCC AGT ATC CCC AGT ATC TCA CCT CTC GCA ATT TTC ATT TGC ATA AAA GCC TGT CTC
3001
TGT TCC GGT GTA AGC AAT TCT CTA CCT CTC GCA ATT TTC ATT CAG TAT CAT TCC ATT TCT
3061
GTA TTT TCA ATT TAT TAG TTC AAT TAT ATA TCA CCT CTC GCA ATT TTC ATT CAG TGT ACT CTA TTG ATA CAA ATG
3121
TAG TAG ACT GAT AAA ATC ATA GTT AAG AGC GTC TCA TAA GAC TTG TCT CAA AAA TGA GGT
```

FIG. 8D

```
3181       resolvase
           LEU ARG LYS ILE GLY TYR ILE ARG VAL SER SER THR ASN GLN ASN PRO SER ARG
           GAT ATT TTG CGG AAA ATC GGT TAT ATT CGT GTC AGT TCG ACT AAC CAG AAT CCT TCA AGA
3241
           GLN PHE GLN GLN LEU ASN GLU ILE GLY MET ASP ILE ILE TYR GLU GLU LYS VAL SER GLY
           CAA TTT CAG CAG TTG AAC GAG ATC GGA ATG GAT ATT ATA TAT GAA GAG AAA GTT TCA GGA
3301
           ALA THR LYS ASP ARG GLU GLN LEU GLN LYS VAL LEU ASP ASP LEU GLN GLU ASP ASP ILE
           GCA ACA AAG GAT CGC GAG CAA CTT CAA AAA GTG TTA GAC GAT TTA CAG GAA GAT GAC ATC
3361
           ILE TYR VAL THR ASP LEU THR ARG ILE THR ARG SER THR ARG ASP LEU PHE GLU LEU ILE
           ATT TAT GTT ACA GAC TTA ACT CGA ATC ACT CGT AGT ACA CAA GAT CTA TTT GAA TTA ATC
3421
           ASP ASN ILE ARG ASP LYS LYS ALA SER LEU LYS SER LEU LYS ASP THR TRP LEU ASP LEU
           GAT AAC ATA CGA GAT AAA AAG GCA AGT TTA AAA TCA CTA AAA GAT ACA TGG CTT GAT TTA
3481
           SER GLU ASP ASN PRO TYR SER GLN PHE LEU ILE THR VAL MET ALA GLY VAL ASN GLN LEU
           TCA GAA GAT AAT CCA TAC AGC CAA TTC TTA ATT ACT GTA ATG GCT GGT GTT AAC CAA TTA
3541
           GLU ARG ASP LEU ILE ARG MET ARG GLN ARG GLU GLY ILE GLU LEU ALA LYS LYS GLU GLY
           GAG CGA GAT CTT ATT CGG ATG AGA CAA CGT GAA GGG ATT GAA TTG GCT AAG AAA GAA GGA
3601
           LYS PHE LYS GLY ARG LEU LYS LYS TYR HIS ASN ASN HIS ALA GLY VAL MET ASN TYR ALA VAL
           AAG TTT AAA GGT CGA TTA AAG AAG TAT CAT AAA AAT CAC GCA GGA ATG AAT TAT GCG GTA
3661
           LYS LEU TYR LYS GLU GLY ASN MET THR VAL ASN GLN ILE CYS GLU ILE THR ASN VAL SER
           AAG CTA TAT AAA GAA GGA AAT ATG ACT GTA AAT CAA ATT TGT GAA ATT ACT AAT GTA TCT
3721
           ARG ALA SER LEU TYR ARG LYS LEU LEU SER GLU VAL ASN ASN
           AGG GCT TCA TTA TAC AGG AAA TTA TCA GAA GTG AAT AAT TAG CCA TTC TGT ATT CCG CTA
```

FIG. 8E

```
3781
ATG GGC AAT ATT TTT AAA GAA GAA AAG GAA ACT ATA AAA TAT TAA CAG CCT CCT AGC GAT
3841
GCC GAA AAG CCC TTT GAT AAA AAA AGA ATC ATC ATC TTA AGA AAT TCT TAG TCA TTT ATT
3901
ATG TAA ATG CTT ATA AAT TCG GCC CTA TAA TCT GAT AAA TTA TTA AGG GCA AAC TTA TGT
         VanR MET SER ASP LYS ILE LEU ILE VAL ASP ASP GLU HIS GLU ILE ALA
3961
GAA AGG GTG ATA ACT ATG AGC GAT AAA ATA CTT ATT GTG GAT GAT GAA CAT GAA ATT GCC
     ASP LEU VAL GLU LEU TYR LEU LYS ASN TYR THR VAL PHE LYS TYR TYR THR ALA
4021
GAT TTG GTT GAA TTA TAC CTT AAA AAC TAC ACG GTT TTC AAA TAC TAT ACC GCC
     LYS GLU ALA LEU GLU CYS ILE ASP LYS SER GLU ILE ALA ILE LEU ASP ILE MET
4081
AAA GAA GCA TTG GAA TGT ATA GAC AAG TCT GAG ATT GCC CTT GAC ATA TTG GAC ATC ATG
     LEU PRO GLY THR SER GLY LEU THR ILE CYS GLN LYS ILE ARG ASP LYS HIS THR TYR PRO
4141
CTT CCC GGC ACA AGC GGC CTT ACT ATC ATC TGT CAA AAA ATA AGG GAC AAG CAC TAT CCG
     ILE ILE MET LEU THR GLY LYS ASP THR GLU VAL ASP LYS ILE THR GLY LEU THR ILE GLY
4201
ATT ATC ATG CTG ACC GGG AAA GAT ACA GAG GTA GAT AAA ATT ACA GGG TTA ACA ATC GGC
     ALA ASP ASP TYR ILE THR LYS PRO PHE ARG PRO LEU GLU LEU ILE ALA ARG VAL LYS ALA
4261
GCG GAT GAT TAT ATA ACG AAG CCC TTT CGC CCA CTG GAG TTA ATT GCT CGG GTA AAG GCC
     GLN LEU ARG ARG TYR LYS LYS PHE SER GLY VAL LYS GLU GLN ASN VAL ILE VAL
4321
CAG TTG CGC CGA TAC AAA AAA TTC AGT GGA GTA AAG GAG CAG AAC GAA GTT ATC GTC
```

FIG. 8F

```
4381
HIS SER GLY LEU VAL ILE ASN VAL ASN THR HIS GLU CYS TYR LEU ASN GLU LYS GLN LEU
CAC TCC GGC CTT GTC ATT AAT GTT AAC ACC CAT GAG TGT TAT CTG AAC GAG AAG CAG TTA
4441
SER LEU THR PRO THR GLU PHE HIS SER ILE LEU ARG ILE LEU CYS GLU ASN LYS GLY ASN VAL
TCC CTT ACT CCC ACC GAG TTT TCA CAG ATC CTG CGA ATC CTC TGT GAA AAC AAG GGG AAT GTG
4501
VAL SER SER GLU LEU LEU PHE HIS GLU ILE TRP GLY ASP GLU TYR PHE SER LYS SER ASN
GTT AGC TCC GAG CTG CTA TTT CAT GAG ATA TGG GGC GAA TAT TTC AGC AAG AGC AAC
4561
ASN THR ILE THR VAL HIS ILE ARG HIS GLU LYS MET ASN ASP THR ILE ASP ASN
AAC ACC ATC ACC GTG CAT ATC CGG CAT TTG CGC GAA AAA ATG AAC GAC ACC ATT GAT AAT
4621
PRO LYS TYR ILE LYS THR VAL TRP GLY VALGLYTYRLYSILEGLULYS
CCG AAA TAT ATA AAA ACG GTA TGG GGG GTTGGTTATAAAATTGAAAAAT AAA AAA AAC GAC
                                    VanS              LEUVALILELYSLEULYSASN LYS LYS ASN ASP
4682
TYR SER LYS LEU GLU ARG LYS LEU TYR MET TYR ILE VAL ALA ILE VAL VAL ALA ILE
TAT TCC AAA CTA GAA CGA AAA CTT TAC ATG TAT ATC GTT GCA ATT GTT GTG GTA GCA ATT
4742
VAL PHE VAL LEU TYR ILE ARG SER MET ILE ARG GLY LYS LEU GLY ASP TRP ILE LEU SER
GTA TTC GTG TTG TAT CGT TCA ATG ATC CGA GGG AAA CTT GGG GAT TGG ATC TTA AGT
4802
ILE LEU GLU ASN LYS TYR ASP LYS MET LYS LEU ASP ALA MET LYS VAL ILE SER ILE LEU LEU
ATT TTG GAA AAC TAT GAC AAA ATG AAA CTG GAC GCG ATG AAA TTA TCA ATT CTT ATT CTA
4862
ILE ARG ASN ASN ILE ASP PHE ILE TYR VAL ALA ILE VAL SER LYS PHE ALA LYS TYR PHE ASP GLU ILE ASN THR GLY ILE ILE ASP
ATA CGG AAC AAT ATA GAT ATC TTT TAT GTG GCG ATT GTC AGT AAA TTC GCA AAA TAC TTT GAC GAG ATA AAT ACC GGC ATT GAT
4922
CYS ARG VAL MET LEU SER LYS
TGT CGC GTC ATG CTT TCA AAA
```

FIG. 8G

```
4982
     VAL LEU ILE GLN ASN GLU ASP LYS GLN ILE GLU LEU SER ALA GLU MET ASP VAL MET GLU
     GTA CTT ATT CAG AAC GAA GAT AAA CAA ATT GAG CTT TCT GCG GAA ATG GAT GTT ATG GAA
5042
     GLN LYS LEU ASN THR LEU LYS ARG THR LEU GLU LYS ARG GLU GLN ASP ALA LYS LEU ALA
     CAA AAG CTC AAC ACA TTA AAA CGG ACT CTG GAA AAG CGA GAG CAG GAT GCA AAG CTG GCC
5102
     GLU GLN ARG LYS ASN ASP VAL VAL MET TYR LEU ALA HIS ASP ILE LYS THR PRO LEU THR
     GAA CAA AGA AAA AAT GAC GTT GTT ATG TAC TTG GCG CAC GAT ATT AAA ACG CCC CTT ACA
5162
     SER ILE ILE GLY TYR LEU SER LEU LEU ASP GLU ALA PRO ASP MET PRO VAL ASP GLN LYS
     TCC ATT ATC GGT TAT TTG AGC CTG CTT GAC GAG GCT CCA GAC ATG CCG GTA GAT CAA AAG
5222
     ALA LYS TYR VAL HIS ILE THR ARG TYR ASN LEU GLN THR ASP LYS ALA TYR ARG LEU ILE ASP GLU
     GCA AAG TAT GTG CAT ATC ACG CGG TAT AAC CTA CAA ACA GAC AAA GCG TAT CGA CTC GAA CAG GAG
5282
     PHE PHE GLU ILE THR ILE THR LEU THR LEU THR LYS THR HIS ILE ASP
     TTT TTT GAG ATT ACA ATA GAC ACA ACG CAC ATA GAC
5342
     LEU TYR TYR MET LEU VAL GLN MET THR ASP GLU PHE TYR PRO GLN LEU SER ALA HIS GLY
     CTA TAC TAT ATG CTG GTG CAG ATG ACC GAT GAA TTT TAT CCT CAG CTT TCC GCA CAT GGA
5402
     LYS GLN ALA VAL ILE HIS ALA PRO GLU ASP LEU THR VAL SER GLY ASP PRO ASP LYS LEU
     AAA CAG GCG GTT ATT CAC GCC CCC GAG GAT CTG ACC GTG TCC GGC GAC CCT GAT AAA CTC
5462
     ALA ARG VAL PHE ASN ASN ILE LEU LYS ASN ALA ALA TYR SER GLU ASP ASN SER ILE
     GCG AGA GTC TTT AAC AAC ATT TTG AAA AAC GCC GCT GCA TAC AGT GAG GAT AAC AGC ATC
```

FIG. 8H

```
5522
ILE ASP ILE THR ALA GLY LEU SER GLY ASP VAL VAL SER ILE GLU PHE LYS ASN THR GLY
ATT GAC ATT ACC GCG GGC CTC TCC GGG GAT GTG GTG TCA ATC GAA TTC AAG AAC ACT GGA
5582
SER ILE PRO LYS ASP LYS LEU ALA ALA ILE PHE GLU LYS PHE TYR ARG LEU ASP ASN ALA
AGC ATC CCA AAA GAT AAG CTA GCT GCC ATA TTT GAA AAG TTC TAT AGG CTG GAC AAT GCT
5642
ARG SER SER ASP THR GLY GLY LEU ALA GLY LEU ALA ILE ALA LYS GLU ILE ILE VAL
CGT TCT TCC GAT ACG GGT GGC GCG CTT GGA TTG GCG ATT GCA AAA GAA ATT ATT GTT
5702
GLN HIS GLY GLN ILE TYR ALA GLU SER ASN ASP ASN TYR THR THR PHE ARG VAL GLU
CAG CAT GGA GGG CAG ATT TAC GCG GAA AGC AAT GAT AAC TAT ACG TTT AGG GTA GAG
5762
LEU PRO ALA MET PRO ASP LEU VAL ASP LYS ARG ARG SER
CTT CCA GCG ATG CCA GAC TTG GTT GAT AAA AGG AGG TCC TAA GA GAT GTA TAT AAT TTT
5821
TTA GGA AAA TCT CAA GGT TAT CTT TAC ACT TAA GGA AAT TAA CAA TTT AAT ATT AAG
5881
AAA CGG CTC GTT CTT ACA CGG TAG ACT TAA TAC CGT AAG AAC GAG CCG TTT TCG TTC TTC
5941
AGA GAA AGA TTT GAC AAG ATT ACC ATT GGC ATC CCC GTT TTA TTT GGT GCC TTT CAC AGA
6001
          VanH    MET ASN ASN ILE GLY ILE THR VAL TYR GLY CYS GLU GLN ASP GLU
AAGGGTTGG TCT TAA TT ATG AAT AAC ATC GGC ATT ACT GTT TAT GGA TGT GAG CAG GAT GAG
6063
ALA ASP ALA PHE HIS ALA LEU SER PRO ARG PHE GLY VAL MET ALA THR ILE ILE ASN ALA
GCA GAT GCA TTC CAT GCT CTT TCG CCT CGC TTT GGC GTT ATG GCA ACG ATA ATT AAC GCC
6123
```

FIG. 8 I

```
       ASN VAL SER GLU SER ASN ALA LYS SER ALA PRO PHE ASN GLN CYS ILE SER VAL GLY HIS
       AAC GTG TCG GAA TCC AAC GCC AAA TCC GCG CCT TTC AAT CAA TGT ATC AGT GTG GGA CAT
6183
       LYS SER GLU ILE SER ALA SER ILE LEU LEU ALA LEU LYS ARG ALA GLY VAL LYS TYR ILE
       AAA TCA GAG ATT TCC GCC TCT ATT CTT CTT GCG CTG AAG AGA GCC GGT GTG AAA TAT ATT
6243
       SER THR ARG SER ILE GLY CYS ASN HIS ILE ASP THR THR ALA LYS ARG MET GLY ILE
       TCT ACC CGA AGC ATC GGC TGC AAT CAT ATA GAT ACA ACT GCT AAG AGA ATG GGC ATC
6303
       THR VAL ASP ASN VAL ALA TYR SER PRO ASP TYR MET MET LEU ILE
       ACT GTC GAC AAT GTG GCG TAC TCG CCG GAT TAT ACT ATG ATG CTA ATT
6363
       LEU MET ALA VAL ARG ASN VAL LYS SER ILE VAL ARG SER VAL GLY VAL THR GLY
       CTT ATG GCA GTA CGC AAC GTA AAA TCG ATT GTG CGC TCT GTG GGT GTG ACG GGC
6423
       LEU ASP SER ASP ARG GLY LYS VAL ILE LEU SER ASP MET THR THR VAL GLY PHE GLY THR GLY
       TTG GAC AGC GAC CGT GGC AAG GTA CTC AGC GAC ATG ACA GTT GGT GTG GGA ACG GGC
6483
       GLN ILE GLY LYS LYS ALA VAL ILE GLU ARG LEU ARG GLY PHE ASP GLU LEU LEU GLN ASN SER
       CAG ATA GGC AAA GCG GTT ATT GAG CGG CTG CGA GGA TTT GAT GAG TTG CTG CAA AAT AGC
6543
       SER ARG SER ARG SER ILE GLU VAL ASN TYR VAL PRO PHE ASP THR HIS TYR ILE ILE SER HIS GLU
       AGT CGC AGC AGT ATA GAG GTA AAC TAT GTA CCG TTT GAT ACG CAC TAT ATC AGC CAC GAA
6603
       ASP ILE VAL THR LEU HIS VAL PRO LEU ASN THR ASN THR GLY ARG GLY LEU VAL
       GAT ATC GTT ACG CTT CAT GTG CCG CTC AAT ACG AAT ACT GGG CGC GGT CCA CTT GTA
6663
       GLN ILE GLN ARG MET LYS GLN GLY ALA PHE LEU ILE ASN THR GLY ARG GLY LEU VAL
       CAA ATA CAG AGA ATG AAG CAA GGA GCA TTT CTT ATC AAT ACT GGG CGC GGT CCA CTT GTA
```

FIG. 8J

```
6723
ASP THR TYR GLU LEU VAL LYS ALA LEU GLY ASN GLY LYS LEU GLY ALA ALA LEU ASP
GAT ACC TAT GAG TTG GTT AAA GCA TTA GAA AAC GGG AAA CTG GGC GGT GCC GCA TTG GAT
6783
VAL LEU GLU GLY GLU GLU PHE PHE TYR SER ASP CYS THR GLN LYS PRO ILE ASP ASN
GTA TTG GAA GGA GAG GAG TTT TTC TAC TCT GAT TGC ACC CAA AAA CCA ATT GAT AAT
6843
GLN PHE LEU LEU LYS LEU GLN ARG MET PRO ASN VAL ILE THR PRO HIS THR ALA TYR
CAA TTT TTA CTT AAA CTT CAA AGA ATG CCT AAC GTG ATA ATC ACA CCG CAT ACG TAT
6903
TYR THR GLN ALA LEU ARG ASP THR VAL GLU LYS THR ILE LYS ASN CYS LEU ASP PHE
TAT ACC GAG CAA GCG TTG CGT GAT ACC GTT GAA AAA ACC ATT AAA AAC TGT TTG GAT TTT
6963
                VanA
                MET ASN ARG ILE LYS VAL ALA ILE LEU PHE GLY GLY CYS SER
                CAT GAAT AGA ATA AAA GTT GCA ATA CTG TTT GGG GGT TGC TCA
GAA AGG AGA CAG GAG
GLU ARG ARG GLN GLU HIS GLU
7021
GLU GLU HIS ASP VAL SER VAL LYS SER ALA ILE GLU ILE ALA ALA ASN ILE ASN LYS GLU
GAG GAG CAT GAC GTA TCG GTA AAA TCT GCA ATA GAG ATA GCC GCT AAC ATT AAT AAA GAA
7081
LYS TYR GLU PRO LEU TYR ILE GLY ILE THR LYS SER GLY VAL TRP LYS MET CYS GLU LYS
AAA TAC GAG CCG TTA TAC ATT GGA ATT ACG AAA TCT GGT GTA TGG AAA ATG TGC GAA AAA
7141
PRO CYS ALA GLU TRP GLU ASN ASP ASN CYS TYR SER ALA VAL LEU SER PRO ASP LYS LYS
CCT TGC GCG GAA TGG GAA AAC GAC AAT TGC TAT TCA GCT GTA CTC TCG GAT AAA AAA
7201
MET HIS GLY LEU LEU VAL LYS LYS ASN HIS GLU TYR GLU ILE ASN HIS VAL ASP VAL ALA
ATG CAC GGA TTA CTT GTT AAA AAG CAT GAA TAT GAA ATC AAC CAT GTT GAT GTA GCA
7261
```

FIG. 8K

```
PHE SER ALA LEU HIS GLY LYS SER GLY ASP GLY GLU ILE GLN GLY LEU PHE GLU LEU
TTT TCA GCT TTG CAT GGC AAG TCA GGT GAT GGA GAA ATA CAA GGT CTG TTT GAA TTG
7321
SER GLY ILE PRO PHE VAL GLY CYS ASP ILE SER SER ALA ILE CYS MET ASP LYS SER
TCC GGT ATC CCT TTT GTA GGC TGC GAT ATT CAA AGC TCA GCA ATT TGT ATG GAC AAA TCG
7381
LEU THR TYR ILE VAL ALA LYS ASN ALA GLY ILE ALA THR PRO ALA PHE TRP VAL ILE ASN
TTG ACA TAC ATC GTT GCG AAA AAT GCT GGG ATA GCT ACT CCC GCC TTT TGG GTT ATT AAT
7441
LYS ASP ASP ARG PRO VAL ALA ALA THR PHE THR TYR PRO VAL PHE VAL LYS PRO ALA ARG
AAA GAT GAT AGG CCG GTG GCA GCT ACG TTT ACC TAT CCT GTT TTT GTT AAG CCG GCG CGT
7501
SER GLY SER SER PHE GLY VAL LYS LYS VAL ASN SER ALA ASP GLU LEU ASP TYR ALA ILE
TCA GGC TCA TCC TTC GTG AAA AAA GTC AAT AGC GCG GAC GAA TTG GAC TAC GCA ATT
7561
GLU SER ALA ARG GLN TYR ASP SER LYS ASN SER ALA LEU ILE GLU GLN ALA VAL SER GLY CYS GLU
GAA TCG GCA AGA CAA TAT GAC AGC AGT GCC TTA ATT GAG CAG GCT GTT TCG GGC TGT GAG
7621
VAL GLY CYS ALA VAL LEU GLY ASN SER ALA ALA LEU VAL VAL GLY GLU VAL ASP GLN ILE
GTC GGT TGT GCG GTA TTG GGA AAC AGT GCC GCG CTT GTT GTT GGC GAG GTG GAC CAA ATC
7681
ARG LEU GLN TYR GLY ILE PHE ARG ILE HIS GLN GLU VAL GLU PRO GLU LYS GLY LYS SER GLU
AGG CTG CAG TAC GGA ATC TTT CGT CAT CAG GAA GTC GAG CCG GAA AAA GGC TCT GAA
7741
ASN ALA VAL ILE THR VAL PRO ALA ASP LEU SER ALA GLU GLU ALA ARG GLY ILE GLN GLU
AAC GCA GTT ACC GTT CCC GAC CTT TCA GCA GAG GAG GCA CGA GGA CGG ATA CAG GAA
7801
THR ALA LYS LYS ILE TYR LYS ALA LEU GLY CYS ARG GLY LEU ALA ARG VAL ASP MET PHE
ACG GCA AAA AAA ATA TAT AAA GCG CTC GGC TGT AGA GGT CTA GCC CGT GTG GAT ATG TTT
```

FIG. 8L

```
7861
LEU GLN ASP ASN GLY ARG ILE VAL LEU ASN GLU VAL ASN THR LEU PRO GLY PHE THR SER
TTA CAA GAT AAC GGC CGC ATT GTA CTG AAC GAA GTC AAT ACT CTG CCC GGT TTC ACG TCA
7921
TYR SER ARG TYR PRO ARG MET MET ALA ALA GLY ILE ALA LEU PRO GLU LEU ILE ASP
TAC AGT CGT TAT CCC CGT ATG ATG GCC GCT GCA GGT ATT GCA CTT CCC GAA CTG ATT GAC
7981
ARG LEU ILE VAL LEU ALA LEU LYS GLY
CGC TTG ATC GTA TTA GCG TTA AAG GGG TGATAAGC ATG GAA ATA GGA TTT ACT TTT TTA GAT
                                    VanX   MET GLU ILE GLY PHE THR PHE LEU ASP
8043
GLU ILE VAL HIS GLY VAL ARG TRP ASP ALA LYS TYR ALA THR TRP ASP ASN PHE THR GLY
GAA ATA GTA CAC GGT GTT CGT TGG GAC GCT AAA TAT GCC ACT TGG GAT AAT TTC ACC GGA
8103
LYS PRO VAL ASP GLY TYR GLU VAL ASN ARG ILE VAL GLY THR TYR GLU LEU ALA GLU SER
AAA CCG GTT GAC GGT TAT GAA GTA AAT CGC ATT GTA GGG ACA TAC GAG TTG GCT GAA TCG
8163
LEU LEU LYS ALA LYS GLU LEU ALA ALA THR GLN GLY TYR GLY LEU LEU LEU TRP ASP GLY
CTT TTG AAG GCA AAA GAA CTG GCT GCT ACC CAA GGG TAC GGA TTG CTT CTA TGG GAC GGT
8223
TYR ARG PRO LYS ARG ALA VAL ASN CYS PHE MET TRP ALA ALA GLN PRO GLU ASN ASN
TAC CGT CCT AAG CGT GCT GTA AAC TGT TTT ATG TGG GCA CAG CCG GAA AAT AAC
8283
LEU THR LYS GLU SER TYR TYR PRO ASN ILE ASP ARG THR GLU MET ILE SER LYS GLY TYR
CTG ACA AAG GAA AGT TAT TAT CCC AAT ATT GAC CGA ACT GAG ATG ATT TCA AAA GGA TAC
8343
VAL ALA SER LYS SER SER HIS SER ARG GLY SER ALA ILE ASP LEU THR LEU TYR ARG LEU
GTG GCT TCA AAA TCA AGC CAT AGC CGC GGC AGT GCC ATT GAT CTT ACG CTT TAT CGA TTA
8403
ASP THR GLY GLU LEU VAL PRO MET GLY SER ARG PHE MET ASP GLU ARG SER HIS
GAC ACG GGT GAG CTT GTA CCA ATG GGG AGC CGA TTT ATG GAT GAA CGC TCT CAT
```

FIG. 8M

```
8463
HIS ALA ALA ASN GLY ILE SER CYS ASN GLU ALA GLN ASN ARG ARG ARG LEU ARG SER ILE
CAT GCG GCA AAT GGA ATA TCA TGC AAT GAA GCG CAA AAT CGC AGA CGT TTG CGC TCC ATC
8523
MET GLU ASN SER GLY PHE GLU ALA TYR SER LEU GLU TRP TRP HIS TYR VAL LEU ARG ASP
ATG GAA AAC AGT GGG TTT GAA GCA TAT AGC CTC GAA TGG TGG CAC TAT GTA TTA AGA GAC
8583
GLU PRO TYR PRO ASN SER TYR PHE ASP PHE PRO VAL LYS
GAA CCA TAC CCC AAT AGC TAT TTT GAT TTC CCC GTT AAA TAAA CTT TTA ACC GTT GCA
8641
CGG ACA AAC TAT ATA AGC TAA CTC TTT CGG CAG GAA ACC CGA CGT ATG TAA CTG GTT CTT
8701
AGG GAA TTT ATA TAT AGT AGA TAG TAT TGA AGA TGT AAG GCA GAG CGA TAT TGC GGT CAT
8761
TAT CTG CGT GCG CTG CGG CAA GAT AGC AGT TCA ACA GGC AGT TCA GCA TAG AGG GGT GGT
8821
ATT TCA CAC CGC CCA TTG TCA CAT CTA CAT TGG TGA TAA TAG TAA ATC CAG TAG GAA ATA ATT GAC
8881
CTT ATG AAA ATT CAT CTA CAT TGG TGA TAA TAG TAA ATC CAG TAG GAA ATA ATT GAC
```

```
9121
ALA LEU PHE SER GLN GLU LYS VAL GLU PHE GLN ASN TYR ASP GLN ASN PRO LYS GLU HIS
GCA CTG TTT TCT CAG GAA AAA GTC GAA TTT CAA AAT TAT GAT CAA AAT CCC AAA GAA CAT
9181
LEU GLU ASN SER GLY THR SER GLU ASN THR GLN GLU THR ILE THR GLU GLU GLN VAL
TTA GAA AAT AGT GGG ACT TCT GAA AAT ACC CAA GAG ACA ATT ACA GAA CAG GTT
9241
TYR GLN GLY ASN LEU LEU ILE LEU ASN SER LYS TYR PRO VAL ARG GLN GLU SER VAL LYS
TAT CAA GGA AAT CTG CTA TTA ATC AAT AGT AAA TAT CCT GTT CGC CAA GAA AGT GTG AAG
9301
SER ASP ILE VAL ASN LEU SER LYS HIS ASP GLU LEU ILE ASN GLY TYR GLY LEU LEU ASP
TCA GAT ATC GTG AAT TTA TCT AAA CAT GAC GAA TTA ATA AAT GGA TAC GGG TTG CTT GAT
9361
SER ASN ILE TYR MET SER LYS GLU ILE ALA GLN LYS PHE SER GLU MET VAL ASN ASP ALA
AGT AAT ATT TAT ATG TCA AAA GAA ATA GCA CAA AAA TTT TCA GAG ATG GTC AAT GAT GCT
9421
VAL LYS GLY VAL SER HIS PHE ILE ILE ASN SER GLY TYR ARG ASP PHE ASP GLU GLN
GTA AAG GGT GTT AGT CAT TTT ATT AAT AGT GGC TAT CGA GAC TTT GAT GAG CAA
9481
SER VAL LEU TYR GLN GLU MET GLY ALA LEU PRO ALA GLY TYR SER GLU HIS
AGT GTG CTT TAC CAA GAA ATG GGG GCT TTA CCA GCA GGT TAT AGT GAG CAT
9541
ASN SER GLY LEU SER LEU ASP VAL GLY SER SER LEU THR LYS MET GLU ARG ALA PRO GLU
AAT TCA GGT TTA TCA CTA GAT GTA GGA TCA AGC TTG ACG AAA ATG GAA CGA GCC CCT GAA
9601
GLY LYS TRP ILE GLU GLU ASN ALA TRP LYS TYR GLY PHE ILE LEU ARG TYR PRO GLU ASP
GGA AAG TGG ATA GAA GAA AAT GCT TGG AAA TAC GGG TTC ATT TTA CGT TAT CCA GAG GAC
9661
LYS THR GLU LEU THR GLY ILE GLN TYR GLU PRO TRP HIS ILE ARG TYR VAL GLY LEU PRO
AAA ACA GAG TTA ACA GGA ATT CAA TAT GAA CCA TGG CAT ATT CGC TAT GTT GGT TTA CCA
9721
```

FIG. 80

```
     HIS SER ALA ILE MET LYS GLU LYS ASN PHE VAL LEU GLU GLU TYR MET ASP TYR LEU LYS
     CAT AGT GCG ATT ATG AAA GAA AAG AAT TTC GTT CTC GAG GAA TAT ATG GAT TAC CTA AAA
9781
     GLU LYS THR ILE SER VAL SER VAL ASN GLY GLU LYS TYR GLU ILE PHE TYR TYR PRO
     GAA AAA ACC ATT TCT GTT AGT GTA AAT GGG GAA AAA TAT GAG ATC TTT TAT TAT CCT
9841
     VAL THR LYS ASN THR THR ILE HIS VAL PRO THR ASN LEU ARG TYR GLU ILE SER GLY ASN
     GTT ACT AAA AAT ACC ACC ATT CAT GTG CCG ACT AAT CTT CGT TAT GAG ATA TCA GGA AAC
9901
     ASN ILE ASP GLY VAL ILE VAL THR VAL PHE PRO GLY SER THR HIS THR ASN SER ARG ARG
     AAT ATA GAC GGT GTA ATT GTG ACA GTG TTT CCC GGA TCA ACA CAT ACT AAT TCA AGG AGG
9961
     TAA GGA TGG CGG AAT GAA ACC AAC GAA ATT AAT GAA CAG CAT TAT TGT ACT AGC ACT TTT
10021
     GGG GTA ACG TTA GCT TTT TAA TTT AAA ACC CAC GTT AAC TAG GAC ATT GCT ATA CTA ATG
10081
     ATA CAA CTT AAA CAA AAG AATTAGAGG AAA TTA TA TTG GGA AAA ATA TCT AGA GGA TTG
10143       Vanz      LEU GLY LYS ILE LEU SER ARG GLY LEU
     LEU ALA LEU TYR LEU VAL THR LEU ILE TRP LEU VAL LEU PHE LYS LEU GLN TYR ASN ILE
     CTA GCT TTA TAT TTA GTG ACA CTA ATC TGG TTA GTG TTA CAA TAC AAT ATT
10203
     LEU SER VAL PHE ASN TYR HIS GLN ARG SER LEU ASN LEU THR PRO PHE THR ALA THR GLY
     TTA TCA GTA TTT AAT TAT CAT CAA AGA AGT CTT AAC TTG ACT CCA TTT ACT GCT ACT GGG
10263
     ASN PHE ARG GLU MET ILE ILE ASP ASN VAL ILE ILE PHE ILE PRO PHE GLY LEU LEU ASN
     AAT TTC AGA GAG ATG ATA ATA GAT AAT GTT ATA ATC ATT CCA TTT GGC TTG CTT TTG AAT
```

FIG. 8P

```
       VAL ASN PHE LYS GLU ILE GLY PHE LEU PRO LYS PHE ALA PHE VAL LEU SER LEU
10323  GTC AAT TTT AAA GAA ATC GGA TTT TTA CCT AAG TTT GCT TTT GTA CTG TTA AGT CTT
       THR PHE GLU ILE ILE GLN PHE ILE PHE ALA ILE GLY ALA THR ASP ILE VAL ILE
10383  ACT TTT GAA ATA ATT CAA TTT ATC GCT ATT GGA GCG ACA GAC ATA ACA GTA ATT
       THR ASN THR VAL GLY GLY PHE LEU GLY PHE LEU LYS LEU TYR GLY LEU SER ASN LYS HIS MET
10443  ACA AAT ACT GTT GGA GGC TTT CTT GGA CTG AAA TTA TAT GGT TTA AGC AAT AAG CAT ATG
       ASN GLN LYS LYS LEU ASP ARG VAL ILE ILE PHE VAL GLY ILE LEU LEU VAL LEU LEU
10503  AAT CAA AAA AAA TTA GAC AGA GTT ATT ATT TTT GTA GGT ATA CTT TTG CTC GTA TTA TTG
       LEU VAL TYR ARG THR HIS LEU ARG ILE ASN TYR VAL
10563  CTC GTT TAC CGT ACC CAT TTA AGA ATA AAT TAC GTG TAAG ATG TCT AAA TCA AGC AAT
10621  CTG ATC TTT CAT ACA CAT AAA GAT ATT GAA TGA ATT GGA TTA GAT GGA AAA CGG GAT GTG
10681  GGG AAA CTC GCC CGT AGG TGT GAA GTG AGG GGA AAA CCG GTG ATA AAG TAA AAA GCT TAC
10741  CTA ACA CTA TAG TAA CAA AGA AAG CCC AAT TAT CAA TTT TAG TGC TGA GGA ATT GGT CTC
10801  TTT AAT AAA TTT CCT TAA CGT TGT AAA TCC GCA TTT TCC TGA CGG TAC CCC
```

FIG. 8Q

Ib brin(-)
1
CAA AAT ATC ACC TCA TTT TTG AGA CAA GTC TTA TGA GAC GCT CTT AAC TAT GAT TTT ATC
61
AGT CTA CTA CAT TTG TAT CAA TAG AGT ACA CTC TAT TGA TAT ATA ATT GAA CTA ATA AAT
                                                        MET LYS ILE ALA ARG GLY ARG GLU LEU LEU THR
121                                  Transposase         MET LYS ILE ALA ARG GLY ARG GLU LEU LEU THR
TGA AAA TAC AGA AAT GGA ATGATACTG AA ATG AAA ATT GCG AGA GGT AGA GAA TTG CTT ACA
182
PRO GLU GLN ARG GLN ALA PHE MET GLN ILE PRO GLU ASP GLU TRP ILE LEU GLY THR TYR
CCG GAA CAG AGA CAG GCT TTT ATG CAA ATC CCT GAA GAT GAA TGG ATA CTG GGG ACC TAC
242
PHE THR PHE SER LYS ARG ASP LEU GLU ILE VAL ASN LYS ARG ARG ARG GLU GLU ASN ARG
TTC ACT TTT TCC AAA CGG GAT TTA GAA ATA GTT AAT AAG CGA AGG AGG GAA GAA AAC CGT
302
LEU GLY PHE ALA VAL GLN LEU ALA VAL LEU ARG TYR PRO GLY TRP PRO TYR THR HIS ILE
TTA GGA TTT GCT GTT CAA TTA GCT GTT CTT CGG TAT CCC GGT TGG CCA TAC ACT CAT ATC
362
LYS SER ILE PRO ASP SER VAL ILE GLN TYR ILE SER LYS VAL LEU GLY VAL SER PRO SER
AAA AGC ATC CCA GAT TCG GTC ATA CAA TAT ATA TCG AAA CAG ATT GGT GTT AGT CCA TCC
422
SER LEU ASP HIS TYR PRO GLN ARG GLU ASN THR LEU TRP ASP HIS LEU LYS GLU ILE ARG
TCG CTT GAT CAT TAT CCT CAA AGG GAA AAT ACA CTT TGG GAT CAT TTG AAA GAA ATT CGA

FIG. 8R

```
482
    SER GLU TYR ASP PHE VAL THR PHE THR LEU SER GLU TYR ARG MET THR PHE LYS TYR LEU
    AGT GAA TAC GAC TTT GTA ACT TTT ACC CTG AGT GAA TAT CGA ATG ACA TTT AAG TAC CTT
542
    HIS GLN LEU ALA LEU GLU ASN GLY ASP ALA ILE HIS LEU LEU HIS GLU CYS ILE ASP PHE
    CAT CAA TTA GCT TTG GAA AAT GGT GAT GCC ATT CAT CTA CTG CAT GAA TGC ATA GAT TTT
602
    LEU ARG LYS ASN LYS ILE LEU PRO ALA ILE LEU THR THR LEU GLU ARG MET VAL TRP GLU
    CTA AGA AAA AAC ATA ATT CTG CCT GCT ATC ACT ACA CTT GAA AGA ATG GTG TGG GAA
662
    ALA ARG ALA MET ALA GLU LYS LYS LEU PHE ASN THR VAL SER LYS SER LEU THR ASN GLU
    GCA AGG GCA ATG GCT GAA AAG AAG CTA TTT AAT ACG GTT AGT AAA TCT CTA ACA AAT GAG
722
    GLN LYS GLU LYS LEU GLU GLY ILE ILE THR SER GLN HIS PRO SER GLU SER ASN LYS THR
    CAA AAA GAA AAG CTT GAA GGG ATT ATT ACC TCG CAG CAT CCA TCA GAA TCC AAT AAA ACG
782
    ILE LEU GLY TRP LEU LYS GLU PRO PRO GLY HIS PRO SER PRO GLU THR PHE LEU LYS ILE
    ATA TTG GGT TGG TTA AAA GAG CCA CCG GGT CAT CCT TCA CCC GAA ACT TTT CTA AAA ATA
842
    ILE GLU ARG LEU GLU TYR ILE ARG GLY MET ASP LEU GLU THR VAL GLN ILE SER HIS LEU
    ATA GAA CGA CTC GAA TAC ATA CGA GGA ATG GAT TTA GAA ACA GTG CAA ATT AGT CAT TTG
902
    HIS ARG ASN ARG LEU LEU GLN LEU SER ARG LEU GLY SER ARG TYR GLU PRO TYR ALA PHE
    CAC CGT AAC CGC CTG TTG CAG CTG TCT CGC TTA GGC AGA TAC GAG CCG TAT GCA TTC
962
    ARG ASP PHE GLN GLU ASN LYS ARG TYR SER ILE LEU TYR ILE TYR LEU LEU GLN LEU THR
    CGT GAC TTT CAA GAA AAT AAA CGT TAT TCG ATA TTA ACC ATC TAT TTA TTA CAA CTT ACT
1022
    GLN GLU LEU THR ASP LYS ALA PHE GLU ILE HIS ASP ARG GLN ILE LEU LEU LEU SER
    CAG GAG CTA ACG GAT AAA GCG TTT GAA ATT CAT GAT AGG CAA ATA CTT TTG TTA TCA
```

FIG. 8S

```
1082
LYS GLY ARG LYS ALA GLN GLU ILE GLU LYS GLN ASN GLY LYS LEU LYS LYS LEU ASN GLU LYS
AAA GGT CGT AAG GCT CAA GAG GAA ATC GAG AAA CAA AAC GGT AAA AAG CTA AAT GAG AAA
1142
VAL ILE HIS PHE THR ASN ILE GLY GLN ALA LEU ILE LYS ALA ARG GLU GLU LYS LEU ASP
GTT ATA CAC TTT ACG AAC ATC GGA CAA GCA TTA ATT AAA GCA AGA GAG GAA AAA TTA GAC
1202
VAL PHE LYS VAL LEU GLU SER VAL ILE GLU TRP ASN THR PHE VAL SER SER VAL GLU GLU
GTT TTT AAG GTT TTA GAA TCG GTT ATT GAA TGG AAT ACC TTT GTC TCT TCA GTA GAA GAG
1262
ALA GLN GLU LEU ALA ARG PRO ALA ASP TYR LEU ARG VAL LEU GLN LYS ARG PHE
GCT CAG GAA CTT GCA CGT CCT GCC GAC TAT TTA AGA GTA CTA CAA AAA CGG TTT
1322
TYR SER LEU ARG LYS TYR THR PRO THR LEU LEU ARG GLY MET ASN GLU SER GLY LYS
TAT TCA CTA AGA AAA TAT ACG CCA ACG CTA TTA AGA GGA ATG AAC GAA TCT GGA AAG
1382
ALA ASN GLU PRO LEU LEU GLN ALA VAL GLU ILE ILE ARG ASP PHE ILE SER LYS ARG TRP LYS
GCA AAT GAG CCA CTT TTA CAA GCT GTT GAG ATT ATC CGA GAT TTT ATT TCA AAA CGA TGG
1442
ARG LYS VAL PRO ASP SER PRO VAL ASP PHE ILE ASN ARG HIS TYR TYR GLU MET ALA VAL LEU THR GLU
CGA AAA GTG CCT GAT TCA CCT GTG GAT TTT ATT AAT CGT CAT TAC TAT GAA ATG GCT GTT TTA ACA GAA
1502
TYR GLU ASP ASP GLY THR THR ILE THR THR GLY ASP LEU THR GLU
TAC GAG GAT GAT GGT ACA ACA ATT ACA GGT GAT CTT ACA GAA
1562
LEU ARG GLU HIS VAL ARG ALA GLY ASP VAL SER ILE VAL GLY SER ARG GLN TYR ARG ASP
CTT CGG GAG CAT GTT CGG GCA GGA GAT GTT TCC ATT GTT GGC AGC AGA CAA TAT AGG GAT
```

FIG. 8T

```
1622
PHE GLU TYR LEU PHE SER GLU ASP THR TRP ASN GLN SER LYS GLY ASN THR ARG LEU
TTT GAG TAT TTG TTT TCG GAA GAT ACA TGG AAT CAA TCG AAG GGG AAT ACG AGA TTA
1682
SER VAL SER LEU SER PHE GLU ASP TYR ILE THR ARG GLU THR SER PHE ASN GLU ARG
TCA GTT AGT TTA TCA TTC GAA GAT TAT ATA ACG GAG AGA ACC AGC TTT AAT GAA AGG
1742
LEU LYS TRP LEU ALA ALA ASN SER ASN LYS LEU ASP GLY VAL SER LEU GLU LYS GLY LYS
TTA AAG TGG TTA GCT GCC AAT TCC AAT AAG TTA GAT GGG GTT TCT CTT GAA AAA GGA AAG
1802
LEU SER LEU ALA ARG LEU GLU LYS ASP VAL PRO GLU GLU ALA LYS LYS PHE SER ALA SER
CTA TCA CTT GCA CGC CTT GAA AAA GAT GTT CCA GAA GCA AAA TTT AGT GCA AGC
1862
LEU TYR GLN MET LEU PRO ARG ILE LYS LEU THR ASP LEU LEU MET ASP LEU ALA HIS ILE
CTT TAT CAG ATG CTA CCA AGA ATA AAA TTA ACT GAT TTA CTC ATG GAT GCC CAT ATA
1922
THR GLY PHE HIS GLU GLN PHE HIS ALA SER ASN ASN ARG LYS PRO ASP LYS GLU GLU LYS MET
ACA GGA TTT CAT GAG CAA TTC ACT GCT TCC AAT AAT CGA AAA CCA GAT AAG GAA GAA
1982
THR ILE ILE MET ALA LEU ALA LEU THR TYR LYS GLN LEU ASN ILE GLY LEU SER LYS MET
ACA ATC ATT ATG GCT CTT GCT CTT ACA TAT AAG CAA CTA AAT ATT GGC TTG AGC AAG ATG
2042
ALA GLU ALA THR PRO GLY LEU MET ASN LYS ALA GLN ALA ILE LEU VAL ASN VAL SER GLN TRP ARG MET
GCC GAA GCA ACA CCC GGA CTT ATG AAT AAA GCC CAA GCC ATA TTA AAC GTA TCT CAA TGG CGC ATG
2102
TYR GLU ASP ALA MET ASN LYS ALA GLN ALA ILE LEU VAL ASN PHE HIS HIS LYS LEU GLN
TAT GAA GAT GCC ATG AAT AAA GCC CAA GCC ATA TTA GTA AAC TTT CAT CAT AAA TTA CAA
2162
LEU PRO PHE TYR TRP GLY ASP GLY MET ARG MET MET GLN LEU
TTG CCT TTC TAT TGG GGC GAC GGT ATG AGA ATG CAG CTA
```

FIG. 8U

```
2222
GLY VAL SER SER LEU HIS ALA ASP ALA ASN PRO HIS TYR GLY THR GLY LYS GLY ALA THR
GGT GTT TCA TCA CTA CAT GCA GAT GCA AAT CCA CAT TAT GGA ACT GGA AAA GGA GCC ACC
2282
ILE TYR ARG PHE THR ASP GLN PHE SER ASP GLY TYR THR LYS ILE ILE HIS THR ASN
ATC TAC CGA TTT ACA GAT CAA TTC TCT GAT GGT TAC ACA AAG ATT CAT ACT AAT
2342
SER ARG ASP ALA ILE HIS VAL LEU ASP GLY LEU LEU HIS HIS GLU THR ASP LEU ASN ILE
TCA AGA GAT GCG ATT CAT GTT TTG GAT GGT TTA CTA CAT CAT GAG ACG GAT CTA AAC ATA
2402
GLU HIS TYR THR ASP THR ALA GLY TYR THR ASP GLN ILE PHE GLY LEU THR HIS LEU
GAG CAT TAT ACA GAC ACT GCC GGT TAC ACT GAC CAA CAA ATA TTC GGA CTG ACT CAT TTA
2462
LEU GLY PHE LYS PHE ALA PRO ARG ILE ARG ASP SER LYS LEU PHE THR ILE
TTA GGA TTT AAA TTT GCC CCA AGA ATA AGG GAT TCG GAC TCA AAA TTA TTT ACG ATA
2522
ASP LYS ALA SER GLU TYR PRO LYS LEU ARG GLY GLN ILE ASN THR LYS
GAT AAA GCA AGT GAG TAT CCA AAA CTA GAA CGT GGA CAA ATA AAT ACA AAG
2582
VAL ILE LYS GLU ASN TYR GLU ASP VAL LEU ARG LEU ALA HIS SER ILE ARG GLU GLY THR
GTC ATT AAA GAA AAT TAT GAG GAT GTT TTG CGA TTA GCT CAT TCT ATA AGG GAG GGA ACA
2642
SER PHE SER ILE PRO TYR GLU ALA ARG PHE LEU TYR LYS THR PHE ASN THR LYS
AGT TTC AGC ATC CCT TAT GAA GCT AGG TTC CTA TTC AAG ACA AAA CAG CTT AGC
VAL SER ALA SER LEU ILE MET GLY LYS LEU GLY TYR SER ARG GLN ASN SER LEU ALA
GTT TCA GCA TCC CTT ATT ATG GGG AAG CTA GGT TCA AGA CAA AAC AGC TTA GCT
2702
THR ALA LEU ARG GLU MET GLY ARG ILE GLU LYS THR ILE PHE ILE LEU ASN TYR ILE SER
ACA GCC TTA CGT GAG ATG GGC CGA ATA GAA AAA ACG ATC TTT ATT TTG AAT TAT ATA TCG
```

FIG. 8V

```
2762
ASP GLU SER LEU ARG ARG LYS ILE GLN ARG GLY LEU ASN LYS GLY ALA MET ASN GLY
GAT GAA TCA TTA AGA AGA AAA ATA CAA AGA GGA TTG AAT AAA GGA GCC ATG AAT GGA
2822
LEU ALA ARG ALA ILE PHE PHE GLY LYS GLN GLY GLU LEU ARG GLY ARG THR ILE GLN HIS
TTG GCA AGA GCT ATT TTC TTC GGA AAA CAA GGT GAG CTT AGA GAA CGC ACC ATA CAG CAT
2882
GLN LEU GLN ARG ALA SER ALA LEU ASN ILE ILE ASN ALA ILE SER ILE TRP ASN THR
CAA TTG CAA AGA GCC AGT GCT TTA AAC ATA ATT ATC AAT GCT ATA AGT ATT TGG AAT ACT
2942
SER PRO ASN ASN SER SER THR THR ALA VAL SER ALA VAL PRO LEU GLY LEU GLN GLN LEU ALA SER PHE ASN GLU ASP LEU
TCT CCA AAC AAC AGC AGT ACA ACA GCA GTT GAA TAT AGT TGA CTT TAA TGA AGA TTT
LEU HIS LEU THR THR ALA VAL SER ALA VAL GLU TYR SER ARG GLY SER PHE ASN GLU ASP LEU
CTC CAC CTA ACA ACA GCA GTT GAA TAT AGT TGA CTT TAA TGA AGA TTT
LEU HIS HIS MET SER PRO LEU GLY TRP GLU HIS ILE ASN LEU LEU GLY GLU TYR HIS PHE
TTA CAC CAT ATG TCG CCC TTA GGT TGG GAA CAT ATT AAT TTA CTA GGA GAA TAC CAT TTT
3062
ASN SER GLU LYS VAL VAL SER LEU ASN SER LEU ARG PRO LEU LYS LEU SER
AAC TCA GAG AAA GTA GTC TCA TCA TTA AAT TCT TTA AGA CCA CTA AAA CTT TCT TAA CGT TG
3121
TTA AAA ACG AGG GAT TCG TCA GGA AAA TAG GCT TAG CGT TGT AAA TCC GCA TTT TCC TGA
3181
CGC TAC CCC
```

FIG. 8W

```
                                                                              SacI
CATTGATCACTAACAATAGCTTCCCCTGCTTTCTTCAAGCCCTTTGTCATAAAATCGTTAGATTTCA  42

CATTGATCACTAACAATAGCTTCCCCTGCTTTCTTCAAGCCCTTTGTCATAAAATCGTTAGATTTCA  111

RBS                    M  K  K  I  A  V  L  F  G  G
TCATAAAATACGAGAAGACACAGGAAGACCGCAAATTTCTTTTTCTTTCCTAGTACACTGAATG     180

N  S  P  E  Y  S  V  S  L  T  S  A  A  S  V  I  Q  A  I  D
TAACCTTAAAGAAAAAATGATGAAAAAAATTGCCGTTTTATTTGGAGGG                    244

P  L  K  Y  E  V  M  T  I  G  I  A  P  T  M  D  W  Y  W  Y
AATTCTCCAGAATACTCAGTGTCACTAACCTCAGCAGCAAGTGTGATCCAAGCTATTGAC         304

Q  G  N  L  A  N  V  R  N  D  T  W  L  E  D  H  K  N  C  H
CCGCTGAAATATGAAGTAATGACCATTGGCATCGCCACAATGGATTGGTATTGGTAT            364

Q  L  T  F  S  S  Q  G  F  I  L  G  E  K  R  I  V  P  D  V
CAAGGAAACCTCGCGAATGTTCGCAATGATACTTGGCTAGAAGATCACAAAAACTGTCAC         424

L  F  P  V  L  H  H  G  K  Y  G  E  D  G  C  I  Q  G  L  L  E
CAGCTGACTTTTTCTAGCCAAGGATTTATATTAGGAGAGAAAAACGAATCGTCCCCTGATGTC      484

L  M  N  L  P  Y  V  G  C  H  V  A  A  S  A  L  C  M  N  K
CTCTTTCCAGTCTTGCATCATGGCAAGTATGGGCGAGGATGGCTGTATCCAAGGACTGCTTGAA     544

CTAATGAACCTGCCTTATGTTGGTTGCCATGTCGCTGCCTCCGCATTATGTATGAACAAA         604
```

FIG. 9A

```
W  L  L  H  Q  L  A  D  T  M  G  I  A  S  A  P  T  L  L  L
TGGCTCTTGCATCAACTTGCTGATACCATGGGAATCGCTAGTGCTCCCACTTTGCTTTTA   664

S  R  Y  E  N  D  P  A  T  I  D  R  F  I  Q  D  H  G  F  P
TCCCGCTATGAAAACGATCCTGCCACAATCGATCGTTTATTCAAGACCATGGATTCCCG   724

I  F  I  K  P  N  E  A  G  S  S  K  G  I  T  K  V  T  D  K
ATCTTTATCAAGCCGAATGAAGCCGGTTCTTCAAAAGGATCACAAAAGTAACTGACAAA   784

T  A  L  Q  S  A  L  T  A  F  A  Y  G  S  T  V  L  I  Q
ACAGCGCTCCAATCTGCATTAACGACTGCTTTTGCTTACGGTTCTACTGTTGATCCAA   844

K  A  I  A  G  I  E  I  G  C  G  I  L  G  N  E  Q  L  T  I
AAGGCGATAGCGGGTATTGAAATTGGCTGCGGCATCTTAGGAAATGAGCAATTGACGATT   904

G  A  C  D  A  I  S  L  V  D  G  F  F  D  F  F  E  E  K  Y  Q
GGTGCTTGTGATGCGATTTCTCTTGTCGACGGTTTTTTTGATTTTGAAGAGAAATACCAA   964

L  I  S  A  T  I  T  V  P  A  P  L  P  L  A  L  E  S  Q  I
TTAATCAGCGCCACGATCACTGTCCCAGCACCATTGCCTCTCGCGCTTGAATCACAGATC   1024

K  E  Q  A  Q  L  Y  R  N  L  G  L  T  G  L  A  R  I  D
AAGGAGCAAGCACAGCTGTATCGAAACTTGGGATTGACGGGTCTGGCTCGAATCGAT   1084

F  F  V  T  N  Q  G  A  I  Y  L  N  E  I  N  T  M  P  G  F
TTTTTCGTCACCAATCAAGGAGCGATTTATTTAAACGAAATCAACACCATGCCGGGATTT   1144
```

FIG. 9B

```
T  G  H  S  R  Y  P  A  M  M  A  E  V  G  L  S  Y  E  I  L
ACTGGGCACTCCCGCTACCCAGCTATGATGGCGGAAGTCGGGGTTATCCTACGAAATATTA      1204

V  E  Q  L  E  A  L  A  E  E  D  K  R  *
GTAGAGCAATTGATTGCACTGGCAGAGGAGGACAAACGATGAACACATTACAATTGATCAATA    1267

AAACCATCCATTGAAAAAAATCAAGAGCCCCCGCACTTAGTGCTAGCTCCTTTTAGCGATCACGATG  1336

TTTACCTGCAG    1347
PstI
```

```
VanS  126 EMDVMEQKLNTLKRTLEKREQDAKLAEQRKNDVVMYLAHDIKTPLTSIIGYLISLLDEAP  184
PhoR  176 EIRVMPYTHKQLLMVARDVTQMHQLEGARRN-FFANVSHELRTPLTVLQGYLEMMNEQP  233
EnvZ  210 ASEVRSVTRAFNHMAA---GVKQLADDRTL-LMAGVSHDLRTPLTRRLATEMMSEQD  263

VanS      DMPVDQKAKYVHITLDKAYRLEQLIDEFFEITRYNLQTITITKTHIDLYYMLVQMTDEF  243
PhoR      LEGAV-REKALHTMREQTQRMEGLVKQLLTLSKIEAAPTHLLNEKVDVPMMLRVVEREA  291
EnvZ      GYLAESINK-----DIEECNAIIEQFIDYLRTGQEMPM--EMADLNAVLGEVIAAE  312
                                         I

VanS      YPQLSAHGKQAVIHAPEDLTVSGDPDKLARVFNNILKNAAAYSEDNSIIDITAGLSG--  300
PhoR      -QTLSQKKQTFTFEIDNGLKVSGNEDQLRSAISNLVYNAVNHTPEGTHITVRWQRVPHG  349
EnvZ      ---SGYEREIETALYPGSIEVKMHPLSIKRAVANMVVNAARYG--NGWIKVSGTEPNR  366
                                         II

VanS      DVVSIEFKNTGSIPKDKLAAIFEKFYRLDNARSSDTGGAGLGLATAKEIIVQHGGQIYA  359
PhoR      AEFSVEDNGPGIAPEHI-PRLTERFYRVDKARSRQIGGSGLGLAIVKHAVNHHESRLNI  407
EnvZ      AWFQVEDDGPGIAPEQR-KHLFQPFVRGDSART--TSGTGLGLAIVQRIVDNHNGMLEL  422
             IIIa                              IIIb

VanS      ESNDNYIT-FRVELPAMPDLVDKRRS                                   384
PhoR      ESTVGKGTRFSFVIPERLIAKNSD                                     432
EnvZ      GTSERGGLSIRAWLPVPVTRAQGTTKEG                                 450
```

VanR ---MSDKIL----IVDDEHEIADLVELYLKNENYIVFK--YYTAKEALECIDKSEIDLAILDIML
OmpR MQENYKIL----VVDDDMRLRALLERYLITEQGFQVRS--VANAEQMDRLLTRESFHLMVLDLML
PhoB ---MARRIL----VVEDEAPIREMVCFVLEQNGFQPVE--AEDYDSAVNQLNEPWPDLILLDWML
CheY ---MADKELKFLVVDDFSTMRRIVRNLLKELGFNNVEEAEDGVDALNKLQAGGFGFIISDWNM

VanR PGTSGLITCQKIRDKHTY---PIIMLTGKDTEVDKITGLTIGADDYITKPFRPLELIARVKA
OmpR PGEDGLSICRRLRSQSNPM--PIIMVTAKGEEVDRIVGLEIGADDYIPKPFNPRELLARIRA
PhoB PGGSGIQFIKHLKRESMTRDIPVVMLTARGEEDRVRGLETGADDYITKPFSPKELVARIKA
CheY PNMDGLELLKTIRADSAMSALPVLMVTAEAKKENIIAAAQAGASGYVVKPFTAATLEEKLNK

VanR QLRRYKK-FSGVKEQNENVIVHSGLVINVNTHECYLNEKQLSLTPTEFSILRILCENKGNVV
OmpR VLRRQANELPGAPSQEEAVIAFGKFKLNLGTREMFREDEPMPLTISGEFAVLKALVSHPREPL
PhoB VMRRISP----MAVEEVIEMQGLSLDPTSHRVMAGEEPLEMGPTEFKLLHFFMTHPERVY
CheY IFEKLGM 129

VanR RSELLFHEIWGDEYFSKSNNTIIVHIRHLREKMNDTIDNPKYIKTVWGVGYKIEK
OmpR RDKLMNLARGREYSAMER-SIDVQISRLRRMVEEDPAHPRYIQTVWGLGYVFVPDGSKA
PhoB REQLLNHVWGTNVYVEDR-ITVDVHIRRLR-KALEPGGHDRMVQTVRGTGYRFSTRF
```

FIG.15

POLYPEPTIDES IMPLICATED IN THE EXPRESSION OF RESISTANCE TO GLYCOPEPTIDES, IN PARTICULAR IN GRAM-POSITIVE BACTERIA, NUCLEOTIDE SEQUENCE CODING FOR THESE POLYPEPTIDES AND USE FOR DIAGNOSIS

This is a divisional of application Ser. No. 08/286,819 filed on Aug. 5, 1994, U.S. Pat. No. 5,871,910, which is a continuation of application Ser. No. 08/174,682 filed on Dec. 28, 1993, abandoned, which is a continuation of application Ser. No. 07/917,146 filed on Aug. 10, 1992, abandoned which is a 371 of PCT/FR91/00855 filed Oct. 29, 1991.

The invention relates to the polypeptides associated with the expression of resistance to antibiotics of the glycopeptide family, in particular in Gram-positive bacteria, in particular in the family of the Gram-positive cocci. The invention also relates to a nucleotide sequence coding for these polypeptides. It also relates to the use of these polypeptides and their nucleotide sequence as agents for the in vitro detection of resistance to glycopeptides. Among the Gram-positive cocci, the invention relates most particularly to the enterococci, the streptococci and the staphylococci which are of particular importance for the implementation of the invention.

The glycopeptides, which include vancomycin and teicoplanin are antibiotics which inhibit the synthesis of the bacterial cell wall. These antibiotics are very much used for the treatment of severe infections due to Gram-positive cocci (enterococci, streptococci and staphylococci), in particular in light of allergy and resistance to the penicillins. In spite of long clinical usage of vancomycin, this antibiotic has remained active towards almost all of the strains up to 1986, the date at which the first resistant-strains were isolated. Since then, resistance to the glycopeptides has been detected by many microbiologists in Europe and in the United States, in particular in strains isolated from immunodepressive patients, making necessary a systematic evaluation of the sensitivity of the microbes in hospital environments.

The activity of the glycopeptides depends on the formation of a complex between the antibiotic and the precursors of the peptidoglycan, more than on the direct interaction with enzymes of cell wall metabolism. In particular, it has been observed that the glycopeptides bind to the terminal D-alanyl-D-alanine residues (D-ala-D-ala) of the precursors of the peptidoglycan.

The recent emergence of resistance to the glycopeptides, in particular in the enterococci, has led to certain results being obtained with regard to knowledge of the factors conferring this resistance.

For example it has been observed in a particular strain of enterococci, *Enterococcus faecium* BM4147, that the determinant of resistance to the glycopeptides is localized on a plasmid of 34 kb, the plasmid pIP816. This determinant has been cloned in *E.coli* (Brisson Noel et al., 1990, Antimicrob Agents Chemother 34, 924–927).

According to the results hitherto obtained, the resistance to the glycopeptides is associated with the production of a protein of molecular weight of about 40 kDa, the synthesis of this protein being induced by sub-inhibitory concentrations of certain glycopeptides such as vancomycin.

By carrying out a more detailed study of the resistance of certain strains of Gram-positive cocci towards glycopeptides, in particular vancomycin or teicoplanin, the inventors have observed that this resistance might be linked to the expression of several proteins or polypeptides encoded in sequences usually borne by plasmids in the resistant strains. The recent results obtained by the inventors also make it possible to distinguish the genes coding for two phenotypes of resistance, on the one hand strains highly resistant to the glycopeptides, and, on the other, strains with a low level of resistance.

By strain with a high level of resistance is meant a strain of bacteria, in particular a strain of Gram-positive cocci, for which the minimal inhibitory concentrations (MIC) of vancomycin and teichoplanin are higher than 32 and 8 µg/ml, respectively. The MIC of vancomycin towards strains with low-level resistance are included between 16 and 32 µg/ml. These strains are apparently sensitive to teicoplanin.

The inventors have isolated and purified, among the components necessary for the expression of the resistance to the glycopeptides, a particular protein designated VANA or VanA which exhibits a certain homology with D-alanine-D-alanine ligases. VanA is nonetheless functionally distinct from the ligases.

In principle, a gene sequence will be designated by "van . . ." and an amino acid sequence by "Van . . ."

The invention relates to polypeptides or proteins implicated in the expression of resistance to antibiotics of the glycopeptide family and, in particular, to vancomycin and/or teicoplanin as well as to the nucleotide sequences coding for such complexes.

The invention also relates to nucleotide probes which can be used for the detection of resistance to the glycopeptides, in particular by means of the polymerase chain reaction (PCR), or by tests involving antibodies.

The invention relates to a composition of polypeptides, characterized in that it contains at least one protein or part of a protein selected from the amino acid sequences identified in the list of the sequences as SEQ ID NO 2 (VanH), SEQ ID NO 4 (VanA), SEQ ID NO 6 (VanX) or SEQ ID NO 8 (VanC), or any protein or part of a protein recognized by the antibodies directed against VanH, VanA, VanX or VanC, or any protein or part of a protein encoded in a sequence hybridizing with one of the nucleotide sequences identified in the list of the sequences as SEQ ID NO 1, SEQ ID NO 3, SEQ ID NO 5 or SEQ ID NO 7 or with one of the following sequences V1 (SEQ ID NO: 9) or V2 (SEQ ID NO: 10) under stringent or only slightly stringent conditions:

```
V1 : GGX GAA GAT GGX TCX TTX CAA GGX
         G   C       AG  C       G
                         A

V2 : AAT ACX ATX CCX GGX TTT AC
         C   T           C
             C
```

A first particular composition according to the invention implicated in the expression of the resistance to the glycopeptides is characterized in that it comprises at least 3 proteins or any part of one or more of these proteins necessary to confer to Gram-positive bacteria the resistance to antibiotics of the glycopeptide family, in particular to vancomycin and/or teicoplanin or to promote this resistance, in particular in strains of the family of the Gram-positive cocci, these proteins or parts of proteins being a) recognized by antibodies directed against one of the sequences identified in the list of the sequences as SEQ ID NO 2, SEQ ID NO 4, SEQ ID NO 6, b) or encoded in genes containing a sequence identified as SEQ ID NO 1, SEQ ID NO 3 or SEQ ID NO 5 or hybridizing with one of these sequences or its complementary sequence or with the sequences V1 (SEQ ID NO: 9) or V2(SEQ ID NO: 10), under stringent or only slightly stringent conditions.

These sequences are also designated, respectively, by ORF3, ORF1 containing the gene VanH, vanA (or ORF2); they characterize the proteins responsible for resistance as obtained from the strain *Enterococcus faecium* BM4147 described by Leclerq et al (N. Engl. J. Med. 319:157–161).

Another protein, VanC (SEQ ID NO: 8), related to the D-Ala-D-Ala ligases but of different specificity has been characterized in *Enterococcus gallinarum* BM4173; the vanC gene (SEQ ID NO: 7) possesses domains having sufficient homology with the vanA gene for probes corresponding to defined regions of vanA to make possible its detection.

*E.gallinarum* is a constitutive isolate resistant to low levels of vancomycin (Dutka-Malen et al., Antimicrob. Agents Chemother 34 (1990b) 1875–1879).

By the expression "polypeptides" is meant any sequence of amino acids constituting proteins or being of a size less than that of a protein.

The stringent conditions mentioned above are defined according to the usual conditions pertaining to the hybridization of nucleotide sequences. As an example, in the case of the sequences which hybridize with the sequence of the vanA gene (SEQ ID NO 1) it will be possible to apply the following conditions:

for hybridization under conditions of high stringency: * a reaction temperature of 65° C. overnight in a solution containing 0.1% SDS, 0.7% skimmed milk powder, 6×SSC (1×SSC=0.15 M NaCl and 0.015 M sodium citrate at pH=7.0) * washes at 65° C. in 2×SSC–0.1% SDS;

for hybridization under slightly stringent conditions, the hybridization temperature is 60° C. overnight and the temperature of the washings is 45° C.

The expression of resistance to glycopeptides may be expressed by the persistence of an infection due to microbes usually sensitive to the glycopeptides.

A polypeptide or a protein is necessary for the expression of resistance to the glycopeptides, if its absence makes the strain which contains this polypeptide or this protein more sensitive to the glycopeptides and if this polypeptide or protein is not present in sensitive strains.

Different levels of resistance to the glycopeptides exist in the strains of Gram-positive cocci, in particular.

According to a preferred embodiment of the invention, the polypeptides included in the composition defined above correspond to the combination of the proteins identified in the list of the sequences as SEQ ID NO 2 (VanH), SEQ ID NO 4 (VanA), SEQ ID NO 6 (VanX).

The inventors have thus observed that the expression of resistance to the glycopeptides in Gram-positive bacteria requires the expression of at least three proteins or of polypeptides derived from these proteins.

According to a first particular embodiment of the invention, the polypeptides of the composition are also characterized in that the amino acid sequences necessary for the expression of resistance to antibiotics of the glycopeptide family are under the control of regulatory elements, in particular of the proteins corresponding to the sequences designated by SEQ ID NO 12 and SEQ ID NO 14 in the list of the sequences, and which correspond to a regulatory sequence R and to a sensor sequence S, respectively.

VanS and VanR constitute a two-component regulatory system, VanR being an activator of transcription and VanS stimulating the transcription dependent on VanR. VanS is capable of modulating the level of phosphorylation of VanR in response to the vancomycin present in the external medium and is thus involved in the control of the transcription of the genes for resistance to vancomycin.

These regulatory sequences are in particular capable of increasing the level of resistance, to the extent to which they promote the expression of the proteins responsible for resistance comprised in the polypeptides of the invention.

According to another advantageous embodiment of the invention, the polypeptides of the above composition are encoded in the sequence SEQ ID NO 15 identified in the list of the sequences, which represents the sequence coding for the 5 proteins previously described.

Another sequence according to the invention is designated by SEQ ID NO 16 which contains the sequence SEQ ID NO 15 as well as a sequence upstream from SEQ ID NO 15 coding for a transposase (encoded in the (−) strand of the sequence, and a sequence downstream from SEQ ID NO 15 corresponding to the genes vanY and vanZ and at each end reverse repeated sequences of 38 bp. SEQ ID NO 16 constitutes a transposon, the genes of which are implicated at different levels in the establishment of resistance to the glycopeptides.

The invention also relates to the purified proteins belonging to the composition and to the polypeptides described previously. In particular, the invention relates to the purified protein VanA, characterized in that it corresponds to the amino acid sequence SEQ ID NO 4 in the list of the sequences or a protein VanC, encoded in a gene capable of hybridizing with the vanA gene.

The protein VanA contains 343 amino acids and has a calculated molecular mass of 37400 Da. The protein VanC contains 343 amino acids and has a calculated molecular mass of 37504 Da.

Other interesting proteins in the framework of the invention correspond to the sequences identified as SEQ ID NO 2 (VanH), SEQ ID NO 6 (VanX), SEQ ID NO 12 (VanR), SEQ ID NO 14 (VanS) in the list of the sequences.

The sequence identified by the abbreviation SEQ ID NO 1 contains the protein VanH encoded in the gene vanH, this protein contains 322 amino acids and begins with a methionine. This protein is an enzyme implicated in the synthesis of the peptidoglycan and has a molecular mass of 35,754 kDA. VanH exhibits some similarities to dehydrogenases which catalyze the $NAD^+$-dependent oxidation of 2-hydroxy-carboxylic acids to form the corresponding 2-keto-carboxylic acids. In fact, the VanH protein might use $NADP^+$ rather than $NAD^+$. The VanH protein also contains several residues of reactive sites which probably participate directly in the binding of the substrate and in catalysis. VanH might be implicated in the synthesis of a substrate of the ligase VanA. This substrate of VanA might be a D-α-hydroxy-carboxylic acid, which might be condensed by VanA with D-alanine in the place of a D-amino acid, which might affect the binding of the precursor of the peptidoglycan with vancomycin, as a result of the loss of a hydrogen bond because one of the hydrogen bonds formed between vancomycin and N-acetyl-D-Ala-D-Ala occurs with the NH group of the terminal D-alanine residue. Let it be recalled that "Ala" is the abbreviation for "alanine".

The inventors have been able to detect some interactions between the proteins VanA and VanH and have in particular been able to describe the following : the nature of the VanA protein (D-alanine: D-alanine ligase with reduced specificity for its substrate) which has made possible resistance to glycopeptides, implies the biosynthesis by VanA of a novel compound different from D-Ala-D-Ala, a peptide which may be incorporated into the peptidoglycans but which is not recognized by vancomycin. In particular, the observation of similarities between the product of the vanH gene and the D-specific α-keto-acid reductases has made it possible to determine that this compound cannot be a D-amino acid but is a D-hydroxy acid, which when it is bound to D-alanine by VanH, can generate the novel depsipeptide precursor of the peptidoglycan.

The invention also relates to any combination of these different proteins in a resistance complex, as well as to hybrid proteins comprising one or several of the above proteins, or part of these proteins, in combination with a defined amino acid sequence.

Also included in the framework of the invention are nucleotide sequences coding for one of the amino acid sequences described above.

A particular sequence is the nucleotide sequence of about 7.3 kb, corresponding to the HindIII-EcoRI restriction fragment, such as that obtained starting from the plasmid pIP816 described in the publication of Leclerq et al—1988, cited above.

This sequence of 7.3 kb comprises the nucleotide sequence coding for the 3 resistance proteins and the 2 regulatory proteins referred to above. This coding sequence is included in an internal BglII-XbaI fragment. It also comprises a part of the sequences coding for the transposase and the resolvase.

The invention also relates to any nucleotide fragment comprising the above-mentioned restriction fragment as well as any part of the HindIII-EcoRI fragment, in particular the EcoRI-XbaI fragment of about 3.4 kb coding for the 3 resistance proteins or the EcoRV-SacII fragment of about 1.7 kb coding for VanA or also HindIII-EcoRI fragment of about 3.3 kb coding for the 2 regulatory proteins VanR and VanS.

Another definition of a nucleotide sequence of the invention corresponds to a nucleotide fragment containing the following restriction sites in the following order, such as obtained starting from pIP816 mentioned above:
HindIII, BglII, BglII, EcoRI, BamHI, XbaI, EcoRI.

Another nucleotide sequence according to the invention is characterized in that it corresponds to a sequence selected from the sequences identified as SEQ ID NO 15, SEQ ID NO 17, or SEQ ID NO 16, or in that it includes this sequence or any part of this sequence, or also any sequence or part of the sequence of the complementary DNA or any sequence of RNA corresponding to one of these DNAs, capable, either of constituting a hybridization probe for the detection of resistance to antibiotics of the glycopeptide family, in particular to vancomycin and/or teicoplanin in particular in strains of the family of the Gram-positive cocci, or of coding for a sequence necessary or associated with the expression of resistance to antibiotics of the glycopeptide family, in particular to vancomycin and/or teicoplanin., in particular in strains of the family of the Gram-positive cocci.

The sequence SEQ ID NO 17 codes for the 3 resistance proteins VanH, VanA and VanX.

The sequence SEQ ID NO 16 includes a transposon shown in FIG. 7a; this transposon contains the genes necessary for the expression of resistance to the glycopeptides as well as the genes associated with this resistance implicated, for example, in the regulation of the expression of the genes necessary to produce the resistance phenotype or implicated in the amount of resistance polypeptide produced.

A specific sequence corresponding to the above definition is one of the following sequences:

```
V1 (SEQ ID NO:9) : GGX GAA GAT GGX TCX TTX CAA GGX
                    G   C       AG  C       G
                                    A
or

V2 (SEQ ID NO:10) : AAT ACX ATX CCX GGX TTT AC
                        C   T           T
                            C
```

V1 and V2 make possible the constitution of probes, if necessary, in combination with other nucleotides, depending on the degree of specificity desired in order to detect vanA and vanC and may also be used as primers in polymerase chain reactions.

Other preferred nucleotide sequences are the sequences SEQ ID NO 1, SEQ ID NO 3, SEQ ID NO 5, SEQ ID NO 7, SEQ ID NO 10 (transposase), SEQ ID NO 20 (resolvase), SEQ ID NO 22 (vanY), SEQ ID NO 15 (vanZ), SEQ ID NO 4 (vanR), SEQ ID NO 13 (vanS) or a variant of one of these sequences provided that it codes for a protein having immunological and/or functional properties similar to those of the proteins encoded in the sequences SEQ ID NO 1 (vanA), SEQ ID NO 3 (vanH), SEQ ID NO 5 (vanX), or SEQ ID NO 7 (vanC), SEQ ID NO 10 (transposase), SEQ ID NO 20 (resolvase), SEQ ID NO 22 (vanY), SEQ ID NO 24 (vanZ), SEQ ID NO 11 (vanR), SEQ ID NO 13 (vanS) or in that it makes possible the detection of strains resistant to antibiotics of the glycopeptide family.

Variants include all of the fragments of the sequences having the following properties.

These sequences code for the resistance proteins VanH, VanA and VanX.

The nucleotide sequence designated by SEQ ID NO 1 corresponds to a DNA fragment of 1029 bp situated between the ATG codon at position 377 and the TGA codon at position 1406 on the plasmid pAT214 (FIG. 6).

The invention also relates to a nucleotide sequence coding for the sequence SEQ ID NO 15 corresponding to the sequence coding for the 5 proteins (2 regulatory proteins and 3 resistance proteins), and also comprising the flanking sequences associated with these coding sequences, or comprising this sequence.

Also included in the framework of the invention is a sequence modified with respect to SEQ ID NO 15, characterized in that it lacks the flanking sequences. These flanking sequences are the sequences shown in the following pages and defined as follows:

sequence upstream from the sequence coding for R: between the bases 1 and 1476 of the sequence shown in FIG. 5, sequence between the sequence coding for the sensor protein S and ORF1: between the bases 3347 and 3500 of the sequence shown in FIG. 5, sequence downstream from the sequence coding for ORF3: between the bases 6168 and 7227 of the sequence shown in FIG. 5.

The sequence designated by SEQ ID NO 6 is also characterized by the fragment bearing the restriction sites in the following order:
BglIII-EcoRI-BamHI-EcoRI The location of the regulatory proteins and the resistance proteins is shown in FIG. 3.

The inventors have identified upstream and downstream from the genes vanR, vanS, vanH, vanA and vanX, which are necessary for or associated with the expression of resistance to glycopeptides at a given level, genes coding for a transposase and a resolvase (upstream from the group previously mentioned) and genes vanY and vanZ, downstream from this group. The genes for the transposase and resolvase might be implicated in transposition functions and the vanY gene coding for a D,D-carboxy peptidase might be implicated in the metabolism of the peptidoglycan, and might contribute to resistance to the glycopeptides in *E. faecium* BM4147 even though vanR, vanS, vanH, vanA and vanX borne by a plasmid in a high number of copies, alone confer a high level of resistance.

Let it be noted that the sequence coding for the transposase (SEQ ID NO: 9) is located on the (−) strand of the sequence ID NO 16 which codes for vanR, vanS, vanH, vanA, vanX, vanY, vanZ and the resolvase.

The invention relates not only to the DNA sequences identified in the list of the sequences but also to the complementary DNA sequences and the corresponding RNA sequences. The invention concerns in addition sequences which are equivalent to the former, either in terms of expression of proteins, polypeptides or their fragments described above, or in terms of the capacity to detect, for example by chain polymerization procedures, strains of Gram-positive bacteria exhibiting resistance to antibiotics of the glycopeptide family such as vancomycin or teicoplanin.

Recombinant sequences characterized in that they comprise one of the above nucleotide sequences also form part of the invention.

The invention also relates to a recombinant vector characterized in that it includes one of the above nucleotide sequences at a site inessential for its replication, under the control of regulatory elements likely to be implemented in the expression of the resistance to antibiotics of the glycopeptide family, in particular to vancomycin or teicoplanin, in a defined host.

Particularly advantageous recombinant vectors for the implementation of the invention are the following vectors: pAT214 containing the EcoRV-SacII fragment of 1761 bp containing a nucleotide sequence coding for the VanA protein; in these vectors the sequences of the invention are advantageously placed under the control of promoters such as the lac promoter.

The invention also relates to a recombinant cell host containing a nucleotide sequence such as that previously described or a vector such as that described above under conditions which make possible the expression of resistance to antibiotics of the glycopeptide family, in particular resistance to vancomycin and/or this host being for example selected from the bacteria, in particular the Gram-positive cocci.

In certain applications it is also possible to use yeasts, fungi, insect or mammalian cells.

The invention also relates to a nucleotide probe characterized in that it is capable of hybridizing with a sequence previously described, this probe being labelled if necessary. These probes may or may not be specific for the proteins of resistance to glycopeptides.

Labels which can be used for the requirements of the invention are the known radioactive labels as well as other labels such as enzymatic labels or chemoluminescent labels.

Probes thus labelled may be used in hybridization tests in order to detect resistance to glycopeptides in Gram-positive bacteria. In this case, conditions of low stringency will be used.

Nucleotide probes according to the invention may be characterized in that they are specific in Gram-positive bacteria for the sequences coding for a resistance protein to the glycopeptides, in particular to vancomycin and/or teicoplanin these probes being in addition universal among these sequences.

By these specific probes is meant any oligonucleotide hybridizing with a nucleotide sequence coding for one of the proteins according to the invention, such as described in the preceding pages, and not exhibiting a cross hybridization reaction or amplification reaction (PCR) with sequences present in all of the sensitive strains.

The universal character of the oligonucleotide which can be used in PCR is defined by their capacity to promote specifically the amplification of a nucleotide sequence implicated in resistance in any one strain of Gram-positive bacteria, resistant to the antibiotics of the glycopeptide family.

The size of the nucleotide probes according to the invention may vary depending on the use desired. For the oligonucleotides which are used in PCR, recourse will be had to fragments of a length which is usual in this procedure. In order to construct probes, it is possible to take any part of the sequences of the invention, for example probe fragments of 200 nucleotides.

According to a particular embodiment of the invention, a nucleotide probe is selected for its specificity towards a nucleotide sequence coding for a protein necessary for the expression in Gram-positive bacteria of a high level of resistance to antibiotics of the glycopeptide family, in particular to vancomycin and teicoplanin.

As examples, useful probes may be selected from the intragenic part of the vanA gene.

Other useful probes for carrying out the invention are characterized by their universal character, according to the preceding definition, but are not specific for the resistance genes. They may also be used as primers in PCR, and are for example:

```
V1 (SEQ ID NO:9)  : GGX GAA GAT GGX TCX TTX CAA GGX
                        G   C       AG  C       G
                                        A

V2 (SEQ ID NO:10) : AAT ACX ATX CCX GGX TTT AC
                        C   T           C
                        C
```

V1 and V2 hybridize with vanA and vanC and are capable of leading to the detection of proteins associated with resistance to glycopeptides in other micro-organisms.

Other particular probes of the invention have the specific character of a nucleotide sequence coding for a protein necessary for the expression in Gram-positive bacteria of a low level of resistance to antibiotics of the glycopeptide family, in particular to vancomycin in Gram-positive bacteria.

It should also be mentioned that oligonucleotide probes which might be derived from the sequence of the vanA gene coding for the VanA protein may be used indiscriminantly to detect high-level or low-level resistance.

In a particularly preferred manner, a probe of the invention is characterized in that it hybridizes with a chromosomal or non-chromosomal nucleotide sequence of a Gram-positive strain resistant to glycopeptides, in particular to vancomycin and/or teicoplanin r in particular in that it hybridizes with a chromosomal or non-chromosomal nucleotide sequence of a strain of Gram-positive cocci, for example an enterococcal strain and preferably *E. faecium* 4147 or *E. gallinarum*.

In order to distinguish strains with a high level of resistance from strains with a low level of resistance it is possible to carry out a hybridization test using conditions of high stringency.

The oligonucleotides of the invention may be obtained from the sequences of the invention by cutting with restriction enzymes, or by chemical synthesis according to the standard methods.

Furthermore, the invention relates to polyclonal or monoclonal antibodies, characterized in that they recognize the polypeptide(s) described above or an amino acid sequence described above.

These antibodies may be obtained according to standard methods for antibody production. In particular, in the case of the preparation of monoclonal antibodies, recourse will be had to the method of Köhler and Milstein according to which monoclonal antibodies are prepared by cell fusion between myeloma cells and mouse spleen cells previously immunized with a polypeptide or a composition according to the invention, in conformity with the standard procedure.

The antibodies of the invention can advantageously be used for the detection of the presence of proteins characteristic of resistance to the glycopeptides, in particular to vancomycin and teicoplanin.

Particularly useful antibodies are polyclonal or monoclonal antibodies directed against the protein VanA or VanC. Such antibodies advantageously make it possible to detect strains of bacteria, in particular Gram-positive cocci, exhibiting high-level resistance to the antibiotics of the glycopeptide family. If necessary, a step entailing lysis of the cells of the sample undergoing detection is performed prior to the placing in contact of the sample with the antibodies.

In order to carry out this detection, recourse will advantageously be had to antibodies labelled for example with a radioactive substance or other type of label.

Hence, tests for the detection in Gram-positive bacteria of resistance to the glycopeptides, in particular tests making use of the ELISA procedures, are included in the framework of the invention.

A kit for the in vitro diagnosis of the presence of Gram-positive strains, resistant to the glycopeptides, in particular to vancomycin and/or teicoplanin, these strains belonging in particular to the Gram-positive cocci for example enterococci, for example *E. faecium* or *E. gallinarum* is characterized in that it comprises:

antibodies corresponding to the above definition, labelled if necessary, a reagent for the detection of an immunological reaction of the antigen-antibody type, if necessary, reagents to effect the lysis of the cells of the sample to be tested.

Furthermore, the agents developed by the inventors offer the very useful advantage of being suitable for the development of a rapid and reliable test or kit for the detection of Gram-positive strains resistant to the glycopeptides by means of the polymerase chain reaction (PCR). Such a test makes it possible to improve the sensitivity of the existing tests which remain rather unreliable and, in certain cases, may make possible the detection of all of the representatives of the family of the genes coding for resistance proteins to the glycopeptides in Gram-positive bacteria.

The carrying out of a test by means of the method of amplification of the genes of these proteins is done by the PCR procedure or by the RPCR procedure (RPCR: abbreviation for reverse polymerase chain reaction).

The RPCR technique makes possible the amplification of the NH$_2$ and COOH terminal regions of the genes it is desired to detect.

Some specific primers make it possible to amplify the genes of the strains with low-level resistance. These primers are selected, for example, from the sequence coding for the resistance protein VanA.

As examples, the following sequences can be used as primers for the preparation of probes for the detection of an amplification by means of the PCR or RPCR method.

```
V1 (SEQ ID NO:9) : GGX GAA GAT GGX TCX TTX CAA GGX
                    G        C      AG  C       G
                                             A

V2 (SEQ ID NO:10) : AAT ACX ATX CCX GGX TTT AC
                        C   T              C
                            C
```

X represents one of the bases A,T,C or G or also corresponds in all cases to inosine.

Naturally, the invention relates to the complementary probes of the oligonucleotides previously described as well as possibly to the RNA probes which correspond to them.

A kit for the in vitro diagnosis of the presence of strains of Gram-positive bacteria resistant to the glycopeptides, in particular resistant to vancomycin and/or teicoplanin these strains belonging in particular to the Gram-positive cocci, in particular that they are strains of enterococci, for example *E. faecium* or *E. gallinarum*, is characterized in that it contains:

a nucleotide probe complying with the above specifications and if necessary, oligonucleoside triphosphates in an amount sufficient to make possible the amplification of the desired sequence, a hybridization buffer, a DNA polymerization agent.

The invention also relates to a procedure for the in vitro detection of the presence of Gram-positive strains resistant to the glycopeptides, in particular to vancomycin and/or teicoplanin these strains belonging in particular to the family of the Gram-positive cocci, in particular in that they are strains of enterococci, for example *E. faecium* or *E. gallinarum*, characterized in that it comprises:

a) the placing of a biological sample likely to contain the resistant strains in contact with a primer constituted by a nucleotide sequence described above, or any part of a sequence previously described, capable of hybridizing with a desired nucleotide sequence necessary for the expression of resistance to the glycopeptides, this sequence being used as matrix in the presence of the 4 different nucleoside triphosphates and a polymerization agent under conditions of hybridization such that for each nucleotide sequence which has hybridized with a primer, an elongation product of each primer complementary to the matrix is synthesized, b) the separation of the matrix from the elongation product obtained, this latter then also being capable of behaving as a matrix, c) the repetition of step a) so as to produce a detectable amount of the desired nucleotide sequences, d) the detection of the product of amplification of the nucleotide sequences.

The detection of the elongation products of the desired sequence may be carried out by a probe identical with the primers used to carry out the PCR or RPCR procedure, or also by a probe different from these primers, this probe being labelled if necessary.

Details relating to the implementation of the PCR procedures may be obtained from the patent applications EP 0229701 and EP 0200362.

Other advantages and characteristics of the invention will become apparent in the examples which follow and from the figures.

BRIEF DESCRIPTION OF THE DRAWINGS

FIG. 2A: Restriction maps of the inserts of the plasmids pAT213 and pAT214. The vector and the DNA insert are distinguished by light and dark segments, respectively. The open arrow represents the vanA gene.

FIG. 2B: Strategy for the nucleotide sequencing of the insert of 1761 bp in the plasmid pAT214. The arrows indicate the direction and extent of the sequencing reactions by the dideoxy method. The synthetic oligonucleotide primer (5' ATGCTCCTGTCTCCTTTC 3' OH; SEQ ID NO: 27) is complementary to the sequence between the positions 361 and 378. Only the pertinent restriction sites are given.

FIG. 4: representation of SEQ ID NO 15.

FIG. 5: representation of SEQ ID NO 6 and the corresponding protein (SEQ ID NOS: 27, 28 and 29).

FIG. 6: sequence of the vanA gene and the corresponding protein.

FIG. 7:

FIG. 7b: Mapping of the plasmids. (A) Polylinker pAT29 and derivatives constructed in this study. The arrow labelled P2 indicates the position and orientation of the P2 promoter of aphA-3 (Caillaud et al., 1987, Mol. Gen. Genet. 207:509–513). (B) Insert pAT80. The white rectangles indicate the DNA of pAT29 but they are not shown to scale. The rectangles terminating in an arrow indicate the coding sequences. The arrows shown in vertical and horizontal full lines indicate the position and orientation, respectively, of the apha-1 gene in the derivatives of pAT80. Restriction sites: Ac, AccI; B, BamHI; Bg, BglII; Bs, BssHII; E, EcoRI; H, HindIII; Hc, HincII; K, KpnI; P, PstI; S, SmaI; SI, SacI, SII, SacII; Sa, SaII; Sp, SphI; Xb, XbaI. (C) Inserts in pAT86, pAT87, pAT88 and pAT89. The inserts are shown by full lines and the corresponding vectors are indicated in parentheses.

FIG. 8: nucleotide sequence of the transposon shown in FIG. 7 (SEQ ID NOS: 2, 4, 6, 12, 14, 19 and 21) and amino acid sequence of the corresponding proteins. The nucleotide sequence is shown for the (+) strand (SEQ ID NO: 16) and for the (−) strand (SEQ ID NO: 30) (corresponding to the complementary sequence of the (+) strand for the positions 1 to 3189) on which the coding sequence of the transposase is located.

FIG. 9: Nucleotide sequence of the SacI-PstI fragment of 1347 bp of the plasmid pAT216 containing the vanC gene (SEQ ID NO: 31). The numbering starts at the first base G of the SacI restriction site. The potential RBS sequence upstream from the initiation codon ATG of translation at position 215 is underlined. The STOP codon (TGA) is indicated by *. The region coding for the vanC and the deduced amino acid sequence are indicated in bold characters. Sequential overlapping clones were generated by restriction fragments of subcloning of pAT216 in the bacteriophage M13mp10 (Amersham, England). The universal primer (New England Biolabs Beverly Mass.) was used to sequence the insert in the recombinant phages. The sequencing was performed by the enzymatic dideoxy nucleotide method (Sanger et al., 1977 PNAS 74: 5463–5467) by using the T7 DNA polymerase (Sequenase US B CORP, Cleveland, Ohio) and [α-$^{35}$S] dATP (Amersham, England). The reaction products were loaded onto 6% denaturing polyacrylamide gels.

FIG. 10: alignment of the amino acid sequences of VanC (SEQ ID NO: 2), VanA (SEQ ID NO: 4), DdlA (SEQ ID NO: 32) and DdlB (SEQ ID NO: 33). The identical (I) amino acids and the conservative (C) substitutions in the 4 sequences are indicated in the alignment. In order to classify the conservative substitutions, the amino acids were grouped as follows: RK, LFPMVI (SEQ ID NO: 34), STQNC (SEQ ID NO: 35), AGW, H, ED and Y. The regions of high homology corresponding to the domains 1, 2, 3 and 4 are underlined. The sequences corresponding to the peptides 1 and 2 are indicated by the arrows.

FIG. 11A: Amino acid sequence of the peptides 1 (SEQ ID NO: 36) and 2 (SEQ ID NO: 37) of VanA and of the D-Ala-D-Ala ligases (SEQ ID NO: 36 –39). The number of amino acids between the N-terminus and peptide 1, between the peptides 1 and 2 and the peptide 2 and the C-terminus is indicated. The identical amino acids between at least 2 of the 3 sequences are indicated in bold characters.

FIG. 11B: Target peptides (SEQ ID NO: 36–39) and deduced nucleotide sequence. X represents any base of the DNA. Peptide 2 in DdlB (SEQ ID NO: 39) differs from the target peptide at 2 positions (*).

FIG. 11C: Nucleotide sequence of V1 (SEQ ID NO: 9) and V2 (SEQ ID NO: 10). Alternate nucleotides and deoxyinosine (I) which may correspond to any base in the DNA, were used at the positions at which the nucleotide sequences coding for the target peptides vary. The arrows indicate the direction of DNA synthesis. The oligonucleotides were synthesized by the methoxy-phosphoramidite method with a Biosystem DNA 380B machine (Applied Biosystem, Foster City, Calif.). The DNA was isolated from bacterial lysates by extraction with hexadecyl trimethyl ammonium bromide (Inst. biotechnologies, Inc., New Haven, Colo.) (Le Bouguénec et al., 1990, J. Bacteriol. 172:727–734) and used as matrix for the amplification by means of PCR with a controlled heating system "Intelligent Heating Block" IBH101 (Hybarid Ltd., GB) according to the description of Mabilat et al. (1990, Plasmid 23:27–34). The amplification products were revealed by electrophoresis on a 0.8% gel, after staining with ethidium bromide.

FIG. 12A: The plasmid pAT217 was constructed by ligation of the EcoRI-HincII fragment of pAT216 to the suicide vector pAT114 (Trieu-Cuot et al., 1991, Gene 106:21–27), digested with EcoRI and SmaI.

FIG. 12B: vanC region of the chromosomal DNA of BM4174.

FIG. 12C: vanC region after integration of pAT217.

Figure 1:
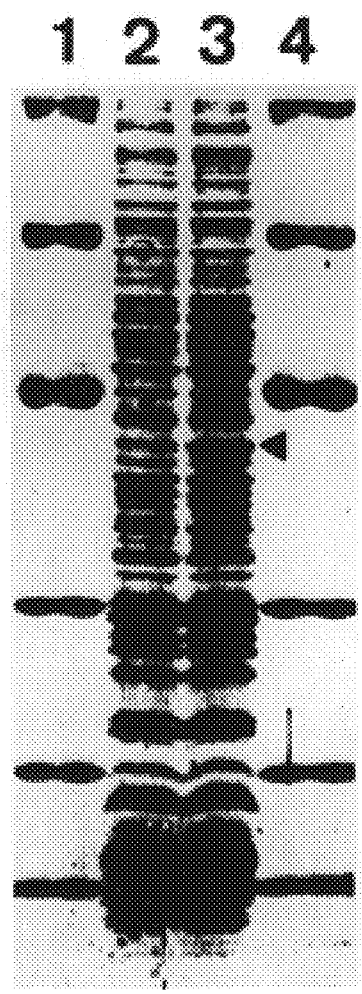
FIG. 1: electrophoresis on SDS-polyacrylamide gel (SDS-PAGE) of the proteins of the membrane fractions line 1 and line 4, molecular weight standards; line 2, *E. faecium* BM4147 placed in culture in the absence of vancomycin; line 3, BM4147 placed in culture in the presence of 10 μg/ml of vancomycin. The head of the arrow indicates the position of the VanA protein.

Total DNA of BM4175 (line 2) and BM4174 (line 3) digested with EcoRI and resolved by means of electrophoresis on a 1% agarose gel. The DNA of the bacteriophage lambda digested with PstI was used as molecular mass standard (line 1). The DNA was transferred under vacuum to a Nytran membrane (Schleicher and Schül, Germany) by using a Trans-Vac TE80 apparatus (Höfer Scientific Instruments, San Francisco, Calif.) and bound to the membrane through the intermediary of UV light. The hybridization was carried out with the probe C (Middle) or the probe aphA-3 specific for pAT114 (Lambert et al., 1985, Annales de l'Institut Pasteur/Microbiol. 136(b): 135–150). (right hand side): the probes were labelled with $^{32}$P by nick translation. The molecular masses (kb) are indicated.

FIG. 14: alignment of the deduced amino acid sequences of VanS derived from E. faecium BM4147 (SEQ ID NO: 40) and of PhoR (SEQ ID NO: 41) and EnvZ (SEQ ID NO: 42) from E.coli. The numbers on the left refer to the position of the first amino acid in the alignment. The numbers on the right refer to the position of the last amino acid of the corresponding line. The identical amino acids are placed in boxes. The dotted lines indicate gaps introduced in order to optimize their similarity. The dashes indicate the positions of the amino acid residues conserved in other HPK. The histidine residues in bold characters in section 1 are potential sites of auto-phosphorylation.

FIG. 15: alignment of the deduced amino acid sequences of VanR from E. faecium BM4147 (SEQ ID NO: 43), OmpR (SEQ ID NO: 44) and PhoB (SEQ ID NO: 45) from E. coli as well as that of CheY from Salmonella typhimurium (SEQ ID NO: 46). The numbers on the right indicate the position of the last amino acid of the corresponding line. The identical amino acids are placed in boxes. The dotted lines indicate the gaps introduced in order to optimize the homologies. The residues in bold characters correspond to the amino acids strongly conserved in the effector domains of other RR. The aspartic acid residue 57 of CheY is phosphorylated by the HPK associated with CheA.

I—IDENTIFICATION OF vanA

Materials and Methods for the Identification and Characterization of the vanA Gene Bacterial Strains and Plasmids The origin of the plasmids used is given in the table below.

| Strain or plasmid | Source or reference |
| --- | --- |
| Escherichia coli | |
| JM83 | Messing (1979) |
| AR1062 | Rambach and Hogness (1977) |
| JM103 | Hannshan (1983) |
| ST640 | Lugtenberg and van Schijndel van-Dam (1973) |
| Enterococcus faecium | |
| BM4147 | Leclercq et al (1988) |
| Plasmid pUC18 | Norrander et al (1983) |
| pAT213 | Brisson-Noel et al (1990) |
| pAT214 | Described in this text |

Preparation of the Enterococcal Membranes

Enterococcus faecium BM4147 was cultivated in 500 ml of heart-brain broth (BHI broth medium) until the optical density ($OD_{600}$) reached 0.7. Induction was effected with 10 µg/ml of vancomycin (Eli Lilly Indianapolis Ind.). The subsequent steps were performed at 4° C. The cells were recovered by centrifugation for 10 minutes at 6000 g, washed with a TE buffer (0.01 M TRIS-HCl, 0.002 M EDTA, pH 7.0) and lysed by glass beads (100 µm in diameter) in a Braun apparatus for 2 minutes. The cell debris were separated by centrifugation for 10 minutes at 6000 g. The membranes were collected by centrifugation for 1 hour at 65000 g and resuspended in 0.5 ml of TE buffer.

Preparation of the Minicells

Plasmids were introduced by transformation into the strain E. coli AR1062 prepared in the form of bacterial vesicles. The bacterial vesicles were recovered on sucrose gradients and the proteins were labelled with 50 µCi of [$^{35}$S]-L-methionine (Amersham, Great Britain) according to the method of Rambach and Hogness (1977, P.N.A.S. USA, 74; 5041–5045).

Preparation of the Membrane Fractions and the Cytoplasmic Fractions of E. coli

E. coli JM83 and strains derived from it were placed in culture in BHI medium until an optical density ($OD_{600}$) of 0.7 was attained, washed and suspended in a TE buffer. The ell suspension was treated by sonication (ultrasound) for 20 seconds at doses of 50 W in a cell fragmentation apparatus in a Branson B7 sonication apparatus and the intact cells were removed by centrifugation for 10 minutes at 6000 g. The supernatant was fractionated into membrane and cytoplasmic fractions by means of centrifugation for 1 hour at 100,000 g Electrophoresis on SDS-polyacrylamide Gel (SDS-PAGE)

The proteins from the bacterial fractions were separated by means of SDS-PAGE on linear gradients of polyacrylamide gels (7.5%–15%) (Laemmli 1970, Nature 227: 680–685). The electrophoresis was carried out for 1 hour at 200 V, then for 3 hours at 350 V. The gels were stained with Coomassie blue. The proteins of the extracts were separated on 10% polyacrylamide gels and visualized by means of autoradiography.

Purification of the Protein Band and Determination of the N-terminal Sequence

The proteins of the membrane fractions of an induced culture of E. faecium BM4147 were separated by means of SDS-PAGE. The gel was electrotransferred for 1 hour at 200 mA to a polyvinylidene difluoride membrane (Immobilon Transfer, Millipore) by using a transfer apparatus (Electrophoresis Unit LKB 2117 Multiphor II) in accordance with the instructions of the manufacturer. The transferred proteins were stained with Ponceau red. The portion of membrane bearing the protein of interest was excised, centered on a Teflon filter and placed in the cartridge of a sequencer (Sequencer Applied Biosystems model 470A). The protein was sequenced by means of the automated Edman degradation (1967, Eur. J. Biochem. 1; 80–81).

Construction of Plasmids

Figure 2:
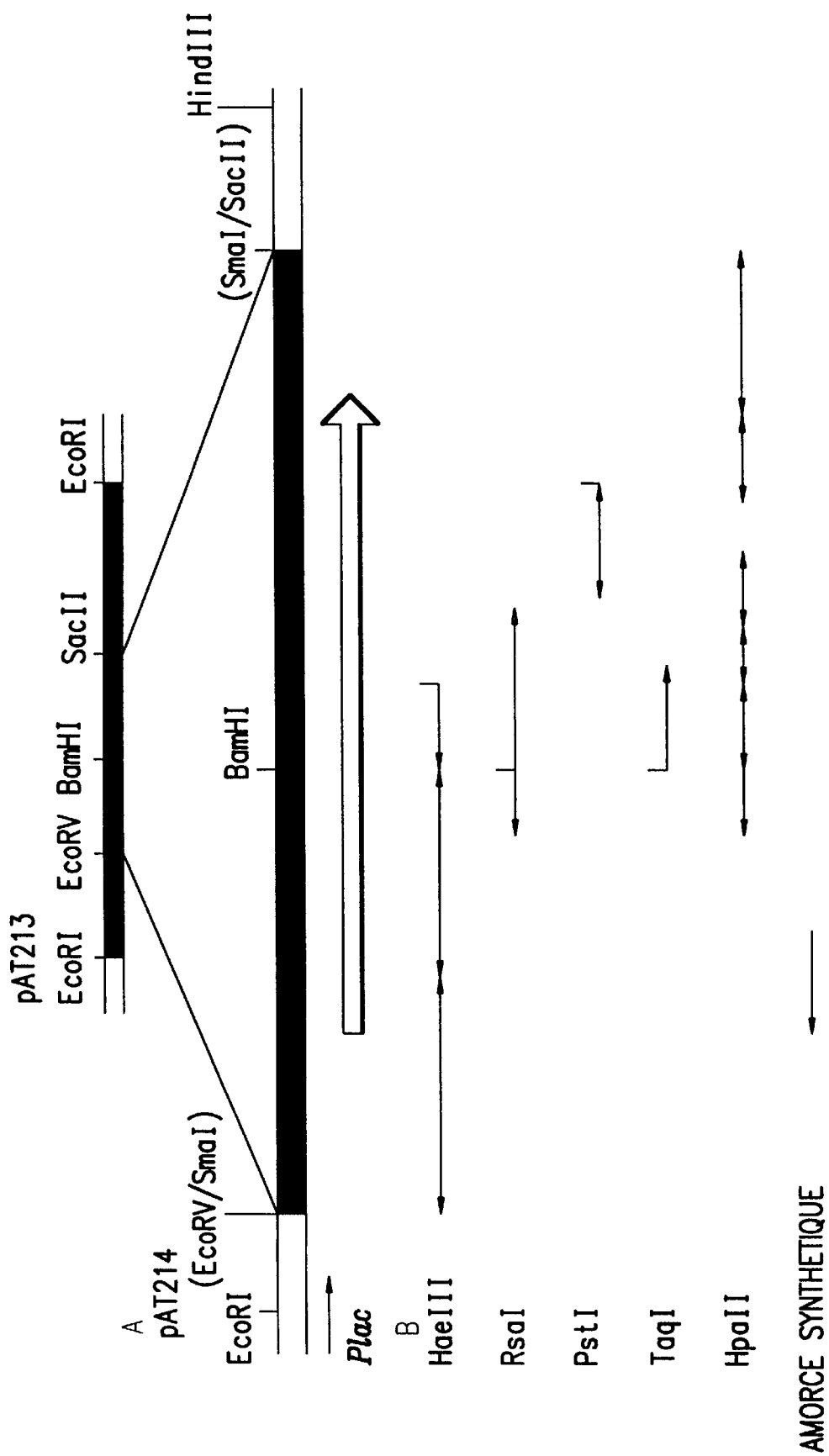
FIG. 2.

The plasmid pAT213 (Brisson-Noel et al., 1990, Antimicrob. Agents Chemother., 34; 924–927) consists of a EcoRI fragment of DNA of 4.0 kb of the enterococcal plasmid pIP816 cloned at the EcoRI site of a Gram-positive-Gram-negative shuttle vector pAT187 (Trieu-Cuot et al., 1987, FEMS Microbiol. Lett. 48; 289–294). In order to construct pAT214, the EcoRV-SacII DNA fragment of 1761 bp of pAT213 was purified, treated with the Klenow fragment of the DNA polymerase I of E. coli and ligated to the DNA of pUC18 which had previously been digested with SmaI and dephosphorylated (FIG. 2). The cloning (Maniatis et al., 1982 Cold Spring Harbor Laboratory Press) was carried out with restriction endonucleases (Boehringer Mannheim and Pharmacia), with the T4 DNA ligase (Pharmacia) and alkaline phosphatase (Pharmacia) according to the instructions of the manufacturer.

Subcloning in M13 and Nucleotide Sequence

The DNA restriction fragments were subcloned in the polylinker of the replicative forms of the derivatives mp18 and mp19 of the bacteriophage M13 (Norrander et al., 1983, Gene 26; 101–106), obtained from Pharmacia P-L Biochemicals. E.coli JM103 was transfected with recombinant phages and the single-stranded DNA was prepared. The nucleotide sequencing was carried out by the enzymatic di-deoxy nucleotide method (Sanger et al., 1977, P.N.A.S. USA 74; 5463–5467) by using a T7 DNA polymerase (Sequenase, United States Biochemical Corporation, Cleveland, Ohio) and [$\alpha$-$^{35}$S] dATP (Amersham, Great Britain). The reaction products were revealed on 6% polyacrylamide gels containing a denaturing buffer.

Data-processing Analysis and Data on the Sequence

The complete DNA sequence was assembled by using the computer programs DBCOMP and DBUTIL (Staden, 1980, Nucleic Acids Res 8; 3673–3694). The protein data bank PSEQIP of the Pasteur Institute was screened using an algorithm developed by Claverie (1984, Nucleic Acids Res 12; 397–407). The alignments between the pairs of amino acid sequences were constructed using the algorithm of Wilbur et al (1983, P.N.A.S. USA 80; 726–730). The statistical significance of the homology was evaluated with the algorithm of Lipman and Pearson (1985, Science 227; 1435–1440).

For each comparison 20 amino acid sequences were used to calculate the mean values and the standard deviations of the random results.

Genetic complementation tests

The plasmids were introduced by transformation into E.coli ST640, a temperature-sensitive mutant with an unmodified D-ala-D-ala ligase (Lugtenberg et al 1973, J. Bacteriol 110; 26–34). The transformants were selected at 30° C. on plates containing 100 μg/ml of ampicillin and the presence of the plasmid DNA of the expected size and the restriction maps were verified. Single colonies grown at 30° C. in BHI broth medium containing ampicillin were placed on a BHI agar medium containing both 100 μg/ml of ampicillin and 50 μM of isopropyl-1-thio-β-D-galactopyranoside (IPTG) and the plates were incubated at a permissive temperature of 30° C. and at a non-permissive temperature of 42° C. The complementation test was considered to be positive if the colonies were present after 18 hours of incubation at 42° C.

RESULTS

Identification of the VanA Protein and its N-terminal Sequence

The membrane fractions of the E. faecium BM4147 cells placed in culture, on the one hand, under conditions of induction, and, on the other, in the absence of induction, were analysed by means of SDS-PAGE. The sole difference which could be detected, related to the exposure to subinhibitory concentrations of vancomycin, was the marked intensification of a band which corresponded to a protein of an estimated molecular weight of about 40 kDa. In the induced cells and in the non-induced cells, the protein band represents the same protein because this band is absent from membranes of a derivative of BM4147 which has lost the pIP816 plasmid. The inducible protein, designated as VanA, was purified after SDS-PAGE and automated Edman degradation was carried out on a 50 pmol. sample. Nine amino acids of the N-terminal sequence of VanA were identified: Met Asn Arg Ile Lys Val Ala Ile Leu (SEQ ID NO: 47).

Sub-Cloning of the vanA Gene

The insert of 4.0 kb of the plasmid pAT213 bears the determinant for resistance to the glycopeptides of E. faecium BM4147. Various restriction fragments of this insert were subcloned in pUC18 and the recombinant plasmids specific for vanA in E. coli were identified by SDS-PAGE analysis of the proteins of the cytoplasmic and membrane fractions or of the extracts of the bacterial vesicles. This approach was used since E. coli is intrinsically resistant to the glycopeptide. The EcoRV-SacII insert of the pAT214 plasmid (FIG. 2) codes for a unique polypeptide of 40 kDa which migrates together with VanA, derived from the membrane preparations of E. faecium BM4147.

Figure 3A:
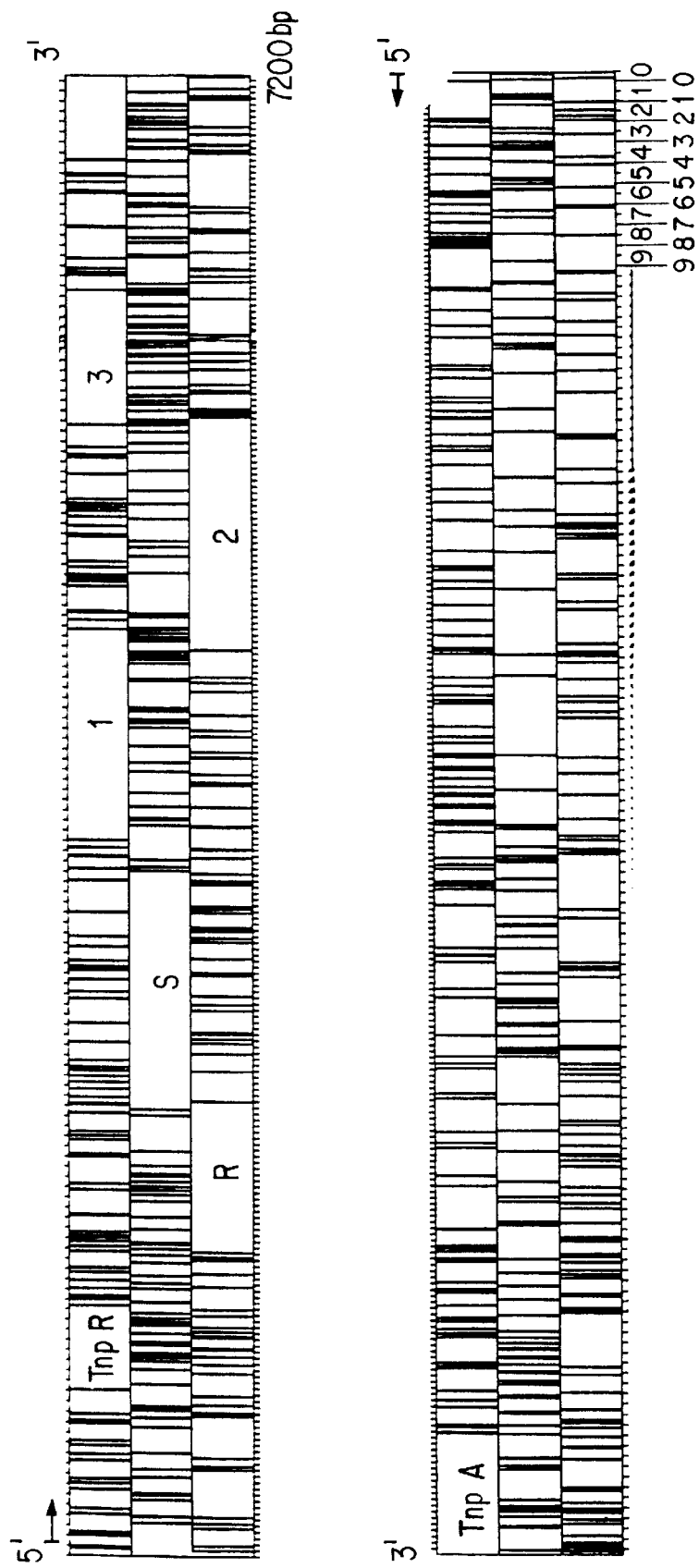
FIG. 3: position of the sequences R, S, ORF1, ORF2, ORF3.
Figure 3B:
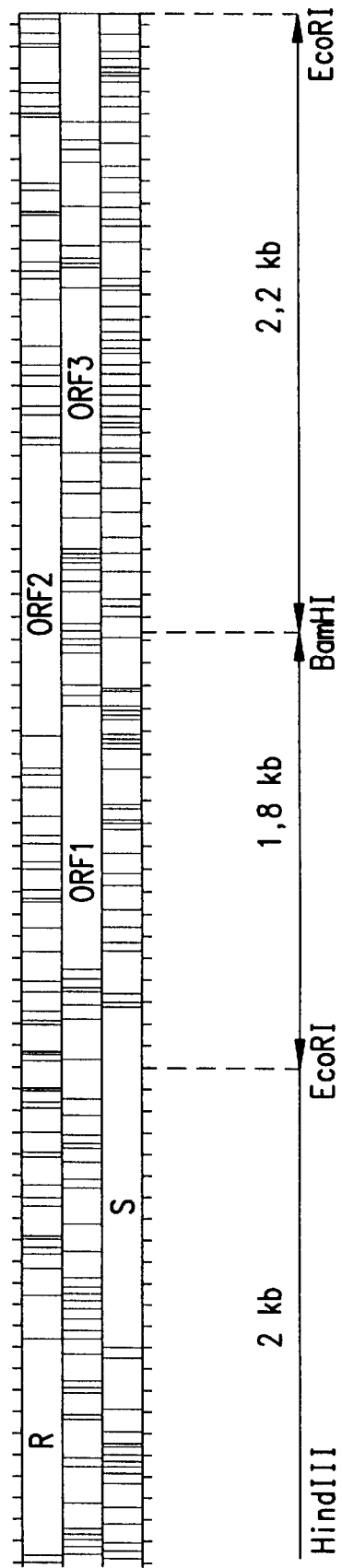
Figure 7A:
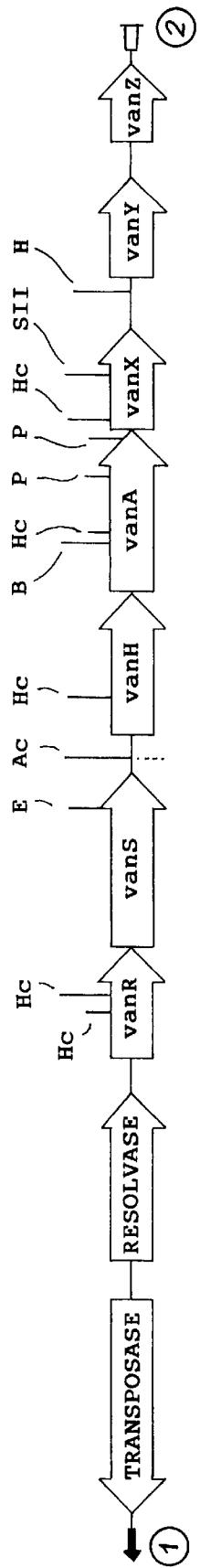
FIG. 7a: Localization of the genes vanR, vanS, vanH, vanA, vanX, vanY, vanZ of the gene for the transposase and of the gene for the resolvase as well as the repeated reverse terminal sequences of 38 bp at the end of the transposon.
Figure 11:
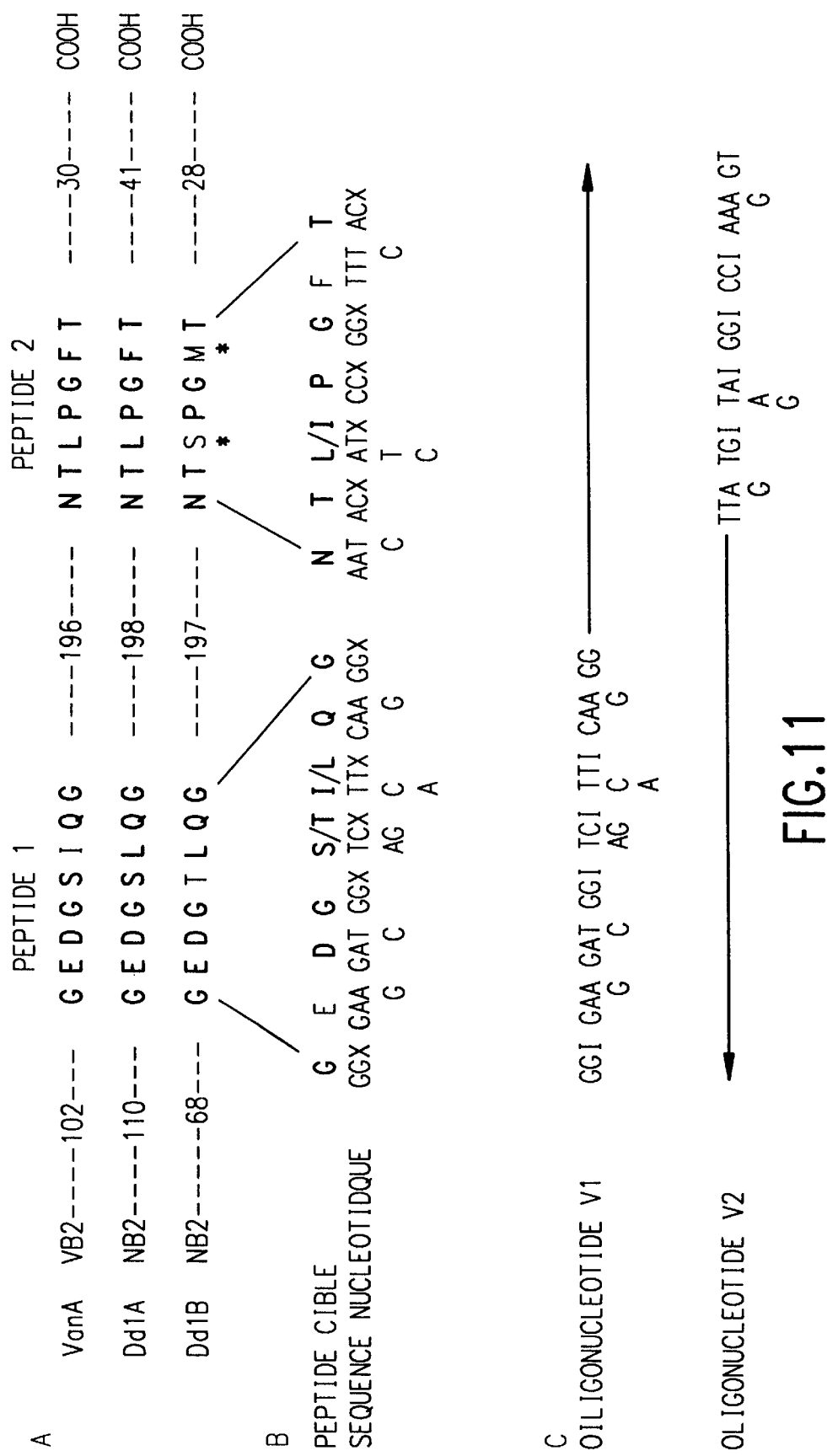
FIG. 11: description of the oligonucleotides V1 (SEQ ID NO: 9) and V2 (SEQ ID NO: 10)
Figure 12:
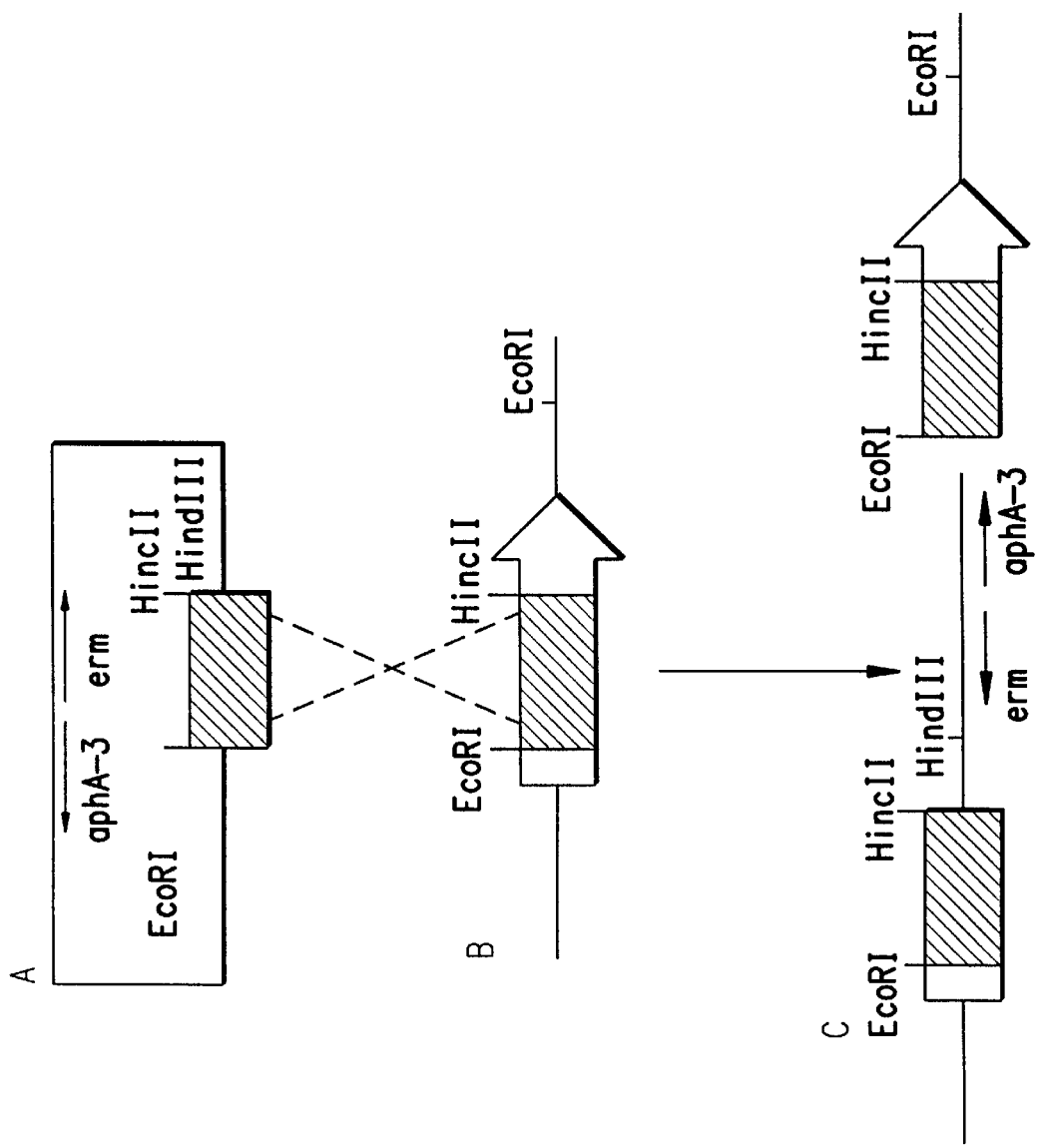
FIG. 12: Inactivation by insertion of vanC. The vanC gene is shown by an open arrow and the internal EcoRI-HincII fragment of 690 bp is hatched. The DNA of pAT114 is shown by a thin line; the chromosomal DNA of PM4174 by a thick line; the arrows indicate the genes for resistance to the antibiotics: aphA-3 is the gene coding for the 3'-aminoglycoside phosphotransferase; erm is the gene coding for the ER$^R$ methyl transferase.
Figure 13:
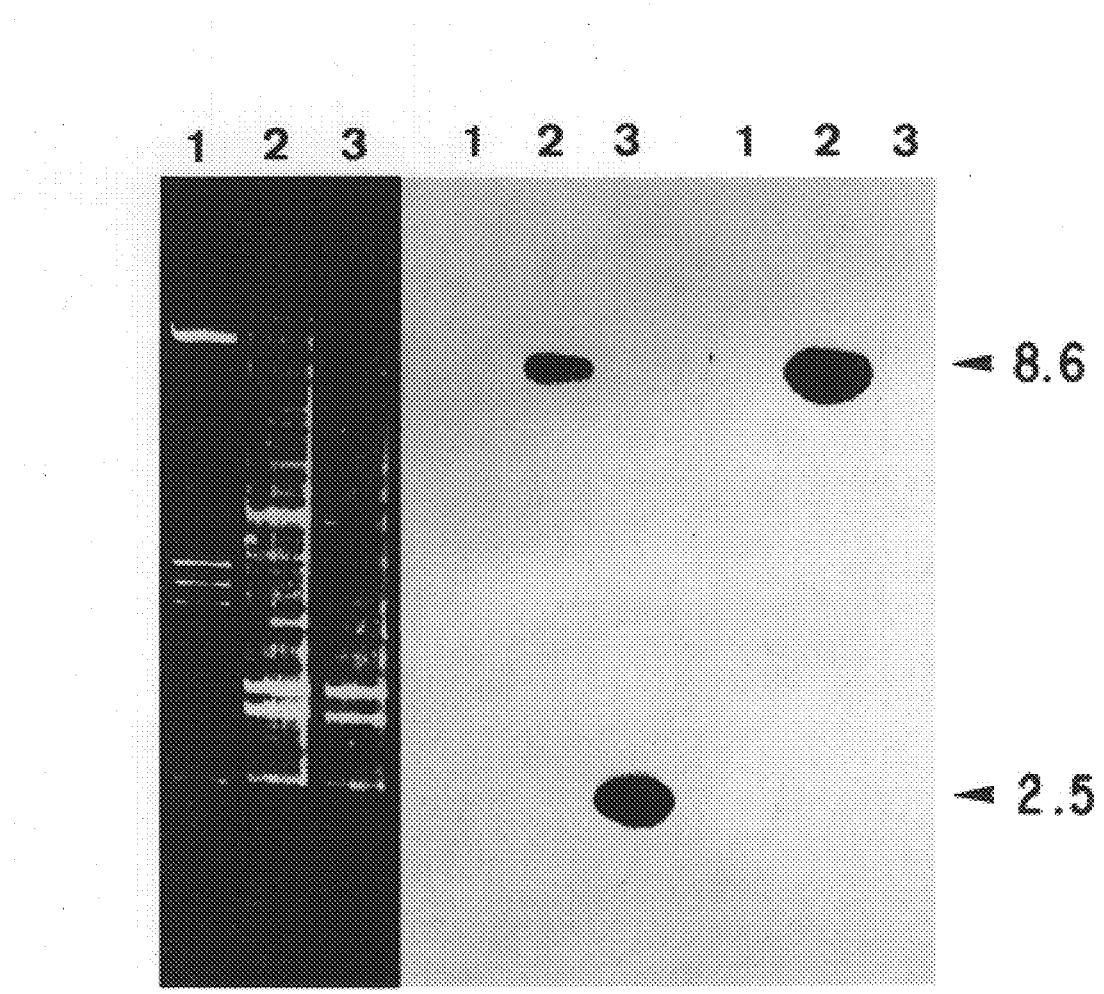
FIG. 13: Southern blot analysis of the integration of pAT217 into the vanC gene of BM4174. (left hand side)

Nucleotide Sequence of the Insert in pAT214 and Identification of the vanA Coding Sequence The nucleotide sequence of the EcoRV-SacII insert of 1761 bp in pAT214 was determined on both strands of the DNA according to the strategy described in FIG. 2. The location of the termination codons (TGA, TAA, TAG) in three reading frames on each DNA strand showed the presence of a unique open reading frame (ORF) which was sufficiently long to code for the VanA protein. This reading frame ORF is located between the TAA codon at position 281 and the TAG codon at position 1406. The amino acid sequence deduced for ORF was compared with that of the N-terminus of VanA. The nine amino acids identified by protein sequencing are encoded in the nucleotide sequence beginning with the ATG (methionine) codon at position 377 (FIG. 3). This codon for the initiation of translation is preceded by a sequence (TGAAAGGAGA (SEQ ID NO: 48)), characteristic of a ribosomal binding site (RBS) in Gram-positive bacteria which is complementary to the 8 bases of the rRNA of the 16S subunit of Bacillus subtilis in its sequence (3'OH UCUUUCCUDCC (SEQ ID NO: 49) 5') (Moran et al., 1982, Mol. Gen. Genet. 186; 339–346). In this ORF, there is no other ATG or GTG initiation codon between the positions 281 and 377. The sequence of 1029 bp which extends from the ATG codon at position 377 to the TGA codon at position 1406 codes for a protein containing 343 amino acid residues. The calculated molecular weight of this protein is 37400 Da, which is in agreement with the estimation of 40 kDa obtained by SDS-PAGE analysis.

Homology of the Amino Acid Sequences of VanA and the D-ala-D-ala Ligase Enzymes

The screening of the protein data bank PSEQIP has shown the existence of a sequence homology between VanA and the D-ala-D-ala ligases of E.coli (ECOALA, Robinson et al., 1986, J. Bacteriol. 167; 809–817) and of Salmonella typhimurium (DALIG, Daub et al., 1988, Biochemistry 27; 3701–3708). The calculated percentage of homology between pairs of proteins was included between 28% and 36% for the identical amino acids and between 48% and 55% by taking into consideration homologous amino acids. VanA (SEQ ID NO: 4) and DALIG are more closely related. The statistical significance of these similarities wa evaluated by aligning VANA and sequences containing the same composition of amino acids as DALIG or ECOALA (Lipman and Pearson, 1985, Science 227; 1435–1440).

Genetic Complementation Test for the Activity of D-ala-D-ala Ligase

The E.coli strain ST640 is a thermosensitive mutant exhibiting a deficient D-ala-D-ala ligase activity (Lugtenberg et al., 1973, J. Bacteriol. 113: 96–104). The plasmids pUC18 and pAT214 were introduced into E.coli ST640 by transformation. The strains ST640 and ST640 (pUC18) grew normally only at the permissive temperature (30° C.) whereas E.coli ST640 (pAT214) grew both at the permissive temperature and at the non-permissive temperature (42° C.).

This test shows that VANA is functionally related to the D-Ala-D-Ala ligases in *E.coli* and is probably capable of catalysing the same ligation reaction as DALIG.

II—VanS-VanR Two-Component Regulation System for the Control of the Synthesis of Depsipeptides of the Precursor of Peptidoglycans

MATERIALS AND METHODS

Strains, Plasmids and Conditions of Culture

The restriction fragments of pIP816 (Tra⁻, Mob⁺, Vmʳ) were cloned in derivatives of the vector pAT29 which constitutes a shuttle vector between the Gram-positive and Gram-negative bacteria (oriR pAMβ1, oriR pUC, oriT RK2, spc, lacZ ) (Trieu-Cuot et al., 1990, Nucleic Acids Res. 18:4296). This vector was constructed by the inventors and used to transform the strain *E.coli* JM103 ( (lac-proAB), supE, thi, strA, sbcB15, endA, hspR4, F traD36, proAB, LacI$^q$, lacZ M15) (Messing et al., 1983, Methods Enzymol. 101:20–78). The plasmid DNA was prepared by an alkaline lysis protocol on a small scale (Sambrook et al., 1982, Molecular cloning, a laboratory manual. Cold Spring Harbor Laboratory, Cold Spring Harbor N.Y.) and introduced by electroporation (Cruz-Rodz A. L. et al., 1990, Mol. Gen. Genet. 224: 152–154) in *E.faecalis* JH2-2 (Fus$^R$, Rif$^R$) (Jacob A. E. et al., 1974, J. Bacteriol. 117: 360–372), by using a Gene Pulser apparatus (Bio-Rad Laboratories, Richmond, Calif.). The restriction profiles of the purified plasmids from *E. faecalis* and *E. coli* were compared in order to detect possible rearrangements of DNA.

The integrative plasmid pAT113 (Mob⁺, Em$^R$, Km$^R$, oriR PACYC184, attTn1545, LacZ) (Trieu-Cuot et al., Gene 106: 21–27) carries the joined ends of the transposon Tn1545. This vector does not replicate in Gram-positive bacteria but is integrated into the chromosome of the host by illegitimate recombination mediated by the integrase of Tn1545 or of Tn916 (Trieu-Cuot et al. previously mentioned). The integrative plasmids were introduced into *E. faecalis* BM4148 (strain JH2-2::Tn916) by means of electroporation. This strain is modified by the transposon Tn917 described by Franque A. E. et al. (1981, J. Bacteriol. 145: 494–502).

The cultures were grown in brain-heart broth (BHI—Brain Heart Infusion Broth) or on agar at 37° C. The method of Steers et al (Antibiot. Chemother. Basel. 9: 307–311) was used to determine the minimal inhibitory concentrations (MICs) of the antibiotics on a Mueller-Hinton gelose agar medium.

Recombinant DNA Procedures

The cleavage of DNA with restriction endonucleases (Boehringer Mannheim and Pharmacia), the purification of the DNA restriction fragments from agarose gels, the conversion of the cohesive ends to blunt ends with the Klenow fragment of the DNA polymerase I of *E.coli* (Boehringer Mannheim), the dephosphorylation of the ends of the DNA with calf intestinal phosphatase (Boehringer Mannheim), the ligation of the DNA fragments with the T4 DNA ligase (Amersham) were carried out according to the standard methods of Sambrook et al (1982, Molecular Cloning, a Laboratory Manual. Cold Spring Harbor Laboratory. Cold Spring Harbor N.Y.).

Construction of Plasmids

The origin of the vectors and the inserts used for the recombinant plasmids constructed here is the following:

(i) vector pAT78 for the recognition of the promoter: the amplified DNA of the cat gene for chloramphenicol acetyltransferase of the plasmid pC194 of *Staphylococcus aureus* (Horinouchi et al., 1982, J. Bacteriol. 150: 815–825) was inserted between the PstI and SphI restriction sites of the shuttle vector pAT29. Amplification by means of the polymerase chain reaction was carried out by means of primers A1 and A2 which were synthesized by the methoxy phoshoramidite method (Mabilat et al., 1990, Plasmid 23: 27–34). The sequence of the primer A1 (SEQ ID NO: 50) (5' G CTGCAGATAAAAATTTAGGAGG) is composed of a PstI recognition site (underlined) and 18 bases (positions 6 to 23) of pC194 which include the ribosomal binding site (RBS; AGGAGG positions 18 to 23) of the cat gene. The sequence of the primer A2 (SEQ ID NO: 51) (5' CGCATGCTATTATAAAA GCCAGTC) contains the SphI cleavage site (underlined) and is complementary (positions 8 to 24) to 17 bases at the 3' end of the cat gene. The triplet ATT at positions 9 to 11 correponds to the TAA stop codon of cat. The DNA fragments amplified with the primers A1 and A2 hence consist of an open reading frame (orf) and a ribosomal binding site for CAT (positions 1234 to 1912 according to the numbering of Horinouchi et al. (1982, J. Bacteriol. 150: 815–825) flanked by the PstI and SphI sites. The position 1234 is located at the interior of the loop of the secondary structure of the mRNA which blocks translation in the absence of chloramphenicol. Thus, the amplified sequence does not contain the cat promoter nor the sequence complementary to the RBS which is essential for the regulation of translation Ambulos, N. P. et al., 1984, Gene 28: 171–176).

(ii) expression vector pAT79: the ClaI-BssHII fragment of 243 bp bearing the P2 promoter of the aphA-3 gene of the enterococcal plasmid pJH1 (Caillaud et al., 1987, Mol. Gen. Genet. 207: 509–513) was inserted between the EcoRI and SacI restriction sites of pAT78.

(iii) plasmid pAT80 and its derivatives: the BglII-XbaI fragment of 5.5 kb of pIP816 was inserted between the BamHI and XbaI sites of pAT78. The resulting plasmid, designated as pAT80 was partially digested with HincII and ligated with the EcoRV fragment containing a gene related to the apha-I gene of the transposon Tn903 (Oka A. et al., 1981, J. Mol. Biol. 147:217–226. This fragment contains the aphA-I gene which codes for the 3'aminoglycoside phosphotransferase of type I conferring resistance to kanamycin. The insertion of aphaI was carried out at three different sites in pAT80, generating the plasmids pAT81, pAT83 and pAT85. The cassettes BamHI and EcoRI containing aphA-I were inserted at the BamHI (to form the plasmid pAT84) and EcoRI (to form the plasmid pAT82) sites of pAT80.

(iv) plasmids pAT86, pAT87, pAT88 and pAT89: the plasmid pAT86 was constructed by cloning the EcoRI-SacII fragment of 2.803 bp of pAT80 coding for VanH and VanA at a SmaI site of pAT79. pAT87 was obtained by inserting the EcoRI-XbaI fragment of 3.4 kb of pAT80 upstream from the cat gene of the detection vector of promoter pAT78. The plasmid pAT88 resulted from the ligation of pAT78 digested with EcoRI and BamHI to the EcoRI-BamHI fragment of 1.731 bp of pAT80. The BglII-AccI fragment (positions 1 to 2356) of pAT80 was inserted into the polylinker of the integrative vector pAT113, generating pAT89.

Sub-cloning in M13 and Sequencing

The DNA restriction fragments were subcloned in a polylinker of replicative derivatives of the bacteriophage M13, these derivatives being called mp18 and mp19 (Norrander et al., 1983, Gene 26:101–106). *E.coli* JM103 was transfected with the recombinant phages and a single-stranded DNA was prepared. The sequencing of the nucleotides was carried out according to the conditions described by Sanger et al. (Proc. Natl. Acad. Sci. USA, 1977, 74: 5463–5467) by using the modified T7 DNA polymerase (Sequenase, United States, Biochemical Corporation Cleveland Ohio) and [α-$^{35}$S] dATP (Amersham). The reaction products were resolved on gradient gels of polyacrylamide in a 6% buffer.

Enzymatic Test The JH2-2 derivatives of E. faecalis were grown to an optical density $OD_{600}$ of 0.7 in a BHI broth supplemented with spectinomycin (300 μg/ml). The cells were treated with lysozyme, lysed by sonication and the cell debris were centrifuged for 45 minutes at 100,000 g according to the description given by Courvalin et al. (1978, Antimicrob. Agents Chemother. 13:716–725). The formation of 5-thio-2-nitrobenzoate was measured at 37° C. in the presence and in the absence of chloramphenicol and the specific CAT activity was expressed in micromole per minute and per milligram of proteins (Shaw et al., 1975, Methods Enzymol. 43:737–755).

RESULTS

The vanH and vanA genes of pIP816 were cloned in a plasmid pAT79 under the control of the heterologous promoter P2 (Caillaud et al., 1987, Mol. Gen. Genet. 207:509–513) and the plasmid pAT86 formed did not confer resistance to vancomycin on the strain E. faecalis JH2-2. These genes are thus not sufficient for the synthesis of peptoglycan in the absence of the antibiotic. Different restriction fragments of pIP816 were cloned in the vector pAT78. The BglII-XbaI fragment of 5.5 kb of pAT80 is the smallest fragment obtained which conferred resistance to vancomycin.

Nucleotide Sequence of the VanR and VanS Genes

The sequence of the insert in pAT80 was determined on both strands of the DNA from the BglII site to the ATG initiation codon for the translation of VanH. Two open reading frames (orf) were detected within the sequence of 2475 bp: the first open reading frame extends from the nucleotide 386 to the nucleotide 1123; at position 431 a sequence characteristic of the RBS sequences in Gram-positive bacteria is found, 6 base pairs upstream from the ATG initiation codon for translation (TGAAAGGGTG (SEQ ID NO: 52); the other initiation codons for translation in this orf are not preceded by this type of sequence. The sequence of 693 bp extending from the ATG codon at position 431 to the TAA codon at position 1124 is capable of coding for a protein of 231 amino acids with a molecular mass of 26,612 Da which is designated as VanR.

In the case of the second open reading frame (from nucleotide 1089 to nucleotide 2255) the amino acid sequence deduced from the first initiation codon in phase (TTG at position 1104) would code for a protein of 384 amino acids having a molecular mass of 43,847 Da and designated as VanS. The TTG codon at position 1116 and the ATG codon at position 1164 are in-phase initiation codons for translation preceded by sequences with low complementarity with the 3'OH terminus of the 16S sub-unit of the rRNA of B. subtilis (GGGGGGTTGG-N8-TTG (SEQ ID NO: 53) and AGAACGAAAA-N6-ATG (SEQ ID NO: 54), respectively).

Between the last codon of vanS and the initiation codon ATG for the translation of vanH a sequence of 217 bp is to be observed which contains a repeated reverse sequence of 17 bp. This sequence does not function as a terminator of strong transcription.

The comparison of the sequences obtained with data bases has shown that the conserved amino acid residues identified by Stock et al. (1989, Microbiol. Rev. 53:450–490) in the kinase domain of 16 HPK (Histidine Protein Kinase) were detected in the C-terminal part of VanS (SEQ ID NO: 14). VanS possesses two groups of hydrophobic amino acids in the N-terminal region. The histidine residue 164 of VAnS is aligned with the residue His216 of PhoR (SEQ ID NO: 41) (Makino et al., 1986, J. Mol. Biol. 192: 549–556) and His 243 of EnvZ (SEQ ID NO: 42) (Comeau et al., 1985, 164:578–584) which are presumed sites of autophosphorylation in these proteins.

Similarly, the amino acids 1 to 122 of VanR (SEQ ID NO: 12) exhibit similarities with the effector domains of response regulators RR. The aspartic acid 53 of VanR might be a phosphorylation site because this residue is aligned with Asp 57 of Che Y (SEQ ID NO: 46) which is phosphorylated by HPK associated with CheA and corresponds to an invariant position in other proteins of the RR type (Stock et al previously mentioned). VanR might belong to the sub-class OmpR-PhoB of RR which activates the initiation of transcription mediated by the RNA polymerase containing the 70S factor of E.coli (Stock et al. previously mentioned).

Inactivation of the van Genes By Insertion

Cassettes of resistance to kanamycin inserted in the group of van genes in the plasmid pAT80 have shown the following: the insertion in vanR suppresses resistance to vancomycin and chloramphenicol; VanR is an activator of transcription necessary for the expression of the genes for resistance to vancomycin. The inactivation of vanS leads to a two-fold reduction of the minimal inhibitory concentration (MIC) of chloramphenicol and to a three-fold reduction of the specific CAT activity but the minimal inhibitory concentration of vancomycin remains unchanged. Hence, VanS is necessary to produce a high level of transcription of the genes for resistance to vancomycin although it is not required for the expression of the phenotype of resistance to vancomycin.

Derivatives of pAT80 bearing insertions in vanH (pAT83), vanA (pAT84) or in the region 1.0 kb downstream from vanA (pAT85) have made it possible to obtain resistance to chloramphenicol but not to vancomycin. This dissociated phenotype corresponds to the inactivation of genes coding for enzymes which synthesize the depsipeptide precursors necessary for the assembly of the bacterial cell walls in the presence of vancomycin.

Downstream from the vanA gene the presence of an inactivated orf has been detected in pAT85 in the region of the sequence of 365 bp after the TGA codon of vanA and before the SacII site and this orf contains an in-phase ATG initiation codon preceded by a RBS-like sequence. This sequence codes for a protein necessary for resistance to the glycopeptide, designated as VanX and which comprises maximally about 330 amino acids.

Trans-activation of the Transcription of the van Genes

The integrative plasmid pAT89 coding for VanR and VanS was introduced into the chromosome of E. faecalis BM4138. The plasmid pAT87 bearing the genes vanH, vanA and vanX cloned upstream from the cat gene lacking the promoter for pAT78 conferred resistance to vancomycin on this strain but not to E. faecalis JH2-2. The level of expression of the cat gene of pAT87 in the strains BM4138::pATS9 and JH2-2 indicated that VanR activates the transcription of the reporter gene localized at the 3' end of the group of van genes. Similar levels of CAT synthesis were observed for pAT88 which bears a transcription fusion between the 5' parts of vanA and the cat gene. These results show that in E. faecalis BM4138: pAT89 (pAT87) VanR and VanS encoded in the chromosome activate in a trans manner the transcription of vanA, vanH and vanX of pAT87 making possible the production of resistance to vancomycin.

Moreover, it has been observed that the expression of the gene was essentially constitutive when vanR and vanS were borne by a multicopy plasmid pAT80 and weakly inducible by vancomycin when the genes for the regulatory proteins were present on the chromosome of the host.

III—Characterization of the sequence of the vanC Gene of *Enterococcus gallinarum* BM4174

Definition and use of Universal Primers for the Amplification of Genes Coding for D-Ala-D-Ala Ligases and Related Proteins Implicated in Resistance to Vancomycin The protein VanA necessary for the expression of a high level of resistance to the glycopeptides in *E. faecium* BM4147 shares a similarity of about 28 to 36% as regards its amino acids with the D-Ala-D-Ala ligases of *E.coli* but possesses a different substrate specificity from that of these ligases. Peptides designated as 1 and 2 which are conserved in the sequences of the DdlA and DdlB ligases (Zawadzke, 1991 Biochemistry 30:1673–1682) of *E.coli* and in the protein VanA were selected in order to synthesize universal primers intended to amplify internal fragments of genes coding for D-Ala-D-Ala ligases or related enzymes. The peptide targets GEDG(S/T) (I/L)QG and NT(I/L)PGFT were translated back as is shown in FIG. IV.1 in order to obtain degenerate oligonucleotides V1 and V2. As the peptides 1 and 2 of VanA, DdlA and DdlB are separated by amino acid sequences of similar length, the predicted size for the amplification product was about 640 bp.

Amplification by means of PCR with the DNA of *E.coli* JM83 and of *E. faecium* BM4147 made it possible to amplify products corresponding to the expected size which have then been purified and cloned in the bacteriophage M13mp10 (Norrander et al., 1983, Gene 26:101–106). The sequencing of the insert obtained with *E.coli* JM83 has shown that the product of PCR was an internal fragment of ddlA. A probe generated starting from a recombinant phage obtained with the amplification fragment of BM4147 was used for the Southern blot analysis of a DNA of BM4147 and BM4147-1 which is a derivative of BM4147 sensitive to vancomycin and which lacks the plasmid pIP816 (Leclercq et al., 1988, N. Engl. J. Med. 319:157–161). The probe hybridized with the EcoRI DNA fragment of 4 kb from BM4147 but not with the DNA from *E. faecium* BM4147-1. As the vanA gene is borne by the EcoRI fragment of 4 kb from pIP816, these results indicate that the primers also make possible the amplification of a part of vanA. Thus the oligonucleotides V1 and V2 may amplify fragments of genes coding for different proteins related to the D-Ala-D-Ala ligases, and may do this in different species.

Amplification, Cloning and Sequencing of the vanC Gene

Amplification by means of PCR was carried out on the total DNA of *E. gallinarum* BM4174 and the amplification product obtained of about 640 bp was cloned in the bacteriophage M13mp10. The single-stranded DNA isolated from the recombinant phage was used to construct a probe C (Hu et al., 1982, Gene 17:2171–2177). In Southern analysis the probe hybridized with a PstI fragment of 1.7 kb from BM4174 but not with the DNA of BM4147 and BM4147-1.

The DNA of BM4174 was digested with PstI and fragments of 1.5 and 2 kb were purified by electrophoresis on agarose gel and cloned in pUC18 (Norrander et al., 1983, mentioned previously). The recombinant plasmids were introduced into *E.coli* JM83 by transformation and screened by hybridization on colonies (Sambrook et al., 1989, Molecular cloning, a laboratory manual. Cold Spring Harbor Laboratory Press, Cold Spring Harbor, N.Y.) by using the probe C. A homology was detected with a transformant harbouring a plasmid called pAT216 which contained a PstI insert of 1.7 kb. The sequence of the SacI-PstI part of 1347 bp of the insert of pAT216 was determined on both strands of the DNA. The location of the termination codons in the three reading frames of each strand of DNA revealed the presence of an ORF phase located between the TGA codons at positions 47 and 1244. The initiation codon of transcription ATG at position 215 is preceded by a sequence GAAAGGAAGA characteristic of the RBS sequences complementary to the RNA of the 16S subunit of *B. subtilis* (Moran et al., 1982, Mol. Gen. Genet. 186:339–346). The sequence of 1029 bp which extends from the ATG codon at position 215 to the TGA codon at position 1244 might code for a protein of 343 amino acids having a calculated molecular mass of 37504 Da designated as VanC. A sequence homology was detected between VanC, VanA and the D-Ala-D-Ala ligases of *E.coli*. In particular, four domains of strong homology previously found between VanA and the D-Ala-D-Ala ligases of the enterobacteria are also present in VanC. The percentage of identical amino acids calculated for these proteins taken two at a time varied between 29 and 38%. The alignment of the four sequences revealed the presence of 57 invariant amino acids which include the conserved residues of the peptides 1 and 2 used to define the oligonucleotide probes V1 and V2.

Inactivation of the vanC Gene by Insertion

In order to evaluate the contribution of vanC to resistance to vancomycin in *E. gallinarum* BM4174, the vanC gene was inactivated by insertion. A EcoRI-HincII fragment of 690 bp, internal to vanC was cloned in pAT114 which does not replicate in Gram-positive bacteria. The resulting pAT217 plasmid was introduced into BM4174 by electroporation (Cruz-Rodz et al., 1990, Mol. Gen. Genet. 224:152–154) and the clones supposed to result from a homologous recombination leading to the integration of pAT217 into vanC were selected on erythromycin. The clone BM4175 was compared with BM4174 by Southern hybridization using the probe C and aphA-3 specific for pAT114. The two probes hybridized with the EcoRI fragment of 8.6 kb from BM4175. The probe C hybridized with a fragment of 2.5 kb from BM4174 whereas no signal was observed with the probe aphA-3. The results indicate that the plasmid pAT217 of 6.1 kb was integrated into the vanC gene. The determination of the minimal inhibitory concentration of vancomycin for BM4174 (16 mg/l) and BM4175 (2 mg/l) indicated that the inactivation by insertion in vanC abolishes resistance to vancomycin.

VanC is thus required for resistance to vancomycin. It may thus be supposed that this protein synthesizes a dipeptide or a depsipeptide which is incorporated into the precursors of peptidoglycans and is not recognized by vancomycin.

The sequences which are the object of the invention are given in the following pages after the list of the sequences containing the description of these sequences. In this list of the sequences, the proteins are identified with respect to the position of the nucleotide bases corresponding to the amino acids of the extremities of the proteins.

List of the Sequences (contained in the sequences I (Ia, Ib), II presented below or in the sequence shown in FIG. 5).

Amino acid sequences

SEQ ID NO 2 (VanH): sequence of the first resistance protein, corresponding to the amino acid sequence of the open reading frame No. 3, starting at the base 3501 and terminating at the base 4529, containing the sequence coding for the vanH gene between the bases 3564 and 4529 with respect to the sequence shown in FIG. 5 or corresponding to the sequence between the positions of the nucleotides 6018 and 6983 of the sequence Ia.

SEQ ID NO 4 (VanA): sequence of the VanA protein, corresponding to the amino acid sequence of the open reading frame No. 1, starting at the base 4429 and terminating at the base 5553 with respect to the sequence shown in FIG. 5 or corresponding to the sequence between the positions of the nucleotides 6977 and 7807 of the sequence Ia.

SEQ ID NO 6 (VanX): sequence of the third resistance protein, corresponding to the amino acid sequence of the open reading frame No. 3, starting at the base 5526 and terminating at the base 6167 with respect to the sequence shown in FIG. 5 or corresponding to the sequence between the positions of the nucleotides 7816 and 8621 of the sequence Ia.

SEQ ID NO 12 (VanR): sequence of the regulatory protein R, corresponding to the amino acid sequence of the open reading frame No. 1, starting at the base 1477 and terminating at the base 2214 with respect to the sequence shown in FIG. 5 or corresponding to the sequence between the positions of the nucleotides 3976 and 4668 of the sequence Ia.

SEQ ID NO 14 (VanS): sequence of the sensor protein S, corresponding to the amino acid sequence of the open reading frame No. 2, starting at the base 2180 and terminating at the base 3346 with respect to the sequence shown in FIG. 5 or corresponding to the sequence between the positions of the nucleotides 4648 and 5800 of the sequence Ia.

SEQ ID NO 19: sequence of the transposase corresponding to the amino acids included between the nucleotides 150 and 3112 of the sequence Ib.

SEQ ID NO 21: sequence of the resolvase comprising the amino acids situated between the positions of the nucleotides 3187 and 3759 of the sequence Ia.

SEQ ID NO 23: VanY sequence comprising the amino acids situated between the positions of the nucleotides 9046 and 9960 of the sequence Ia.

SEQ ID NO 25: VanZ sequence comprising the amino acids situated between the positions of the nucleotides 10116 and 10598 of the sequence Ia.

SEQ ID NO 8: VanC amino acid sequence shown in list II. Nucleotide sequences

SEQ ID NO 15: nucleotide sequence containing the sequence coding for the 5 proteins as well as the flanking sequences, shown in FIG. 5.

SEQ ID NO 17: sequence containing the sequence coding for the 3 resistance proteins as well as the flanking sequences and starting at the base 3501 and terminating at the base 6167, shown in FIG. 5.

SEQ ID NO 3: sequence of the vanA gene, starting at the base 4429 and terminating at the base 5553 of the sequence shown in FIG. 5, or corresponding to the nucleotide sequence situated between the nucleotides 6977 and 7807 of the sequence Ia.

SEQ ID NO 1: sequence coding for the first resistance protein called VanH, starting at the base 3501 and terminating at the base 4529, in particular the sequence vanH, the coding sequence of which is located between the bases 3564 and 45–29 of the sequence shown in FIG. 5, or corresponding to the nucleotide sequence situated between the nucleotides 6018 and 6983 of the sequence Ia.

SEQ ID NO 5: sequence coding for the third resistance protein VanX, starting at the base 5526 and terminating at the base 6167 of the sequence shown in FIG. 5, or corresponding to the nucleotide sequence situated between the nucleotides 7816 and 8621 of the sequence Ia.

SEQ ID NO 16: sequence of the transposon coding for the transposase, the resolvase, vanR, VAnS, VanH, VanA, VanX, VanY and VanZ and containing the repeated reverse sequence of 38 bp at its N- and C-termini and corresponding to the sequence Ia.

SEQ ID NO 18: sequence coding for the transposase, starting at the base 150 and terminating at the base 3112 of the sequence Ib.

SEQ ID NO 20: sequence coding for the resolvase, starting at the base 3187 and terminating at the base 3759 of the sequence Ia.

SEQ ID NO 22: sequence coding for VanY, starting at the base 9046 and terminating at the base 9960 of the sequence Ia.

SEQ ID NO 24: sequence coding for VanZ, starting at the base 10116 and terminating at the base 10598 of the sequence Ia.

SEQ ID NO 7: sequence coding for VanC, shown in the list II in relation to the protein VanC.

SEQ ID NO 16: complete sequence Ia of the transposon of *E. faecium*, starting at the base 1 and terminating at the base 10851.

SEQ ID NO 11: sequence coding for the protein VanR, starting at the base 3976 and terminating at the base 4668 of the sequence Ia.

SEQ ID NO 13 sequence coding for the protein VanS, starting at the base 4648 and terminating at the base 5800 of the sequence Ia.

I. Nucleotide sequence of the transposon and translation

Ia. (+) Strand

```
1
GGG GTA GCG TCA GGA AAA TGC GGA TTT ACA ACG CTA AGC CTA TTT TCC TGA CGA ATC CCT

61
CGT TTT TAA CAA CGT TAA GAA AGT TTT AGT GGT CTT AAA GAA TTT AAT GAG ACT ACT TTC

121
TCT GAG TTA AAA TGG TAT TCT CCT AGT AAA TTA ATA TGT TCC CAA CCT AAG GGC GAC ATA

181
TGG TGT AAC AAA TCT TCA TTA AAG CTA CCT GTC CGT TTT TTA TAT TCA ACT GCT GTT GTT

241
AGG TGG AGA GTA TTC CAA ATA CTT ATA GCA TTG ATA ATT ATG TTT AAA GCA CTG GCT CTT
```

-continued

```
301
TGC AAT TGA TGC TGT ATG GTG CGT TCT CTA AGC TCA CCT TGT TTT CCG AAG AAA ATA GCT

361
CTT GCC AAT CCA TTC ATG GCT TCT CCT TTA TTC AAT CCT CTT TGT ATT TTT CTT CTT AAT

421
GAT TCA TCC GAT ATA TAA TTC AAA ATA AAG ATC GTT TTT TCT ATT CGG CCC ATC TCA CGT

481
AAG GCT GTA GCT AAG CTG TTT TGT CTT GAA TAG GAA CCT AGC TTC CCC ATA ATA AGG GAT

541
GCT GAA ACT GTT CCC TCC CTT ATA GAA TGA GCT AAT CGC AAA ACA TCC TCA TAA TTT TCT

601
TTA ATG ACC TTT GTA TTT ATT TGT CCA CGT AAA ATG GCT TCT AGT TTT GGA TAC TCA CTT

661
GCT TTA TCT ATC GTA AAT AAT TTT GAG TCC GAT AAA TCC CTT ATT CTT GGG GCA AAT TTA

721
AAT CCT AAT AAA TGA GTC AGT CCG AAT ATT TGG TCA GTG TAA CCG GCA GTG TCT GTA TAA

781
TGT TCC TCT ATG TTT AGA TCC GTC TCA TGA TGT AAC AAA CCA TCC AAA ACA TGA ATC GCA

841
TCT CTT GAA TTA GTA TGA ATA ATC TTT GTG TAG TAA GAA GAG AAT TGA TCA CTT GTA AAT

901
CGG TAG ATG GTG GCT CCT TTT CCA GTT CCA TAA TGT GGA TTT GCA TCT GCA TGT AGT GAT

961
GAA ACA CCT AGC TGC ATT CTC ATA CCA TCT GAC GAA GAT GTT GTA CCG TCG CCC CAA TAG

1021
AAA GGC AAT TGT AAT TTA TGA TGA AAG TTT ACT AAT ATG GCT TGG GCT TTA TTC ATG GCA

1081
TCT TCA TAC ATG CGC CAT TGA GAT ACA TTG GCT AGT TGC TTA TAT GTA AGT CCG GGT GTG

1141
GCT TCG GCC ATC TTG CTC AAG CCA ATA TTC ATT CCC ATT CCT AAA AGG GCA GCC ATG ATA

1201
ATG ATT GTT TCT TCC TTA TCT GGT TTT CGA TTA TTG GAA GCA TGA GTG AAT TGC TCA TGA

1261
AAT CCT GTT ATA TGG GCC ACA TCC ATG AGT AAA TCA GTT AAT TTT ATT CTT GGT AGC ATC

1321
TGA TAA AGG CTT GCA CTA AAT TTT TTT GCT TCT TCT GGA ACA TCT TTT TCT AAG CGT GCA

1381
AGT GAT AGC TTT CCT TTT TCA AGA GAA ACC CCA TCT AAC TTA TTG GAA TTG GCA GCT AAC

1441
CAC TTT AAC CTT TCA TTA AAG CTG CTG GTT CTC TCC GTT ATA TAA TCT TCG AAT GAT AAA

1501
CTA ACT GAT AAT CTC GTA TTC CCC TTC GAT TGA TTC CAT GTA TCT TCC GAA AAC AAA TAT

1561
TCC TCA AAA TCC CTA TAT TGT CTG CTG CCA ACA ATG GAA ACA TCT CCT GCC CGA ACA TGC

1621
TCC CGA AGT TCT GTT AAA ACA GCC ATT TCA TAG TAA TGA CGA TTA ATT GTT GTA CCA TCA

1681
TCC TCG TAT AAA TGT CTT TTC CAT CGT TTT GAA ATA AAA TCC ACA GGT GAG TCA TCA GGC

1741
ACT TTT CGC TTT CCA GAT TCG TTC ATT CCT CGG ATA ATC TCA ACA GCT TGT AAA AGT GGC

1801
TCA TTT GCC TTT GTA GAA TGA AAT TCC AAT ACT CTT AAT AGC GTT GGC GTA TAT TTT CTT

1861
AGT GAA TAA AAC CGT TTT TGC AGT AAG TCT AAA TAA TCA TAG TCG GCA GGA CGT GCA AGT
```

```
1921
TCC TGA GCC TCT TCT ACT GAA GAG ACA AAG GTA TTC CAT TCA ATA ACC GAT TCT AAA ACC

1981
TTA AAA ACG TCT AAT TTT TCC TCT CTT GCT TTA ATT AAT GCT TGT CCG ATG TTC GTA AAG

2041
TGT ATA ACT TTC TCA TTT AGC TTT TTA CCG TTT TGT TTC TGG ATT TCC TCT TGA GCC TTA

2101
CGA CCT TTT GAT AAC AAA CTA AGT ATT TGC CTA TCA TGA ATT CAA AAC GCT TTA TCC GTT

2161
AGC TCC TGA GTA AGT TGT AAT AAA TAG ATG GTT AAT ATC GAA TAA CGT TTA TTT TCT TGA

2221
AAG TCA CGG AAT GCA TAC GGC TCG TAT CTT GAG CCT AAG CGA GAC AGC TGC AAC AGG CGG

2281
TTA CGG TGC AAA TGA CTA ATT TGC ACT GTT TCT AAA TCC ATT CCT CGT ATG TAT TCG AGT

2341
CGT TCT ATT ATT TTT AGA AAA GTT TCG GGT GAA GGA TGA CCC GGT GGC TCT TTT AAC CAA

2401
CCC AAT ATC GTT TTA TTG GAT TCG GAT GGA TGC TGC GAG GTA ATA ATC CCT TCA AGC TTT

2461
TCT TTT TGC TCA TTT GTT AGA GAT TTA CTA ACC GTA AAT AAT AGC TTC TTT TCA GCC ATT

2521
GCC CTT GCT TCC CAC ACC ATT CTT TCA AGT GTA GTG ATA GCA GGC AGT ATA ATT TTG TTT

2641
AAT TGA TGA AGG TAC TTA AAT GTC ATT CGA TAT TCA CTC AGG GTA AAA GTT ACA AAG TCG

2701
TAT TCA CTT CGA ATT TCT TTC AAA TGA TCC CAA AGT GTA TTT TCC CTT TGA GGA TAA TGA

2761
TCA AGC GAG GAT GGA CTA ACA CCA ATC TGT TTC GAT ATA TAT TGT ATG ACC GAA TCT GGG

2821
ATG CTT TTG ATA TGA GTG TAT GGC CAA CCG GGA TAC CGA AGA ACA GCT AAT GAA ACA GCA

2881
AAT CCT AAA CGG TTT TCT TCC CTC CTT CGC TTA TTA ACT ATT TCT AAA TCC CGT TTG GAA

2941
AAA GTG AAG TAG GTC CCC AGT ATC CAT TCA TCT TCA GGG ATT TGC ATA AAA GCC TGT CTC

3001
TGT TCC GGT GTA AGC AAT TCT CTA CCT CTC GCA ATT TTC ATT CAG TAT CAT TCC ATT TCT

3061
GTA TTT TCA ATT TAT TAG TTC AAT TAT ATA TCA ATA GAG TGT ACT CTA TTG ATA CAA ATG

3121
TAG TAG ACT GAT AAA ATC ATA GTT AAG AGC GTC TCA TAA GAC TTG TCT CAA AAA TGA GGT 3181      resolvase
          LEU ARG LYS ILE GLY TYR ILE ARG VAL SER SER THR ASN GLN ASN PRO SER ARG
GAT ATT TTG CGG AAA ATC GGT TAT ATT CGT GTC AGT TCG ACT AAC CAG AAT CCT TCA AGA 3241
GLN PHE GLN GLN LEU ASN GLU ILE GLY MET ASP ILE ILE TYR GLU GLU LYS VAL SER GLY
CAA TTT CAG CAG TTG AAC GAG ATC GGA ATG GAT ATT ATA TAT GAA GAG AAA GTT TCA GGA 3301
ALA THR LYS ASP ARG GLU GLN LEU GLN LYS VAL LEU ASP ASP LEU GLN GLU ASP ASP ILE
GCA ACA AAG GAT CGC GAG CAA CTT CAA AAA GTG TTA GAC GAT TTA CAG GAA GAT GAC ATC 3361
ILE TYR VAL THR ASP LEU THR ARG ILE THR ARG SER THR GLN ASP LEU PHE GLU LEU ILE
ATT TAT GTT ACA GAC TTA ACT CGA ATC ACT CGT AGT ACA CAA GAT CTA TTT GAA TTA ATC

3421
```

```
ASP ASN ILE ARG ASP LYS LYS ALA SER LEU LYS SER LEU LYS ASP THR TRP LEU ASP LEU
GAT AAC ATA CGA GAT AAA AAG GCA AGT TTA AAA TCA CTA AAA GAT ACA TGG CTT GAT TTA

3481
SER GLU ASP ASN PRO TYR SER GLN PHE LEU ILE THR VAL MET ALA GLY VAL ASN GLN LEU
TCA GAA GAT AAT CCA TAC AGC CAA TTC TTA ATT ACT GTA ATG GCT GGT GTT AAC CAA TTA

3541
GLU ARG ASP LEU ILE ARG MET ARG GLN ARG GLU GLY ILE GLU LEU ALA LYS LYS GLU GLY
GAG CGA GAT CTT ATT CGG ATG AGA CAA CGT GAA GGG ATT GAA TTG GCT AAG AAA GAA GGA

3601
LYS PHE LYS GLY ARG LEU LYS LYS TYR HIS LYS ASN HIS ALA GLY MET ASN TYR ALA VAL
AAG TTT AAA GGT CGA TTA AAG AAG TAT CAT AAA AAT CAC GCA GGA ATG AAT TAT GCG GTA

3661
LYS LEU TYR LYS GLU GLY ASN MET THR VAL ASN GLN ILE CYS GLU ILE THR ASN VAL SER
AAG CTA TAT AAA GAA GGA AAT ATG ACT GTA AAT CAA ATT TGT GAA ATT ACT AAT GTA TCT

3721
ARG ALA SER LEU TYR ARG LYS LEU SER GLU VAL ASN ASN
AGG GCT TCA TTA TAC AGG AAA TTA TCA GAA GTG AAT AAT TAG CCA TTC TGT ATT CCG CTA

3781
ATG GGC AAT ATT TTT AAA GAA GAA AAG GAA ACT ATA AAA TAT TAA CAG CCT CCT AGC GAT

3841
GCC GAA AAG CCC TTT GAT AAA AAA AGA ATC ATC ATC TTA AGA AAT TCT TAG TCA TTT ATT

3901
ATG TAA ATG CTT ATA AAT TCG GCC CTA TAA TCT GAT AAA TTA TTA AGG GCA AAC TTA TGT

3961      VanR  MET SER ASP LYS ILE LEU ILE VAL ASP ASP GLU HIS ILE ALA
GAA AGG GTG ATA ACT ATG AGC GAT AAA ATA CTT ATT GTG GAT GAT GAA CAT GAA ATT GCC

4021
ASP LEU VAL GLU LEU TYR LEU LYS ASN GLU ASN TYR THR VAL PHE LYS TYR TYR THR ALA
GAT TTG GTT GAA TTA TAC TTA AAA AAC GAG AAT TAT ACG GTT TTC AAA TAC TAT ACC GCC

4081
LYS GLU ALA LEU GLU CYS ILE ASP LYS SER GLU ILE ASP LEU ALA ILE LEU ASP ILE MET
AAA GAA GCA TTG GAA TGT ATA GAC AAG TCT GAG ATT GAC CTT GCC ATA TTG GAC ATC ATG

4141
LEU PRO GLY THR SER GLY LEU THR ILE CYS GLN LYS ILE ARG ASP LYS HIS THR TYR PRO
CTT CCC GGC ACA AGC GGC CTT ACT ATC TGT CAA AAA ATA AGG GAC AAG CAC ACC TAT CCG

4201
ILE ILE MET LEU THR GLY LYS ASP THR GLU VAL ASP LYS ILE THR GLY LEU THR ILE GLY
ATT ATC ATG CTG ACC GGG AAA GAT ACA GAG GTA GAT AAA ATT ACA GGG TTA ACA ATC GGC

4261
ALA ASP ASP TYR ILE THR LYS PRO PHE ARG PRO LEU GLU LEU ILE ALA ARG VAL LYS ALA
GCG GAT GAT TAT ATA ACG AAG CCC TTT CGC CCA CTG GAG TTA ATT GCT CGG GTA AAG GCC

4321
GLN LEU ARG ARG TYR LYS LYS PHE SER GLY VAL LYS GLU GLN ASN GLU ASN VAL ILE VAL
CAG TTG CGC CGA TAC AAA AAA TTC AGT GGA GTA AAG GAG CAG AAC GAA AAT GTT ATC GTC

4381
HIS SER GLY LEU VAL ILE ASN VAL ASN THR HIS GLU CYS TYR LEU ASN GLU LYS GLN LEU
CAC TCC GGC CTT GTC ATT AAT GTT AAC ACC CAT GAG TGT TAT CTG AAC GAG AAG CAG TTA

4441
SER LEU THR PRO THR GLU PHE SER ILE LEU ARG ILE LEU CYS GLU ASN LYS GLY ASN VAL
TCC CTT ACT CCC ACC GAG TTT TCA ATA CTG CGA ATC CTC TGT GAA AAC AAG GGG AAT GTG
```

```
4501
VAL SER SER GLU LEU LEU PHE HIS GLU ILE TRP GLY ASP GLU TYR PHE SER LYS SER ASN

GTT AGC TCC GAG CTG CTA TTT CAT GAG ATA TGG GGC GAC GAA TAT TTC AGC AAG AGC AAC

4561
ASN THR ILE THR VAL HIS ILE ARG HIS LEU ARG GLU LYS MET ASN ASP THR ILE ASP ASN

AAC ACC ATC ACC GTG CAT ATC CGG CAT TTG CGC GAA AAA ATG AAC GAC ACC ATT GAT AAT

4621
PRO LYS TYR ILE LYS THR VAL TRP GLY VALGLYTYRLYSILEGLULYS

CCG AAA TAT ATA AAA ACG GTA TGG GGG GTTGGTTATAAAATTGAAAAAT AAA AAA AAC GAC

VanS    LEUVALILELYSLEULYSASN  LYS LYS ASN ASP

4682
TYR SER LYS LEU GLU ARG LYS LEU TYR MET TYR ILE VAL ALA ILE VAL VAL VAL ALA ILE

TAT TCC AAA CTA GAA CGA AAA CTT TAC ATG TAT ATC GTT GCA ATT GTT GTG GTA GCA ATT

4742
VAL PHE VAL LEU TYR ILE ARG SER MET ILE ARG GLY LYS LEU GLY ASP TRP ILE LEU SER

GTA TTC GTG TTG TAT ATT CGT TCA ATG ATC CGA GGG AAA CTT GGG GAT TGG ATC TTA AGT

4802
ILE LEU GLU ASN LYS TYR ASP LEU ASN HIS LEU ASP ALA MET LYS LEU TYR GLN TYR SER

ATT TTG GAA AAC AAA TAT GAC TTA AAT CAC CTG GAC GCG ATG AAA TTA TAT CAA TAT TCC

4862
ILE ARG ASN ASN ILE ASP ILE PHE ILE TYR VAL ALA ILE VAL ILE SER ILE LEU ILE LEU

ATA CGG AAC AAT ATA GAT ATC TTT ATT TAT GTG GCG ATT GTC ATT AGT ATT CTT ATT CTA

4922
CYS ARG VAL MET LEU SER LYS PHE ALA LYS TYR PHE ASP GLU ILE ASN THR GLY ILE ASP

TGT CGC GTC ATG CTT TCA AAA TTC GCA AAA TAC TTT GAC GAG ATA AAT ACC GGC ATT GAT

4982
VAL LEU ILE GLN ASN GLU ASP LYS GLN ILE GLU LEU SER ALA GLU MET ASP VAL MET GLU

GTA CTT ATT CAG AAC GAA GAT AAA CAA ATT GAG CTT TCT GCG GAA ATG GAT GTT ATG GAA

5042
GLN LYS LEU ASN THR LEU LYS ARG THR LEU GLU LYS ARG GLU GLN ASP ALA LYS LEU ALA

CAA AAG CTC AAC ACA TTA AAA CGG ACT CTG GAA AAG CGA GAG CAG GAT GCA AAG CTG GCC

5102
GLU GLN ARG LYS ASN ASP VAL VAL MET TYR LEU ALA HIS ASP ILE LYS THR PRO LEU THR

GAA CAA AGA AAA AAT GAC GTT GTT ATG TAC TTG GCG CAC GAT ATT AAA ACG CCC CTT ACA

5162
SER ILE ILE GLY TYR LEU SER LEU LEU ASP GLU ALA PRO ASP MET PRO VAL ASP GLN LYS

TCC ATT ATC GGT TAT TTG AGC CTG CTT GAC GAG GCT CCA GAC ATG CCG GTA GAT CAA AAG

5222
ALA LYS TYR VAL HIS ILE THR LEU ASP LYS ALA TYR ARG LEU GLU GLN LEU ILE ASP GLU

GCA AAG TAT GTG CAT ATC ACG TTG GAC AAA GCG TAT CGA CTC GAA CAG CTA ATC GAC GAG

5282
PHE PHE GLU ILE THR ARG TYR ASN LEU GLN THR ILE THR LEU THR LYS THR HIS ILE ASP

TTT TTT GAG ATT ACA CGG TAT AAC CTA CAA ACG ATA ACG CTA ACA AAA ACG CAC ATA GAC

5342
LEU TYR TYR MET LEU VAL GLN MET THR ASP GLU PHE TYR PRO GLN LEU SER ALA HIS GLY

CTA TAC TAT ATG CTG GTG CAG ATG ACC GAT GAA TTT TAT CCT CAG CTT TCC GCA CAT GGA

5402
LYS GLN ALA VAL ILE HIS ALA PRO GLU ASP LEU THR VAL SER GLY ASP PRO ASP LYS LEU
```

```
AAA CAG GCG GTT ATT CAC GCC CCC GAG GAT CTG ACC GTG TCC GGC GAC CCT GAT AAA CTC
5462
ALA ARG VAL PHE ASN ASN ILE LEU LYS ASN ALA ALA ALA TYR SER GLU ASP ASN SER ILE
GCG AGA GTC TTT AAC AAC ATT TTG AAA AAC GCC GCT GCA TAC AGT GAG GAT AAC AGC ATC
5522
ILE ASP ILE THR ALA GLY LEU SER GLY ASP VAL VAL SER ILE GLU PHE LYS ASN THR GLY
ATT GAC ATT ACC GCG GGC CTC TCC GGG GAT GTG GTG TCA ATC GAA TTC AAG AAC ACT GGA
5582
SER ILE PRO LYS ASP LYS LEU ALA ALA ILE PHE GLU LYS PHE TYR ARG LEU ASP ASN ALA
AGC ATC CCA AAA GAT AAG CTA GCT GCC ATA TTT GAA AAG TTC TAT AGG CTG GAC AAT GCT
5642
ARG SER SER ASP THR GLY GLY ALA GLY LEU GLY LEU ALA ILE ALA LYS GLY ILE ILE VAL
CGT TCT TCC GAT ACG GGT GGC GCG GGA CTT GGA TTG GCG ATT GCA AAA GAA ATT ATT GTT
5702
GLN HIS GLY GLY GLN ILE TYR ALA GLU SER ASN ASP ASN TYR THR THR PHE ARG VAL GLU
CAG CAT GGA GGG CAG ATT TAC GCG GAA AGC AAT GAT AAC TAT ACG ACG TTT AGG GTA GAG
5762
LEU PRO ALA MET PRO ASP LEU VAL ASP LYS ARG ARG SER
CTT CCA GCG ATG CCA GAC TTG GTT GAT AAA AGG AGG TCC TAA GA GAT GTA TAT AAT TTT
5821
TTA GGA AAA TCT CAA GGT TAT CTT TAC TTT TTC TTA GGA AAT TAA CAA TTT AAT ATT AAG
5881
AAA CGG CTC GTT CTT ACA CGG TAG ACT TAA TAC CGT AAG AAC GAG CCG TTT TCG TTC TTC
5941
AGA GAA AGA TTT GAC AAG ATT ACC ATT GGC ATC CCC GTT TTA TTT GGT GCC TTT CAC AGA
6001
        VanH      MET ASN ASN ILE GLY ILE THR VAL TYR GLY CYS GLU GLN ASP GLU
AAGGGTTGG TCT TAA TT ATG AAT AAC ATC GGC ATT ACT GTT TAT GGA TGT GAG CAG GAT GAG
6063
ALA ASP ALA PHE HIS ALA LEU SER PRO ARG PHE GLY VAL MET ALA THR ILE ILE ASN ALA
GCA GAT GCA TTC CAT GCT CTT TCG CCT CGC TTT GGC GTT ATG GCA ACG ATA ATT AAC GCC
6123
ASN VAL SER GLU SER ASN ALA LYS SER ALA PRO PHE ASN GLN CYS ILE SER VAL GLY HIS
AAC GTG TCG GAA TCC AAC GCC AAA TCC GCG CCT TTC AAT CAA TGT ATC AGT GTG GGA CAT
6183
LYS SER GLU ILE SER ALA SER ILE LEU LEU ALA LEU LYS ARG ALA GLY VAL LYS TYR ILE
AAA TCA GAG ATT TCC GCC TCT ATT CTT CTT GCG CTG AAG AGA GCC GGT GTG AAA TAT ATT
6243
SER THR ARG SER ILE GLY CYS ASN HIS ILE ASP THR THR ALA ALA LYS ARG MET GLY ILE
TCT ACC CGA AGC ATC GGC TGC AAT CAT ATA GAT ACA ACT GCT GCT AAG AGA ATG GGC ATC
6303
THR VAL ASP ASN VAL ALA TYR SER PRO ASP SER VAL ALA ASP TYR THR MET MET LEU ILE
ACT GTC GAC AAT GTG GCG TAC TCG CCG GAT AGC GTT GCC GAT TAT ACT ATG ATG CTA ATT
6363
LEU MET ALA VAL ARG ASN VAL LYS SER ILE VAL ARG SER VAL GLU LYS HIS ASP PHE ARG
CTT ATG GCA GTA CGC AAC GTA AAA TCG ATT GTG CGC TCT GTG GAA AAA CAT GAT TTC AGG
6423
LEU ASP SER ASP ARG GLY LYS VAL LEU SER ASP MET THR VAL GLY VAL VAL GLY THR GLY
TTG GAC AGC GAC CGT GGC AAG GTA CTC AGC GAC ATG ACA GTT GGT GTG GTG GGA ACG GGC
```

```
6483
GLN ILE GLY LYS ALA VAL ILE GLU ARG LEU ARG GLY PHE GLY CYS LYS VAL LEU ALA TYR
CAG ATA GGC AAA GCG GTT ATT GAG CGG CTG CGA GGA TTT GGA TGT AAA GTG TTG GCT TAT
6543
SER ARG SER ARG SER ILE GLU VAL ASN TYR VAL PRO PHE ASP GLU LEU LEU GLN ASN SER
AGT CGC AGC CGA AGT ATA GAG GTA AAC TAT GTA CCG TTT GAT GAG TTG CTG CAA AAT AGC
6603
ASP ILE VAL THR LEU HIS VAL PRO LEU ASN THR ASP THR HIS TYR ILE ILE SER HIS GLU
GAT ATC GTT ACG CTT CAT GTG CCG CTC AAT ACG GAT ACG CAC TAT ATT ATC AGC CAC GAA
6663
GLN ILE GLN ARG MET LYS GLN GLY ALA PHE LEU ILE ASN THR GLY ARG GLY PRO LEU VAL
CAA ATA CAG AGA ATG AAG CAA GGA GCA TTT CTT ATC AAT ACT GGG CGC GGT CCA CTT GTA
6723
ASP THR TYR GLU LEU VAL LYS ALA LEU GLU ASN GLY LYS LEU GLY GLY ALA ALA LEU ASP
GAT ACC TAT GAG TTG GTT AAA GCA TTA GAA AAC GGG AAA CTG GGC GGT GCC GCA TTG GAT
6783
VAL LEU GLU GLY GLU GLU GLU PHE PHE TYR SER ASP CYS THR GLN LYS PRO ILE ASP ASN
GTA TTG GAA GGA GAG GAA GAG TTT TTC TAC TCT GAT TGC ACC CAA AAA CCA ATT GAT AAT
6843
GLN PHE LEU LEU LYS LEU GLN ARG MET PRO ASN VAL ILE ILE THR PRO HIS THR ALA TYR
CAA TTT TTA CTT AAA CTT CAA AGA ATG CCT AAC GTG ATA ATC ACA CCG CAT ACG GCC TAT
6903
TYR THR GLU GLN ALA LEU ARG ASP THR VAL GLU LYS THR ILE LYS ASN CYS LEU ASP PHE
TAT ACC GAG CAA GCG TTG CGT GAT ACC GTT GAA AAA ACC ATT AAA AAC TGT TTG GAT TTT
6963
           VanA    METASN ARG ILE LYS VAL ALA ILE LEU PHE GLY GLY CYS SER
GAA AGG AGA CAG GAG CATGAAT AGA ATA AAA GTT GCA ATA CTG TTT GGG GGT TGC TCA
GLU ARG ARG GLN GLU HISGLU
7021
GLU GLU HIS ASP VAL SER VAL LYS SER ALA ILE GLU ILE ALA ALA ASN ILE ASN LYS GLU
GAG GAG CAT GAC GTA TCG GTA AAA TCT GCA ATA GAG ATA GCC GCT AAC ATT AAT AAA GAA
7081
LYS TYR GLU PRO LEU TYR ILE GLY ILE THR LYS SER GLY VAL TRP LYS MET CYS GLU LYS
AAA TAC GAG CCG TTA TAC ATT GGA ATT ACG AAA TCT GGT GTA TGG AAA ATG TGC GAA AAA
7141
PRO CYS ALA GLU TRP GLU ASN ASP ASN CYS TYR SER ALA VAL LEU SER PRO ASP LYS LYS
CCT TGC GCG GAA TGG GAA AAC GAC AAT TGC TAT TCA GCT GTA CTC TCG CCG GAT AAA AAA
7201
MET HIS GLY LEU LEU VAL LYS LYS ASN HIS GLU TYR GLU ILE ASN HIS VAL ASP VAL ALA
ATG CAC GGA TTA CTT GTT AAA AAG AAC CAT GAA TAT GAA ATC AAC CAT GTT GAT GTA GCA
7261
PHE SER ALA LEU HIS GLY LYS SER GLY GLU ASP GLY SER ILE GLN GLY LEU PHE GLU LEU
TTT TCA GCT TTG CAT GGC AAG TCA GGT GAA GAT GGA TCC ATA CAA GGT CTG TTT GAA TTG
7321
SER GLY ILE PRO PHE VAL GLY CYS ASP ILE GLN SER SER ALA ILE CYS MET ASP LYS SER
TCC GGT ATC CCT TTT GTA GGC TGC GAT ATT CAA AGC TCA GCA ATT TGT ATG GAC AAA TCG
7381
LEU THR TYR ILE VAL ALA LYS ASN ALA GLY ILE ALA THR PRO ALA PHE TRP VAL ILE ASN
```

-continued

```
           TTG ACA TAC ATC GTT GCG AAA AAT GCT GGG ATA GCT ACT CCC GCC TTT TGG GTT ATT AAT
7441
           LYS ASP ASP ARG PRO VAL ALA ALA THR PHE THR TYR PRO VAL PHE VAL LYS PRO ALA ARG
           AAA GAT GAT AGG CCG GTG GCA GCT ACG TTT ACC TAT CCT GTT TTT GTT AAG CCG GCG CGT
7501
           SER GLY SER SER PHE GLY VAL LYS LYS VAL ASN SER ALA ASP GLU LEU ASP TYR ALA ILE
           TCA GGC TCA TCC TTC GGT GTG AAA AAA GTC AAT AGC GCG GAC GAA TTG GAC TAC GCA ATT
7561
           GLU SER ALA ARG GLN TYR ASP SER LYS ILE LEU ILE GLU GLN ALA VAL SER GLY CYS GLU
           GAA TCG GCA AGA CAA TAT GAC AGC AAA ATC TTA ATT GAG CAG GCT GTT TCG GGC TGT GAG
7621
           VAL GLY CYS ALA VAL LEU GLY ASN SER ALA ALA LEU VAL VAL GLY GLU VAL ASP GLN ILE
           GTC GGT TGT GCG GTA TTG GGA AAC AGT GCC GCG TTA GTT GTT GGC GAG GTG GAC CAA ATC
7681
           ARG LEU GLN TYR GLY ILE PHE ARG ILE HIS GLN GLU VAL GLU PRO GLU LYS GLY SER GLU
           AGG CTG CAG TAC GGA ATC TTT CGT ATT CAT CAG GAA GTC GAG CCG GAA AAA GGC TCT GAA
7741
           ASN ALA VAL ILE THR VAL PRO ALA ASP LEU SER ALA GLU GLU ARG GLY ARG ILE GLN GLU
           AAC GCA GTT ATA ACC GTT CCC GCA GAC CTT TCA GCA GAG GAG CGA GGA CGG ATA CAG GAA
7801
           THR ALA LYS LYS ILE TYR LYS ALA LEU GLY CYS ARG GLY LEU ALA ARG VAL ASP MET PHE
           ACG GCA AAA AAA ATA TAT AAA GCG CTC GGC TGT AGA GGT CTA GCC CGT GTG GAT ATG TTT
7861
           LEU GLN ASP ASN GLY ARG ILE VAL LEU ASN GLU VAL ASN THR LEU PRO GLY PHE THR SER
           TTA CAA GAT AAC GGC CGC ATT GTA CTG AAC GAA GTC AAT ACT CTG CCC GGT TTC ACG TCA
7921
           TYR SER ARG TYR PRO ARG MET MET ALA ALA ALA GLY ILE ALA LEU PRO GLU LEU ILE ASP
           TAC AGT CGT TAT CCC CGT ATG ATG GCC GCT GCA GGT ATT GCA CTT CCC GAA CTG ATT GAC
7981
           ARG LEU ILE VAL LEU ALA LEU LYS GLY
           CGC TTG ATC GTA TTA GCG TTA AAG GGG TGATAAGC ATG GAA ATA GGA TTT ACT TTT TTA GAT
                                                VanX     MET GLU ILE GLY PHE THR PHE LEU ASP
8043
           GLU ILE VAL HIS GLY VAL ARG TRP ASP ALA LYS TYR ALA THR TRP ASP ASN PHE THR GLY
           GAA ATA GTA CAC GGT GTT CGT TGG GAC GCT AAA TAT GCC ACT TGG GAT AAT TTC ACC GGA
8103
           LYS PRO VAL ASP GLY TYR GLU VAL ASN ARG ILE VAL GLY THR TYR GLU LEU ALA GLU SER
           AAA CCG GTT GAC GGT TAT GAA GTA AAT CGC ATT GTA GGG ACA TAC GAG TTG GCT GAA TCG
8163
           LEU LEU LYS ALA LYS GLU LEU ALA ALA THR GLN GLY TYR GLY LEU LEU LEU TRP ASP GLY
           CTT TTG AAG GCA AAA GAA CTG GCT GCT ACC CAA GGG TAC GGA TTG CTT CTA TGG GAC GGT
8223
           TYR ARG PRO LYS ARG ALA VAL ASN CYS PHE MET GLN TRP ALA ALA GLN PRO GLU ASN ASN
           TAC CGT CCT AAG CGT GCT GTA AAC TGT TTT ATG CAA TGG GCT GCA CAG CCG GAA AAT AAC
8283
           LEU THR LYS GLU SER TYR TYR PRO ASN ILE ASP ARG THR GLU MET ILE SER LYS GLY TYR
           CTG ACA AAG GAA AGT TAT TAT CCC AAT ATT GAC CGA ACT GAG ATG ATT TCA AAA GGA TAC
8343
           VAL ALA SER LYS SER SER HIS SER ARG GLY SER ALA ILE ASP LEU THR LEU TYR ARG LEU
```

```
GTG GCT TCA AAA TCA AGC CAT AGC CGC GGC AGT GCC ATT GAT CTT AGC CTT TAT CGA TTA
8403
ASP THR GLY GLU LEU VAL PRO MET GLY SER ARG PHE ASP PHE MET ASP GLU ARG SER HIS
GAC ACG GGT GAG CTT GTA CCA ATG GGG AGC CAG TTT GAT TTT ATG GAT GAA CGC TCT CAT
8463
HIS ALA ALA ASN GLY ILE SER CYS ASN GLU ALA GLN ASN ARG ARG ARG LEU ARG SER ILE
CAT GCG GCA AAT GGA ATA TCA TGC AAT GAA GCG CAA AAT CGC AGA CGT TTG CGC TCC ATC
8523
MET GLU ASN SER GLY PHE GLU ALA TYR SER LEU GLU TRP TRP HIS TYR VAL LEU ARG ASP
ATG GAA AAC AGT GGG TTT GAA GCA TAT AGC CTC GAA TGG TGG CAC TAT GTA TTA AGA GAC
8583
GLU PRO TYR PRO ASN SER TYR PHE ASP PHE PRO VAL LYS
GAA CCA TAC CCC AAT AGC TAT TTT GAT TTC CCC GTT AAA TAAA CTT TTA ACC GTT GCA
8641
CGG ACA AAC TAT ATA AGC TAA CTC TTT CGG CAG GAA ACC CGA CGT ATG TAA CTG GTT CTT
8701
AGG GAA TTT ATA TAT AGT AGA TAG TAT TGA AGA TGT AAG GCA GAG CGA TAT TGC GGT CAT
8761
TAT CTG CGT GCG CTG CGG CAA GAT AGC CTG ATA ATA AGA CTG ATC GCA TAG AGG GGT GGT
8821
ATT TCA CAC CGC CCA TTG TCA ACA GGC AGT TCA GCC TCG TTA AAT TCA GCA TGG GTA TCA
8881
CTT ATG AAA ATT CAT CTA CAT TGG TGA TAA TAG TAA ATC CAG TAG GGC GAA ATA ATT GAC
8941
TGT AAT TTA CGG GGC AAA ACG GCA CAA TCT CAA ACG AGA TTG TGC CGT TTA AGG GGA AGA
9001
                                                          VanY    MET LYS LYS
TTC TAG AAA TAT TTC ATA CTT CCA ACT ATA TAG TTA AGG AGG AGA CTG AAA ATG AAG AAG
9061
LEU PHE PHE LEU LEU LEU LEU LEU PHE LEU ILE TYR LEU GLY TYR ASP TYR VAL ASN GLU
TTG TTT TTT TTA TTG TTA TTG TTA TTC TTA ATA TAC TTA GGT TAT GAC TAC GTT AAT GAA
9121
ALA LEU PHE SER GLN GLU LYS VAL GLU PHE GLN ASN TYR ASP GLN ASN PRO LYS GLU HIS
GCA CTG TTT TCT CAG GAA AAA GTC GAA TTT CAA AAT TAT GAT CAA AAT CCC AAA GAA CAT
9181
LEU GLU ASN SER GLY THR SER GLU ASN THR GLN GLU LYS THR ILE THR GLU GLU GLN VAL
TTA GAA AAT AGT GGG ACT TCT GAA AAT ACC CAA GAG AAA ACA ATT ACA GAA GAA CAG GTT
9241
TYR GLN GLY ASN LEU LEU LEU ILE ASN SER LYS TYR PRO VAL ARG GLN GLU SER VAL LYS
TAT CAA GGA AAT CTG CTA TTA ATC AAT AGT AAA TAT CCT GTT CGC CAA GAA AGT GTG AAG
9301
SER ASP ILE VAL ASN LEU SER LYS HIS ASP GLU LEU ILE ASN GLY TYR GLY LEU LEU ASP
TCA GAT ATC GTG AAT TTA TCT AAA CAT GAC GAA TTA ATA AAT GGA TAC GGG TTG CTT GAT
9361
SER ASN ILE TYR MAT SER LYS GLU ILE ALA GLN LYS PHE SER GLU MET VAL ASN ASP ALA
AGT AAT ATT TAT ATG TCA AAA GAA ATA GCA CAA AAA TTT TCA GAG ATG GTC AAT GAT GCT
9421
VAL LYS GLY GLY VAL SER HIS PHE ILE ILE ASN SER GLY TYR ARG ASP PHE ASP GLU GLN
GTA AAG GGT GGC GTT AGT CAT TTT ATT ATT AAT AGT GGC TAT CGA GAC TTT GAT GAG CAA
```

-continued

```
9481
SER VAL LEU TYR GLN GLU MET GLY ALA GLU TYR ALA LEU PRO ALA GLY TYR SER GLU HIS

AGT GTG CTT TAC CAA GAA ATG GGG GCT GAG TAT GCC TTA CCA GCA GGT TAT AGT GAG CAT

9541
ASN SER GLY LEU SER LEU ASP VAL GLY SER SER LEU THR LYS MET GLU ARG ALA PRO GLU

AAT TCA GGT TTA TCA CTA GAT GTA GGA TCA AGC TTG ACG AAA ATG GAA CGA GCC CCT GAA

9601
GLY LYS TRP ILE GLU GLU ASN ALA TRP LYS TYR GLY PHE ILE LEU ARG TYR PRO GLU ASP

GGA AAG TGG ATA GAA GAA AAT GCT TGG AAA TAC GGG TTC ATT TTA CGT TAT CCA GAG GAC

9661
LYS THR GLU LEU THR GLY ILE GLN TYR GLU PRO TRP HIS ILE ARG TYR VAL GLY LEU PRO

AAA ACA GAG TTA ACA GGA ATT CAA TAT GAA CCA TGG CAT ATT CGC TAT GTT GGT TTA CCA

9721
HIS SER ALA ILE MET LYS GLU LYS ASN PHE VAL LEU GLU GLU TYR MET ASP TYR LEU LYS

CAT AGT GCG ATT ATG AAA GAA AAG AAT TTC GTT CTC GAG GAA TAT ATG GAT TAC CTA AAA

9781
GLU GLU LUS THR ILE SER VAL SER VAL ASN GLY GLU LYS TYR GLU ILE PHE TYR TYR PRO

GAA GAA AAA ACC ATT TCT GTT AGT GTA AAT GGG GAA AAA TAT GAG ATC TTT TAT TAT CCT

9841
VAL THR LYS ASN THR THR ILE HIS VAL PRO THR ASN LEU ARG TYR GLU ILE SER GLY ASN

GTT ACT AAA AAT ACC ACC ATT CAT GTG CCG ACT AAT CTT CGT TAT GAG ATA TCA GGA AAC

9901
ASN ILE ASP GLY VAL ILE VAL THR VAL PHE PRO GLY SER THR HIS THR ASN SER ARG ARG

AAT ATA GAC GGT GTA ATT GTG ACA GTG TTT CCC GGA TCA ACA VAT ACT AAT TCA AGG AGG

9961
TAA GGA TGG CGG AAT GAA ACC AAC GAA ATT AAT GAA CAG CAT TAT TGT ACT AGC ACT TTT

10021
GGG GTA ACG TTA GCT TTT TAA TTT AAA ACC CAC GTT AAC TAG GAC ATT GCT ATA CTA ATG

10081                    VanZ    LEU GLY LYS ILE LEU SER ARG GLY LEU

ATA CAA CTT AAA CAA AAG AATTAGAGG AAA TTA TA TTG GGA AAA ATA TTA TCT AGA GGA TTG

10143
LEU ALA LEU TYR LEU VAL THR LEU ILE TRP LEU VAL LEU PHE LYS LEU GLN TYR ASN ILE

CTA GCT TTA TAT TTA GTG ACA CTA ATC TGG TTA GTG TTA TTC AAA TTA CAA TAC AAT AAT

10203
LEU SER VAL PHE ASN TYR HIS GLN ARG SER LEU ASN LEU THR PRO PHE THR ALA THR GLY

TTA TCA GTA TTT AAT TAT CAT CAA AGA AGT CTT AAC TTG ACT CCA TTT ACT GCT ACT GGG

10263
ASN PHE ARG GLU MET ILE ASP ASN VAL ILE ILE PHE ILE PRO PHE GLY LEU LEU LEU ASN

AAT TTC AGA GAG ATG ATA GAT AAT GTT ATA ATC TTT ATT CCA TTT GGC TTG CTT TTG AAT

10323
VAL ASN PHE LYS GLU ILE GLY PHE LEU PRO LYS PHE ALA PHE VAL LEU VAL LEU SER LEU

GTC AAT TTT AAA GAA ATC GGA TTT TTA CCT AAG TTT GCT TTT GTA CTG GTT TTA AGT CTT

10383
THR PHE GLU ILE ILE GLN PHE ILE PHE ALA ILE GLY ALA THR ASP ILE THR ASP VAL ILE

ACT TTT GAA ATA ATT CAA TTT ATC TTC GCT ATT GGA GCG ACA GAC ATA ACA GAT GTA ATT

10443
THR ASN THR VAL GLY GLY PHE LEU GLY LEU LYS LEU TYR GLY LEU SER ASN LYS HIS MET

ACA AAT ACT GTT GGA GGC TTT CTT GGA CTG AAA TTA TAT GGT TTA AGC AAT AAG CAT ATG

10503
```

```
ASN GLN LYS LYS LEU ASP ARG VAL ILE ILE PHE VAL GLY ILE LEU LEU LEU VAL LEU LEU
AAT CAA AAA AAA TTA GAC AGA GTT ATT ATT TTT GTA GGT ATA CTT TTG CTC GTA TTA TTG
10563
LEU VAL TYR ARG THR HIS LEU ARG ILE ASN TYR VAL
CTC GTT TAC CGT ACC CAT TTA AGA ATA AAT TAC GTG TAAG ATG TCT AAA TCA AGC AAT
10621
CTG ATC TTT CAT ACA CAT AAA GAT ATT GAA TGA ATT GGA TTA GAT GGA AAA CGG GAT GTG
10681
GGG AAA CTC GCC CGT AGG TGT GAA GTG AGG GGA AAA CCG GTG ATA AAG TAA AAA GCT TAC
10741
CTA ACA CTA TAG TAA CAA AGA AAG CCC AAT TAT CAA TTT TAG TGC TGA GGA ATT GGT CTC
10801
TTT AAT AAA TTT CCT TAA CGT TGT AAA TCC GCA TTT TCC TGA CGG TAC CCC
```

Ib (−) Strand (corresponds to the sequence of the strand complementary to the (+) strand from 1 to 3189.

```
1
CAA AAT ATC ACC TCA TTT TTG AGA CAA GTC TTA TGA GAC GCT CTT AAC TAT GAT TTT ATC
61
AGT CTA CTA CAT TTG TAT CAA TAG AGT ACA CTC TAT TGA TAT ATA ATT GAA CTA ATA AAT
121          Transposase       MET LYS ILE ALA ARG GLY ARG GLU LEU LEU THR
TGA AAA TAC AGA AAT GGA ATGATACTG AA ATG AAA ATT GCG AGA GGT AGA GAA TTG CTT ACA
182
PRO GLU GLN ARG GLN ALA PHE MET GLN ILE PRO GLU ASP GLU TRP ILE LEU GLY THR TYR
CCG GAA CAG AGA CAG GCT TTT ATG CAA ATC CCT GAA GAT GAA TGG ATA CTG GGG ACC TAC
242
PHE THR PHE SER LYS ARG ASP LEU GLU ILE VAL ASN LYS ARG ARG ARG GLU GLU ASN ARG
TTC ACT TTT TCC AAA CGG GAT TTA GAA ATA GTT AAT AAG CGA AGG AGG GAA GAA AAC GCT
302
LEU GLY PHE ALA VAL GLN LEU ALA VAL LEU ARG TYR PRO GLY TRP PRO TYR THR HIS ILE
TTA GGA TTT GCT GTT CAA TTA GCT GTT CTT CGG TAT CCC GGT TGG CCA TAC ACT CAT ATC
362
LYS SER ILE PRO ASP SER VAL ILE GLN TYR ILE SER LYS GLN ILE GLY VAL SER PRO SER
AAA AGC ATC CCA GAT TCG GTC ATA CAA TAT ATA TCG AAA CAG ATT GGT GTT AGT CCA TCC
422
SER LEU ASP HIS TYR PRO GLN ARG GLU ASN THR LEU TRP ASP HIS LEU LYS GLU ILE ARG
TCG CTT GAT CAT TAT CCT CAA AGG GAA AAT ACA CTT TGG GAT CAT TTG AAA GAA ATT CGA
482
SER GLU TYR ASP PHE VAL THR PHE THR LEU SER GLU TYR ARG MET THR PHE LYS TYR LEU
AGT GAA TAC GAC TTT GTA ACT TTT ACC CTG AGT GAA TAT CGA ATG ACA TTT AAG TAC CTT
542
HIS GLN LEU ALA LEU GLU ASN GLY ASP ALA ILE HIS LEU LEU HIS GLU CYS ILE ASP PHE
CAT CAA TTA GCT TTG GAA AAT GGT GAT GCC ATT CAT CTA CTG CAT GAA TGC ATA GAT TTT
602
LEU ARG LYS ASN LYS ILE ILE LEU PRO ALA ILE THR THR LEU GLU ARG MET VAL TRP GLU
CTA AGA AAA AAC AAA ATT ATA CTG CCT GCT ATC ACT ACA CTT GAA AGA ATG GTG TGG GAA
662
ALA ARG ALA MET ALA GLU LYS LYS LEU PHE ASN THR VAL SER LYS SER LEU THR ASN GLU
GCA AGG GCA ATG GCT GAA AAG AAG CTA TTT AAT ACG GTT AGT AAA TCT CTA ACA AAT GAG
722
```

```
        GLN LYS GLU LYS LEU GLU GLY ILE ILE THR SER GLN HIS PRO SER GLU SER ASN LYS THR
        CAA AAA GAA AAG CTT GAA GGG ATT ATT ACC TCG CAG CAT CCA TCC GAA TCC AAT AAA ACG
782
        ILE LEU GLY TRP LEU LYS GLU PRO PRO GLY HIS PRO SER PRO GLU THR PHE LEU LYS ILE
        ATA TTG GGT TGG TTA AAA GAG CCA CCG GGT CAT CCT TCA CCC GAA ACT TTT CTA AAA ATA
842
        ILE GLU ARG LEU GLU TYR ILE ARG GLY MET ASP LEU GLU THR VAL GLN ILE SER HIS LEU
        ATA GAA CGA CTC GAA TAC ATA CGA GGA ATG GAT TTA GAA ACA GTG CAA ATT AGT CAT TTG
902
        HIS ARG ASN ARG LEU LEU GLN LEU SER ARG LEU GLY SER ARG TYR GLU PRO TYR ALA PHE
        CAC CGT AAC CGC CTG TTG CAG CTG TCT CGC TTA GGC TCA AGA TAC GAG CCG TAT GCA TTC
962
        ARG ASP PHE GLN GLU ASN LYS ARG TYR SER ILE LEU THR ILE TYR LEU LEU GLN LEU THR
        CGT GAC TTT CAA GAA AAT AAA CGT TAT TCG ATA TTA ACC ATC TAT TTA TTA CAA CTT ACT
1022
        GLN GLU LEU THR ASP LYS ALA PHE GLU ILE HIS ASP ARG GLN ILE LEU SER LEU LEU SER
        CAG GAG CTA ACG GAT AAA GCG TTT GAA ATT CAT GAT AGG CAA ATA CTT AGT TTG TTA TCA
1082
        LYS GLY ARG LYS ALA GLN GLU GLU ILE GLN LYS GLN ASN GLY LYS LYS LEU ASN GLU LYS
        AAA GGT CGT AAG GCT CAA GAG GAA ATC CAG AAA CAA AAC GGT AAA AAG CTA AAT GAG AAA
1142
        VAL ILE HIS PHE THR ASN ILE GLY GLN ALA LEU ILE LYS ALA ARG GLU GLU LYS LEU ASP
        GTT ATA CAC TTT ACG AAC ATC GGA CAA GCA TTA ATT AAA GCA AGA GAG GAA AAA TTA GAC
1202
        VAL PHE LYS VAL LEU GLU SER VAL ILE GLU TRP ASN THR PHE VAL SER SER VAL GLU GLU
        GTT TTT AAG GTT TTA GAA TCG GTT ATT GAA TGG AAT ACC TTT GTC TCT TCA GTA GAA GAG
1262
        ALA GLN GLU LEU ALA ARG PRO ALA ASP TYR ASP TYR LEU ASP LEU LEU GLN LYS ARG PHE
        GCT CAG GAA CTT GCA CGT CCT GCC GAC TAT GAT TAT TTA GAC TTA CTG CAA AAA CGG TTT
1322
        TYR SER LEU ARG LYS TYR THR PRO TYR LEU LEU ARG VAL LEU GLU PHE HIS SER THR LYS
        TAT TCA CTA AGA AAA TAT ACG CCA ACG CTA TTA AGA GTA TTG GAA TTT CAT TCT ACA AAG
1382
        ALA ASN GLU PRO LEU LEU GLN ALA VAL GLU ILE ILE ARG GLY MET ASN GLU SER GLY LYS
        GCA AAT GAG CCA CTT TTA CAA GCT GTT GAG ATT ATC CGA GGA ATG AAC GAA TCT GGA AAG
1442
        ARG LYS VAL PRO ASP ASP SER PRO VAL ASP PHE ILE SER LYS ARG TRP LYS ARG HIS LEU
        CGA AAA GTG CCT GAT GAC TCA CCT GTG GAT TTT ATT TCA AAA CGA TGG AAA AGA CAT TTA
1502
        TYR GLU ASP ASP GLY THR THR ILE ASN ARG HIS TYR TYR GLU MET ALA VAL LEU THR GLU
        TAC GAG GAT GAT GGT ACA ACA ATT AAT CGT CAT TAC TAT GAA ATG GCT GTT TTA ACA GAA
1562
        LEU ARG GLU HIS VAL ARG ALA GLY ASP VAL SER ILE VAL GLY SER ARG GLN TYR ARG ASP
        CTT CGG GAG CAT GTT CGG GCA GGA GAT GTT TCC ATT GTT GGC AGC AGA CAA TAT AGG GAT
1622
        PHE GLU GLU TYR LEU PHE SER GLU ASP THR TRP ASN GLN SER LYS GLY ASN THR ARG LEU
        TTT GAG GAA TAT TTG TTT TCG GAA GAT ACA TGG AAT CAA TCG AAG GGG AAT ACG AGA TTA
1682
        SER VAL SER LEU SER PHE GLU ASP TYR ILE THR GLU ARG THR SRE SER PHE ASN GLU ARG
```

-continued

```
TCA GTT AGT TTA TCA TTC GAA GAT TAT ATA ACG GAG AGA ACC AGC AGC TTT AAT GAA AGG
1742
LEU LYS TRP LEU ALA ALA ASN SER ASN LYS LEU ASP GLY VAL SER LEU GLU LYS GLY LYS
TTA AAG TGG TTA GCT GCC AAT TCC AAT AAG TTA GAT GGG GTT TCT CTT GAA AAA GGA AAG
1802
LEU SER LEU ALA ARG LEU GLU LYS ASP VAL PRO GLU GLU ALA LYS LYS PHE SER ALA SER
CTA TCA CTT GCA CGC TTA GAA AAA GAT GTT CCA GAA GAA GCA AAA AAA TTT AGT GCA AGC
1862
LEU TYR GLN MET LEU PRO ARG ILE LYS LEU THR ASP LEU LEU MET ASP VAL ALA HIS ILE
CTT TAT CAG ATG CTA CCA AGA ATA AAA TTA ACT GAT TTA ATC ATG GAT GTG GCC CAT ATA
1922
THR GLY PHE HIS GLU GLN PHE THR HIS ALA SER ASN ASN ARG LYS PRO ASP LYS GLU GLU
ACA GGA TTT CAT GAG CAA TTC ACT CAT GCT TCC AAT AAT CGA AAA CCA GAT AAG GAA GAA
1982
THR ILE ILE ILE MET ALA ALA LEU LEU GLY MET GLY MET ASN ILE GLY LEU SER LYS MET
ACA ATC ATT ATC ATG GCT GCC CTT TTA GGA ATG GGA ATG AAT ATT GGC TTG AGC AAG ATG
2042
ALA GLU ALA THR PRO GLY LEU THR TYR LYS GLN LEU ALA ASN VAL SER GLN TRP ARG MET
GCC GAA GCC ACA CCC GGA CTT ACA TAT AAG CAA CTA GCC AAT GTA TCT CAA TGG CGC ATG
2102
TYR GLU ASP ALA MET ASN LYS ALA GLN ALA ILE LEU VAL ASN PHE HIS HIS LYS LEU GLN
TAT GAA GAT GCC ATG AAT AAA GCC CAA GCC ATA TTA GTA AAC TTT CAT CAT AAA TTA CAA
2162
LEU PRO PHE TYR TRP GLY ASP GLY THR THR SER SER SER ASP GLY MET ARG MET GLN LEU
TTG CCT TTC TAT TGG GGC GAC GGT ACA ACA TCT TCG TCA GAT GGT ATG AGA ATG CAG CTA
2222
GLY VAL SER SER LEU HIS ALA ASP ALA ASN PRO HIS TYR GLY THR GLY LYS GLY ALA THR
GGT GTT TCA TCA CTA CAT GCA GAT GCA AAT CCA CAT TAT GGA ACT GGA AAA GGA GCC ACC
2282
ILE TYR ARG PHE THR SER ASP GLN PHE SER SER TYR TYR THR LYS ILE ILE HIS THR ASN
ATC TAC CGA TTT ACA AGT GAT CAA TTC TCT TCT TAC TAC ACA AAG ATT ATT CAT ACT AAT
2342
SER ARG ASP ALA ILE HIS VAL LEU ASP GLY LEU LEU HIS HIS GLU THR ASP LEU ASN ILE
TCA AGA GAT GCG ATT CAT GTT TTG GAT GGT TTG TTA CAT CAT GAG ACG GAT CTA AAC ATA
2402
GLU GLU HIS TYR THR ASP THR ALA GLY TYR THR ASP GLN ILE PHE GLY LEU THR HIS LEU
GAG GAA CAT TAT ACA GAC ACT GCC GGT TAC ACT GAC CAA ATA TTC GGA CTG ACT CAT TTA
2462
LEU GLY PHE LYS PHE ALA PRO ARG ILE ARG ASP LEU SER ASP SER LYS LEU PHE THR ILE
TTA GGA TTT AAA TTT GCC CCA AGA ATA AGG GAT TTA TCG GAC TCA AAA TTA TTT ACG ATA
2522
ASP LYS ALA SER GLU TYR PRO LYS LEU GLU ALA ILE LEU ARG GLY GLN ILE ASN THR LYS
GAT AAA GCA AGT GAG TAT CCA AAA CTA GAA GCC ATT TTA CGT GGA CAA ATA AAT ACA AAG
2582
VAL ILE LYS GLU ASN TYR GLU ASP VAL LEU ARG LEU ALA HIS SER ILE ARG GLU GLY THR
GTC ATT AAA GAA AAT TAT GAG GAT GTT TTG CGA TTA GCT CAT TCT ATA AGG GAG GGA ACA
2642
SER PHE SER ILE PRO TYR TYR GLY GLU ALA ARG PHE LEU PHE LYS THR LYS GLN LEU SER
AGT TTC AGC ATC CCT TAT TAT GGG GAA GCT AGG TTC CTA TTC AAG ACA AAA CAG CTT AGC
```

```
                    VAL SER ALA SER LEU ILE MET GLY LYS LEU GLY SER TYR SER ARG GLN ASN SER LEU ALA
                    GTT TCA GCA TCC CTT ATT ATG GGG AAG CTA GGT TCC TAT TCA AGA CAA AAC AGC TTA GCT
2702
THR ALA LEU ARG GLU MET GLY ARG ILE GLU LYS THR ILE PHE ILE LEU ASN TYR ILE SER
ACA GCC TTA CGT GAG ATG GGC CGA ATA GAA AAA ACG ATC TTT ATT TTG AAT TAT ATA TCG
2762
ASP GLU SER LEU ARG ARG LYS ILE GLN ARG GLY LEU ASN LYS GLY GLU ALA MET ASN GLY
GAT GAA TCA TTA AGA AGA AAA ATA CAA AGA GGA TTG AAT AAA GGA GAA GCC ATG AAT GGA
2822
LEU ALA ARG ALA ILE PHE PHE GLY LYS GLN GLY GLU LEU ARG GLU ARG THR ILE GLN HIS
TTG GCA AGA GCT ATT TTC TTC GGA AAA CAA GGT GAG CTT AGA GAA CGC ACC ATA CAG CAT
2882
GLN LEU GLN ARG ALA SER ALA LEU ASN ILE ILE ILE ASN ALA ILE SER ILE TRP ASN THR
CAA TTG CAA AGA GCC AGT GCT TTA AAC ATA ATT ATC AAT GCT ATA AGT ATT TGG AAT ACT
2942
TCT CCA CCT AAC AAC AGC AGT TGA ATA TAA AAA ACG GAC AGG TAG CTT TAA TGA AGA TTT
LEU HIS LEU THR THR ALA VAL GLU TYR LYS LSY ARG THR GLY SRE PHE ASN GLU ASP LEU
CTC CAC CTA ACA ACA GCA GTT GAA TAT AAA AAA CGG ACA GGT AGC TTT AAT GAA GAT TTG
3002
LEU HIS HIS MET SER PRO LEU GLY TRP GLU HIS ILE ASN LEU LEU GLY GLU TYR HIS PHE
TTA CAC CAT ATG TCG CCC TTA GGT TGG GAA CAT ATT AAT TTA CTA GGA GAA TAC CAT TTT
3062
ASN SER GLU LYS VAL VAL SER LEU ASN SER LEU ARG PRO LEU LYS LEU SER
AAC TCA GAG AAA GTA GTC TCA TTA AAT TCT TTA AGA CCA CTA AAA CTT TCT TAA CGT TG
3121
TTA AAA ACG AGG GAT TCG TCA GGA AAA TAG CTA TAG CGT TGT AAA TCC GCA TTT TCC TGA
3181
CGC TAC CCC
```

LIST OF SEQUENCES : ii     SacI
                           GAGCTCTTCCTTCAACGCACTTCTGTACCAAGAGTTGTTGTC 42

CATTTGATCACTAACAATAGCTTCCCCTGCTTTCTTCAAGCCCTTTGTCATAAAATCGTTAGATTTTCA 111

TCATAAAAATACGAGAAAGACAACAGGAAGACCGCAAATTTTCTTTTCTTTTCCTAGGTACACTGAATG 180

```
                     RBS       M  K  K  I  A  V  L  F  G  G
TAACCTTAAAAGAAAAAAGGAAAGGAAGAAAATGATGAAAAAAATTGCCGTTTTATTTGGAGGG         244

N  S  P  K  Y  S  V  S  L  T  S  A  A  S  V  I  Q  A  I  D
AATTCTCCAGAATACTCAGTGTCACTAACCTCAGCAGCAAGTGTGATCCAAGCTATTGAC             304

P  L  K  Y  E  V  M  T  I  G  I  A  P  T  M  D  W  Y  W  Y
CCGCTGAAATATGAAGTAATGACCATTGGCATCGCACCAACAATGGATTGGTATTGGTAT             364

Q  G  N  L  A  N  V  R  N  D  T  W  L  E  D  H  K  N  C  H
CAAGGAAACCTCGCGAATGTTCGCAATGATACTTGGCTAGAAGATCACAAAAACTGTCAC             424

Q  L  T  F  S  S  Q  G  F  I  L  G  E  K  R  I  V  P  D  V
CAGCTGACTTTTTCTAGCCAAGGATTTATATTAGGAGAAAAAACGAATCGTCCCTGATGTC            484

L  F  P  V  L  H  G  K  Y  G  E  D  G  C  I  Q  G  L  L  E
CTCTTTCCAGTCTTGCATGGGAAGTATGGCGAGGATGGCTGTATCCAAGGACTGCTTGAA             544

L  M  N  L  P  Y  V  G  C  H  V  A  A  S  A  L  C  M  N  K
CTAATGAACCTGCCTTATGTTGGTTGCCATGTCGCTGCCTCCGCATTATGTATGAACAAA             604

W  L  L  H  Q  L  A  D  T  M  G  I  A  S  A  P  T  L  L  L
TGGCTCTTGCATCAACTTGCTGATACCATGGGAATCGCTAGTGCTCCCACTTTGCTTTTA             664

S  R  Y  E  N  D  P  A  T  I  D  R  F  I  Q  D  H  G  F  P
TCCCGCTATGAAAACGATCCTGCCACAATCGATCGTTTTATTCAAGACCATGGATTCCCG            724
```

```
        I   F   I   K   P   N   E   A   G   S   S   K   G   I   T   K   V   T   D   K
        ATCTTTATCAAGCCGAATGAAGCCGGTTCTTCAAAAGGGATCACAAAAGTAACTGACAAA                  784

T   A   L   Q   S   A   L   T   T   A   F   A   Y   G   S   T   V   L   I   Q
        ACAGCGCTCCAATCTGCATTAACGACTGCTTTTGCTTACGGTTCTACTGTGTTGATCCAA                  844

K   A   I   A   G   I   E   I   G   C   G   I   L   G   N   E   Q   L   T   I
        AAGGCGATAGCGGGTATTGAAATTGGCTGCGGCATCTTAGGAAATGAGCAATTGACGATT                  904

G   A   C   D   A   I   S   L   V   D   G   F   F   D   F   E   E   K   Y   Q
        GGTGCTTGTGATGCGATTTCTCTTGTCGACGGTTTTTTTGATTTTGAAGAGAAATACCAA                  964

L   I   S   A   T   I   T   V   P   A   P   L   P   L   A   L   E   S   Q   I
        TTAATCAGCGCCACGATCACTGTCCCAGCACCATTGCCTCTCGCGCTTGAATCACAGATC                 1024

K   E   Q   A   Q   L   L   Y   R   N   L   G   L   T   G   L   A   R   I   D
        AAGGAGCAGGCACAGCTGCTTTATCGAAACTTGGGATTGACGGGTCTGGCTCGAATCGAT                 1084

F   F   V   T   N   Q   G   A   I   Y   L   N   E   I   N   T   M   P   G   F
        TTTTTCGTCACCAATCAAGGAGCGATTTATTTAAACGAAATCAACACCATGCCGGGATTT                 1144

T   G   H   S   R   Y   P   A   M   M   A   E   V   G   L   S   Y   E   I   L
        ACTGGGCACTCCCGCTACCCAGCTATGATGGCGGAAGTCGGGTTATCCTACGAAATATTA                 1204

V   E   Q   L   E   A   L   A   E   E   D   K   R   *
        GTAGAGCAATTGATTGCACTGGCAGAGGAGGACAAACGATGAACACATTACAATTGATCAATA              1267

AAAACCATCCATTGAAAAAAATCAAGAGCCCCCGCACTTAGTGCTAGCTCCTTTTAGCGATCACGATG          1336

TTTACCTGCAG                                                                  1347
            PstI
```

---

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
       (A) LENGTH: 966 base pairs
       (B) TYPE: nucleic acid
       (C) STRANDEDNESS: unknown
       (D) TOPOLOGY: linear (ii) MOLECULE TYPE: DNA (genomic)

(ix) FEATURE:
       (A) NAME/KEY: CDS
       (B) LOCATION: 1..966

(xi) SEQUENCE DESCRIPTION: SEQ ID NO:1:

```
ATG AAT AAC ATC GGC ATT ACT GTT TAT GGA TGT GAG CAG GAT GAG GCA        48
Met Asn Asn Ile Gly Ile Thr Val Tyr Gly Cys Glu Gln Asp Glu Ala
 1               5                  10                  15

GAT GCA TTC CAT GCT CTT TCG CCT CGC TTT GGC GTT ATG GCA ACG ATA        96
Asp Ala Phe His Ala Leu Ser Pro Arg Phe Gly Val Met Ala Thr Ile
                20                  25                  30

ATT AAC GCC AAC GTG TCG GAA TCC AAC GCC AAA TCC GCG CCT TTC AAT       144
Ile Asn Ala Asn Val Ser Glu Ser Asn Ala Lys Ser Ala Pro Phe Asn
            35                  40                  45

CAA TGT ATC AGT GTG GGA CAT AAA TCA GAG ATT TCC GCC TCT ATT CTT       192
Gln Cys Ile Ser Val Gly His Lys Ser Glu Ile Ser Ala Ser Ile Leu
        50                  55                  60

CTT GCG CTG AAG AGA GCC GGT GTG AAA TAT ATT TCT ACC CGA AGC ATC       240
Leu Ala Leu Lys Arg Ala Gly Val Lys Tyr Ile Ser Thr Arg Ser Ile
65                  70                  75                  80

GGC TGC AAT CAT ATA GAT ACA ACT GCT GCT AAG AGA ATG GGC ATC ACT       288
Gly Cys Asn His Ile Asp Thr Thr Ala Ala Lys Arg Met Gly Ile Thr
                85                  90                  95
```

| | | |
|---|---|---|
| GTC GAC AAT GTG GCG TAC TCG CCG GAT AGC GTT GCC GAT TAT ACT ATG<br>Val Asp Asn Val Ala Tyr Ser Pro Asp Ser Val Ala Asp Tyr Thr Met<br>              100                        105                      110 | 336 |
| ATG CTA ATT CTT ATG GCA GTA CGC AAC GTA AAA TCG ATT GTG CGC TCT<br>Met Leu Ile Leu Met Ala Val Arg Asn Val Lys Ser Ile Val Arg Ser<br>       115                       120                       125 | 384 |
| GTG GAA AAA CAT GAT TTC AGG TTG GAC AGC GAC CGT GGC AAG GTA CTC<br>Val Glu Lys His Asp Phe Arg Leu Asp Ser Asp Arg Gly Lys Val Leu<br>130                         135                       140 | 432 |
| AGC GAC ATG ACA GTT GGT GTG GTG GGA ACG GGC CAG ATA GGC AAA GCG<br>Ser Asp Met Thr Val Gly Val Val Gly Thr Gly Gln Ile Gly Lys Ala<br>145                       150                     155                160 | 480 |
| GTT ATT GAG CGG CTG CGA GGA TTT GGA TGT AAA GTG TTG GCT TAT AGT<br>Val Ile Glu Arg Leu Arg Gly Phe Gly Cys Lys Val Leu Ala Tyr Ser<br>               165                       170                       175 | 528 |
| CGC AGC CGA AGT ATA GAG GTA AAC TAT GTA CCG TTT GAT GAG TTG CTG<br>Arg Ser Arg Ser Ile Glu Val Asn Tyr Val Pro Phe Asp Glu Leu Leu<br>              180                       185                    190 | 576 |
| CAA AAT AGC GAT ATC GTT ACG CTT CAT GTG CCG CTC AAT ACG GAT ACG<br>Gln Asn Ser Asp Ile Val Thr Leu His Val Pro Leu Asn Thr Asp Thr<br>             195                        200                   205 | 624 |
| CAC TAT ATT ATC AGC CAC GAA CAA ATA CAG AGA ATG AAG CAA GGA GCA<br>His Tyr Ile Ile Ser His Glu Gln Ile Gln Arg Met Lys Gln Gly Ala<br>210                       215                     220 | 672 |
| TTT CTT ATC AAT ACT GGG CGC GGT CCA CTT GTA GAT ACC TAT GAG TTG<br>Phe Leu Ile Asn Thr Gly Arg Gly Pro Leu Val Asp Thr Tyr Glu Leu<br>225                       230                     235                 240 | 720 |
| GTT AAA GCA TTA GAA AAC GGG AAA CTG GGC GGT GCC GCA TTG GAT GTA<br>Val Lys Ala Leu Glu Asn Gly Lys Leu Gly Gly Ala Ala Leu Asp Val<br>                   245                     250                    255 | 768 |
| TTG GAA GGA GAG GAA GAG TTT TTC TAC TCT GAT TGC ACC CAA AAA CCA<br>Leu Glu Gly Glu Glu Glu Phe Phe Tyr Ser Asp Cys Thr Gln Lys Pro<br>              260                       265                    270 | 816 |
| ATT GAT AAT CAA TTT TTA CTT AAA CTT CAA AGA ATG CCT AAC GTG ATA<br>Ile Asp Asn Gln Phe Leu Leu Lys Leu Gln Arg Met Pro Asn Val Ile<br>             275                        280                   285 | 864 |
| ATC ACA CCG CAT ACG GCC TAT TAT ACC GAG CAA GCG TTG CGT GAT ACC<br>Ile Thr Pro His Thr Ala Tyr Tyr Thr Glu Gln Ala Leu Arg Asp Thr<br>290                       295                     300 | 912 |
| GTT GAA AAA ACC ATT AAA AAC TGT TTG GAT TTT GAA AGG AGA CAG GAG<br>Val Glu Lys Thr Ile Lys Asn Cys Leu Asp Phe Glu Arg Arg Gln Glu<br>305                       310                     315                320 | 960 |
| CAT GAA<br>His Glu | 966 |

(2) INFORMATION FOR SEQ ID NO:2:

(i) SEQUENCE CHARACTERISTICS:
        (A) LENGTH: 322 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Asn Ile Gly Ile Thr Val Tyr Gly Cys Glu Gln Asp Glu Ala
1                 5                     10                    15

Asp Ala Phe His Ala Leu Ser Pro Arg Phe Gly Val Met Ala Thr Ile
                 20                     25                    30

Ile Asn Ala Asn Val Ser Glu Ser Asn Ala Lys Ser Ala Pro Phe Asn
                 35                     40                    45

```
Gln Cys Ile Ser Val Gly His Lys Ser Glu Ile Ser Ala Ser Ile Leu
 50                  55                  60
Leu Ala Leu Lys Arg Ala Gly Val Lys Tyr Ile Ser Thr Arg Ser Ile
 65                  70                  75                  80
Gly Cys Asn His Ile Asp Thr Thr Ala Ala Lys Arg Met Gly Ile Thr
                 85                  90                  95
Val Asp Asn Val Ala Tyr Ser Pro Asp Ser Val Ala Asp Tyr Thr Met
            100                 105                 110
Met Leu Ile Leu Met Ala Val Arg Asn Val Lys Ser Ile Val Arg Ser
        115                 120                 125
Val Glu Lys His Asp Phe Arg Leu Asp Ser Asp Arg Gly Lys Val Leu
    130                 135                 140
Ser Asp Met Thr Val Gly Val Val Gly Thr Gly Gln Ile Gly Lys Ala
145                 150                 155                 160
Val Ile Glu Arg Leu Arg Gly Phe Gly Cys Lys Val Leu Ala Tyr Ser
                165                 170                 175
Arg Ser Arg Ser Ile Glu Val Asn Tyr Val Pro Phe Asp Glu Leu Leu
            180                 185                 190
Gln Asn Ser Asp Ile Val Thr Leu His Val Pro Leu Asn Thr Asp Thr
        195                 200                 205
His Tyr Ile Ile Ser His Glu Gln Ile Gln Arg Met Lys Gln Gly Ala
    210                 215                 220
Phe Leu Ile Asn Thr Gly Arg Gly Pro Leu Val Asp Thr Tyr Glu Leu
225                 230                 235                 240
Val Lys Ala Leu Glu Asn Gly Lys Leu Gly Gly Ala Ala Leu Asp Val
                245                 250                 255
Leu Glu Gly Glu Glu Glu Phe Phe Tyr Ser Asp Cys Thr Gln Lys Pro
            260                 265                 270
Ile Asp Asn Gln Phe Leu Leu Lys Leu Gln Arg Met Pro Asn Val Ile
        275                 280                 285
Ile Thr Pro His Thr Ala Tyr Tyr Thr Glu Gln Ala Leu Arg Asp Thr
    290                 295                 300
Val Glu Lys Thr Ile Lys Asn Cys Leu Asp Phe Glu Arg Arg Gln Glu
305                 310                 315                 320
His Glu (2) INFORMATION FOR SEQ ID NO:3:

(i) SEQUENCE CHARACTERISTICS:
        (A) LENGTH: 1029 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..1029

(xi) SEQUENCE DESCRIPTION: SEQ ID NO:3:

ATG AAT AGA ATA AAA GTT GCA ATA CTG TTT GGG GGT TGC TCA GAG GAG      48
Met Asn Arg Ile Lys Val Ala Ile Leu Phe Gly Gly Cys Ser Glu Glu
 1               5                  10                  15

CAT GAC GTA TCG GTA AAA TCT GCA ATA GAG ATA GCC GCT AAC ATT AAT      96
His Asp Val Ser Val Lys Ser Ala Ile Glu Ile Ala Ala Asn Ile Asn
                20                  25                  30

AAA GAA AAA TAC GAG CCG TTA TAC ATT GGA ATT ACG AAA TCT GGT GTA     144
```

```
                    Lys Glu Lys Tyr Glu Pro Leu Tyr Ile Gly Ile Thr Lys Ser Gly Val
                             35                  40                  45

TGG AAA ATG TGC GAA AAA CCT TGC GCG GAA TGG GAA AAC GAC AAT TGC              192
Trp Lys Met Cys Glu Lys Pro Cys Ala Glu Trp Glu Asn Asp Asn Cys
 50                  55                  60

TAT TCA GCT GTA CTC TCG CCG GAT AAA AAA ATG CAC GGA TTA CTT GTT              240
Tyr Ser Ala Val Leu Ser Pro Asp Lys Lys Met His Gly Leu Leu Val
 65                  70                  75                  80

AAA AAG AAC CAT GAA TAT GAA ATC AAC CAT GTT GAT GTA GCA TTT TCA              288
Lys Lys Asn His Glu Tyr Glu Ile Asn His Val Asp Val Ala Phe Ser
                 85                  90                  95

GCT TTG CAT GGC AAG TCA GGT GAA GAT GGA TCC ATA CAA GGT CTG TTT              336
Ala Leu His Gly Lys Ser Gly Glu Asp Gly Ser Ile Gln Gly Leu Phe
            100                 105                 110

GAA TTG TCC GGT ATC CCT TTT GTA GGC TGC GAT ATT CAA AGC TCA GCA              384
Glu Leu Ser Gly Ile Pro Phe Val Gly Cys Asp Ile Gln Ser Ser Ala
        115                 120                 125

ATT TGT ATG GAC AAA TCG TTG ACA TAC ATC GTT GCG AAA AAT GCT GGG              432
Ile Cys Met Asp Lys Ser Leu Thr Tyr Ile Val Ala Lys Asn Ala Gly
    130                 135                 140

ATA GCT ACT CCC GCC TTT TGG GTT ATT AAT AAA GAT GAT AGG CCG GTG              480
Ile Ala Thr Pro Ala Phe Trp Val Ile Asn Lys Asp Asp Arg Pro Val
145                 150                 155                 160

GCA GCT ACG TTT ACC TAT CCT GTT TTT GTT AAG CCG GCG CGT TCA GGC              528
Ala Ala Thr Phe Thr Tyr Pro Val Phe Val Lys Pro Ala Arg Ser Gly
                165                 170                 175

TCA TCC TTC GGT GTG AAA AAA GTC AAT AGC GCG GAC GAA TTG GAC TAC              576
Ser Ser Phe Gly Val Lys Lys Val Asn Ser Ala Asp Glu Leu Asp Tyr
            180                 185                 190

GCA ATT GAA TCG GCA AGA CAA TAT GAC AGC AAA ATC TTA ATT GAG CAG              624
Ala Ile Glu Ser Ala Arg Gln Tyr Asp Ser Lys Ile Leu Ile Glu Gln
        195                 200                 205

GCT GTT TCG GGC TGT GAG GTC GGT TGT GCG GTA TTG GGA AAC AGT GCC              672
Ala Val Ser Gly Cys Glu Val Gly Cys Ala Val Leu Gly Asn Ser Ala
    210                 215                 220

GCG TTA GTT GTT GGC GAG GTG GAC CAA ATC AGG CTG CAG TAC GGA ATC              720
Ala Leu Val Val Gly Glu Val Asp Gln Ile Arg Leu Gln Tyr Gly Ile
225                 230                 235                 240

TTT CGT ATT CAT CAG GAA GTC GAG CCG GAA AAA GGC TCT GAA AAC GCA              768
Phe Arg Ile His Gln Glu Val Glu Pro Glu Lys Gly Ser Glu Asn Ala
                245                 250                 255

GTT ATA ACC GTT CCC GCA GAC CTT TCA GCA GAG GAG CGA GGA CGG ATA              816
Val Ile Thr Val Pro Ala Asp Leu Ser Ala Glu Glu Arg Gly Arg Ile
            260                 265                 270

CAG GAA ACG GCA AAA AAA ATA TAT AAA GCG CTC GGC TGT AGA GGT CTA              864
Gln Glu Thr Ala Lys Lys Ile Tyr Lys Ala Leu Gly Cys Arg Gly Leu
        275                 280                 285

GCC CGT GTG GAT ATG TTT TTA CAA GAT AAC GGC CGC ATT GTA CTG AAC              912
Ala Arg Val Asp Met Phe Leu Gln Asp Asn Gly Arg Ile Val Leu Asn
    290                 295                 300

GAA GTC AAT ACT CTG CCC GGT TTC ACG TCA TAC AGT CGT TAT CCC CGT              960
Glu Val Asn Thr Leu Pro Gly Phe Thr Ser Tyr Ser Arg Tyr Pro Arg
305                 310                 315                 320

ATG ATG GCC GCT GCA GGT ATT GCA CTT CCC GAA CTG ATT GAC CGC TTG             1008
Met Met Ala Ala Ala Gly Ile Ala Leu Pro Glu Leu Ile Asp Arg Leu
                325                 330                 335

ATC GTA TTA GCG TTA AAG GGG                                                 1029
Ile Val Leu Ala Leu Lys Gly
            340
```

(2) INFORMATION FOR SEQ ID NO:4:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Arg Ile Lys Val Ala Ile Leu Phe Gly Gly Cys Ser Glu Glu
 1               5                  10                  15

His Asp Val Ser Val Lys Ser Ala Ile Glu Ile Ala Ala Asn Ile Asn
            20                  25                  30

Lys Glu Lys Tyr Glu Pro Leu Tyr Ile Gly Ile Thr Lys Ser Gly Val
        35                  40                  45

Trp Lys Met Cys Glu Lys Pro Cys Ala Glu Trp Glu Asn Asp Asn Cys
     50                  55                  60

Tyr Ser Ala Val Leu Ser Pro Asp Lys Lys Met His Gly Leu Leu Val
 65                  70                  75                  80

Lys Lys Asn His Glu Tyr Glu Ile Asn His Val Asp Val Ala Phe Ser
                85                  90                  95

Ala Leu His Gly Lys Ser Gly Glu Asp Gly Ser Ile Gln Gly Leu Phe
            100                 105                 110

Glu Leu Ser Gly Ile Pro Phe Val Gly Cys Asp Ile Gln Ser Ser Ala
        115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
    210                 215                 220

Ala Leu Val Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
                245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340
```

(2) INFORMATION FOR SEQ ID NO:5:

(i) SEQUENCE CHARACTERISTICS:
        (A) LENGTH: 606 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..606

(xi) SEQUENCE DESCRIPTION: SEQ ID NO:5:

```
ATG GAA ATA GGA TTT ACT TTT TTA GAT GAA ATA GTA CAC GGT GTT CGT        48
Met Glu Ile Gly Phe Thr Phe Leu Asp Glu Ile Val His Gly Val Arg
 1               5                  10                  15

TGG GAC GCT AAA TAT GCC ACT TGG GAT AAT TTC ACC GGA AAA CCG GTT        96
Trp Asp Ala Lys Tyr Ala Thr Trp Asp Asn Phe Thr Gly Lys Pro Val
                20                  25                  30

GAC GGT TAT GAA GTA AAT CGC ATT GTA GGG ACA TAC GAG TTG GCT GAA       144
Asp Gly Tyr Glu Val Asn Arg Ile Val Gly Thr Tyr Glu Leu Ala Glu
            35                  40                  45

TCG CTT TTG AAG GCA AAA GAA CTG GCT GCT ACC CAA GGG TAC GGA TTG       192
Ser Leu Leu Lys Ala Lys Glu Leu Ala Ala Thr Gln Gly Tyr Gly Leu
        50                  55                  60

CTT CTA TGG GAC GGT TAC CGT CCT AAG CGT GCT GTA AAC TGT TTT ATG       240
Leu Leu Trp Asp Gly Tyr Arg Pro Lys Arg Ala Val Asn Cys Phe Met
 65                  70                  75                  80

CAA TGG GCT GCA CAG CCG GAA AAT AAC CTG ACA AAG GAA AGT TAT TAT       288
Gln Trp Ala Ala Gln Pro Glu Asn Asn Leu Thr Lys Glu Ser Tyr Tyr
                85                  90                  95

CCC AAT ATT GAC CGA ACT GAG ATG ATT TCA AAA GGA TAC GTG GCT TCA       336
Pro Asn Ile Asp Arg Thr Glu Met Ile Ser Lys Gly Tyr Val Ala Ser
            100                 105                 110

AAA TCA AGC CAT AGC CGC GGC AGT GCC ATT GAT CTT ACG CTT TAT CGA       384
Lys Ser Ser His Ser Arg Gly Ser Ala Ile Asp Leu Thr Leu Tyr Arg
        115                 120                 125

TTA GAC ACG GGT GAG CTT GTA CCA ATG GGG AGC CGA TTT GAT TTT ATG       432
Leu Asp Thr Gly Glu Leu Val Pro Met Gly Ser Arg Phe Asp Phe Met
130                 135                 140

GAT GAA CGC TCT CAT CAT GCG GCA AAT GGA ATA TCA TGC AAT GAA GCG       480
Asp Glu Arg Ser His His Ala Ala Asn Gly Ile Ser Cys Asn Glu Ala
145                 150                 155                 160

CAA AAT CGC AGA CGT TTG CGC TCC ATC ATG GAA AAC AGT GGG TTT GAA       528
Gln Asn Arg Arg Arg Leu Arg Ser Ile Met Glu Asn Ser Gly Phe Glu
                165                 170                 175

GCA TAT AGC CTC GAA TGG TGG CAC TAT GTA TTA AGA GAC GAA CCA TAC       576
Ala Tyr Ser Leu Glu Trp Trp His Tyr Val Leu Arg Asp Glu Pro Tyr
            180                 185                 190

CCC AAT AGC TAT TTT GAT TTC CCC GTT AAA                               606
Pro Asn Ser Tyr Phe Asp Phe Pro Val Lys
        195                 200
```

(2) INFORMATION FOR SEQ ID NO:6:

(i) SEQUENCE CHARACTERISTICS:
        (A) LENGTH: 202 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Ile Gly Phe Thr Phe Leu Asp Glu Ile Val His Gly Val Arg
 1               5                  10                  15
```

```
Trp Asp Ala Lys Tyr Ala Thr Trp Asp Asn Phe Thr Gly Lys Pro Val
                 20                  25                  30

Asp Gly Tyr Glu Val Asn Arg Ile Val Gly Thr Tyr Glu Leu Ala Glu
             35                  40                  45

Ser Leu Leu Lys Ala Lys Glu Leu Ala Ala Thr Gln Gly Tyr Gly Leu
 50                  55                  60

Leu Leu Trp Asp Gly Tyr Arg Pro Lys Arg Ala Val Asn Cys Phe Met
 65                  70                  75                  80

Gln Trp Ala Ala Gln Pro Glu Asn Asn Leu Thr Lys Glu Ser Tyr Tyr
             85                  90                  95

Pro Asn Ile Asp Arg Thr Glu Met Ile Ser Lys Gly Tyr Val Ala Ser
            100                 105                 110

Lys Ser Ser His Ser Arg Gly Ser Ala Ile Asp Leu Thr Leu Tyr Arg
            115                 120                 125

Leu Asp Thr Gly Glu Leu Val Pro Met Gly Ser Arg Phe Asp Phe Met
            130                 135                 140

Asp Glu Arg Ser His His Ala Ala Asn Gly Ile Ser Cys Asn Glu Ala
145                 150                 155                 160

Gln Asn Arg Arg Arg Leu Arg Ser Ile Met Glu Asn Ser Gly Phe Glu
                165                 170                 175

Ala Tyr Ser Leu Glu Trp Trp His Tyr Val Leu Arg Asp Glu Pro Tyr
            180                 185                 190

Pro Asn Ser Tyr Phe Asp Phe Pro Val Lys
            195                 200
```

(2) INFORMATION FOR SEQ ID NO:7:

(i) SEQUENCE CHARACTERISTICS:
        (A) LENGTH: 1347 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 215..1243

(xi) SEQUENCE DESCRIPTION: SEQ ID NO:7:

```
GAGCTCTTCC TTCAACGCAC TTCTGTACCA AGAGTTGTTG TCCATTTGAT CACTAACAAT      60

AGCTTCCCCT GCTTTCTTCA AGCCCTTTGT CATAAAATCG TTAGATTTTC ATCATAAAAA     120

TACGAGAAAG ACAACAGGAA GACCGCAAAT TTTCTTTTCT TTTCCTAGGT ACACTGAATG     180

TAACCTTAAA AGAAAAAAGG AAAGGAAGAA AATG ATG AAA AAA ATT GCC GTT         232
                                  Met Lys Lys Ile Ala Val
                                    1               5

TTA TTT GGA GGG AAT TCT CCA GAA TAC TCA GTG TCA CTA ACC TCA GCA       280
Leu Phe Gly Gly Asn Ser Pro Glu Tyr Ser Val Ser Leu Thr Ser Ala
         10                  15                  20

GCA AGT GTG ATC CAA GCT ATT GAC CCG CTG AAA TAT GAA GTA ATG ACC       328
Ala Ser Val Ile Gln Ala Ile Asp Pro Leu Lys Tyr Glu Val Met Thr
             25                  30                  35

ATT GGC ATC GCA CCA ACA ATG GAT TGG TAT TGG TAT CAA GGA AAC CTC       376
Ile Gly Ile Ala Pro Thr Met Asp Trp Tyr Trp Tyr Gln Gly Asn Leu
         40                  45                  50

GCG AAT GTT CGC AAT GAT ACT TGG CTA GAA GAT CAC AAA AAC TGT CAC       424
Ala Asn Val Arg Asn Asp Thr Trp Leu Glu Asp His Lys Asn Cys His
 55                  60                  65                  70
```

```
CAG CTG ACT TTT TCT AGC CAA GGA TTT ATA TTA GGA GAA AAA CGA ATC      472
Gln Leu Thr Phe Ser Ser Gln Gly Phe Ile Leu Gly Glu Lys Arg Ile
            75                  80                  85

GTC CCT GAT GTC CTC TTT CCA GTC TTG CAT GGG AAG TAT GGC GAG GAT      520
Val Pro Asp Val Leu Phe Pro Val Leu His Gly Lys Tyr Gly Glu Asp
        90                  95                 100

GGC TGT ATC CAA GGA CTG CTT GAA CTA ATG AAC CTG CCT TAT GTT GGT      568
Gly Cys Ile Gln Gly Leu Leu Glu Leu Met Asn Leu Pro Tyr Val Gly
            105                 110                 115

TGC CAT GTC GCT GCC TCC GCA TTA TGT ATG AAC AAA TGG CTC TTG CAT      616
Cys His Val Ala Ala Ser Ala Leu Cys Met Asn Lys Trp Leu Leu His
120                 125                 130

CAA CTT GCT GAT ACC ATG GGA ATC GCT AGT GCT CCC ACT TTG CTT TTA      664
Gln Leu Ala Asp Thr Met Gly Ile Ala Ser Ala Pro Thr Leu Leu Leu
135                 140                 145                 150

TCC CGC TAT GAA AAC GAT CCT GCC ACA ATC GAT CGT TTT ATT CAA GAC      712
Ser Arg Tyr Glu Asn Asp Pro Ala Thr Ile Asp Arg Phe Ile Gln Asp
                155                 160                 165

CAT GGA TTC CCG ATC TTT ATC AAG CCG AAT GAA GCC GGT TCT TCA AAA      760
His Gly Phe Pro Ile Phe Ile Lys Pro Asn Glu Ala Gly Ser Ser Lys
            170                 175                 180

GGG ATC ACA AAA GTA ACT GAC AAA ACA GCG CTC CAA TCT GCA TTA ACG      808
Gly Ile Thr Lys Val Thr Asp Lys Thr Ala Leu Gln Ser Ala Leu Thr
            185                 190                 195

ACT GCT TTT GCT TAC GGT TCT ACT GTG TTG ATC CAA AAG GCG ATA GCG      856
Thr Ala Phe Ala Tyr Gly Ser Thr Val Leu Ile Gln Lys Ala Ile Ala
200                 205                 210

GGT ATT GAA ATT GGC TGC GGC ATC TTA GGA AAT GAG CAA TTG ACG ATT      904
Gly Ile Glu Ile Gly Cys Gly Ile Leu Gly Asn Glu Gln Leu Thr Ile
215                 220                 225                 230

GGT GCT TGT GAT GCG ATT TCT CTT GTC GAC GGT TTT TTT GAT TTT GAA      952
Gly Ala Cys Asp Ala Ile Ser Leu Val Asp Gly Phe Phe Asp Phe Glu
                235                 240                 245

GAG AAA TAC CAA TTA ATC AGC GCC ACG ATC ACT GTC CCA GCA CCA TTG     1000
Glu Lys Tyr Gln Leu Ile Ser Ala Thr Ile Thr Val Pro Ala Pro Leu
            250                 255                 260

CCT CTC GCG CTT GAA TCA CAG ATC AAG GAG CAG GCA CAG CTG CTT TAT     1048
Pro Leu Ala Leu Glu Ser Gln Ile Lys Glu Gln Ala Gln Leu Leu Tyr
            265                 270                 275

CGA AAC TTG GGA TTG ACG GGT CTG GCT CGA ATC GAT TTT TTC GTC ACC     1096
Arg Asn Leu Gly Leu Thr Gly Leu Ala Arg Ile Asp Phe Phe Val Thr
280                 285                 290

AAT CAA GGA GCG ATT TAT TTA AAC GAA ATC AAC ACC ATG CCG GGA TTT     1144
Asn Gln Gly Ala Ile Tyr Leu Asn Glu Ile Asn Thr Met Pro Gly Phe
295                 300                 305                 310

ACT GGG CAC TCC CGC TAC CCA GCT ATG ATG GCG GAA GTC GGG TTA TCC     1192
Thr Gly His Ser Arg Tyr Pro Ala Met Met Ala Glu Val Gly Leu Ser
                315                 320                 325

TAC GAA ATA TTA GTA GAG CAA TTG ATT GCA CTG GCA GAG GAG GAC AAA     1240
Tyr Glu Ile Leu Val Glu Gln Leu Ile Ala Leu Ala Glu Glu Asp Lys
            330                 335                 340

CGA TGAACACATT ACAATTGATC AATAAAAACC ATCCATTGAA AAAAAATCAA          1293
Arg

GAGCCCCCGC ACTTAGTGCT AGCTCCTTTT AGCGATCACG ATGTTTACCT GCAG         1347

(2) INFORMATION FOR SEQ ID NO:8:

(i) SEQUENCE CHARACTERISTICS:
        (A) LENGTH: 343 amino acids
        (B) TYPE: amino acid
        (D) TOPOLOGY: linear
```

(ii) MOLECULE TYPE: protein (xi) SEQUENCE DESCRIPTION: SEQ ID NO:8:

| Met | Lys | Lys | Ile | Ala | Val | Leu | Phe | Gly | Gly | Asn | Ser | Pro | Glu | Tyr | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Ser Leu Thr Ser Ala Ala Ser Val Ile Gln Ala Ile Asp Pro Leu
              20                  25                  30

Lys Tyr Glu Val Met Thr Ile Gly Ile Ala Pro Thr Met Asp Trp Tyr
         35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
             100                 105                 110

Asn Leu Pro Tyr Val Gly Cys His Val Ala Ala Ser Ala Leu Cys Met
         115                 120                 125

Asn Lys Trp Leu Leu His Gln Leu Ala Asp Thr Met Gly Ile Ala Ser
130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                 165                 170                 175

Glu Ala Gly Ser Ser Lys Gly Ile Thr Lys Val Thr Asp Lys Thr Ala
             180                 185                 190

Leu Gln Ser Ala Leu Thr Thr Ala Phe Ala Tyr Gly Ser Thr Val Leu
         195                 200                 205

Ile Gln Lys Ala Ile Ala Gly Ile Glu Ile Gly Cys Gly Ile Leu Gly
         210                 215                 220

Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                 245                 250                 255

Thr Val Pro Ala Pro Leu Pro Leu Ala Leu Glu Ser Gln Ile Lys Glu
             260                 265                 270

Gln Ala Gln Leu Leu Tyr Arg Asn Leu Gly Leu Thr Gly Leu Ala Arg
         275                 280                 285

Ile Asp Phe Phe Val Thr Asn Gln Gly Ala Ile Tyr Leu Asn Glu Ile
290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                 325                 330                 335

Leu Ala Glu Glu Asp Lys Arg
             340

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GGNGARGAYG GNWSNHTNCA RGGN                                      24
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
AAYACNHTNC CNGGNTTYAC                                           20
```

(2) INFORMATION FOR SEQ ID NO:11:

(i) SEQUENCE CHARACTERISTICS:
        (A) LENGTH: 693 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..693

(xi) SEQUENCE DESCRIPTION: SEQ ID NO:11:

```
ATG AGC GAT AAA ATA CTT ATT GTG GAT GAT GAA CAT GAA ATT GCC GAT      48
Met Ser Asp Lys Ile Leu Ile Val Asp Asp Glu His Glu Ile Ala Asp
 1               5                  10                  15

TTG GTT GAA TTA TAC TTA AAA AAC GAG AAT TAT ACG GTT TTC AAA TAC      96
Leu Val Glu Leu Tyr Leu Lys Asn Glu Asn Tyr Thr Val Phe Lys Tyr
             20                  25                  30

TAT ACC GCC AAA GAA GCA TTG GAA TGT ATA GAC AAG TCT GAG ATT GAC     144
Tyr Thr Ala Lys Glu Ala Leu Glu Cys Ile Asp Lys Ser Glu Ile Asp
         35                  40                  45

CTT GCC ATA TTG GAC ATC ATG CTT CCC GGC ACA AGC GGC CTT ACT ATC     192
Leu Ala Ile Leu Asp Ile Met Leu Pro Gly Thr Ser Gly Leu Thr Ile
     50                  55                  60

TGT CAA AAA ATA AGG GAC AAG CAC ACC TAT CCG ATT ATC ATG CTG ACC     240
Cys Gln Lys Ile Arg Asp Lys His Thr Tyr Pro Ile Ile Met Leu Thr
 65                  70                  75                  80

GGG AAA GAT ACA GAG GTA GAT AAA ATT ACA GGG TTA ACA ATC GGC GCG     288
Gly Lys Asp Thr Glu Val Asp Lys Ile Thr Gly Leu Thr Ile Gly Ala
                 85                  90                  95

GAT GAT TAT ATA ACG AAG CCC TTT CGC CCA CTG GAG TTA ATT GCT CGG     336
Asp Asp Tyr Ile Thr Lys Pro Phe Arg Pro Leu Glu Leu Ile Ala Arg
            100                 105                 110

GTA AAG GCC CAG TTG CGC CGA TAC AAA AAA TTC AGT GGA GTA AAG GAG     384
Val Lys Ala Gln Leu Arg Arg Tyr Lys Lys Phe Ser Gly Val Lys Glu
        115                 120                 125

CAG AAC GAA AAT GTT ATC GTC CAC TCC GGC CTT GTC ATT AAT GTT AAC     432
Gln Asn Glu Asn Val Ile Val His Ser Gly Leu Val Ile Asn Val Asn
    130                 135                 140

ACC CAT GAG TGT TAT CTG AAC GAG AAG CAG TTA TCC CTT ACT CCC ACC     480
Thr His Glu Cys Tyr Leu Asn Glu Lys Gln Leu Ser Leu Thr Pro Thr
145                 150                 155                 160

GAG TTT TCA ATA CTG CGA ATC CTC TGT GAA AAC AAG GGG AAT GTG GTT     528
Glu Phe Ser Ile Leu Arg Ile Leu Cys Glu Asn Lys Gly Asn Val Val
```

```
                      165                 170                 175
AGC TCC GAG CTG CTA TTT CAT GAG ATA TGG GGC GAC GAA TAT TTC AGC          576
Ser Ser Glu Leu Leu Phe His Glu Ile Trp Gly Asp Glu Tyr Phe Ser
            180                 185                 190

AAG AGC AAC AAC ACC ATC ACC GTG CAT ATC CGG CAT TTG CGC GAA AAA          624
Lys Ser Asn Asn Thr Ile Thr Val His Ile Arg His Leu Arg Glu Lys
            195                 200                 205

ATG AAC GAC ACC ATT GAT AAT CCG AAA TAT ATA AAA ACG GTA TGG GGG          672
Met Asn Asp Thr Ile Asp Asn Pro Lys Tyr Ile Lys Thr Val Trp Gly
            210                 215                 220

GTT GGT TAT AAA ATT GAA AAA                                              693
Val Gly Tyr Lys Ile Glu Lys
225                 230

(2) INFORMATION FOR SEQ ID NO:12:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO:12:

Met Ser Asp Lys Ile Leu Ile Val Asp Asp Glu His Glu Ile Ala Asp
  1               5                  10                  15

Leu Val Glu Leu Tyr Leu Lys Asn Glu Asn Tyr Thr Val Phe Lys Tyr
                 20                  25                  30

Tyr Thr Ala Lys Glu Ala Leu Glu Cys Ile Asp Lys Ser Glu Ile Asp
             35                  40                  45

Leu Ala Ile Leu Asp Ile Met Leu Pro Gly Thr Ser Gly Leu Thr Ile
 50                  55                  60

Cys Gln Lys Ile Arg Asp Lys His Thr Tyr Pro Ile Ile Met Leu Thr
 65                  70                  75                  80

Gly Lys Asp Thr Glu Val Asp Lys Ile Thr Gly Leu Thr Ile Gly Ala
                 85                  90                  95

Asp Asp Tyr Ile Thr Lys Pro Phe Arg Pro Leu Glu Leu Ile Ala Arg
            100                 105                 110

Val Lys Ala Gln Leu Arg Arg Tyr Lys Lys Phe Ser Gly Val Lys Glu
        115                 120                 125

Gln Asn Glu Asn Val Ile Val His Ser Gly Leu Val Ile Asn Val Asn
130                 135                 140

Thr His Glu Cys Tyr Leu Asn Glu Lys Gln Leu Ser Leu Thr Pro Thr
145                 150                 155                 160

Glu Phe Ser Ile Leu Arg Ile Leu Cys Glu Asn Lys Gly Asn Val Val
                165                 170                 175

Ser Ser Glu Leu Leu Phe His Gly Ile Trp Gly Asp Glu Tyr Phe Ser
            180                 185                 190

Lys Ser Asn Asn Thr Ile Thr Val His Ile Arg His Leu Arg Glu Lys
            195                 200                 205

Met Asn Asp Thr Ile Asp Asn Pro Lys Tyr Ile Lys Thr Val Trp Gly
            210                 215                 220

Val Gly Tyr Lys Ile Glu Lys
225                 230

(2) INFORMATION FOR SEQ ID NO:13:

(i) SEQUENCE CHARACTERISTICS:
        (A) LENGTH: 1152 base pairs
```

(B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..1152

(xi) SEQUENCE DESCRIPTION: SEQ ID NO:13:

| | | | | | | | | | | | | | | | | |
|---|---|---|---|---|---|---|---|---|---|---|---|---|---|---|---|---|
| TTG | GTT | ATA | AAA | TTG | AAA | AAT | AAA | AAA | AAC | GAC | TAT | TCC | AAA | CTA | GAA | 48 |
| Leu | Val | Ile | Lys | Leu | Lys | Asn | Lys | Lys | Asn | Asp | Tyr | Ser | Lys | Leu | Glu | |
| 1 | | | | 5 | | | | | 10 | | | | | 15 | | |
| CGA | AAA | CTT | TAC | ATG | TAT | ATC | GTT | GCA | ATT | GTT | GTG | GTA | GCA | ATT | GTA | 96 |
| Arg | Lys | Leu | Tyr | Met | Tyr | Ile | Val | Ala | Ile | Val | Val | Val | Ala | Ile | Val | |
| | | | 20 | | | | | 25 | | | | | 30 | | | |
| TTC | GTG | TTG | TAT | ATT | CGT | TCA | ATG | ATC | CGA | GGG | AAA | CTT | GGG | GAT | TGG | 144 |
| Phe | Val | Leu | Tyr | Ile | Arg | Ser | Met | Ile | Arg | Gly | Lys | Leu | Gly | Asp | Trp | |
| | | 35 | | | | | 40 | | | | | 45 | | | | |
| ATC | TTA | AGT | ATT | TTG | GAA | AAC | AAA | TAT | GAC | TTA | AAT | CAC | CTG | GAC | GCG | 192 |
| Ile | Leu | Ser | Ile | Leu | Glu | Asn | Lys | Tyr | Asp | Leu | Asn | His | Leu | Asp | Ala | |
| | 50 | | | | | 55 | | | | | 60 | | | | | |
| ATG | AAA | TTA | TAT | CAA | TAT | TCC | ATA | CGG | AAC | AAT | ATA | GAT | ATC | TTT | ATT | 240 |
| Met | Lys | Leu | Tyr | Gln | Tyr | Ser | Ile | Arg | Asn | Asn | Ile | Asp | Ile | Phe | Ile | |
| 65 | | | | | 70 | | | | | 75 | | | | | 80 | |
| TAT | GTG | GCG | ATT | GTC | ATT | AGT | ATT | CTT | ATT | CTA | TGT | CGC | GTC | ATG | CTT | 288 |
| Tyr | Val | Ala | Ile | Val | Ile | Ser | Ile | Leu | Ile | Leu | Cys | Arg | Val | Met | Leu | |
| | | | | 85 | | | | | 90 | | | | | 95 | | |
| TCA | AAA | TTC | GCA | AAA | TAC | TTT | GAC | GAG | ATA | AAT | ACC | GGC | ATT | GAT | GTA | 336 |
| Ser | Lys | Phe | Ala | Lys | Tyr | Phe | Asp | Glu | Ile | Asn | Thr | Gly | Ile | Asp | Val | |
| | | | 100 | | | | | 105 | | | | | 110 | | | |
| CTT | ATT | CAG | AAC | GAA | GAT | AAA | CAA | ATT | GAG | CTT | TCT | GCG | GAA | ATG | GAT | 384 |
| Leu | Ile | Gln | Asn | Glu | Asp | Lys | Gln | Ile | Glu | Leu | Ser | Ala | Glu | Met | Asp | |
| | | 115 | | | | | 120 | | | | | 125 | | | | |
| GTT | ATG | GAA | CAA | AAG | CTC | AAC | ACA | TTA | AAA | CGG | ACT | CTG | GAA | AAG | CGA | 432 |
| Val | Met | Glu | Gln | Lys | Leu | Asn | Thr | Leu | Lys | Arg | Thr | Leu | Glu | Lys | Arg | |
| | 130 | | | | | 135 | | | | | 140 | | | | | |
| GAG | CAG | GAT | GCA | AAG | CTG | GCC | GAA | CAA | AGA | AAA | AAT | GAC | GTT | GTT | ATG | 480 |
| Glu | Gln | Asp | Ala | Lys | Leu | Ala | Glu | Gln | Arg | Lys | Asn | Asp | Val | Val | Met | |
| 145 | | | | | 150 | | | | | 155 | | | | | 160 | |
| TAC | TTG | GCG | CAC | GAT | ATT | AAA | ACG | CCC | CTT | ACA | TCC | ATT | ATC | GGT | TAT | 528 |
| Tyr | Leu | Ala | His | Asp | Ile | Lys | Thr | Pro | Leu | Thr | Ser | Ile | Ile | Gly | Tyr | |
| | | | | 165 | | | | | 170 | | | | | 175 | | |
| TTG | AGC | CTG | CTT | GAC | GAG | GCT | CCA | GAC | ATG | CCG | GTA | GAT | CAA | AAG | GCA | 576 |
| Leu | Ser | Leu | Leu | Asp | Glu | Ala | Pro | Asp | Met | Pro | Val | Asp | Gln | Lys | Ala | |
| | | | 180 | | | | | 185 | | | | | 190 | | | |
| AAG | TAT | GTG | CAT | ATC | ACG | TTG | GAC | AAA | GCG | TAT | CGA | CTC | GAA | CAG | CTA | 624 |
| Lys | Tyr | Val | His | Ile | Thr | Leu | Asp | Lys | Ala | Tyr | Arg | Leu | Glu | Gln | Leu | |
| | | 195 | | | | | 200 | | | | | 205 | | | | |
| ATC | GAC | GAG | TTT | TTT | GAG | ATT | ACA | CGG | TAT | AAC | CTA | CAA | ACG | ATA | ACG | 672 |
| Ile | Asp | Glu | Phe | Phe | Glu | Ile | Thr | Arg | Tyr | Asn | Leu | Gln | Thr | Ile | Thr | |
| | 210 | | | | | 215 | | | | | 220 | | | | | |
| CTA | ACA | AAA | ACG | CAC | ATA | GAC | CTA | TAC | TAT | ATG | CTG | GTG | CAG | ATG | ACC | 720 |
| Leu | Thr | Lys | Thr | His | Ile | Asp | Leu | Tyr | Tyr | Met | Leu | Val | Gln | Met | Thr | |
| 225 | | | | | 230 | | | | | 235 | | | | | 240 | |
| GAT | GAA | TTT | TAT | CCT | CAG | CTT | TCC | GCA | CAT | GGA | AAA | CAG | GCG | GTT | ATT | 768 |
| Asp | Glu | Phe | Tyr | Pro | Gln | Leu | Ser | Ala | His | Gly | Lys | Gln | Ala | Val | Ile | |
| | | | | 245 | | | | | 250 | | | | | 255 | | |
| CAC | GCC | CCC | GAG | GAT | CTG | ACC | GTG | TCC | GGC | GAC | CCT | GAT | AAA | CTC | GCG | 816 |
| His | Ala | Pro | Glu | Asp | Leu | Thr | Val | Ser | Gly | Asp | Pro | Asp | Lys | Leu | Ala | |
| | | | 260 | | | | | 265 | | | | | 270 | | | |

```
AGA GTC TTT AAC AAC ATT TTG AAA AAC GCC GCT GCA TAC AGT GAG GAT        864
Arg Val Phe Asn Asn Ile Leu Lys Asn Ala Ala Ala Tyr Ser Glu Asp
        275                 280                 285

AAC AGC ATC ATT GAC ATT ACC GCG GGC CTC TCC GGG GAT GTG GTG TCA        912
Asn Ser Ile Ile Asp Ile Thr Ala Gly Leu Ser Gly Asp Val Val Ser
290                 295                 300

ATC GAA TTC AAG AAC ACT GGA AGC ATC CCA AAA GAT AAG CTA GCT GCC        960
Ile Glu Phe Lys Asn Thr Gly Ser Ile Pro Lys Asp Lys Leu Ala Ala
305                 310                 315                 320

ATA TTT GAA AAG TTC TAT AGG CTG GAC AAT GCT CGT TCT TCC GAT ACG       1008
Ile Phe Glu Lys Phe Tyr Arg Leu Asp Asn Ala Arg Ser Ser Asp Thr
                325                 330                 335

GGT GGC GCG GGA CTT GGA TTG GCG ATT GCA AAA GAA ATT ATT GTT CAG       1056
Gly Gly Ala Gly Leu Gly Leu Ala Ile Ala Lys Glu Ile Ile Val Gln
            340                 345                 350

CAT GGA GGG CAG ATT TAC GCG GAA AGC AAT GAT AAC TAT ACG ACG TTT       1104
His Gly Gly Gln Ile Tyr Ala Glu Ser Asn Asp Asn Tyr Thr Thr Phe
        355                 360                 365

AGG GTA GAG CTT CCA GCG ATG CCA GAC TTG GTT GAT AAA AGG AGG TCC       1152
Arg Val Glu Leu Pro Ala Met Pro Asp Leu Val Asp Lys Arg Arg Ser
370                 375                 380
```

(2) INFORMATION FOR SEQ ID NO:14:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:14:

```
Leu Val Ile Lys Leu Lys Asn Lys Lys Asn Asp Tyr Ser Lys Leu Glu
1               5                   10                  15

Arg Lys Leu Tyr Met Tyr Ile Val Ala Ile Val Val Ala Ile Val
                20                  25                  30

Phe Val Leu Tyr Ile Arg Ser Met Ile Arg Gly Lys Leu Gly Asp Trp
            35                  40                  45

Ile Leu Ser Ile Leu Glu Asn Lys Tyr Asp Leu Asn His Leu Asp Ala
50                  55                  60

Met Lys Leu Tyr Gln Tyr Ser Ile Arg Asn Asn Ile Asp Ile Phe Ile
65                  70                  75                  80

Tyr Val Ala Ile Val Ile Ser Ile Leu Ile Leu Cys Arg Val Met Leu
                85                  90                  95

Ser Lys Phe Ala Lys Tyr Phe Asp Glu Ile Asn Thr Gly Ile Asp Val
            100                 105                 110

Leu Ile Gln Asn Glu Asp Lys Gln Ile Glu Leu Ser Ala Glu Met Asp
        115                 120                 125

Val Met Glu Gln Lys Leu Asn Thr Leu Lys Arg Thr Leu Glu Lys Arg
130                 135                 140

Glu Gln Asp Ala Lys Leu Ala Glu Gln Arg Lys Asn Asp Val Val Met
145                 150                 155                 160

Tyr Leu Ala His Asp Ile Lys Thr Pro Leu Thr Ser Ile Ile Gly Tyr
                165                 170                 175

Leu Ser Leu Leu Asp Glu Ala Pro Asp Met Pro Val Asp Gln Lys Ala
            180                 185                 190

Lys Tyr Val His Ile Thr Leu Asp Lys Ala Tyr Arg Leu Glu Gln Leu
        195                 200                 205

Ile Asp Glu Phe Phe Glu Ile Thr Arg Tyr Asn Leu Gln Thr Ile Thr
```

```
                210                 215                 220
Leu Thr Lys Thr His Ile Asp Leu Tyr Tyr Met Leu Val Gln Met Thr
225                 230                 235                 240

Asp Glu Phe Tyr Pro Gln Leu Ser Ala His Gly Lys Gln Ala Val Ile
                245                 250                 255

His Ala Pro Glu Asp Leu Thr Val Ser Gly Asp Pro Asp Lys Leu Ala
                260                 265                 270

Arg Val Phe Asn Asn Ile Leu Lys Asn Ala Ala Ala Tyr Ser Glu Asp
                275                 280                 285

Asn Ser Ile Ile Asp Ile Thr Ala Gly Leu Ser Gly Asp Val Val Ser
                290                 295                 300

Ile Glu Phe Lys Asn Thr Gly Ser Ile Pro Lys Asp Lys Leu Ala Ala
305                 310                 315                 320

Ile Phe Glu Lys Phe Tyr Arg Leu Asp Asn Ala Arg Ser Ser Asp Thr
                325                 330                 335

Gly Gly Ala Gly Leu Gly Leu Ala Ile Ala Lys Glu Ile Ile Val Gln
                340                 345                 350

His Gly Gly Gln Ile Tyr Ala Glu Ser Asn Asp Asn Tyr Thr Thr Phe
                355                 360                 365

Arg Val Glu Leu Pro Ala Met Pro Asp Leu Val Asp Lys Arg Arg Ser
370                 375                 380
```

(2) INFORMATION FOR SEQ ID NO:15:

(i) SEQUENCE CHARACTERISTICS:
        (A) LENGTH: 7225 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:15:

```
AAGCTTTTCT TTTTGCTCAT TGTTAGAGA TTTACTAACC GTATTAAATA GCTTCTTTTC      60
AGCCATTGCC CTTGCTTCCC ACACCATTCT TTCAAGTGTA GTGATAGCAG GCAGTATAAT    120
TTTGTTTTTT CTTAGAAAAT CTATGCATTC ATGCAGTAGA TGAATGGCAT CACCATTTTC    180
CAAAGCTAAT TGATGAAGGT ACTTAAATGT CATTCGATAT TCACTCAGGG TAAAAGTTAC    240
AAAGTCGTAT TCACTTCGAA TTTCTTTCAA ATGATCCCAA AGTGTATTTT CCCTTTGAGG    300
ATAATGATCA AGCGAGGATG GACTAACACC AATCTGTTTC GATATATATT GTATGACCGA    360
ATCTGGGATG CTTTTGATAT GAGTGTATGG CCAACCGGGA TACCGAAGAA CAGCTAATTG    420
AACAGCAAAT CCTAAACGGT TTTCTTCCCT CCTTCGCTTA TTAACTATTT CTAAATCCCG    480
TTTGGAAAAA GTGAAGTAGG TCCCCAGTAT CCATTCATCT TCAGGGATTT GCATAAAAGC    540
CTGTCTCTGT TCCGGTGTAA GCAATTCTCT ACCTCTCGCA ATTTTCATTC AGTATCATTC    600
CATTTCTGTA TTTTCAATTT ATTAGTTCAA TTATATATCA ATAGAGTGTA CTCTATTGAT    660
ACAAATGTAG TAGACTGATA AAATCATAGT TAAGAGCGTC TCATAAGACT TGTCTCAAAA    720
ATGAGGTGAT ATTTTGCGGA AAATCGGTTA TATTCGTGTC AGTTCGACTA ACCAGAATCC    780
TTCAAGACAA TTTCAGCAGT TGAACAGAGAT CGGAATGGAT ATTATATAAA GAGAAAGTTT    840
CAGGAGCAAC AAAGGATCGC GAGCAACTTC AAAAAGTGTT AGACGATTTA CAGGAAGATG    900
ACATCATTTA TGTTACAGAC TTAACTCGAA TCACTCGTAG TACACAAGAT CTATTTGAAT    960
TAATCGATAA CATACGAGAT AAAAAGGCAA GTTTAAAATC ACTAAAAGAT ACATGGCTTG   1020
ATTTATCAGA AGATAATCCA TACAGCCAAT TCTTAATTAC TGTAATGGCT GGTGTTAACC   1080
```

```
AATTAGAGCG AGATCTTATT CGGATGAGAC AACGTGAAGG GATTGAATTG GCTAAGAAAG    1140

AAGGAAAGTT TAAAGGTCGA TTAAAGAAGT ATCATAAAAA TCACGCAGGA ATGAATTATG    1200

CGGAAAGCTA TATAAAGAAG GAAATATGAC TGTAAATCAA ATTTGTGAAA TTACTAATGT    1260

ATCTAGGGCT TCATTATACA GGAAATTATC AGAAGTGAAT AATTAGCCAT TCTGTATTCC    1320

GCTAATGGGC AATATTTTTA AAGAAGAAAA GGAAACTATA AAATATTAAC AGCCTCCTAG    1380

CGATGCCGAA AAGCCCTTTG ATAAAAAAAG AATCATCATC TTAAGAAATT CTTAGTCATT    1440

TATTATGTAA ATGCTTATAA ATTCGGCCCT ATAATCTGAT AAATTATTAA GGGCAAACTT    1500

ATGTGAAAGG GTGATAACTA TGAGCGATAA AATACTTATT GTGGATGATG AACATGAAAT    1560

TGCCGATTTG GTTGAATTAT ACTTAAAAAA CGAGAATTAT ACGGTTTTCA AATACTATAC    1620

CGCCAAAGAA GCATTGGAAT GTATAGACAA GTCTGAGATT GACCTTGCCA TATTGGACAT    1680

CATGCTTCCC GGCACAAGCG GCCTTACTAT CTGTCAAAAA ATAAGGGACA AGCACACCTA    1740

TCCGATTATC ATGCTGACCG GGAAAGATAC AGAGGTAGAT AAAATTACAG GGTTAACAAT    1800

CGGCGCGGAT GATTATATAA CGAAGCCCTT TCGCCCACTG GAGTTAATTG CTCGGGTAAA    1860

GGCCCAGTTG CGCCGATACA AAAAATTCAG TGGAGTAAAG GAGCAGAACG AAAATGTTAT    1920

CGTCCACTCC GGCCTTGTCA TTAATGTTAA CACCCATGAG TGTTATCTGA ACGAGAAGCA    1980

GTTATCCCTT ACTCCCACCG AGTTTTCAAT ACTGCGAATC CTCTGTGAAA ACAAGGGGAA    2040

TGTGGTTAGC TCCGAGCTGC TATTTCATGA GATATGGGGC GACGAATATT TCAGCAAGAG    2100

CAACAACACC ATCACCGTGC ATATCCGGCA TTTGCGCGAA AAAATGAACG ACACCATTGA    2160

TAATCCGAAA TATATAAAAA CGGTATGGGG GGTTGGTTAT AAAATTGAAA ATAAAAAAA    2220

ACGACTATTC CAAACTAGAA CGAAAACTTT ACATGTATAT CGTTGCAATT GTTGTGGTAG    2280

CAATTGTATT CGTGTTGTAT ATTCGTTCAA TGATCCGAGG GAAACTTGGG GATTGGATCT    2340

TAAGTATTTT GGAAAACAAA TATGACTTAA ATCACCTGGA CGCGATGAAA TTATATCAAT    2400

ATTCCATACG GAACAATATA GATATCTTTA TTTATGTGGC GATTGTCATT AGTATTCTTA    2460

TTCTATGTCG CGTCATGCTT TCAAAATTCG CAAAATACTT TGACGAGATA AATACCGGCA    2520

TTGATGTACT TATTCAGAAC GAAGATAAAC AAATTGAGCT TTCTGCGGAA ATGGATGTTA    2580

TGGAACAAAA GCTCAACACA TTAAAACGGA CTCTGGAAAA GCGAGAGCAG GATGCAAAGC    2640

TGGCCGAACA AAGAAAAAAT GACGTTGTTA TGTACTTGGC GCACGATATT AAAACGCCCC    2700

TTACATCCAT TATCGGTTAT TTGAGCCTGC TTGACGAGGC TCCAGACATG CCGGTAGATC    2760

AAAAGGCAAA GTATGTGCAT ATCACGTTGG ACAAAGCGTA TCGACTCGAA CAGCTAATCG    2820

ACGAGTTTTT TGAGATTACA CGGTATAACC TACAAACGAT AACGCTAACA AAAACGCACA    2880

TAGACCTATA CTATATGCTG GTGCAGATGA CCGATGAATT TTATCCTCAG CTTTCCGCAC    2940

ATGGAAAACA GGCGGTTATT CACGCCCCCG AGGATCTGAC CGTGTCCGGC GACCCTGATA    3000

AACTCGCGAG AGTCTTTAAC AACATTTTGA AAAACGCCGC TGCATACAGT GAGGATAACA    3060

GCATCATTGA CATTACCGCG GGCCTCTCCG GGGATGTGGT GTCAATCGAA TTCAAGAACA    3120

CTGGAAGCAT CCCAAAAGAT AAGCTAGCTG CCATATTTGA AAAGTTCTAT AGGCTGGACA    3180

ATTCTCGTTC TTCCGATACG GGTGGCGCGG GACTTGGATT GGCGATTGCA AAAGAAATTA    3240

TTGTTCAGCA TGGAGGGCAG ATTTACGCGG AAAGCTATGA TAACTATACG ACGTTTAGGG    3300

TAGAGCTTCC AGCGATGCCA GACTTGGTTG ATAAAAGGAG GTCCTAAGAG ATGTATATAA    3360

TTTTTTAGGA AAATCTCAAG GTTATCTTTA CTTTTTCTTA GGAAATTAAC AATTTAATAT    3420

TAAGAAACGG CTCGTTCTTA CACGGTAGAC TTAATACCGT AAGAACGAGC CGTTTTCGTT    3480
```

```
CTTCAGAGAA AGATTTGACA AGATTACCAT TGGCATCCCC GTTTTATTTG GTGCCTTTCA    3540

CAGAAAGGGT TGGTCTTAAT TATGAATAAC ATCGGCATTA CTGTTTATGG ATGTGAGCAG    3600

GATGAGGCAG ATGCATTCCA TGCTCTTTCG CCTCGCTTTG GCGTTATGGC AACGATAATT    3660

AACGCCAACG TGTCGGAATC AACGCCAAA TCCGCGCCTT TCAATCAATG TATCAGTGTG     3720

GGACATAAAT CAGAGATTTC CGCCTCTATT CTTCTTGCGC TGAAGAGAGC CGGTGTGAAA    3780

TATATTTCTA CCCGAAGCAT CGGCTGCAAT CATATAGATA CAACTGCTGC TAAGAGAATG    3840

GGCATCACTG TCGACAATGT GGCGTACTCG CCGGATAGCG TTGCCGATTA TACTATGATG    3900

CTAATTCTTA TGGCAGTACG CAACGTAAAA TCGATTGTGC GCTCTGTGGA AAAACATGAT    3960

TTCAGGTTGG ACAGCGACCG TGGCAAGGTA CTCAGCGACA TGACAGTTGG TGTGGTGGGA    4020

ACGGGCCAGA TAGGCAAAGC GGTTATTGAG CGGCTGCGAG GATTTGGATG TAAAGTGTTG    4080

GCTTATAGTC GCAGCCGAAG TATAGAGGTA AACTATGTAC CGTTTGATGA GTTGATGCAA    4140

AATAGCGATA TCGTTACGCT TCATGTGCCG CTCAATACGG ATACGCACTA TATTATCAGC    4200

CACGAACAAA TACAGAGAAT GAAGCAAGGA GCATTTCTTA TCAATACTGG GCGCGGTCCA    4260

CTTGTAGATA CCTATGAGTT GGTTAAAGCA TTAGAAAACG GGAAACTGGG CGGTGCCGCA    4320

TTGGATGTAT TGGAAGGAGA GGAAGAGTTT TTCTACTCTG ATTGCACCCA AAAACCAATT    4380

GATAATCAAT TTTTACTTAA ACTTCAAAGA ATGCCTAACG TGATAATCAC ACCGCATACG    4440

GCCTATTATA CCGAGCAAGC GTTGCGTGAT ACCGTTGAAA AAACCATTAA AAACTGTTTG    4500

GATTTTGAAA GGAGACAGGA GCATGAATAG AATAAAAGTT GCAATACTGT TTGGGGGTTG    4560

CTCAGAGGAG CATGACGTAT CGGTAAAATC TGCAATAGAG ATAGCCGCTA ACATTAATAA    4620

AGAAAAATAC GAGCCGTTAT ACATTGGAAT TACGAAATCT GGTGTATGGA AAATGTGCGA    4680

AAAACCTTGC GCGGAATGGG AAAACGACAA TTGCTATTCA GCTGTACTCT CGCCGGATAA    4740

AAAAATGCAC GGATTACTTG TTAAAAAGAA CCATGAATAT GAAATCAACC ATGTTGATGT    4800

AGCATTTTCA GCTTTGCATG GCAAGTCAGG TGAAGATGGA TCCATACAAG GTCTGTTTGA    4860

ATTGTCCGGT ATCCCTTTTG TAGGCTGCGA TATTCAAAGC TCAGCAATTT GTATGGACAA    4920

ATCGTTGACA TACATCGTTG CGAAAAATGC TGGGATAGCT ACTCCCGCCT TTTGGGTTAT    4980

TAATAAAGAT GATAGGCCGG TGGCAGCTAC GTTTACCTAT CCTGTTTTTG TTAAGCCGGC    5040

GCGTTCAGGC TCATCCTTCG GTGTGAAAAA AGTCAATAGC GCGGACGAAT TGGACTACGC    5100

AATTGAATCG GCAAGACAAT ATGACAGCAA AATCTTAATT GAGCAGGCTG TTTCGGGCTG    5160

TGAGGTCGGT TGTGCGGTAT TGGGAAACAG TGCCGCGTTA GTTGTTGGCG AGGTGGACCA    5220

AATCAGGCTG CAGTACGGAA TCTTTCGTAT TCATCAGGAA GTCGAGCCGG AAAAAGGCTC    5280

TGAAAACGCA GTTATAACCG TTCCCGCAGA CCTTTCAGCA GAGGAGCGAG GACGGATACA    5340

GGAAACGGCA AAAAAAATAT ATAAAGCGCT CGGCTGTAGA GGTCTAGCCC GTGTGGATAT    5400

GTTTTTACAA GATAACGGCC GCATTGTACT GAACGAAGTC AATACTCTGC CCGGTTTCAC    5460

GTCATACAGT CGTTATCCCC GTATGATGGC CGCTGCAGGT ATTGCACTTC CCGAACTGAT    5520

TGACCGCTTG ATCGTATTAG CGTTAAAGGG GTGATAAGCA TGGAAATAGG ATTTACTTTT    5580

TTAGATGAAA TAGTACACGG TGTTCGTTGG ACGCTAAAT ATGCCACTTG GATAATTTC      5640

ACCGGAAAAC CGGTTGACGG TTATGAAGTA AATCGCATTG TAGGGACATA CGAGTTGGCT    5700

GAATCGCTTT TGAAGGCAAA AGAACTGGCT GCTACCCAAG GGTACGGATT GCTTCTATGG    5760

GACGGTTACC GTCCTAAGCG TGCTGTAAAC TGTTTTATGC AATGGGCTGC ACAGCCGGAA    5820

AATAACCTGA CAAAGGAAAG TTATTATCCC AATATTGACC GAACTGAGAT GATTTCAAAA    5880
```

```
GGATACGTGG CTTCAAAATC AAGCCATAGC CGCGGCAGTG CCATTGATCT TACGCTTTAT    5940

CGATTAGACA CGGGTGAGCT TGTACCAATG GGGAGCCGAT TTGATTTTAT GGATGAACGC    6000

TCTCATCATG CGGCAAATGG AATATCATGC AATGAAGCGC AAAATCGCAG ACGTTTGCGC    6060

TCCATCATGG AAAACAGTGG GTTTGAAGCA TATAGCCTCG AATGGTGGCA CTATGTATTA    6120

AGAGACGAAC CATACCCCAA TAGCTATTTT GATTTCCCCG TTAAATAAAC TTTTAACCGT    6180

TGCACGGACA AACTATATAA GCTAACTCTT TCGGCAGGAA ACCCGACGTA TGTAACTGGT    6240

TCTTAGGGAA TTTATATATA GTAGATAGTA TTGAAGATGT AAGGCAGAGC GATATTGCGG    6300

TCATTATCTG CGTGCGCTGC GGCAAGATAG CCTGATAATA AGACTGATCG CATAGAGGGG    6360

TGGTATTTCA CACCGCCCAT TGTCAACAGG CAGTTCAGCC TCGTTAAATT CAGCATGGGT    6420

ATCACTTATG AAAATTCATC TACATTGGTG ATAATAGTAA ATCCAGTAGG GCGAAATAAT    6480

TGACTGTAAT TTACGGGGCA AAACGGCACA ATCTCAAACG AGATTGTGCC GTTTAAGGGG    6540

AAGATTCTAG AAATATTTCA TACTTCCAAC TATATAGTTA AGGAGGAGAC TGAAAATGAA    6600

GAAGTTGTTT TTTTTATTGT TATTGTTATT CTTAATATAC TTAGGTTATG ACTACGTTAA    6660

TGAAGCACTG TTTTCTCAGG AAAAAGTCGA ATTTCAAAAT TATGATCAAA ATCCCAAAGA    6720

ACATTTAGAA AATAGTGGGA CTTCTGAAAA TACCCAAGAG AAAACAATTA CAGAAGAACA    6780

GGTTTATCAA GGAAATCTGC TATTAATCAA TAGTAAATAT CCTGTTCGCC AAGAAGTGTG    6840

AAGTCAGATA TCGTGAATTT ATCTAAACAT GACGAATTAA TAAATGGATA CGGGTTGCTT    6900

GATAGTAATA TTTATATGTC AAAAGAAATA GCACAAAAAT TTTCAGAGAT GGTCAATGAT    6960

GCTGTAAAGG GTGGCGTTAG TCATTTTATT ATTAATAGTG GCTATCGAGA CTTTGATGAG    7020

CAAAGTGTGC TTTACCAAGA AATGGGGGCT GAGTATGCCT TACCAGCAGG TTATAGTGAG    7080

CATAATTCAG GTTATCACT AGATGTAGGA TCAAGCTTGA CGAAAATGGA ACGAGCCCCT    7140

GAAGGAAAGT GGATAGAAGA AAATGCTTGG AAATACGGGT TCATTTTACG TTATCCAGAG    7200

GACAAAACAG AGTTAACAGG AATTC                                         7225

(2) INFORMATION FOR SEQ ID NO:16:

(i) SEQUENCE CHARACTERISTICS:
        (A) LENGTH: 10851 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:16:

GGGGTAGCGT CAGGAAAATG CGGATTTACA ACGCTAAGCC TATTTTCCTG ACGAATCCCT     60

CGTTTTTAAC AACGTTAAGA AAGTTTTAGT GGTCTTAAAG AATTTAATGA GACTACTTTC    120

TCTGAGTTAA AATGGTATTC TCCTAGTAAA TTAATATGTT CCCAACCTAA GGGCGACATA    180

TGGTGTAACA AATCTTCATT AAAGCTACCT GTCCGTTTTT TATATTCAAC TGCTGTTGTT    240

AGGTGGAGAG TATTCCAAAT ACTTATAGCA TTGATAATTA TGTTTAAAGC ACTGGCTCTT    300

TGCAATTGAT GCTGTATGGT GCGTTCTCTA AGCTCACCTT GTTTTCCGAA GAAAATAGCT    360

CTTGCCAATC CATTCATGGC TTCTCCTTTA TTCAATCCTC TTTGTATTTT TCTTCTTAAT    420

GATTCATCCG ATATATAATT CAAAATAAAG ATCGTTTTTT CTATTCGGCC CATCTCACGT    480

AAGGCTGTAG CTAAGCTGTT TTGTCTTGAA TAGGAACCTA GCTTCCCCAT AATAAGGGAT    540

GCTGAAACTG TTCCCTCCCT TATAGAATGA GCTAATCGCA AACATCCTC ATAATTTTCT     600
```

| | |
|---|---|
| TTAATGACCT TTGTATTTAT TTGTCCACGT AAAATGGCTT CTAGTTTTGG ATACTCACTT | 660 |
| GCTTTATCTA TCGTAAATAA TTTTGAGTCC GATAAATCCC TTATTCTTGG GGCAAATTTA | 720 |
| AATCCTAATA AATGAGTCAG TCCGAATATT TGGTCAGTGT AACCGGCAGT GTCTGTATAA | 780 |
| TGTTCCTCTA TGTTTAGATC CGTCTCATGA TGTAACAAAC CATCCAAAAC ATGAATCGCA | 840 |
| TCTCTTGAAT TAGTATGAAT AATCTTTGTG TAGTAAGAAG AGAATTGATC ACTTGTAAAT | 900 |
| CGGTAGATGG TGGCTCCTTT TCCAGTTCCA TAATGTGGAT TTGCATCTGC ATGTAGTGAT | 960 |
| GAAACACCTA GCTGCATTCT CATACCATCT GACGAAGATG TTGTACCGTC GCCCCAATAG | 1020 |
| AAAGGCAATT GTAATTTATG ATGAAAGTTT ACTAATATGG CTTGGGCTTT ATTCATGGCA | 1080 |
| TCTTCATACA TGCGCCATTG AGATACATTG GCTAGTTGCT TATATGTAAG TCCGGGTGTG | 1140 |
| GCTTCGGCCA TCTTGCTCAA GCCAATATTC ATTCCCATTC CTAAAAGGGC AGCCATGATA | 1200 |
| ATGATTGTTT CTTCCTTATC TGGTTTTCGA TTATTGGAAG CATGAGTGAA TTGCTCATGA | 1260 |
| AATCCTGTTA TATGGGCCAC ATCCATGAGT AAATCAGTTA ATTTTATTCT TGGTAGCATC | 1320 |
| TGATAAAGGC TTGCACTAAA TTTTTTTGCT TCTTCTGGAA CATCTTTTTC TAAGCGTGCA | 1380 |
| AGTGATAGCT TTCCTTTTTC AAGAGAAACC CCATCTAACT TATTGGAATT GGCAGCTAAC | 1440 |
| CACTTTAACC TTTCATTAAA GCTGCTGGTT CTCTCCGTTA TATAATCTTC GAATGATAAA | 1500 |
| CTAACTGATA ATCTCGTATT CCCCTTCGAT TGATTCCATG TATCTTCCGA AAACAAATAT | 1560 |
| TCCTCAAAAT CCCTATATTG TCTGCTGCCA ACAATGGAAA CATCTCCTGC CCGAACATGC | 1620 |
| TCCCGAAGTT CTGTTAAAAC AGCCATTTCA TAGTAATGAC GATTAATTGT TGTACCATCA | 1680 |
| TCCTCGTATA AATGTCTTTT CCATCGTTTT GAAATAAAAT CCACAGGTGA GTCATCAGGC | 1740 |
| ACTTTTCGCT TTCCAGATTC GTTCATTCCT CGGATAATCT CAACAGCTTG TAAAAGTGGC | 1800 |
| TCATTTGCCT TTGTAGAATG AAATTCCAAT ACTCTTAATA GCGTTGGCGT ATATTTTCTT | 1860 |
| AGTGAATAAA ACCGTTTTTG CAGTAAGTCT AAATAATCAT AGTCGGCAGG ACGTGCAAGT | 1920 |
| TCCTGAGCCT CTTCTACTGA AGAGACAAAG GTATTCCATT CAATAACCGA TTCTAAAACC | 1980 |
| TTAAAAACGT CTAATTTTTC CTCTCTTGCT TTAATTAATG CTTGTCCGAT GTTCGTAAAG | 2040 |
| TGTATAACTT TCTCATTTAG CTTTTTACCG TTTTGTTTCT GGATTTCCTC TTGAGCCTTA | 2100 |
| CGACCTTTTG ATAACAAACT AAGTATTTGC CTATCATGAA TTTCAAACGC TTTATCCGTT | 2160 |
| AGCTCCTGAG TAAGTTGTAA TAAATAGATG GTTAATATCG AATAACGTTT ATTTTCTTGA | 2220 |
| AAGTCACGGA ATGCATACGG CTCGTATCTT GAGCCTAAGC GAGACAGCTG CAACAGGCGG | 2280 |
| TTACGGTGCA AATGACTAAT TTGCACTGTT TCTAAATCCA TTCCTCGTAT GTATTCGAGT | 2340 |
| CGTTCTATTA TTTTTAGAAA AGTTTCGGGT GAAGGATGAC CCGGTGGCTC TTTTAACCAA | 2400 |
| CCCAATATCG TTTTATTGGA TTCGGATGGA TGCTGCGAGG TAATAATCCC TTCAAGCTTT | 2460 |
| TCTTTTTGCT CATTTGTTAG AGATTACTA ACCGTATTAA ATAGCTTCTT TTCAGCCATT | 2520 |
| GCCCTTGCTT CCCACACCAT TCTTTCAAGT GTAGTGATAG CAGGCAGTAT AATTTTGTTT | 2580 |
| TTTCTTAGAA AATCTATGCA TTCATGCAGT AGATGAATGG CATCACCATT TTCCAAAGCT | 2640 |
| AATTGATGAA GGTACTTAAA TGTCATTCGA TATTCACTCA GGGTAAAAGT TACAAAGTCG | 2700 |
| TATTCACTTC GAATTCTTT CAAATGATCC CAAAGTGTAT TTTCCCTTTG AGGATAATGA | 2760 |
| TCAAGCGAGG ATGGACTAAC ACCAATCTGT TTCGATATAT ATTGTATGAC CGAATCTGGG | 2820 |
| ATGCTTTTGA TATGAGTGTA TGGCCAACCG GGATACCGAA GAACAGCTAA TTGAACAGCA | 2880 |
| AATCCTAAAC GGTTTTCTTC CCTCCTTCGC TTATTAACTA TTTCTAAATC CCGTTTGGAA | 2940 |
| AAAGTGAAGT AGGTCCCCAG TATCCATTCA TCTTCAGGGA TTTGCATAAA AGCCTGTCTC | 3000 |

```
TGTTCCGGTG TAAGCAATTC TCTACCTCTC GCAATTTTCA TTCAGTATCA TTCCATTTCT   3060

GTATTTTCAA TTTATTAGTT CAATTATATA TCAATAGAGT GTACTCTATT GATACAAATG   3120

TAGTAGACTA ATAAAATCAT AGTTAAGAGC GTCTCATAAG ACTTGTCTCA AAAATGAGGT   3180

GATATTTTGC GGAAAATCGG TTATATTCGT GTCAGTTCGA CTAACCAGAA TCCTTCAAGA   3240

CAATTTCAGC AGTTGAACGA GATCGGAATG GATATTATAT ATGAAGAGAA AGTTTCAGGA   3300

GCAACAAAGG ATCGCGAGCA ACTTCAAAAA GTGTTAGACG ATTTACAGGA AGATGACATC   3360

ATTTATGTTA CAGACTTAAC TCGAATCACT CGTAGTACAC AAGATCTATT TGAATTAATC   3420

GATAACATAC GAGATAAAAA GGCAAGTTTA AAATCACTAA AAGATACATG GCTTGATTTA   3480

TCAGAAGATA ATCCATACAG CCAATTCTTA ATTACTGTAA TGGCTGGTGT TAACCAATTA   3540

GAGCGAGATC TTATTCGGAT GAGACAACGT GAAGGGATTG AATTGGCTAA GAAAGAAGGA   3600

AAGTTTAAAG GTCGATTAAA GAAGTATCAT AAAAATCACG CAGGAATGAA TTATGCGGTA   3660

AAGCTATATA AAGAAGGAAA TATGACTGTA AATCAAATTT GTGAAATTAC TAATGTATCT   3720

AGGGCTTCAT TATACAGGAA ATTATCAGAA GTGAATAATT AGCCATTCTG TATTCCGCTA   3780

ATGGGCAATA TTTTTAAAGA AGAAAAGGAA ACTATAAAAT ATTAACAGCC TCCTAGCGAT   3840

GCCGAAAAGC CCTTTGATAA AAAAAGAATC ATCATCTTAA GAAATTCTTA GTCATTTATT   3900

ATGTAAATGC TTATAAATTC GGCCCTATAA TCTGATAAAT TATTAAGGGC AAACTTATGT   3960

GAAAGGGTGA TAACTATGAG CGATAAAATA CTTATTGTGG ATGATGAACA TGAAATTGCC   4020

GATTTGGTTG AATTATACTT AAAAAACGAG AATTATACGG TTTTCAAATA CTATACCGCC   4080

AAAGAAGCAT TGGAATGTAT AGACAAGTCT GAGATTGACC TTGCCATATT GGACATCATG   4140

CTTCCCGGCA CAAGCGGCCT TACTATCTGT CAAAAAATAA GGGACAAGCA CACCTATCCG   4200

ATTATCATGC TGACCGGGAA AGATACAGAG GTAGATAAAA TTACAGGGTT AACAATCGGC   4260

GCGGATGATT ATATAACGAA GCCCTTTCGC CCACTGGAGT TAATTGCTCG GGTAAAGGCC   4320

CAGTTGCGCC GATACAAAAA ATTCAGTGGA GTAAAGGAGC AGAACGAAAA TGTTATCGTC   4380

CACTCCGGCC TTGTCATTAA TGTTAACACC CATGAGTGTT ATCTGAACGA GAAGCAGTTA   4440

TCCCTTACTC CCACCGAGTT TTCAATACTG CGAATCCTCT GTGAAAACAA GGGGAATGTG   4500

GTTAGCTCCG AGCTGCTATT TCATGAGATA TGGGGCGACG AATATTTCAG CAAGAGCAAC   4560

AACACCATCA CCGTGCATAT CCGGCATTTG CGCGAAAAAA TGAACGACAC CATTGATAAT   4620

CCGAAATATA TAAAAACGGT ATGGGGGGTT GGTTATAAAA TTGAAAAATA AAAAAAACGA   4680

CTATTCCAAA CTAGAACGAA AACTTTACAT GTATATCGTT GCAATTGTTG TGGTAGCAAT   4740

TGTATTCGTG TTGTATATTC GTTCAATGAT CCGAGGGAAA CTTGGGGATT GGATCTTAAG   4800

TATTTTGGAA AACAAATATG ACTTAAATCA CCTGGACGCG ATGAAATTAT ATCAATATTC   4860

CATACGGAAC AATATAGATA TCTTTATTTA TGTGGCGATT GTCATTAGTA TTCTTATTCT   4920

ATGTCGCGTC ATGCTTTCAA AATTCGCAAA ATACTTTGAC GAGATAAATA CCGGCATTGA   4980

TGTACTTATT CAGAACGAAG ATAAACAAAT TGAGCTTTCT GCGGAAATGG ATGTTATGGA   5040

ACAAAAGCTC AACACATTAA AACGGACTCT GGAAAAGCGA GAGCAGGATG CAAAGCTGGC   5100

CGAACAAAGA AAAAATGACG TTGTTATGTA CTTGGCGCAC GATATTAAAA CGCCCCTTAC   5160

ATCCATTATC GGTTATTTGA GCCTGCTTGA CGAGGCTCCA GACATGCCGG TAGATCAAAA   5220

GGCAAAGTAT GTGCATATCA CGTTGGACAA AGCGTATCGA CTCGAACAGC TAATCGACGA   5280

GTTTTTTGAG ATTACACGGT ATAACCTACA AACGATAACG CTAACAAAAA CGCACATAGA   5340

CCTATACTAT ATGCTGGTGC AGATGACCGA TGAATTTTAT CCTCAGCTTT CCGCACATGG   5400
```

```
AAAACAGGCG GTTATTCACG CCCCCGAGGA TCTGACCGTG TCCGGCGACC CTGATAAACT    5460

CGCGAGAGTC TTTAACAACA TTTTGAAAAA CGCCGCTGCA TACAGTGAGG ATAACAGCAT    5520

CATTGACATT ACCGCGGGCC TCTCCGGGGA TGTGGTGTCA ATCGAATTCA AGAACACTGG    5580

AAGCATCCCA AAAGATAAGC TAGCTGCCAT ATTTGAAAAG TTCTATAGGC TGGACAATGC    5640

TCGTTCTTCC GATACGGGTG GCGCGGGACT TGGATTGGCG ATTGCAAAAG AAATTATTGT    5700

TCAGCATGGA GGGCAGATTT ACGCGGAAAG CAATGATAAC TATACGACGT TTAGGGTAGA    5760

GCTTCCAGCG ATGCCAGACT TGGTTGATAA AAGGAGGTCC TAAGAGATGT ATATAATTTT    5820

TTAGGAAAAT CTCAAGGTTA TCTTTACTTT TTCTTAGGAA ATTAACAATT TAATATTAAG    5880

AAACGGCTCG TTCTTACACG GTAGACTTAA TACCGTAAGA ACGAGCCGTT TTCGTTCTTC    5940

AGAGAAAGAT TTGACAAGAT TACCATTGGC ATCCCCGTTT TATTTGGTGC CTTTCACAGA    6000

AAGGGTTGGT CTTAATTATG AATAACATCG GCATTACTGT TTATGGATGT GAGCAGGATG    6060

AGGCAGATGC ATTCCATGCT CTTTCGCCTC GCTTTGGCGT TATGGCAACG ATAATTAACG    6120

CCAACGTGTC GGAATCCAAC GCCAAATCCG CGCCTTTCAA TCAATGTATC AGTGTGGGAC    6180

ATAAATCAGA GATTTCCGCC TCTATTCTTC TTGCGCTGAA GAGAGCCGGT GTGAAATATA    6240

TTTCTACCCG AAGCATCGGC TGCAATCATA TAGATACAAC TGCTGCTAAG AGAATGGGCA    6300

TCACTGTCGA CAATGTGGCG TACTCGCCGG ATAGCGTTGC CGATTATACT ATGATGCTAA    6360

TTCTTATGGC AGTACGCAAC GTAAAATCGA TTGTGCGCTC TGTGGAAAAA CATGATTTCA    6420

GGTTGGACAG CGACCGTGGC AAGGTACTCA GCGACATGAC AGTTGGTGTG GTGGGAACGG    6480

GCCAGATAGG CAAAGCGGTT ATTGAGCGGC TGCGAGGATT TGGATGTAAA GTGTTGGCTT    6540

ATAGTCGCAG CCGAAGTATA GAGGTAAACT ATGTACCGTT TGATGAGTTG CTGCAAAATA    6600

GCGATATCGT TACGCTTCAT GTGCCGCTCA ATACGGATAC GCACTATATT ATCAGCCACG    6660

AACAAATACA GAGAATGAAG CAAGGAGCAT TTCTTATCAA TACTGGGCGC GGTCCACTTG    6720

TAGATACCTA TGAGTTGGTT AAAGCATTAG AAAACGGGAA ACTGGGCGGT GCCGCATTGG    6780

ATGTATTGGA AGGAGAGGAA GAGTTTTTCT ACTCTGATTG CACCCAAAAA CCAATTGATA    6840

ATCAATTTTT ACTTAAACTT CAAAGAATGC CTAACGTGAT AATCACACCG CATACGGCCT    6900

ATTATACCGA GCAAGCGTTG CGTGATACCG TTGAAAAAAC CATTAAAAAC TGTTTGGATT    6960

TTGAAAGGAG ACAGGAGCAT GAATAGAATA AAAGTTGCAA TACTGTTTGG GGGTTGCTCA    7020

GAGGAGCATG ACGTATCGGT AAAATCTGCA ATAGAGATAG CCGCTAACAT TAATAAAGAA    7080

AAATACGAGC CGTTATACAT TGGAATTACG AAATCTGGTG TATGGAAAAT GTGCGAAAAA    7140

CCTTGCGCGG AATGGGAAAA CGACAATTGC TATTCAGCTG TACTCTCGCC GGATAAAAAA    7200

ATGCACGGAT TACTTGTTAA AAAGAACCAT GAATATGAAA TCAACCATGT TGATGTAGCA    7260

TTTTCAGCTT TGCATGGCAA GTCAGGTGAA GATGGATCCA TACAAGGTCT GTTTGAATTG    7320

TCCGGTATCC CTTTTGTAGG CTGCGATATT CAAAGCTCAG CAATTTGTAT GGACAAATCG    7380

TTGACATACA TCGTTGCGAA AAATGCTGGG ATAGCTACTC CCGCCTTTTG GGTTATTAAT    7440

AAAGATGATA GGCCGGTGGC AGCTACGTTT ACCTATCCTG TTTTTGTTAA GCCGGCGCGT    7500

TCAGGCTCAT CCTTCGGTGT GAAAAAAGTC AATAGCGCGG ACGAATTGGA CTACGCAATT    7560

GAATCGGCAA GACAATATGA CAGCAAAATC TTAATTGAGC AGGCTGTTTC GGGCTGTGAG    7620

GTCGGTTGTG CGGTATTGGG AAACAGTGCC GCGTTAGTTG TTGGCGAGGT GGACCAAATC    7680

AGGCTGCAGT ACGGAATCTT TCGTATTCAT CAGGAAGTCG AGCCGGAAAA AGGCTCTGAA    7740

AACGCAGTTA TAACCGTTCC CGCAGACCTT TCAGCAGAGG AGCGAGGACG GATACAGGAA    7800
```

```
ACGGCAAAAA AAATATATAA AGCGCTCGGC TGTAGAGGTC TAGCCCGTGT GGATATGTTT      7860

TTACAAGATA ACGGCCGCAT TGTACTGAAC GAAGTCAATA CTCTGCCCGG TTTCACGTCA      7920

TACAGTCGTT ATCCCCGTAT GATGGCCGCT GCAGGTATTG CACTTCCCGA ACTGATTGAC      7980

CGCTTGATCG TATTAGCGTT AAAGGGGTGA TAAGCATGGA AATAGGATTT ACTTTTTTAG      8040

ATGAAATAGT ACACGGTGTT CGTTGGGACG CTAAATATGC CACTTGGGAT AATTTCACCG      8100

GAAAACCGGT TGACGGTTAT GAAGTAAATC GCATTGTAGG GACATACGAG TTGGCTGAAT      8160

CGCTTTTGAA GGCAAAAGAA CTGGCTGCTA CCCAAGGGTA CGGATTGCTT CTATGGGACG      8220

GTTACCGTCC TAAGCGTGCT GTAAACTGTT TTATGCAATG GGCTGCACAG CCGGAAAATA      8280

ACCTGACAAA GGAAAGTTAT TATCCCAATA TTGACCGAAC TGAGATGATT TCAAAAGGAT      8340

ACGTGGCTTC AAAATCAAGC CATAGCCGCG GCAGTGCCAT TGATCTTACG CTTTATCGAT      8400

TAGACACGGG TGAGCTTGTA CCAATGGGGA GCCGATTTGA TTTTATGGAT GAACGCTCTC      8460

ATCATGCGGC AAATGGAATA TCATGCAATG AAGCGCAAAA TCGCAGACGT TTGCGCTCCA      8520

TCATGGAAAA CAGTGGGTTT GAAGCATATA GCCTCGAATG GTGGCACTAT GTATTAAGAG      8580

ACGAACCATA CCCCAATAGC TATTTTGATT TCCCCGTTAA ATAAACTTTT AACCGTTGCA      8640

CGGACAAACT ATATAAGCTA ACTCTTTCGG CAGGAAACCC GACGTATGTA ACTGGTTCTT      8700

AGGGAATTTA TATATAGTAG ATAGTATTGA AGATGTAAGG CAGAGCGATA TTGCGGTCAT      8760

TATCTGCGTG CGCTGCGGCA AGATAGCCTG ATAATAAGAC TGATCGCATA GAGGGGTGGT      8820

ATTTCACACC GCCCATTGTC AACAGGCAGT TCAGCCTCGT TAAATTCAGC ATGGGTATCA      8880

CTTATGAAAA TTCATCTACA TTGGTGATAA TAGTAAATCC AGTAGGGCGA ATAATTGAC      8940

TGTAATTTAC GGGGCAAAAC GGCACAATCT CAAACGAGAT TGTGCCGTTT AAGGGGAAGA      9000

TTCTAGAAAT ATTTCATACT TCCAACTATA TAGTTAAGGA GGAGACTGAA AATGAAGAAG      9060

TTGTTTTTTT TATTGTTATT GTTATTCTTA ATATACTTAG GTTATGACTA CGTTAATGAA      9120

GCACTGTTTT CTCAGGAAAA AGTCGAATTT CAAAATTATG ATCAAAATCC CAAAGAACAT      9180

TTAGAAAATA GTGGGACTTC TGAAAATACC CAAGAGAAAA CAATTACAGA AGAACAGGTT      9240

TATCAAGGAA ATCTGCTATT AATCAATAGT AAATATCCTG TTCGCCAAGA AAGTGTGAAG      9300

TCAGATATCG TGAATTTATC TAAACATGAC GAATTAATAA ATGGATACGG TTGCTTGAT      9360

AGTAATATTT ATATGTCAAA AGAAATAGCA CAAAAATTTT CAGAGATGGT CAATGATGCT      9420

GTAAAGGGTG GCGTTAGTCA TTTTATTATT AATAGTGGCT ATCGAGACTT TGATGAGCAA      9480

AGTGTGCTTT ACCAAGAAAT GGGGGCTGAG TATGCCTTAC CAGCAGGTTA TAGTGAGCAT      9540

AATTCAGGTT TATCACTAGA TGTAGGATCA AGCTTGACGA AAATGGAACG AGCCCCTGAA      9600

GGAAAGTGGA TAGAAGAAAA TGCTTGGAAA TACGGGTTCA TTTTACGTTA TCCAGAGGAC      9660

AAAACAGAGT TAACAGGAAT TCAATATGAA CCATGGCATA TTCGCTATGT TGGTTTACCA      9720

CATAGTGCGA TTATGAAAGA AAAGAATTTC GTTCTCGAGG AATATATGGA TTACCTAAAA      9780

GAAGAAAAAA CCATTTCTGT TAGTGTAAAT GGGAAAAAT ATGAGATCTT TTATTATCCT      9840

GTTACTAAAA ATACCACCAT TCATGTGCCG ACTAATCTTC GTTATGAGAT ATCAGGAAAC      9900

AATATAGACG GTGTAATTGT GACAGTGTTT CCCGGATCAA CACATACTAA TTCAAGGAGG      9960

TAAGGATGGC GGAATGAAAC CAACGAAATT AATGAACAGC ATTATTGTAC TAGCACTTTT      10020

GGGGTAACGT TAGCTTTTTA ATTTAAAACC CACGTTAACT AGGACATTGC TATACTAATG      10080

ATACAACTTA AACAAAAGAA TTAGAGGAAA TTATATTGGG AAAAATATTA TCTAGAGGAT      10140

TGCTAGCTTT ATATTTAGTG ACACTAATCT GGTTAGTGTT ATTCAAATTA CAATACAATA      10200
```

```
TTTTATCAGT ATTTAATTAT CATCAAAGAA GTCTTAACTT GACTCCATTT ACTGCTACTG    10260

GGAATTTCAG AGAGATGATA GATAATGTTA TAATCTTTAT TCCATTTGGC TTGCTTTTGA    10320

ATGTCAATTT TAAAGAAATC GGATTTTTAC CTAAGTTTGC TTTTGTACTG GTTTTAAGTC    10380

TTACTTTTGA AATAATTCAA TTTATCTTCG CTATTGGAGC GACAGACATA ACAGATGTAA    10440

TTACAAATAC TGTTGGAGGC TTTCTTGGAC TGAAATTATA TGGTTTAAGC AATAAGCATA    10500

TGAATCAAAA AAAATTAGAC AGAGTTATTA TTTTTGTAGG TATACTTTTG CTCGTATTAT    10560

TGCTCGTTTA CCGTACCCAT TTAAGAATAA ATTACGTGTA AGATGTCTAA ATCAAGCAAT    10620

CTGATCTTTC ATACACATAA AGATATTGAA TGAATTGGAT TAGATGGAAA ACGGGATGTG    10680

GGGAAACTCG CCCGTAGGTG TGAAGTGAGG GGAAAACCGG TGATAAAGTA AAAAGCTTAC    10740

CTAACACTAT AGTAACAAAG AAAGCCCAAT TATCAATTTT AGTGCTGAGG AATTGGTCTC    10800

TTTAATAAAT TTCCTTAACG TTGTAAATCC GCATTTTCCT GACGGTACCC C             10851

(2) INFORMATION FOR SEQ ID NO:17:

(i) SEQUENCE CHARACTERISTICS:
        (A) LENGTH: 2667 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:17:

CAAGATTACC ATTGGCATCC CCGTTTTATT TGGTGCCTTT CACAGAAAGG GTTGGTCTTA      60

ATTATGAATA ACATCGGCAT TACTGTTTAT GGATGTGAGC AGGATGAGGC AGATGCATTC     120

CATGCTCTTT CGCCTCGCTT TGGCGTTATG GCAACGATAA TTAACGCCAA CGTGTCGGAA     180

TCCAACGCCA AATCCGCGCC TTTCAATCAA TGTATCAGTG TGGGACATAA ATCAGAGATT     240

TCCGCCTCTA TTCTTCTTGC GCTGAAGAGA GCCGGTGTGA AATATATTTC TACCCGAAGC     300

ATCGGCTGCA ATCATATAGA TACAACTGCT GCTAAGAGAA TGGGCATCAC TGTCGACAAT     360

GTGGCGTACT CGCCGGATAG CGTTGCCGAT TATACTATGA TGCTAATTCT TATGGCAGTA     420

CGCAACGTAA AATCGATTGT GCGCTCTGTG GAAAAACATG ATTTCAGGTT GGACAGCGAC     480

CGTGGCAAGG TACTCAGCGA CATGACAGTT GGTGTGGTGG GAACGGGCCA GATAGGCAAA     540

GCGGTTATTG AGCGGCTGCG AGGATTTGGA TGTAAAGTGT TGGCTTATAG TCGCAGCCGA     600

AGTATAGAGG TAAACTATGT ACCGTTTGAT GAGTTGATGC AAAATAGCGA TATCGTTACG     660

CTTCATGTGC CGCTCAATAC GGATACGCAC TATATTATCA GCCACGAACA AATACAGAGA     720

ATGAAGCAAG GAGCATTTCT TATCAATACT GGGCGCGGTC CACTTGTAGA TACCTATGAG     780

TTGGTTAAAG CATTAGAAAA CGGGAAACTG GGCGGTGCCG CATTGGATGT ATTGGAAGGA     840

GAGGAAGAGT TTTTCTACTC TGATTGCACC CAAAAACCAA TTGATAATCA ATTTTTACTT     900

AAACTTCAAA GAATGCCTAA CGTGATAATC ACACCGCATA CGGCCTATTA TACCGAGCAA     960

GCGTTGCGTG ATACCGTTGA AAAAACCATT AAAAACTGTT TGGATTTTGA AAGGAGACAG    1020

GAGCATGAAT AGAATAAAAG TTGCAATACT GTTTGGGGGT TGCTCAGAGG AGCATGACGT    1080

ATCGGTAAAA TCTGCAATAG AGATAGCCGC TAACATTAAT AAAGAAAAAT ACGAGCCGTT    1140

ATACATTGGA ATTACGAAAT CTGGTGTATG GAAAATGTGC GAAAAACCTT GCGCGGAATG    1200

GGAAAACGAC AATTGCTATT CAGCTGTACT CTCGCCGGAT AAAAAAATGC ACGGATTACT    1260

TGTTAAAAAG AACCATGAAT ATGAAATCAA CCATGTTGAT GTAGCATTTT CAGCTTTGCA    1320

TGGCAAGTCA GGTGAAGATG GATCCATACA AGGTCTGTTT GAATTGTCCG GTATCCCTTT    1380
```

-continued

```
TGTAGGCTGC GATATTCAAA GCTCAGCAAT TTGTATGGAC AAATCGTTGA CATACATCGT    1440

TGCGAAAAAT GCTGGGATAG CTACTCCCGC CTTTTGGGTT ATTAATAAAG ATGATAGGCC    1500

GGTGGCAGCT ACGTTTACCT ATCCTGTTTT TGTTAAGCCG GCGCGTTCAG GCTCATCCTT    1560

CGGTGTGAAA AAAGTCAATA GCGCGGACGA ATTGGACTAC GCAATTGAAT CGGCAAGACA    1620

ATATGACAGC AAAATCTTAA TTGAGCAGGC TGTTTCGGGC TGTGAGGTCG GTTGTGCGGT    1680

ATTGGGAAAC AGTGCCGCGT TAGTTGTTGG CGAGGTGGAC CAAATCAGGC TGCAGTACGG    1740

AATCTTTCGT ATTCATCAGG AAGTCGAGCC GGAAAAAGGC TCTGAAAACG CAGTTATAAC    1800

CGTTCCCGCA GACCTTTCAG CAGAGGAGCG AGGACGGATA CAGGAAACGG CAAAAAAAAT    1860

ATATAAAGCG CTCGGCTGTA GAGGTCTAGC CCGTGTGGAT ATGTTTTTAC AAGATAACGG    1920

CCGCATTGTA CTGAACGAAG TCAATACTCT GCCCGGTTTC ACGTCATACA GTCGTTATCC    1980

CCGTATGATG GCCGCTGCAG GTATTGCACT TCCCGAACTG ATTGACCGCT TGATCGTATT    2040

AGCGTTAAAG GGGTGATAAG CATGGAAATA GGATTTACTT TTTTAGATGA AATAGTACAC    2100

GGTGTTCGTT GGGACGCTAA ATATGCCACT TGGGATAATT TCACCGGAAA ACCGGTTGAC    2160

GGTTATGAAG TAAATCGCAT TGTAGGGACA TACGAGTTGG CTGAATCGCT TTTGAAGGCA    2220

AAAGAACTGG CTGCTACCCA AGGGTACGGA TTGCTTCTAT GGGACGGTTA CCGTCCTAAG    2280

CGTGCTGTAA ACTGTTTTAT GCAATGGGCT GCACAGCCGG AAAATAACCT GACAAAGGAA    2340

AGTTATTATC CCAATATTGA CCGAACTGAG ATGATTTCAA AAGGATACGT GGCTTCAAAA    2400

TCAAGCCATA GCCGCGGCAG TGCCATTGAT CTTACGCTTT ATCGATTAGA CACGGGTGAG    2460

CTTGTACCAA TGGGGAGCCG ATTTGATTTT ATGGATGAAC GCTCTCATCA TGCGGCAAAT    2520

GGAATATCAT GCAATGAAGC GCAAAATCGC AGACGTTTGC GCTCCATCAT GGAAAACAGT    2580

GGGTTTGAAG CATATAGCCT CGAATGGTGG CACTATGTAT TAAGAGACGA ACCATACCCC    2640

AATAGCTATT TTGATTTCCC CGTTAAA                                       2667
```

(2) INFORMATION FOR SEQ ID NO:18:

(i) SEQUENCE CHARACTERISTICS:
        (A) LENGTH: 2964 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..2964

(xi) SEQUENCE DESCRIPTION: SEQ ID NO:18:

```
ATG AAA ATT GCG AGA GGT AGA GAA TTG CTT ACA CCG GAA CAG AGA CAG      48
Met Lys Ile Ala Arg Gly Arg Glu Leu Leu Thr Pro Glu Gln Arg Gln
 1               5                  10                  15

GCT TTT ATG CAA ATC CCT GAA GAT GAA TGG ATA CTG GGG ACC TAC TTC      96
Ala Phe Met Gln Ile Pro Glu Asp Glu Trp Ile Leu Gly Thr Tyr Phe
             20                  25                  30

ACT TTT TCC AAA CGG GAT TTA GAA ATA GTT AAT AAG CGA AGG AGG GAA     144
Thr Phe Ser Lys Arg Asp Leu Glu Ile Val Asn Lys Arg Arg Arg Glu
         35                  40                  45

GAA AAC CGT TTA GGA TTT GCT GTT CAA TTA GCT GTT CTT CGG TAT CCC     192
Glu Asn Arg Leu Gly Phe Ala Val Gln Leu Ala Val Leu Arg Tyr Pro
     50                  55                  60

GGT TGG CCA TAC ACT CAT ATC AAA AGC ATC CCA GAT TCG GTC ATA CAA     240
Gly Trp Pro Tyr Thr His Ile Lys Ser Ile Pro Asp Ser Val Ile Gln
```

-continued

|  |  | 65 |  |  |  | 70 |  |  |  | 75 |  |  |  | 80 |  |  |
|---|---|---|---|---|---|---|---|---|---|---|---|---|---|---|---|---|

```
TAT ATA TCG AAA CAG ATT GGT GTT AGT CCA TCC TCG CTT GAT CAT TAT       288
Tyr Ile Ser Lys Gln Ile Gly Val Ser Pro Ser Ser Leu Asp His Tyr
            85                  90                  95

CCT CAA AGG GAA AAT ACA CTT TGG GAT CAT TTG AAA GAA ATT CGA AGT       336
Pro Gln Arg Glu Asn Thr Leu Trp Asp His Leu Lys Glu Ile Arg Ser
                100                 105                 110

GAA TAC GAC TTT GTA ACT TTT ACC CTG AGT GAA TAT CGA ATG ACA TTT       384
Glu Tyr Asp Phe Val Thr Phe Thr Leu Ser Glu Tyr Arg Met Thr Phe
                115                 120                 125

AAG TAC CTT CAT CAA TTA GCT TTG GAA AAT GGT GAT GCC ATT CAT CTA       432
Lys Tyr Leu His Gln Leu Ala Leu Glu Asn Gly Asp Ala Ile His Leu
        130                 135                 140

CTG CAT GAA TGC ATA GAT TTT CTA AGA AAA AAC AAA ATT ATA CTG CCT       480
Leu His Glu Cys Ile Asp Phe Leu Arg Lys Asn Lys Ile Ile Leu Pro
145                 150                 155                 160

GCT ATC ACT ACA CTT GAA AGA ATG GTG TGG GAA GCA AGG GCA ATG GCT       528
Ala Ile Thr Thr Leu Glu Arg Met Val Trp Glu Ala Arg Ala Met Ala
                165                 170                 175

GAA AAG AAG CTA TTT AAT ACG GTT AGT AAA TCT CTA ACA AAT GAG CAA       576
Glu Lys Lys Leu Phe Asn Thr Val Ser Lys Ser Leu Thr Asn Glu Gln
        180                 185                 190

AAA GAA AAG CTT GAA GGG ATT ATT ACC TCG CAG CAT CCA TCC GAA TCC       624
Lys Glu Lys Leu Glu Gly Ile Ile Thr Ser Gln His Pro Ser Glu Ser
195                 200                 205

AAT AAA ACG ATA TTG GGT TGG TTA AAA GAG CCA CCG GGT CAT CCT TCA       672
Asn Lys Thr Ile Leu Gly Trp Leu Lys Glu Pro Pro Gly His Pro Ser
210                 215                 220

CCC GAA ACT TTT CTA AAA ATA ATA GAA CGA CTC GAA TAC ATA CGA GGA       720
Pro Glu Thr Phe Leu Lys Ile Ile Glu Arg Leu Glu Tyr Ile Arg Gly
225                 230                 235                 240

ATG GAT TTA GAA ACA GTG CAA ATT AGT CAT TTG CAC CGT AAC CGC CTG       768
Met Asp Leu Glu Thr Val Gln Ile Ser His Leu His Arg Asn Arg Leu
                245                 250                 255

TTG CAG CTG TCT CGC TTA GGC TCA AGA TAC GAG CCG TAT GCA TTC CGT       816
Leu Gln Leu Ser Arg Leu Gly Ser Arg Tyr Glu Pro Tyr Ala Phe Arg
        260                 265                 270

GAC TTT CAA GAA AAT AAA CGT TAT TCG ATA TTA ACC ATC TAT TTA TTA       864
Asp Phe Gln Glu Asn Lys Arg Tyr Ser Ile Leu Thr Ile Tyr Leu Leu
        275                 280                 285

CAA CTT ACT CAG GAG CTA ACG GAT AAA GCG TTT GAA ATT CAT GAT AGG       912
Gln Leu Thr Gln Glu Leu Thr Asp Lys Ala Phe Glu Ile His Asp Arg
        290                 295                 300

CAA ATA CTT AGT TTG TTA TCA AAA GGT CGT AAG GCT CAA GAG GAA ATC       960
Gln Ile Leu Ser Leu Leu Ser Lys Gly Arg Lys Ala Gln Glu Glu Ile
305                 310                 315                 320

CAG AAA CAA AAC GGT AAA AAG CTA AAT GAG AAA GTT ATA CAC TTT ACG      1008
Gln Lys Gln Asn Gly Lys Lys Leu Asn Glu Lys Val Ile His Phe Thr
                325                 330                 335

AAC ATC GGA CAA GCA TTA ATT AAA GCA AGA GAG GAA AAA TTA GAC GTT      1056
Asn Ile Gly Gln Ala Leu Ile Lys Ala Arg Glu Glu Lys Leu Asp Val
        340                 345                 350

TTT AAG GTT TTA GAA TCG GTT ATT GAA TGG AAT ACC TTT GTC TCT TCA      1104
Phe Lys Val Leu Glu Ser Val Ile Glu Trp Asn Thr Phe Val Ser Ser
                355                 360                 365

GTA GAA GAG GCT CAG GAA CTT GCA CGT CCT GCC GAC TAT GAT TAT TTA      1152
Val Glu Glu Ala Gln Glu Leu Ala Arg Pro Ala Asp Tyr Asp Tyr Leu
        370                 375                 380

GAC TTA CTG CAA AAA CGG TTT TAT TCA CTA AGA AAA TAT ACG CCA ACG      1200
Asp Leu Leu Gln Lys Arg Phe Tyr Ser Leu Arg Lys Tyr Thr Pro Thr
```

-continued

| | | | | | | | | | | | | | |
|---|---|---|---|---|---|---|---|---|---|---|---|---|---|
| | 385 | | | | 390 | | | | 395 | | | | 400 |
| CTA | TTA | AGA | GTA | TTG | GAA | TTT | CAT | TCT | ACA | AAG | GCA | AAT | GAG | CCA | CTT | 1248 |
| Leu | Leu | Arg | Val | Leu | Glu | Phe | His | Ser | Thr | Lys | Ala | Asn | Glu | Pro | Leu |
| | | | | 405 | | | | 410 | | | | 415 | |

```
CTA TTA AGA GTA TTG GAA TTT CAT TCT ACA AAG GCA AAT GAG CCA CTT                1248
Leu Leu Arg Val Leu Glu Phe His Ser Thr Lys Ala Asn Glu Pro Leu
            405             410             415

TTA CAA GCT GTT GAG ATT ATC CGA GGA ATG AAC GAA TCT GGA AAG CGA                1296
Leu Gln Ala Val Glu Ile Ile Arg Gly Met Asn Glu Ser Gly Lys Arg
                420             425             430

AAA GTG CCT GAT GAC TCA CCT GTG GAT TTT ATT TCA AAA CGA TGG AAA                1344
Lys Val Pro Asp Asp Ser Pro Val Asp Phe Ile Ser Lys Arg Trp Lys
            435             440             445

AGA CAT TTA TAC GAG GAT GAT GGT ACA ACA ATT AAT CGT CAT TAC TAT                1392
Arg His Leu Tyr Glu Asp Asp Gly Thr Thr Ile Asn Arg His Tyr Tyr
        450             455             460

GAA ATG GCT GTT TTA ACA GAA CTT CGG GAG CAT GTT CGG GCA GGA GAT                1440
Glu Met Ala Val Leu Thr Glu Leu Arg Glu His Val Arg Ala Gly Asp
465             470             475             480

GTT TCC ATT GTT GGC AGC AGA CAA TAT AGG GAT TTT GAG GAA TAT TTG                1488
Val Ser Ile Val Gly Ser Arg Gln Tyr Arg Asp Phe Glu Glu Tyr Leu
                485             490             495

TTT TCG GAA GAT ACA TGG AAT CAA TCG AAG GGG AAT ACG AGA TTA TCA                1536
Phe Ser Glu Asp Thr Trp Asn Gln Ser Lys Gly Asn Thr Arg Leu Ser
            500             505             510

GTT AGT TTA TCA TTC GAA GAT TAT ATA ACG GAG AGA ACC AGC AGC TTT                1584
Val Ser Leu Ser Phe Glu Asp Tyr Ile Thr Glu Arg Thr Ser Ser Phe
        515             520             525

AAT GAA AGG TTA AAG TGG TTA GCT GCC AAT TCC AAT AAG TTA GAT GGG                1632
Asn Glu Arg Leu Lys Trp Leu Ala Ala Asn Ser Asn Lys Leu Asp Gly
            530             535             540

GTT TCT CTT GAA AAA GGA AAG CTA TCA CTT GCA CGC TTA GAA AAA GAT                1680
Val Ser Leu Glu Lys Gly Lys Leu Ser Leu Ala Arg Leu Glu Lys Asp
545             550             555             560

GTT CCA GAA GAA GCA AAA AAA TTT AGT GCA AGC CTT TAT CAG ATG CTA                1728
Val Pro Glu Glu Ala Lys Lys Phe Ser Ala Ser Leu Tyr Gln Met Leu
                565             570             575

CCA AGA ATA AAA TTA ACT GAT TTA CTC ATG GAT GTG GCC CAT ATA ACA                1776
Pro Arg Ile Lys Leu Thr Asp Leu Leu Met Asp Val Ala His Ile Thr
            580             585             590

GGA TTT CAT GAG CAA TTC ACT CAT GCT TCC AAT AAT CGA AAA CCA GAT                1824
Gly Phe His Glu Gln Phe Thr His Ala Ser Asn Asn Arg Lys Pro Asp
        595             600             605

AAG GAA GAA ACA ATC ATT ATC ATG GCT GCC CTT TTA GGA ATG GGA ATG                1872
Lys Glu Glu Thr Ile Ile Ile Met Ala Ala Leu Leu Gly Met Gly Met
            610             615             620

AAT ATT GGC TTG AGC AAG ATG GCC GAA GCC ACA CCC GGA CTT ACA TAT                1920
Asn Ile Gly Leu Ser Lys Met Ala Glu Ala Thr Pro Gly Leu Thr Tyr
625             630             635             640

AAG CAA CTA GCC AAT GTA TCT CAA TGG CGC ATG TAT GAA GAT GCC ATG                1968
Lys Gln Leu Ala Asn Val Ser Gln Trp Arg Met Tyr Glu Asp Ala Met
                645             650             655

AAT AAA GCC CAA GCC ATA TTA GTA AAC TTT CAT CAT AAA TTA CAA TTG                2016
Asn Lys Ala Gln Ala Ile Leu Val Asn Phe His His Lys Leu Gln Leu
            660             665             670

CCT TTC TAT TGG GGC GAC GGT ACA ACA TCT TCG TCA GAT GGT ATG AGA                2064
Pro Phe Tyr Trp Gly Asp Gly Thr Thr Ser Ser Ser Asp Gly Met Arg
        675             680             685

ATG CAG CTA GGT GTT TCA TCA CTA CAT GCA GAT GCA AAT CCA CAT TAT                2112
Met Gln Leu Gly Val Ser Ser Leu His Ala Asp Ala Asn Pro His Tyr
            690             695             700

GGA ACT GGA AAA GGA GCC ACC ATC TAC CGA TTT ACA AGT GAT CAA TTC                2160
Gly Thr Gly Lys Gly Ala Thr Ile Tyr Arg Phe Thr Ser Asp Gln Phe
```

| | | | | | | | | | | | | | | | |
|---|---|---|---|---|---|---|---|---|---|---|---|---|---|---|---|
| | | | | 705 | | | | | 710 | | | | | 715 | 720 |
| TCT | TCT | TAC | TAC | ACA | AAG | ATT | ATT | CAT | ACT | AAT | TCA | AGA | GAT | GCG | ATT | 2208
| Ser | Ser | Tyr | Tyr | Thr | Lys | Ile | Ile | His | Thr | Asn | Ser | Arg | Asp | Ala | Ile |
| | | | | 725 | | | | | 730 | | | | | 735 | |

```
            705                 710                 715                 720
TCT TCT TAC TAC ACA AAG ATT ATT CAT ACT AAT TCA AGA GAT GCG ATT         2208
Ser Ser Tyr Tyr Thr Lys Ile Ile His Thr Asn Ser Arg Asp Ala Ile
                725                 730                 735

CAT GTT TTG GAT GGT TTG TTA CAT CAT GAG ACG GAT CTA AAC ATA GAG         2256
His Val Leu Asp Gly Leu Leu His His Glu Thr Asp Leu Asn Ile Glu
                740                 745                 750

GAA CAT TAT ACA GAC ACT GCC GGT TAC ACT GAC CAA ATA TTC GGA CTG         2304
Glu His Tyr Thr Asp Thr Ala Gly Tyr Thr Asp Gln Ile Phe Gly Leu
                755                 760                 765

ACT CAT TTA TTA GGA TTT AAA TTT GCC CCA AGA ATA AGG GAT TTA TCG         2352
Thr His Leu Leu Gly Phe Lys Phe Ala Pro Arg Ile Arg Asp Leu Ser
        770                 775                 780

GAC TCA AAA TTA TTT ACG ATA GAT AAA GCA AGT GAG TAT CCA AAA CTA         2400
Asp Ser Lys Leu Phe Thr Ile Asp Lys Ala Ser Glu Tyr Pro Lys Leu
785                 790                 795                 800

GAA GCC ATT TTA CGT GGA CAA ATA AAT ACA AAG GTC ATT AAA GAA AAT         2448
Glu Ala Ile Leu Arg Gly Gln Ile Asn Thr Lys Val Ile Lys Glu Asn
                805                 810                 815

TAT GAG GAT GTT TTG CGA TTA GCT CAT TCT ATA AGG GAG GGA ACA GTT         2496
Tyr Glu Asp Val Leu Arg Leu Ala His Ser Ile Arg Glu Gly Thr Val
                820                 825                 830

TCA GCA TCC CTT ATT ATG GGG AAG CTA GGT TCC TAT TCA AGA CAA AAC         2544
Ser Ala Ser Leu Ile Met Gly Lys Leu Gly Ser Tyr Ser Arg Gln Asn
                835                 840                 845

AGC TTA GCT ACA GCC TTA CGT GAG ATG GGC CGA ATA GAA AAA ACG ATC         2592
Ser Leu Ala Thr Ala Leu Arg Glu Met Gly Arg Ile Glu Lys Thr Ile
        850                 855                 860

TTT ATT TTG AAT TAT ATA TCG GAT GAA TCA TTA AGA AGA AAA ATA CAA         2640
Phe Ile Leu Asn Tyr Ile Ser Asp Glu Ser Leu Arg Arg Lys Ile Gln
865                 870                 875                 880

AGA GGA TTG AAT AAA GGA GAA GCC ATG AAT GGA TTG GCA AGA GCT ATT         2688
Arg Gly Leu Asn Lys Gly Glu Ala Met Asn Gly Leu Ala Arg Ala Ile
                885                 890                 895

TTC TTC GGA AAA CAA GGT GAG CTT AGA GAA CGC ACC ATA CAG CAT CAA         2736
Phe Phe Gly Lys Gln Gly Glu Leu Arg Glu Arg Thr Ile Gln His Gln
                900                 905                 910

TTG CAA AGA GCC AGT GCT TTA AAC ATA ATT ATC AAT GCT ATA AGT ATT         2784
Leu Gln Arg Ala Ser Ala Leu Asn Ile Ile Ile Asn Ala Ile Ser Ile
                915                 920                 925

TGG AAT ACT CTC CAC CTA ACA ACA GCA GTT GAA TAT AAA AAA CGG ACA         2832
Trp Asn Thr Leu His Leu Thr Thr Ala Val Glu Tyr Lys Lys Arg Thr
        930                 935                 940

GGT AGC TTT AAT GAA GAT TTG TTA CAC CAT ATG TCG CCC TTA GGT TGG         2880
Gly Ser Phe Asn Glu Asp Leu Leu His His Met Ser Pro Leu Gly Trp
945                 950                 955                 960

GAA CAT ATT AAT TTA CTA GGA GAA TAC CAT TTT AAC TCA GAG AAA GTA         2928
Glu His Ile Asn Leu Leu Gly Glu Tyr His Phe Asn Ser Glu Lys Val
                965                 970                 975

GTC TCA TTA AAT TCT TTA AGA CCA CTA AAA CTT TCT                         2964
Val Ser Leu Asn Ser Leu Arg Pro Leu Lys Leu Ser
                980                 985
```

(2) INFORMATION FOR SEQ ID NO:19:

(i) SEQUENCE CHARACTERISTICS:
        (A) LENGTH: 988 amino acids
        (B) TYPE: amino acid
        (D) TOPOLOGY: linear (ii) MOLECULE TYPE: protein (xi) SEQUENCE DESCRIPTION: SEQ ID NO:19:

Met Lys Ile Ala Arg Gly Arg Glu Leu Leu Thr Pro Glu Gln Arg Gln
1               5                   10                  15

Ala Phe Met Gln Ile Pro Glu Asp Glu Trp Ile Leu Gly Thr Tyr Phe
            20                  25                  30

Thr Phe Ser Lys Arg Asp Leu Glu Ile Val Asn Lys Arg Arg Arg Glu
        35                  40                  45

Glu Asn Arg Leu Gly Phe Ala Val Gln Leu Ala Val Leu Arg Tyr Pro
    50                  55                  60

Gly Trp Pro Tyr Thr His Ile Lys Ser Ile Pro Asp Ser Val Ile Gln
65              70                  75                  80

Tyr Ile Ser Lys Gln Ile Gly Val Ser Pro Ser Ser Leu Asp His Tyr
                85                  90                  95

Pro Gln Arg Glu Asn Thr Leu Trp Asp His Leu Lys Glu Ile Arg Ser
            100                 105                 110

Glu Tyr Asp Phe Val Thr Phe Thr Leu Ser Glu Tyr Arg Met Thr Phe
        115                 120                 125

Lys Tyr Leu His Gln Leu Ala Leu Glu Asn Gly Asp Ala Ile His Leu
    130                 135                 140

Leu His Glu Cys Ile Asp Phe Leu Arg Lys Asn Lys Ile Ile Leu Pro
145             150                 155                 160

Ala Ile Thr Thr Leu Glu Arg Met Val Trp Glu Ala Arg Ala Met Ala
                165                 170                 175

Glu Lys Lys Leu Phe Asn Thr Val Ser Lys Ser Leu Thr Asn Glu Gln
            180                 185                 190

Lys Glu Lys Leu Glu Gly Ile Ile Thr Ser Gln His Pro Ser Glu Ser
        195                 200                 205

Asn Lys Thr Ile Leu Gly Trp Leu Lys Glu Pro Pro Gly His Pro Ser
    210                 215                 220

Pro Glu Thr Phe Leu Lys Ile Ile Glu Arg Leu Glu Tyr Ile Arg Gly
225             230                 235                 240

Met Asp Leu Glu Thr Val Gln Ile Ser His Leu His Arg Asn Arg Leu
                245                 250                 255

Leu Gln Leu Ser Arg Leu Gly Ser Arg Tyr Glu Pro Tyr Ala Phe Arg
            260                 265                 270

Asp Phe Gln Glu Asn Lys Arg Tyr Ser Ile Leu Thr Ile Tyr Leu Leu
        275                 280                 285

Gln Leu Thr Gln Glu Leu Thr Asp Lys Ala Phe Glu Ile His Asp Arg
    290                 295                 300

Gln Ile Leu Ser Leu Leu Ser Lys Gly Arg Lys Ala Gln Glu Glu Ile
305             310                 315                 320

Gln Lys Gln Asn Gly Lys Lys Leu Asn Glu Lys Val Ile His Phe Thr
                325                 330                 335

Asn Ile Gly Gln Ala Leu Ile Lys Ala Arg Glu Glu Lys Leu Asp Val
            340                 345                 350

Phe Lys Val Leu Glu Ser Val Ile Glu Trp Asn Thr Phe Val Ser Ser
        355                 360                 365

Val Glu Glu Ala Gln Glu Leu Ala Arg Pro Ala Asp Tyr Asp Tyr Leu
    370                 375                 380

Asp Leu Leu Gln Lys Arg Phe Tyr Ser Leu Arg Lys Tyr Thr Pro Thr
385             390                 395                 400

Leu Leu Arg Val Leu Glu Phe His Ser Thr Lys Ala Asn Glu Pro Leu
                405                 410                 415

-continued

```
Leu Gln Ala Val Glu Ile Ile Arg Gly Met Asn Glu Ser Gly Lys Arg
        420                 425                 430

Lys Val Pro Asp Asp Ser Pro Val Asp Phe Ile Ser Lys Arg Trp Lys
            435                 440                 445

Arg His Leu Tyr Glu Asp Gly Thr Thr Ile Asn Arg His Tyr Tyr
        450                 455                 460

Glu Met Ala Val Leu Thr Glu Leu Arg Glu His Val Arg Ala Gly Asp
465                 470                 475                 480

Val Ser Ile Val Gly Ser Arg Gln Tyr Arg Asp Phe Glu Glu Tyr Leu
                485                 490                 495

Phe Ser Glu Asp Thr Trp Asn Gln Ser Lys Gly Asn Thr Arg Leu Ser
                500                 505                 510

Val Ser Leu Ser Phe Glu Asp Tyr Ile Thr Glu Arg Thr Ser Ser Phe
            515                 520                 525

Asn Glu Arg Leu Lys Trp Leu Ala Ala Asn Ser Asn Lys Leu Asp Gly
        530                 535                 540

Val Ser Leu Glu Lys Gly Lys Leu Ser Leu Ala Arg Leu Glu Lys Asp
545                 550                 555                 560

Val Pro Glu Glu Ala Lys Lys Phe Ser Ala Ser Leu Tyr Gln Met Leu
                565                 570                 575

Pro Arg Ile Lys Leu Thr Asp Leu Leu Met Asp Val Ala His Ile Thr
            580                 585                 590

Gly Phe His Glu Gln Phe Thr His Ala Ser Asn Asn Arg Lys Pro Asp
        595                 600                 605

Lys Glu Glu Thr Ile Ile Ile Met Ala Ala Leu Leu Gly Met Gly Met
        610                 615                 620

Asn Ile Gly Leu Ser Lys Met Ala Glu Ala Thr Pro Gly Leu Thr Tyr
625                 630                 635                 640

Lys Gln Leu Ala Asn Val Ser Gln Trp Arg Met Tyr Glu Asp Ala Met
                645                 650                 655

Asn Lys Ala Gln Ala Ile Leu Val Asn Phe His His Lys Leu Gln Leu
            660                 665                 670

Pro Phe Tyr Trp Gly Asp Gly Thr Thr Ser Ser Ser Asp Gly Met Arg
        675                 680                 685

Met Gln Leu Gly Val Ser Ser Leu His Ala Asp Ala Asn Pro His Tyr
        690                 695                 700

Gly Thr Gly Lys Gly Ala Thr Ile Tyr Arg Phe Thr Ser Asp Gln Phe
705                 710                 715                 720

Ser Ser Tyr Tyr Thr Lys Ile Ile His Thr Asn Ser Arg Asp Ala Ile
                725                 730                 735

His Val Leu Asp Gly Leu Leu His Glu Thr Asp Leu Asn Ile Glu
            740                 745                 750

Glu His Tyr Thr Asp Thr Ala Gly Tyr Thr Asp Gln Ile Phe Gly Leu
        755                 760                 765

Thr His Leu Leu Gly Phe Lys Phe Ala Pro Arg Ile Arg Asp Leu Ser
        770                 775                 780

Asp Ser Lys Leu Phe Thr Ile Asp Lys Ala Ser Glu Tyr Pro Lys Leu
785                 790                 795                 800

Glu Ala Ile Leu Arg Gly Gln Ile Asn Thr Lys Val Ile Lys Glu Asn
                805                 810                 815

Tyr Glu Asp Val Leu Arg Leu Ala His Ser Ile Arg Glu Gly Thr Val
            820                 825                 830

Ser Ala Ser Leu Ile Met Gly Lys Leu Gly Ser Tyr Ser Arg Gln Asn
        835                 840                 845
```

```
Ser Leu Ala Thr Ala Leu Arg Glu Met Gly Arg Ile Glu Lys Thr Ile
    850                 855                 860

Phe Ile Leu Asn Tyr Ile Ser Asp Glu Ser Leu Arg Arg Lys Ile Gln
865                 870                 875                 880

Arg Gly Leu Asn Lys Gly Glu Ala Met Asn Gly Leu Ala Arg Ala Ile
                885                 890                 895

Phe Phe Gly Lys Gln Gly Glu Leu Arg Glu Arg Thr Ile Gln His Gln
            900                 905                 910

Leu Gln Arg Ala Ser Ala Leu Asn Ile Ile Ile Asn Ala Ile Ser Ile
        915                 920                 925

Trp Asn Thr Leu His Leu Thr Thr Ala Val Glu Tyr Lys Lys Arg Thr
    930                 935                 940

Gly Ser Phe Asn Glu Asp Leu Leu His His Met Ser Pro Leu Gly Trp
945                 950                 955                 960

Glu His Ile Asn Leu Leu Gly Glu Tyr His Phe Asn Ser Glu Lys Val
                965                 970                 975

Val Ser Leu Asn Ser Leu Arg Pro Leu Lys Leu Ser
                980                 985
```

(2) INFORMATION FOR SEQ ID NO:20:

(i) SEQUENCE CHARACTERISTICS:
        (A) LENGTH: 573 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..573

(xi) SEQUENCE DESCRIPTION: SEQ ID NO:20:

```
TTG CGG AAA ATC GGT TAT ATT CGT GTC AGT TCG ACT AAC CAG AAT CCT       48
Leu Arg Lys Ile Gly Tyr Ile Arg Val Ser Ser Thr Asn Gln Asn Pro
 1               5                  10                  15

TCA AGA CAA TTT CAG CAG TTG AAC GAG ATC GGA ATG GAT ATT ATA TAT       96
Ser Arg Gln Phe Gln Gln Leu Asn Glu Ile Gly Met Asp Ile Ile Tyr
            20                  25                  30

GAA GAG AAA GTT TCA GGA GCA ACA AAG GAT CGC GAG CAA CTT CAA AAA      144
Glu Glu Lys Val Ser Gly Ala Thr Lys Asp Arg Glu Gln Leu Gln Lys
        35                  40                  45

GTG TTA GAC GAT TTA CAG GAA GAT GAC ATC ATT TAT GTT ACA GAC TTA      192
Val Leu Asp Asp Leu Gln Glu Asp Asp Ile Ile Tyr Val Thr Asp Leu
    50                  55                  60

ACT CGA ATC ACT CGT AGT ACA CAA GAT CTA TTT GAA TTA ATC GAT AAC      240
Thr Arg Ile Thr Arg Ser Thr Gln Asp Leu Phe Glu Leu Ile Asp Asn
 65                 70                  75                  80

ATA CGA GAT AAA AAG GCA AGT TTA AAA TCA CTA AAA GAT ACA TGG CTT      288
Ile Arg Asp Lys Lys Ala Ser Leu Lys Ser Leu Lys Asp Thr Trp Leu
                85                  90                  95

GAT TTA TCA GAA GAT AAT CCA TAC AGC CAA TTC TTA ATT ACT GTA ATG      336
Asp Leu Ser Glu Asp Asn Pro Tyr Ser Gln Phe Leu Ile Thr Val Met
            100                 105                 110

GCT GGT GTT AAC CAA TTA GAG CGA GAT CTT ATT CGG ATG AGA CAA CGT      384
Ala Gly Val Asn Gln Leu Glu Arg Asp Leu Ile Arg Met Arg Gln Arg
        115                 120                 125

GAA GGG ATT GAA TTG GCT AAG AAA GAA GGA AAG TTT AAA GGT CGA TTA      432
Glu Gly Ile Glu Leu Ala Lys Lys Glu Gly Lys Phe Lys Gly Arg Leu
    130                 135                 140
```

```
AAG AAG TAT CAT AAA AAT CAC GCA GGA ATG AAT TAT GCG GTA AAG CTA      480
Lys Lys Tyr His Lys Asn His Ala Gly Met Asn Tyr Ala Val Lys Leu
145                 150                 155                 160

TAT AAA GAA GGA AAT ATG ACT GTA AAT CAA ATT TGT GAA ATT ACT AAT      528
Tyr Lys Glu Gly Asn Met Thr Val Asn Gln Ile Cys Glu Ile Thr Asn
                165                 170                 175

GTA TCT AGG GCT TCA TTA TAC AGG AAA TTA TCA GAA GTG AAT AAT          573
Val Ser Arg Ala Ser Leu Tyr Arg Lys Leu Ser Glu Val Asn Asn
        180                 185                 190
```

(2) INFORMATION FOR SEQ ID NO:21:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:21:

```
Leu Arg Lys Ile Gly Tyr Ile Arg Val Ser Ser Thr Asn Gln Asn Pro
1               5                   10                  15

Ser Arg Gln Phe Gln Gln Leu Asn Glu Ile Gly Met Asp Ile Ile Tyr
                20                  25                  30

Glu Glu Lys Val Ser Gly Ala Thr Lys Asp Arg Glu Gln Leu Gln Lys
            35                  40                  45

Val Leu Asp Asp Leu Gln Glu Asp Asp Ile Ile Tyr Val Thr Asp Leu
        50                  55                  60

Thr Arg Ile Thr Arg Ser Thr Gln Asp Leu Phe Glu Leu Ile Asp Asn
65                  70                  75                  80

Ile Arg Asp Lys Lys Ala Ser Leu Lys Ser Leu Lys Asp Thr Trp Leu
                85                  90                  95

Asp Leu Ser Glu Asp Asn Pro Tyr Ser Gln Phe Leu Ile Thr Val Met
                100                 105                 110

Ala Gly Val Asn Gln Leu Glu Arg Asp Leu Ile Arg Met Arg Gln Arg
            115                 120                 125

Glu Gly Ile Glu Leu Ala Lys Lys Glu Gly Lys Phe Lys Gly Arg Leu
        130                 135                 140

Lys Lys Tyr His Lys Asn His Ala Gly Met Asn Tyr Ala Val Lys Leu
145                 150                 155                 160

Tyr Lys Glu Gly Asn Met Thr Val Asn Gln Ile Cys Glu Ile Thr Asn
                165                 170                 175

Val Ser Arg Ala Ser Leu Tyr Arg Lys Leu Ser Glu Val Asn Asn
            180                 185                 190
```

(2) INFORMATION FOR SEQ ID NO:22:

(i) SEQUENCE CHARACTERISTICS:
        (A) LENGTH: 909 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..909

(xi) SEQUENCE DESCRIPTION: SEQ ID NO:22:

```
ATG AAG AAG TTG TTT TTT TTA TTG TTA TTG TTA TTC TTA ATA TAC TTA      48
Met Lys Lys Leu Phe Phe Leu Leu Leu Leu Leu Phe Leu Ile Tyr Leu
```

```
        1               5              10              15
GGT TAT GAC TAC GTT AAT GAA GCA CTG TTT TCT CAG GAA AAA GTC GAA      96
Gly Tyr Asp Tyr Val Asn Glu Ala Leu Phe Ser Gln Glu Lys Val Glu
                 20              25              30

TTT CAA AAT TAT GAT CAA AAT CCC AAA GAA CAT TTA GAA AAT AGT GGG     144
Phe Gln Asn Tyr Asp Gln Asn Pro Lys Glu His Leu Glu Asn Ser Gly
             35              40              45

ACT TCT GAA AAT ACC CAA GAG AAA ACA ATT ACA GAA CAG GTT TAT         192
Thr Ser Glu Asn Thr Gln Glu Lys Thr Ile Thr Glu Gln Val Tyr
         50              55              60

CAA GGA AAT CTG CTA TTA ATC AAT AGT AAA TAT CCT GTT CGC CAA GAA     240
Gln Gly Asn Leu Leu Leu Ile Asn Ser Lys Tyr Pro Val Arg Gln Glu
 65              70              75              80

AGT GTG AAG TCA GAT ATC GTG AAT TTA TCT AAA CAT GAC GAA TTA ATA     288
Ser Val Lys Ser Asp Ile Val Asn Leu Ser Lys His Asp Glu Leu Ile
                 85              90              95

AAT GGA TAC GGG TTG CTT GAT AGT AAT ATT TAT ATG TCA AAA GAA ATA     336
Asn Gly Tyr Gly Leu Leu Asp Ser Asn Ile Tyr Met Ser Lys Glu Ile
            100             105             110

GCA CAA AAA TTT TCA GAG ATG GTC AAT GAT GCT GTA AAG GGT GGC GTT     384
Ala Gln Lys Phe Ser Glu Met Val Asn Asp Ala Val Lys Gly Gly Val
        115             120             125

AGT CAT TTT ATT ATT AAT AGT GGC TAT CGA GAC TTT GAT GAG CAA AGT     432
Ser His Phe Ile Ile Asn Ser Gly Tyr Arg Asp Phe Asp Glu Gln Ser
    130             135             140

GTG CTT TAC CAA GAA ATG GGG GCT GAG TAT GCC TTA CCA GCA GGT TAT     480
Val Leu Tyr Gln Glu Met Gly Ala Glu Tyr Ala Leu Pro Ala Gly Tyr
145             150             155             160

AGT GAG CAT AAT TCA GGT TTA TCA CTA GAT GTA GGA TCA AGC TTG ACG     528
Ser Glu His Asn Ser Gly Leu Ser Leu Asp Val Gly Ser Ser Leu Thr
                165             170             175

AAA ATG GAA CGA GCC CCT GAA GGA AAG TGG ATA GAA GAA AAT GCT TGG     576
Lys Met Glu Arg Ala Pro Glu Gly Lys Trp Ile Glu Glu Asn Ala Trp
            180             185             190

AAA TAC GGG TTC ATT TTA CGT TAT CCA GAG GAC AAA ACA GAG TTA ACA     624
Lys Tyr Gly Phe Ile Leu Arg Tyr Pro Glu Asp Lys Thr Glu Leu Thr
        195             200             205

GGA ATT CAA TAT GAA CCA TGG CAT ATT CGC TAT GTT GGT TTA CCA CAT     672
Gly Ile Gln Tyr Glu Pro Trp His Ile Arg Tyr Val Gly Leu Pro His
    210             215             220

AGT GCG ATT ATG AAA GAA AAG AAT TTC GTT CTC GAG GAA TAT ATG GAT     720
Ser Ala Ile Met Lys Glu Lys Asn Phe Val Leu Glu Glu Tyr Met Asp
225             230             235             240

TAC CTA AAA GAA GAA AAA ACC ATT TCT GTT AGT GTA AAT GGG GAA AAA     768
Tyr Leu Lys Glu Glu Lys Thr Ile Ser Val Ser Val Asn Gly Glu Lys
                245             250             255

TAT GAG ATC TTT TAT TAT CCT GTT ACT AAA AAT ACC ACC ATT CAT GTG     816
Tyr Glu Ile Phe Tyr Tyr Pro Val Thr Lys Asn Thr Thr Ile His Val
            260             265             270

CCG ACT AAT CTT CGT TAT GAG ATA TCA GGA AAC AAT ATA GAC GGT GTA     864
Pro Thr Asn Leu Arg Tyr Glu Ile Ser Gly Asn Asn Ile Asp Gly Val
        275             280             285

ATT GTG ACA GTG TTT CCC GGA TCA ACA CAT ACT AAT TCA AGG AGG         909
Ile Val Thr Val Phe Pro Gly Ser Thr His Thr Asn Ser Arg Arg
    290             295             300
```

(2) INFORMATION FOR SEQ ID NO:23:

(i) SEQUENCE CHARACTERISTICS:
       (A) LENGTH: 303 amino acids
       (B) TYPE: amino acid -continued (D) TOPOLOGY: linear (ii) MOLECULE TYPE: protein (xi) SEQUENCE DESCRIPTION: SEQ ID NO:23:

Met Lys Lys Leu Phe Phe Leu Leu Leu Leu Phe Leu Ile Tyr Leu
 1               5                  10                  15

Gly Tyr Asp Tyr Val Asn Glu Ala Leu Phe Ser Gln Glu Lys Val Glu
                20                  25                  30

Phe Gln Asn Tyr Asp Gln Asn Pro Lys Glu His Leu Glu Asn Ser Gly
                35                  40                  45

Thr Ser Glu Asn Thr Gln Glu Lys Thr Ile Thr Glu Glu Gln Val Tyr
         50                  55                  60

Gln Gly Asn Leu Leu Ile Asn Ser Lys Tyr Pro Val Arg Gln Glu
 65                  70                  75                  80

Ser Val Lys Ser Asp Ile Val Asn Leu Ser Lys His Asp Glu Leu Ile
                85                  90                  95

Asn Gly Tyr Gly Leu Leu Asp Ser Asn Ile Tyr Met Ser Lys Glu Ile
                100                 105                 110

Ala Gln Lys Phe Ser Glu Met Val Asn Asp Ala Val Lys Gly Gly Val
            115                 120                 125

Ser His Phe Ile Ile Asn Ser Gly Tyr Arg Asp Phe Asp Glu Gln Ser
    130                 135                 140

Val Leu Tyr Gln Glu Met Gly Ala Glu Tyr Ala Leu Pro Ala Gly Tyr
145                 150                 155                 160

Ser Glu His Asn Ser Gly Leu Ser Leu Asp Val Gly Ser Ser Leu Thr
                165                 170                 175

Lys Met Glu Arg Ala Pro Glu Gly Lys Trp Ile Glu Glu Asn Ala Trp
            180                 185                 190

Lys Tyr Gly Phe Ile Leu Arg Tyr Pro Glu Asp Lys Thr Glu Leu Thr
        195                 200                 205

Gly Ile Gln Tyr Glu Pro Trp His Ile Arg Tyr Val Gly Leu Pro His
    210                 215                 220

Ser Ala Ile Met Lys Glu Lys Asn Phe Val Leu Glu Glu Tyr Met Asp
225                 230                 235                 240

Tyr Leu Lys Glu Glu Lys Thr Ile Ser Val Ser Val Asn Gly Glu Lys
                245                 250                 255

Tyr Glu Ile Phe Tyr Tyr Pro Val Thr Lys Asn Thr Thr Ile His Val
            260                 265                 270

Pro Thr Asn Leu Arg Tyr Glu Ile Ser Gly Asn Asn Ile Asp Gly Val
        275                 280                 285

Ile Val Thr Val Phe Pro Gly Ser Thr His Thr Asn Ser Arg Arg
    290                 295                 300

(2) INFORMATION FOR SEQ ID NO:24:

(i) SEQUENCE CHARACTERISTICS:
        (A) LENGTH: 483 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: CDS
        (B) LOCATION: 1..483

(xi) SEQUENCE DESCRIPTION: SEQ ID NO:24:

|  |  |  |  |  |  |  |  |  |  |  |  |  |  |  |  |
|---|---|---|---|---|---|---|---|---|---|---|---|---|---|---|---|
| TTG | GGA | AAA | ATA | TTA | TCT | AGA | GGA | TTG | CTA | GCT | TTA | TAT | TTA | GTG | ACA | 48 |
| Leu | Gly | Lys | Ile | Leu | Ser | Arg | Gly | Leu | Leu | Ala | Leu | Tyr | Leu | Val | Thr |  |
| 1 |  |  |  | 5 |  |  |  |  | 10 |  |  |  |  | 15 |  |  |
| CTA | ATC | TGG | TTA | GTG | TTA | TTC | AAA | TTA | CAA | TAC | AAT | ATT | TTA | TCA | GTA | 96 |
| Leu | Ile | Trp | Leu | Val | Leu | Phe | Lys | Leu | Gln | Tyr | Asn | Ile | Leu | Ser | Val |  |
|  |  | 20 |  |  |  |  | 25 |  |  |  |  | 30 |  |  |  |  |
| TTT | AAT | TAT | CAT | CAA | AGA | AGT | CTT | AAC | TTG | ACT | CCA | TTT | ACT | GCT | ACT | 144 |
| Phe | Asn | Tyr | His | Gln | Arg | Ser | Leu | Asn | Leu | Thr | Pro | Phe | Thr | Ala | Thr |  |
|  |  | 35 |  |  |  |  | 40 |  |  |  |  | 45 |  |  |  |  |
| GGG | AAT | TTC | AGA | GAG | ATG | ATA | GAT | AAT | GTT | ATA | ATC | TTT | ATT | CCA | TTT | 192 |
| Gly | Asn | Phe | Arg | Glu | Met | Ile | Asp | Asn | Val | Ile | Ile | Phe | Ile | Pro | Phe |  |
|  | 50 |  |  |  |  | 55 |  |  |  |  | 60 |  |  |  |  |  |
| GGC | TTG | CTT | TTG | AAT | GTC | AAT | TTT | AAA | GAA | ATC | GGA | TTT | TTA | CCT | AAG | 240 |
| Gly | Leu | Leu | Leu | Asn | Val | Asn | Phe | Lys | Glu | Ile | Gly | Phe | Leu | Pro | Lys |  |
| 65 |  |  |  |  | 70 |  |  |  |  | 75 |  |  |  |  | 80 |  |
| TTT | GCT | TTT | GTA | CTG | GTT | TTA | AGT | CTT | ACT | TTT | GAA | ATA | ATT | CAA | TTT | 288 |
| Phe | Ala | Phe | Val | Leu | Val | Leu | Ser | Leu | Thr | Phe | Glu | Ile | Ile | Gln | Phe |  |
|  |  |  |  | 85 |  |  |  |  | 90 |  |  |  |  | 95 |  |  |
| ATC | TTC | GCT | ATT | GGA | GCG | ACA | GAC | ATA | ACA | GAT | GTA | ATT | ACA | AAT | ACT | 336 |
| Ile | Phe | Ala | Ile | Gly | Ala | Thr | Asp | Ile | Thr | Asp | Val | Ile | Thr | Asn | Thr |  |
|  |  |  | 100 |  |  |  |  | 105 |  |  |  |  | 110 |  |  |  |
| GTT | GGA | GGC | TTT | CTT | GGA | CTG | AAA | TTA | TAT | GGT | TTA | AGC | AAT | AAG | CAT | 384 |
| Val | Gly | Gly | Phe | Leu | Gly | Leu | Lys | Leu | Tyr | Gly | Leu | Ser | Asn | Lys | His |  |
|  |  | 115 |  |  |  |  | 120 |  |  |  |  | 125 |  |  |  |  |
| ATG | AAT | CAA | AAA | AAA | TTA | GAC | AGA | GTT | ATT | ATT | TTT | GTA | GGT | ATA | CTT | 432 |
| Met | Asn | Gln | Lys | Lys | Leu | Asp | Arg | Val | Ile | Ile | Phe | Val | Gly | Ile | Leu |  |
| 130 |  |  |  |  |  | 135 |  |  |  |  | 140 |  |  |  |  |  |
| TTG | CTC | GTA | TTA | TTG | CTC | GTT | TAC | CGT | ACC | CAT | TTA | AGA | ATA | AAT | TAC | 480 |
| Leu | Leu | Val | Leu | Leu | Val | Tyr | Arg | Thr | His | Leu | Arg | Ile | Asn | Tyr |  |  |
| 145 |  |  |  |  | 150 |  |  |  |  | 155 |  |  |  |  | 160 |  |
| GTG |  |  |  |  |  |  |  |  |  |  |  |  |  |  |  | 483 |
| Val |  |  |  |  |  |  |  |  |  |  |  |  |  |  |  |  |

(2) INFORMATION FOR SEQ ID NO:25:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:25:

|  |  |  |  |  |  |  |  |  |  |  |  |  |  |  |  |
|---|---|---|---|---|---|---|---|---|---|---|---|---|---|---|---|
| Leu | Gly | Lys | Ile | Leu | Ser | Arg | Gly | Leu | Leu | Ala | Leu | Tyr | Leu | Val | Thr |
| 1 |  |  |  | 5 |  |  |  |  | 10 |  |  |  |  | 15 |  |
| Leu | Ile | Trp | Leu | Val | Leu | Phe | Lys | Leu | Gln | Tyr | Asn | Ile | Leu | Ser | Val |
|  |  | 20 |  |  |  |  | 25 |  |  |  |  | 30 |  |  |  |
| Phe | Asn | Tyr | His | Gln | Arg | Ser | Leu | Asn | Leu | Thr | Pro | Phe | Thr | Ala | Thr |
|  |  | 35 |  |  |  |  | 40 |  |  |  |  | 45 |  |  |  |
| Gly | Asn | Phe | Arg | Glu | Met | Ile | Asp | Asn | Val | Ile | Ile | Phe | Ile | Pro | Phe |
|  | 50 |  |  |  |  | 55 |  |  |  |  | 60 |  |  |  |  |
| Gly | Leu | Leu | Leu | Asn | Val | Asn | Phe | Lys | Glu | Ile | Gly | Phe | Leu | Pro | Lys |
| 65 |  |  |  |  | 70 |  |  |  |  | 75 |  |  |  |  | 80 |
| Phe | Ala | Phe | Val | Leu | Val | Leu | Ser | Leu | Thr | Phe | Glu | Ile | Ile | Gln | Phe |
|  |  |  |  | 85 |  |  |  |  | 90 |  |  |  |  | 95 |  |
| Ile | Phe | Ala | Ile | Gly | Ala | Thr | Asp | Ile | Thr | Asp | Val | Ile | Thr | Asn | Thr |
|  |  |  | 100 |  |  |  |  | 105 |  |  |  |  | 110 |  |  |
| Val | Gly | Gly | Phe | Leu | Gly | Leu | Lys | Leu | Tyr | Gly | Leu | Ser | Asn | Lys | His |
|  |  | 115 |  |  |  |  | 120 |  |  |  |  | 125 |  |  |  |
| Met | Asn | Gln | Lys | Lys | Leu | Asp | Arg | Val | Ile | Ile | Phe | Val | Gly | Ile | Leu |

```
                    130              135             140
Leu Leu Val Leu Leu Val Tyr Arg Thr His Leu Arg Ile Asn Tyr
145                 150             155                 160

Val
```

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:26:

```
ATGCTCCTGT CTCCTTTC                                               18
```

(2) INFORMATION FOR SEQ ID NO:27:

(i) SEQUENCE CHARACTERISTICS:
        (A) LENGTH: 2296 amino acids
        (B) TYPE: amino acid
        (D) TOPOLOGY: linear (ii) MOLECULE TYPE: protein (xi) SEQUENCE DESCRIPTION: SEQ ID NO:27:

```
Lys Leu Phe Phe Leu Leu Ile Cys Arg Phe Thr Asn Arg Ile Lys Leu
1               5                   10                  15

Leu Phe Ser His Cys Pro Cys Phe Pro His His Ser Phe Lys Cys Ser
                20                  25                  30

Asp Ser Arg Gln Tyr Asn Phe Val Phe Ser Lys Ile Tyr Ala Phe Met
            35                  40                  45

Gln Met Asn Gly Ile Thr Ile Phe Gln Ser Leu Met Lys Val Leu Lys
        50                  55                  60

Cys His Ser Ile Phe Thr Gln Gly Lys Ser Tyr Lys Val Val Phe Thr
65                  70                  75                  80

Ser Asn Phe Phe Gln Met Ile Pro Lys Cys Ile Phe Pro Leu Arg Ile
                85                  90                  95

Met Ile Lys Arg Gly Trp Thr Asn Thr Asn Leu Phe Arg Tyr Ile Leu
            100                 105                 110

Tyr Asp Arg Ile Trp Asp Ala Phe Asp Met Ser Val Trp Pro Thr Gly
        115                 120                 125

Ile Pro Lys Asn Ser Leu Asn Ser Lys Ser Thr Val Phe Phe Pro Pro
    130                 135                 140

Ser Leu Ile Asn Tyr Phe Ile Pro Phe Gly Lys Ser Glu Val Gly Pro
145                 150                 155                 160

Gln Tyr Pro Phe Ile Phe Arg Asp Leu His Lys Ser Leu Ser Leu Phe
                165                 170                 175

Arg Cys Lys Gln Phe Ser Thr Ser Arg Asn Phe His Ser Val Ser Phe
            180                 185                 190

His Phe Cys Ile Phe Asn Leu Leu Val Gln Leu Tyr Ile Asn Arg Val
        195                 200                 205

Tyr Ser Ile Asp Thr Asn Val Val Asp Asn His Ser Glu Arg Leu Ile
    210                 215                 220

Arg Leu Val Ser Lys Met Arg Tyr Phe Ala Glu Asn Arg Leu Tyr Ser
225                 230                 235                 240

Cys Gln Phe Asp Pro Glu Ser Phe Lys Thr Ile Ser Ala Val Glu Arg
```

-continued

```
                245                 250                 255
Asp Arg Asn Gly Tyr Tyr Ile Lys Arg Lys Phe Gln Glu Gln Gln Arg
            260                 265                 270

Ile Ala Ser Asn Phe Lys Lys Cys Thr Ile Tyr Arg Lys Met Thr Ser
        275                 280                 285

Phe Met Leu Gln Thr Leu Glu Ser Leu Val Val His Lys Ile Tyr Leu
    290                 295                 300

Asn Ser Ile Thr Tyr Glu Ile Lys Arg Gln Val Asn His Lys Ile His
305                 310                 315                 320

Gly Leu Ile Tyr Gln Lys Ile Ile His Thr Ala Asn Ser Leu Leu Trp
                325                 330                 335

Leu Val Leu Thr Asn Ser Glu Ile Leu Phe Gly Asp Asn Val Lys Gly
            340                 345                 350

Leu Asn Trp Leu Arg Lys Lys Glu Ser Leu Lys Val Asp Arg Ser Ile
        355                 360                 365

Ile Lys Ile Thr Gln Glu Ile Met Arg Arg Lys Leu Tyr Lys Glu Gly
    370                 375                 380

Asn Met Thr Val Asn Gln Ile Cys Glu Ile Thr Asn Val Ser Arg Ala
385                 390                 395                 400

Ser Leu Tyr Arg Lys Leu Ser Glu Val Asn Asn Pro Phe Cys Ile Pro
                405                 410                 415

Leu Met Gly Asn Ile Phe Lys Glu Gly Lys Glu Thr Ile Lys Tyr Gln
            420                 425                 430

Pro Pro Ser Asp Ala Glu Lys Pro Phe Asp Lys Lys Arg Ile Ile Ile
        435                 440                 445

Leu Arg Asn Ser Ser Phe Ile Met Met Leu Ile Asn Ser Ala Leu Ser
    450                 455                 460

Asp Lys Leu Leu Arg Ala Asn Leu Cys Glu Arg Val Ile Thr Met Ser
465                 470                 475                 480

Asp Lys Ile Leu Ile Val Asp Asp Glu His Glu Ile Ala Asp Leu Val
                485                 490                 495

Glu Leu Tyr Leu Lys Asn Glu Asn Tyr Thr Val Phe Lys Tyr Tyr Thr
            500                 505                 510

Ala Lys Glu Ala Leu Glu Cys Ile Asp Lys Ser Glu Ile Asp Leu Ala
        515                 520                 525

Ile Leu Asp Ile Met Leu Pro Gly Thr Ser Gly Leu Thr Ile Cys Gln
    530                 535                 540

Lys Ile Arg Asp Lys His Thr Tyr Pro Ile Ile Met Leu Thr Gly Lys
545                 550                 555                 560

Asp Thr Glu Val Asp Lys Ile Thr Gly Leu Thr Ile Gly Ala Asp Asp
                565                 570                 575

Tyr Ile Thr Lys Pro Phe Arg Pro Leu Glu Leu Ile Ala Arg Val Lys
            580                 585                 590

Ala Gln Leu Arg Arg Tyr Lys Lys Phe Ser Gly Val Lys Glu Gln Asn
        595                 600                 605

Glu Asn Val Ile Val His Ser Gly Leu Val Ile Asn Val Asn Thr His
    610                 615                 620

Glu Cys Tyr Leu Asn Glu Lys Gln Leu Ser Leu Thr Pro Thr Glu Phe
625                 630                 635                 640

Ser Ile Leu Arg Ile Leu Cys Glu Asn Lys Gly Asn Val Val Ser Ser
                645                 650                 655

Glu Leu Leu Phe His Glu Ile Trp Gly Asp Glu Tyr Phe Ser Lys Ser
            660                 665                 670
```

```
Asn Asn Thr Ile Thr Val His Ile Arg His Leu Arg Glu Lys Met Asn
        675                 680                 685
Asp Thr Ile Asp Asn Pro Lys Tyr Ile Lys Thr Val Trp Gly Val Gly
690                 695                 700
Tyr Lys Ile Glu Lys Lys Arg Leu Phe Gln Thr Arg Thr Lys Thr
705                 710                 715                 720
Leu His Val Tyr Arg Cys Asn Cys Gly Ser Asn Cys Ile Arg Val
            725                 730                 735
Val Tyr Ser Phe Asn Asp Pro Arg Glu Thr Trp Gly Leu Asp Leu Lys
            740                 745                 750
Tyr Phe Gly Lys Gln Ile Leu Lys Ser Pro Gly Arg Asp Glu Ile Ile
            755                 760                 765
Ser Ile Phe His Thr Glu Gln Tyr Arg Tyr Leu Tyr Leu Cys Gly Asp
            770                 775                 780
Cys His Tyr Ser Tyr Ser Met Ser Arg His Ala Phe Lys Ile Arg Lys
785                 790                 795                 800
Ile Leu Arg Asp Lys Tyr Arg His Cys Thr Tyr Ser Glu Arg Arg Thr
            805                 810                 815
Asn Ala Phe Cys Gly Asn Gly Cys Tyr Gly Thr Lys Ala Gln His Ile
            820                 825                 830
Lys Thr Asp Ser Gly Lys Ala Arg Ala Gly Cys Lys Ala Gly Arg Thr
            835                 840                 845
Lys Lys Lys Arg Cys Tyr Val Leu Gly Ala Arg Tyr Asn Ala Pro Tyr
850                 855                 860
Ile His Tyr Arg Leu Phe Glu Pro Ala Arg Gly Ser Arg His Ala Gly
865                 870                 875                 880
Arg Ser Lys Gly Lys Val Cys Ala Tyr His Val Gly Gln Ser Val Ser
            885                 890                 895
Thr Arg Thr Ala Asn Arg Arg Val Phe Asp Tyr Thr Val Pro Thr Asn
            900                 905                 910
Asp Asn Ala Asn Lys Asn Ala His Arg Pro Ile Leu Tyr Ala Gly Ala
            915                 920                 925
Asp Asp Arg Ile Leu Ser Ser Ala Phe Arg Thr Trp Lys Thr Gly Gly
            930                 935                 940
Tyr Ser Arg Pro Arg Gly Ser Asp Arg Val Arg Arg Pro Thr Arg Glu
945                 950                 955                 960
Ser Leu Gln His Phe Glu Lys Arg Arg Cys Ile Gln Gly Gln His His
            965                 970                 975
His Tyr Arg Gly Pro Leu Arg Gly Cys Gly Val Asn Arg Ile Gln Glu
            980                 985                 990
His Trp Lys His Pro Lys Arg Ala Ser Cys His Ile Lys Val Leu Ala
            995                 1000                1005
Gly Gln Phe Ser Phe Phe Arg Tyr Gly Trp Arg Gly Thr Trp Ile Gly
            1010                1015                1020
Asp Cys Lys Arg Asn Tyr Cys Ser Ala Trp Arg Ala Asp Leu Arg Gly
1025                1030                1035                1040
Lys Leu Leu Tyr Asp Val Gly Arg Ala Ser Ser Asp Ala Arg Leu Gly
                1045                1050                1055
Lys Glu Val Leu Arg Asp Val Tyr Asn Phe Leu Gly Lys Ser Gln Gly
                1060                1065                1070
Tyr Leu Tyr Phe Phe Leu Gly Asn Gln Phe Asn Ile Lys Lys Arg Leu
                1075                1080                1085
Val Leu Thr Arg Thr Tyr Arg Lys Asn Glu Pro Phe Ser Phe Phe Arg
                1090                1095                1100
```

-continued

```
Glu Arg Phe Asp Lys Ile Thr Ile Gly Ile Pro Val Leu Phe Gly Ala
1105                1110                1115                1120

Phe His Arg Lys Gly Trp Ser Leu Ile Thr Ser Ala Leu Leu Phe Met
                    1125                1130                1135

Asp Val Ser Arg Met Arg Gln Met His Ser Met Leu Phe Arg Leu Ala
                1140                1145                1150

Leu Ala Leu Trp Gln Arg Leu Thr Pro Thr Cys Arg Asn Pro Thr Pro
            1155                1160                1165

Asn Pro Arg Leu Ser Ile Asn Val Ser Val Trp Asp Ile Asn Gln Arg
        1170                1175                1180

Phe Pro Pro Leu Phe Phe Leu Arg Arg Glu Pro Val Asn Ile Phe Leu
1185                1190                1195                1200

Pro Glu Ala Ser Ala Ala Ile Ile Ile Gln Leu Leu Leu Arg Glu Trp
                    1205                1210                1215

Ala Ser Leu Ser Thr Met Trp Arg Thr Arg Arg Ile Ala Leu Pro Ile
                1220                1225                1230

Ile Leu Cys Phe Leu Trp Gln Tyr Ala Thr Asn Arg Leu Cys Ala Leu
            1235                1240                1245

Trp Lys Asn Met Ile Ser Gly Trp Thr Ala Thr Val Ala Arg Tyr Ser
        1250                1255                1260

Ala Thr Gln Leu Val Trp Trp Glu Arg Ala Arg Ala Lys Arg Leu Leu
1265                1270                1275                1280

Ser Gly Cys Glu Asp Leu Asp Val Lys Cys Trp Leu Ile Val Ala Ala
                    1285                1290                1295

Glu Val Arg Thr Met Tyr Arg Leu Met Ser Cys Cys Lys Ile Ala Ile
                1300                1305                1310

Ser Leu Arg Phe Met Cys Arg Ser Ile Arg Ile Arg Thr Ile Leu Ser
            1315                1320                1325

Ala Thr Asn Lys Tyr Arg Glu Ser Lys Glu His Phe Leu Ser Ile Leu
        1330                1335                1340

Gly Ala Val His Leu Ile Pro Met Ser Trp Leu Lys His Lys Thr Gly
1345                1350                1355                1360

Asn Trp Ala Val Pro His Trp Met Tyr Trp Lys Glu Arg Lys Ser Phe
                    1365                1370                1375

Ser Thr Leu Ile Ala Pro Lys Asn Gln Leu Ile Ile Asn Phe Tyr Leu
                1380                1385                1390

Asn Phe Lys Glu Cys Leu Thr Ser His Arg Ile Arg Pro Ile Ile Pro
            1395                1400                1405

Ser Lys Arg Cys Val Ile Pro Leu Lys Lys Pro Leu Lys Thr Val Trp
        1410                1415                1420

Ile Leu Lys Gly Asp Arg Ser Met Asn Arg Ile Lys Val Ala Ile Leu
1425                1430                1435                1440

Phe Gly Gly Cys Ser Glu Glu His Asp Val Ser Val Lys Ser Ala Ile
                    1445                1450                1455

Glu Ile Ala Ala Asn Ile Asn Lys Glu Lys Tyr Glu Pro Leu Tyr Ile
                1460                1465                1470

Gly Ile Thr Lys Ser Gly Val Trp Lys Met Cys Glu Lys Pro Cys Ala
            1475                1480                1485

Glu Trp Glu Asn Asp Asn Cys Tyr Ser Ala Val Leu Ser Pro Asp Lys
        1490                1495                1500

Lys Met His Gly Leu Leu Val Lys Asn His Glu Tyr Glu Ile Asn
1505                1510                1515                1520

His Val Asp Val Ala Phe Ser Ala Leu His Gly Lys Ser Gly Glu Asp
```

-continued

```
                        1525                1530                1535
Gly Ser Ile Gln Gly Leu Phe Glu Leu Ser Gly Ile Pro Phe Val Gly
                1540                1545                1550
Cys Asp Ile Gln Ser Ser Ala Ile Cys Met Asp Lys Ser Leu Thr Tyr
            1555                1560                1565
Ile Val Ala Lys Asn Ala Gly Ile Ala Thr Pro Ala Phe Trp Val Ile
        1570                1575                1580
Asn Lys Asp Asp Arg Pro Val Ala Ala Thr Phe Thr Tyr Pro Val Phe
1585                1590                1595                1600
Val Lys Pro Ala Arg Ser Gly Ser Ser Phe Gly Val Lys Lys Val Asn
                1605                1610                1615
Ser Ala Asp Glu Leu Asp Tyr Ala Ile Glu Ser Ala Arg Gln Tyr Asp
                1620                1625                1630
Ser Lys Ile Leu Ile Glu Gln Ala Val Ser Gly Cys Glu Val Gly Cys
                1635                1640                1645
Ala Val Leu Gly Asn Ser Ala Ala Leu Val Val Gly Glu Val Asp Gln
            1650                1655                1660
Ile Arg Leu Gln Tyr Gly Ile Phe Arg Ile His Gln Glu Val Glu Pro
1665                1670                1675                1680
Glu Lys Gly Ser Glu Asn Ala Val Ile Thr Val Pro Ala Asp Leu Ser
                1685                1690                1695
Ala Glu Glu Arg Gly Arg Ile Gln Glu Thr Ala Lys Lys Ile Tyr Lys
                1700                1705                1710
Ala Leu Gly Cys Arg Gly Leu Ala Arg Val Asp Met Phe Leu Gln Asp
            1715                1720                1725
Asn Gly Arg Ile Val Leu Asn Glu Val Asn Thr Leu Pro Gly Phe Thr
        1730                1735                1740
Ser Tyr Ser Arg Tyr Pro Arg Met Met Ala Ala Ala Gly Ile Ala Leu
1745                1750                1755                1760
Pro Glu Leu Ile Asp Arg Leu Ile Val Leu Ala Leu Lys Gly Ala Trp
                1765                1770                1775
Lys Asp Leu Leu Phe Met Lys Tyr Thr Val Phe Val Gly Thr Leu Asn
            1780                1785                1790
Met Pro Leu Gly Ile Ile Ser Pro Glu Asn Arg Leu Thr Val Met Lys
        1795                1800                1805
Ile Ala Leu Gly His Thr Ser Trp Leu Asn Arg Phe Arg Gln Lys Asn
    1810                1815                1820
Trp Leu Leu Pro Lys Gly Thr Asp Cys Phe Tyr Gly Thr Val Thr Val
1825                1830                1835                1840
Leu Ser Val Leu Thr Val Leu Cys Asn Gly Leu His Ser Arg Lys Ile
                1845                1850                1855
Thr Gln Arg Lys Val Ile Ile Pro Ile Leu Thr Glu Leu Arg Phe Gln
                1860                1865                1870
Lys Asp Thr Trp Leu Gln Asn Gln Ala Ile Ala Ala Val Pro Leu
            1875                1880                1885
Ile Leu Arg Phe Ile Asp Thr Arg Val Ser Leu Tyr Gln Trp Gly Ala
            1890                1895                1900
Asp Leu Ile Leu Trp Met Asn Ala Leu Ile Met Arg Gln Met Glu Tyr
1905                1910                1915                1920
His Ala Met Lys Arg Lys Ile Ala Asp Val Cys Ala Pro Ser Trp Lys
                1925                1930                1935
Thr Val Gly Leu Lys His Ile Ala Ser Asn Gly Gly Thr Met Tyr Glu
            1940                1945                1950
```

-continued

```
Thr Asn His Thr Pro Ile Ala Ile Leu Ile Ser Pro Leu Asn Lys Leu
        1955                1960                1965

Leu Thr Val Ala Arg Thr Asn Tyr Ile Ser Leu Phe Arg Gln Glu Thr
    1970                1975                1980

Arg Arg Met Leu Val Leu Arg Glu Phe Ile Tyr Ser Arg Tyr Arg Cys
1985                1990                1995                2000

Lys Ala Glu Arg Tyr Cys Gly His Tyr Leu Arg Ala Leu Arg Gln Asp
                2005                2010                2015

Ser Leu Ile Ile Arg Leu Ile Ala Arg Gly Gly Ile Ser His Arg Pro
            2020                2025                2030

Leu Ser Thr Gly Ser Ser Ala Ser Leu Asn Ser Ala Trp Val Ser Leu
        2035                2040                2045

Met Lys Ile His Leu His Trp Ile Gln Gly Glu Ile Ile Asp Cys Asn
        2050                2055                2060

Leu Arg Gly Lys Thr Ala Gln Ser Gln Thr Arg Leu Cys Arg Leu Arg
2065                2070                2075                2080

Gly Arg Phe Lys Tyr Phe Ile Leu Pro Thr Ile Leu Arg Arg Arg Leu
                2085                2090                2095

Lys Met Lys Lys Leu Phe Phe Leu Leu Leu Leu Phe Leu Ile Tyr
            2100                2105                2110

Leu Gly Tyr Asp Tyr Val Asn Glu Ala Leu Phe Ser Gln Glu Lys Val
        2115                2120                2125

Glu Phe Gln Asn Tyr Asp Gln Asn Pro Lys Glu His Leu Glu Asn Ser
    2130                2135                2140

Gly Thr Ser Glu Asn Thr Gln Glu Lys Thr Ile Thr Glu Glu Gln Val
2145                2150                2155                2160

Tyr Gln Gly Asn Leu Leu Leu Ile Asn Ser Lys Tyr Pro Val Arg Gln
                2165                2170                2175

Glu Val Ser Gln Ile Ser Ile Tyr Leu Asn Met Thr Asn Met Asp Thr
            2180                2185                2190

Gly Cys Leu Ile Val Ile Phe Ile Cys Gln Lys Lys His Lys Asn Phe
        2195                2200                2205

Gln Arg Trp Ser Met Met Leu Arg Val Ala Leu Val Ile Leu Leu Leu
        2210                2215                2220

Ile Val Ala Ile Glu Thr Leu Met Ser Lys Val Cys Phe Thr Lys Lys
2225                2230                2235                2240

Trp Gly Leu Ser Met Pro Tyr Gln Gln Val Ile Val Ser Ile Ile Gln
                2245                2250                2255

Val Tyr His Met Asp Gln Ala Arg Lys Trp Asn Glu Pro Leu Lys Glu
            2260                2265                2270

Ser Gly Lys Lys Met Leu Gly Asn Thr Gly Ser Phe Tyr Val Ile Gln
        2275                2280                2285

Arg Thr Lys Gln Ser Gln Glu Phe
    2290                2295
```

(2) INFORMATION FOR SEQ ID NO:28:

(i) SEQUENCE CHARACTERISTICS:
        (A) LENGTH: 2254 amino acids
        (B) TYPE: amino acid
        (D) TOPOLOGY: linear (ii) MOLECULE TYPE: protein (xi) SEQUENCE DESCRIPTION: SEQ ID NO:28:

```
Ser Phe Ser Phe Cys Ser Phe Val Arg Asp Leu Leu Thr Val Leu Asn
1               5                   10                  15
```

```
Ser Phe Phe Ser Ala Ile Ala Leu Ala Ser His Thr Ile Leu Ser Ser
             20                  25                  30

Val Val Ile Ala Gly Ser Ile Ile Leu Phe Phe Leu Arg Lys Ser Met
             35                  40                  45

His Ser Cys Ser Arg Met Ala Ser Pro Phe Ser Lys Ala Asn Arg Tyr
 50                  55                  60

Leu Asn Val Ile Arg Tyr Ser Leu Arg Val Lys Val Thr Lys Ser Tyr
 65                  70                  75                  80

Ser Leu Arg Ile Ser Phe Lys Ser Gln Ser Val Phe Ser Leu Gly Ser
                 85                  90                  95

Ser Glu Asp Gly Leu Thr Pro Ile Cys Phe Asp Ile Tyr Cys Met Thr
                100                 105                 110

Glu Ser Gly Met Leu Leu Ile Val Tyr Gly Gln Pro Gly Tyr Arg Arg
            115                 120                 125

Thr Ala Asn Thr Ala Asn Pro Lys Arg Phe Ser Ser Leu Leu Arg Leu
130                 135                 140

Leu Thr Ile Ser Lys Ser Arg Leu Glu Lys Val Lys Val Pro Ser Ile
145                 150                 155                 160

His Ser Ser Ser Gly Ile Cys Ile Lys Ala Cys Leu Cys Ser Gly Val
                165                 170                 175

Ser Asn Ser Leu Pro Leu Ala Ile Phe Ile Gln Tyr His Ser Ile Ser
                180                 185                 190

Val Phe Ser Ile Tyr Phe Asn Tyr Ile Ser Ile Glu Cys Thr Leu Leu
            195                 200                 205

Ile Gln Met Thr Asp Lys Ile Ile Val Lys Ser Val Ser Asp Leu Ser
            210                 215                 220

Gln Lys Gly Asp Ile Leu Arg Lys Ile Gly Tyr Ile Arg Val Ser Ser
225                 230                 235                 240

Thr Asn Gln Asn Pro Ser Arg Gln Phe Gln Gln Leu Asn Glu Ile Gly
                245                 250                 255

Met Asp Ile Ile Arg Glu Ser Phe Arg Ser Asn Lys Gly Ser Arg Ala
                260                 265                 270

Thr Ser Lys Ser Val Arg Arg Phe Thr Gly Arg His His Leu Cys Tyr
            275                 280                 285

Arg Leu Asn Ser Asn His Ser Tyr Thr Arg Ser Ile Ile Asn Arg His
            290                 295                 300

Thr Arg Lys Gly Lys Phe Lys Ile Thr Lys Arg Tyr Met Ala Phe Ile
305                 310                 315                 320

Arg Arg Ser Ile Gln Pro Ile Leu Asn Tyr Cys Asn Gly Trp Cys Pro
                325                 330                 335

Ile Arg Ala Arg Ser Tyr Ser Asp Glu Thr Thr Arg Asp Ile Gly Glu
                340                 345                 350

Arg Arg Lys Val Arg Ser Ile Lys Glu Val Ser Lys Ser Arg Arg Asn
            355                 360                 365

Glu Leu Cys Gly Glu Ser Tyr Ile Lys Lys Glu Ile Leu Ile Lys Phe
    370                 375                 380

Val Lys Leu Leu Met Tyr Leu Gly Leu His Tyr Thr Gly Asn Tyr Gln
385                 390                 395                 400

Lys Ile Ile Ser His Ser Val Phe Arg Trp Ala Ile Phe Leu Lys Lys
                405                 410                 415

Lys Arg Lys Leu Asn Ile Asn Ser Leu Leu Ala Met Pro Lys Ser Pro
            420                 425                 430

Leu Ile Lys Lys Glu Ser Ser Ser Glu Ile Leu Ser His Leu Leu Cys
```

```
                    435                 440                 445
Lys Cys Leu Ile Arg Pro Tyr Asn Leu Ile Asn Tyr Gly Gln Thr Tyr
    450                 455                 460
Val Lys Gly Leu Ala Ile Lys Tyr Leu Leu Trp Met Met Asn Met Lys
465                 470                 475                 480
Leu Pro Ile Trp Leu Asn Tyr Thr Lys Thr Arg Ile Ile Arg Phe Ser
                485                 490                 495
Asn Thr Ile Pro Pro Lys Lys His Trp Asn Val Thr Ser Leu Arg Leu
                500                 505                 510
Thr Leu Pro Tyr Trp Thr Ser Cys Phe Pro Ala Gln Ala Ala Leu Leu
            515                 520                 525
Ser Val Lys Lys Gly Thr Ser Thr Pro Ile Arg Leu Ser Cys Pro Gly
530                 535                 540
Lys Ile Gln Arg Ile Lys Leu Gln Gly Gln Ser Ala Arg Met Ile Ile
545                 550                 555                 560
Arg Ser Pro Phe Ala His Trp Ser Leu Leu Gly Arg Pro Ser Cys Ala
                565                 570                 575
Asp Thr Lys Asn Ser Val Glu Arg Ser Arg Thr Lys Met Leu Ser Ser
                580                 585                 590
Thr Pro Ala Leu Ser Leu Met Leu Thr Pro Met Ser Val Ile Thr Arg
            595                 600                 605
Ser Ser Tyr Pro Leu Leu Pro Pro Ser Phe Gln Tyr Cys Glu Ser Ser
610                 615                 620
Val Lys Thr Arg Gly Met Trp Leu Ala Pro Ser Cys Tyr Phe Met Arg
625                 630                 635                 640
Tyr Gly Ala Thr Asn Ile Ser Ala Arg Ala Thr Thr Pro Ser Pro Cys
                645                 650                 655
Ile Ser Gly Ile Cys Ala Lys Lys Thr Thr Pro Leu Ile Ile Arg Asn
                660                 665                 670
Ile Lys Arg Tyr Gly Gly Leu Val Ile Lys Leu Lys Asn Lys Lys Asn
            675                 680                 685
Asp Tyr Ser Lys Leu Glu Arg Lys Leu Tyr Met Tyr Ile Val Ala Ile
    690                 695                 700
Val Val Val Ala Ile Val Phe Val Leu Tyr Ile Arg Ser Met Ile Arg
705                 710                 715                 720
Gly Lys Leu Gly Asp Trp Ile Leu Ser Ile Leu Glu Asn Lys Tyr Asp
                725                 730                 735
Leu Asn His Leu Asp Ala Met Lys Leu Tyr Gln Tyr Ser Ile Arg Asn
                740                 745                 750
Asn Ile Asp Ile Phe Ile Tyr Val Ala Ile Val Ile Ser Ile Leu Ile
            755                 760                 765
Leu Cys Arg Val Met Leu Ser Lys Phe Ala Lys Tyr Phe Asp Glu Ile
    770                 775                 780
Asn Thr Gly Ile Asp Val Leu Ile Gln Asn Glu Asp Lys Gln Ile Glu
785                 790                 795                 800
Leu Ser Ala Glu Met Asp Val Met Glu Gln Lys Leu Asn Thr Leu Lys
                805                 810                 815
Arg Thr Leu Glu Lys Arg Glu Gln Asp Ala Lys Leu Ala Glu Gln Arg
                820                 825                 830
Lys Asn Asp Val Val Met Tyr Leu Ala His Asp Ile Lys Thr Pro Leu
            835                 840                 845
Thr Ser Ile Ile Gly Tyr Leu Ser Leu Leu Asp Glu Ala Pro Asp Met
    850                 855                 860
```

-continued

```
Pro Val Asp Gln Lys Ala Lys Tyr Val His Ile Thr Leu Asp Lys Ala
865                 870                 875                 880

Tyr Arg Leu Glu Gln Leu Ile Asp Glu Phe Phe Glu Ile Thr Arg Tyr
                885                 890                 895

Asn Leu Gln Thr Ile Thr Leu Thr Lys Thr His Ile Asp Leu Tyr Tyr
            900                 905                 910

Met Leu Val Gln Met Thr Asp Glu Phe Tyr Pro Gln Leu Ser Ala His
        915                 920                 925

Gly Lys Gln Ala Val Ile His Ala Pro Glu Asp Leu Thr Val Ser Gly
    930                 935                 940

Asp Pro Asp Lys Leu Ala Arg Val Phe Asn Asn Ile Leu Lys Asn Ala
945                 950                 955                 960

Ala Ala Tyr Ser Glu Asp Asn Ser Ile Ile Asp Ile Thr Ala Gly Leu
                965                 970                 975

Ser Gly Asp Val Val Ser Ile Glu Phe Lys Asn Thr Gly Ser Ile Pro
            980                 985                 990

Lys Asp Lys Leu Ala Ala Ile Phe Glu Lys Phe Tyr Arg Leu Asp Asn
        995                 1000                1005

Ser Arg Ser Ser Asp Thr Gly Gly Ala Gly Leu Gly Leu Ala Ile Ala
    1010                1015                1020

Lys Glu Ile Ile Val Gln His Gly Gly Gln Ile Tyr Ala Glu Ser Tyr
1025                1030                1035                1040

Asp Asn Tyr Thr Thr Phe Arg Val Glu Leu Pro Ala Met Pro Asp Leu
                1045                1050                1055

Val Asp Lys Arg Arg Ser Glu Met Tyr Ile Ile Phe Glu Asn Leu Lys
            1060                1065                1070

Val Ile Phe Thr Phe Ser Glu Ile Asn Asn Leu Ile Leu Arg Asn Gly
        1075                1080                1085

Ser Phe Leu His Gly Arg Leu Asn Thr Val Arg Thr Ser Arg Phe Arg
    1090                1095                1100

Ser Ser Glu Lys Asp Leu Thr Arg Leu Pro Leu Ala Ser Pro Phe Tyr
1105                1110                1115                1120

Leu Val Pro Phe Thr Glu Arg Val Gly Leu Asn Tyr Glu His Arg His
                1125                1130                1135

Tyr Cys Leu Trp Met Ala Gly Gly Arg Cys Ile Pro Cys Ser Phe Ala
            1140                1145                1150

Ser Leu Trp Arg Tyr Gly Asn Asp Asn Arg Gln Arg Val Gly Ile Gln
        1155                1160                1165

Arg Gln Ile Arg Ala Phe Gln Ser Met Tyr Gln Cys Gly Thr Ile Arg
    1170                1175                1180

Asp Phe Arg Leu Tyr Ser Ser Cys Ala Glu Glu Ser Arg Cys Glu Ile
1185                1190                1195                1200

Tyr Phe Tyr Pro Lys His Arg Leu Gln Ser Tyr Arg Tyr Asn Cys Cys
                1205                1210                1215

Glu Asn Gly His His Cys Arg Gln Cys Gly Val Leu Ala Gly Arg Cys
            1220                1225                1230

Arg Leu Tyr Tyr Asp Ala Asn Ser Tyr Gly Ser Thr Gln Arg Lys Ile
        1235                1240                1245

Asp Cys Ala Leu Cys Gly Lys Thr Phe Gln Val Gly Gln Arg Pro Trp
    1250                1255                1260

Gln Gly Thr Gln Arg His Asp Ser Trp Cys Gly Gly Asn Gly Pro Asp
1265                1270                1275                1280

Arg Gln Ser Gly Tyr Ala Ala Ala Arg Ile Trp Met Ser Val Gly Leu
                1285                1290                1295
```

```
Ser Gln Pro Lys Tyr Arg Gly Lys Leu Cys Thr Val Ala Ala Lys
        1300                1305                1310

Arg Tyr Arg Tyr Ala Ser Cys Ala Ala Gln Tyr Gly Tyr Ala Leu Tyr
        1315                1320                1325

Tyr Gln Pro Arg Thr Asn Thr Glu Asn Glu Ala Arg Ser Ile Ser Tyr
        1330                1335                1340

Gln Tyr Trp Ala Arg Ser Thr Cys Arg Tyr Leu Val Gly Ser Ile Arg
1345                1350                1355                1360

Lys Arg Glu Thr Gly Arg Cys Arg Ile Gly Cys Ile Gly Arg Arg Gly
            1365                1370                1375

Arg Val Phe Leu Leu Leu His Pro Lys Thr Asn Ser Ile Phe Thr Thr
        1380                1385                1390

Ser Lys Asn Ala Arg Asp Asn His Thr Ala Tyr Gly Leu Leu Tyr Arg
        1395                1400                1405

Ala Ser Val Ala Tyr Arg Lys Asn His Lys Leu Phe Gly Phe Lys Glu
        1410                1415                1420

Thr Gly Ala Ile Glu Lys Leu Gln Tyr Cys Leu Gly Val Ala Gln Arg
1425                1430                1435                1440

Ser Met Thr Tyr Arg Asn Leu Gln Arg Pro Leu Thr Leu Ile Lys Lys
            1445                1450                1455

Asn Thr Ser Arg Tyr Thr Leu Glu Leu Arg Asn Leu Val Tyr Gly Lys
        1460                1465                1470

Cys Ala Lys Asn Leu Ala Arg Asn Gly Lys Thr Thr Ile Ala Ile Gln
        1475                1480                1485

Leu Tyr Ser Arg Arg Ile Lys Lys Cys Thr Asp Tyr Leu Leu Lys Arg
        1490                1495                1500

Thr Met Asn Met Lys Ser Thr Met Leu Met His Phe Gln Leu Cys Met
1505                1510                1515                1520

Ala Ser Gln Val Lys Met Asp Pro Tyr Lys Val Cys Leu Asn Cys Pro
            1525                1530                1535

Val Ser Leu Leu Ala Ala Ile Phe Lys Ala Gln Gln Phe Val Trp Thr
        1540                1545                1550

Asn Arg His Thr Ser Leu Arg Lys Met Leu Gly Leu Leu Pro Pro Phe
        1555                1560                1565

Gly Leu Leu Ile Lys Met Ile Gly Arg Trp Gln Leu Arg Leu Pro Ile
        1570                1575                1580

Leu Phe Leu Leu Ser Arg Arg Val Gln Ala His Pro Ser Val Lys Lys
1585                1590                1595                1600

Ser Ile Ala Arg Thr Asn Trp Thr Thr Gln Leu Asn Arg Gln Asp Asn
            1605                1610                1615

Met Thr Ala Lys Ser Leu Ser Arg Leu Phe Arg Ala Val Arg Ser Val
        1620                1625                1630

Val Arg Tyr Trp Glu Thr Val Pro Arg Leu Leu Ala Arg Trp Thr Lys
        1635                1640                1645

Ser Gly Cys Ser Thr Glu Ser Phe Val Phe Ile Arg Lys Ser Ser Arg
        1650                1655                1660

Lys Lys Ala Leu Lys Thr Gln Leu Pro Phe Pro Gln Thr Phe Gln Gln
1665                1670                1675                1680

Arg Ser Glu Asp Gly Tyr Arg Lys Arg Gln Lys Lys Tyr Ile Lys Arg
            1685                1690                1695

Ser Ala Val Glu Val Pro Val Trp Ile Cys Phe Tyr Lys Ile Thr Ala
        1700                1705                1710

Ala Leu Tyr Thr Lys Ser Ile Leu Cys Pro Val Ser Arg His Thr Val
```

```
                    1715                1720                1725
Val Ile Pro Val Trp Pro Leu Gln Val Leu His Phe Pro Asn Leu Thr
        1730                1735                1740
Ala Ser Tyr Arg Arg Gly Asp Lys His Gly Asn Arg Ile Tyr Phe Phe
1745                1750                1755                1760
Arg Asn Ser Thr Arg Cys Ser Leu Gly Arg Ile Cys His Leu Gly Phe
            1765                1770                1775
His Arg Lys Thr Gly Arg Leu Ser Lys Ser His Cys Arg Asp Ile Arg
            1780                1785                1790
Val Gly Ile Ala Phe Glu Gly Lys Arg Thr Gly Cys Tyr Pro Arg Val
            1795                1800                1805
Arg Ile Ala Ser Met Gly Arg Leu Pro Ser Ala Cys Cys Lys Leu Phe
        1810                1815                1820
Tyr Ala Met Gly Cys Thr Ala Gly Lys Pro Asp Lys Gly Lys Leu Leu
1825                1830                1835                1840
Ser Gln Tyr Pro Asn Asp Asp Phe Lys Arg Ile Arg Gly Phe Lys Ile
            1845                1850                1855
Lys Pro Pro Arg Gln Cys His Ser Tyr Ala Leu Ser Ile Arg His Gly
            1860                1865                1870
Ala Cys Thr Asn Gly Glu Pro Ile Phe Tyr Gly Thr Leu Ser Ser Cys
            1875                1880                1885
Gly Lys Trp Asn Ile Met Gln Ser Ala Lys Ser Gln Thr Phe Ala Leu
            1890                1895                1900
His His Gly Lys Gln Trp Val Ser Ile Pro Arg Met Val Ala Leu Cys
1905                1910                1915                1920
Ile Lys Arg Arg Thr Ile Pro Gln Leu Phe Phe Pro Arg Ile Asn Phe
            1925                1930                1935
Pro Leu His Gly Gln Thr Ile Ala Asn Ser Phe Gly Arg Lys Pro Asp
            1940                1945                1950
Val Cys Asn Trp Phe Leu Gly Asn Leu Tyr Ile Val Asp Ser Ile Glu
            1955                1960                1965
Asp Val Arg Gln Ser Asp Ile Ala Val Ile Cys Val Arg Cys Gly
            1970                1975                1980
Lys Ile Ala Asp Ser His Arg Gly Val Val Phe His Thr Ala His Cys
1985                1990                1995                2000
Gln Gln Ala Val Gln Pro Arg Ile Gln Gly Tyr His Leu Lys Phe
            2005                2010                2015
Ile Tyr Ile Gly Asp Asn Ser Lys Ser Ser Arg Ala Lys Leu Thr Val
            2020                2025                2030
Ile Tyr Gly Ala Lys Arg His Asn Leu Lys Arg Asp Cys Ala Val Gly
            2035                2040                2045
Glu Asp Ser Arg Asn Ile Ser Tyr Phe Gln Leu Tyr Ser Gly Gly Asp
            2050                2055                2060
Lys Arg Ser Cys Phe Phe Tyr Cys Tyr Cys Tyr Ser Tyr Thr Val Met
2065                2070                2075                2080
Thr Thr Leu Met Lys His Cys Phe Leu Arg Lys Lys Ser Asn Phe Lys
            2085                2090                2095
Ile Met Ile Lys Ile Pro Lys Asn Ile Lys Ile Val Gly Leu Leu Lys
            2100                2105                2110
Ile Pro Lys Arg Lys Gln Leu Gln Lys Asn Arg Phe Ile Lys Glu Ile
            2115                2120                2125
Cys Tyr Ser Ile Val Asn Ile Leu Phe Ala Lys Lys Cys Glu Val Arg
            2130                2135                2140
```

```
Tyr Arg Glu Phe Ile Thr Arg Ile Asn Lys Trp Ile Arg Val Ala Tyr
2145                2150                2155                2160

Leu Tyr Val Lys Arg Asn Ser Thr Lys Ile Phe Arg Asp Gly Gln Cys
            2165                2170                2175

Cys Lys Gly Trp Arg Ser Phe Tyr Tyr Trp Leu Ser Arg Leu Ala Lys
        2180                2185                2190

Cys Ala Leu Pro Arg Asn Gly Gly Val Cys Leu Thr Ser Arg Leu Ala
    2195                2200                2205

Phe Arg Phe Ile Thr Arg Cys Arg Ile Lys Leu Asp Glu Asn Gly Thr
2210                2215                2220

Ser Pro Arg Lys Val Asp Arg Arg Lys Cys Leu Glu Ile Arg Val His
2225                2230                2235                2240

Phe Thr Leu Ser Arg Gly Gln Asn Arg Val Asn Arg Asn Ser
                2245                2250

(2) INFORMATION FOR SEQ ID NO:29:

(i) SEQUENCE CHARACTERISTICS:
        (A) LENGTH: 2291 amino acids
        (B) TYPE: amino acid
        (D) TOPOLOGY: linear (ii) MOLECULE TYPE: protein (xi) SEQUENCE DESCRIPTION: SEQ ID NO:29:

Ala Phe Leu Phe Ala His Leu Leu Glu Ile Tyr Pro Tyr Ile Ala Ser
1               5                   10                  15

Phe Gln Pro Leu Pro Leu Pro Thr Pro Phe Phe Gln Val Gln Ala
            20                  25                  30

Val Phe Cys Phe Leu Glu Asn Leu Cys Ile His Ala Val Asp Glu
        35                  40                  45

Trp His His His Phe Pro Lys Leu Ile Asp Glu Gly Thr Met Ser Phe
    50                  55                  60

Asp Ile His Ser Gly Lys Leu Gln Ser Arg Ile His Phe Glu Phe Leu
65                  70                  75                  80

Ser Asn Asp Pro Lys Val Tyr Phe Pro Phe Glu Asp Asn Asp Gln Ala
                85                  90                  95

Arg Met Asp His Gln Ser Val Ser Ile Tyr Ile Val Pro Asn Leu Gly
            100                 105                 110

Cys Phe Tyr Glu Cys Met Ala Asn Arg Asp Thr Glu Glu Gln Leu Ile
        115                 120                 125

Glu Gln Gln Ile Leu Asn Gly Phe Leu Pro Ser Phe Ala Tyr Leu Phe
130                 135                 140

Leu Asn Pro Val Trp Lys Lys Ser Arg Ser Pro Val Ser Ile His Leu
145                 150                 155                 160

Gln Gly Phe Ala Lys Pro Val Ser Val Pro Val Ala Ile Leu Tyr Leu
                165                 170                 175

Ser Gln Phe Ser Phe Ser Ile Ile Pro Phe Leu Tyr Phe Gln Phe Ile
            180                 185                 190

Ser Ser Ile Ile Tyr Gln Ser Val Leu Tyr Tyr Lys Cys Ser Arg Leu
        195                 200                 205

Ile Lys Ser Leu Arg Ala Ser His Lys Thr Cys Leu Lys Asn Glu Val
    210                 215                 220

Ile Phe Cys Gly Lys Ser Val Ile Phe Val Ser Val Arg Leu Thr Arg
225                 230                 235                 240

Ile Leu Gln Asp Asn Phe Ser Ser Thr Arg Ser Glu Trp Ile Leu Tyr
                245                 250                 255
```

-continued

Lys Glu Lys Val Ser Gly Ala Thr Lys Asp Arg Glu Gln Leu Gln Lys
            260                 265                 270

Val Leu Asp Asp Leu Gln Glu Asp Asp Ile Ile Tyr Val Thr Asp Leu
            275                 280                 285

Thr Arg Ile Thr Arg Ser Thr Gln Asp Leu Phe Glu Leu Ile Asp Asn
            290                 295                 300

Ile Arg Asp Lys Lys Ala Ser Leu Lys Ser Leu Lys Asp Thr Trp Leu
305                 310                 315                 320

Asp Leu Ser Glu Asp Asn Pro Tyr Ser Gln Phe Leu Ile Thr Val Met
                    325                 330                 335

Ala Gly Val Asn Gln Leu Glu Arg Asp Leu Ile Arg Met Arg Gln Arg
            340                 345                 350

Glu Gly Ile Glu Leu Ala Lys Lys Glu Gly Lys Phe Lys Gly Arg Leu
            355                 360                 365

Lys Lys Tyr His Lys Asn His Ala Gly Met Asn Tyr Ala Ala Lys Ala
            370                 375                 380

Ile Arg Arg Lys Tyr Asp Cys Lys Ser Asn Leu Asn Tyr Cys Ile Gly
385                 390                 395                 400

Phe Ile Ile Gln Glu Ile Ile Arg Ser Glu Leu Ala Ile Leu Tyr Ser
                    405                 410                 415

Ala Asn Gly Gln Tyr Phe Arg Arg Lys Gly Asn Tyr Lys Ile Leu Thr
            420                 425                 430

Ala Ser Arg Cys Arg Lys Ala Leu Lys Lys Asn His His Leu Lys Lys
            435                 440                 445

Phe Leu Val Ile Tyr Tyr Val Asn Ala Tyr Lys Phe Gly Pro Ile Ile
            450                 455                 460

Ile Ile Lys Gly Lys Leu Met Lys Gly Asp Asn Tyr Glu Arg Asn Thr
465                 470                 475                 480

Tyr Cys Gly Thr Asn Cys Arg Phe Gly Ile Ile Leu Lys Lys Arg Glu
                    485                 490                 495

Leu Tyr Gly Phe Gln Ile Leu Tyr Arg Gln Arg Ser Ile Gly Met Tyr
                    500                 505                 510

Arg Gln Val Asp Pro Cys His Ile Gly His His Ala Ser Arg His Lys
            515                 520                 525

Arg Pro Tyr Tyr Leu Ser Lys Asn Lys Gly Gln Ala His Leu Ser Asp
            530                 535                 540

Tyr His Ala Asp Arg Glu Arg Tyr Arg Gly Arg Asn Tyr Arg Val Asn
545                 550                 555                 560

Asn Arg Arg Gly Leu Tyr Asn Glu Ala Leu Ser Pro Thr Gly Val Asn
                    565                 570                 575

Cys Ser Gly Lys Gly Pro Val Ala Pro Ile Gln Lys Ile Gln Trp Ser
            580                 585                 590

Lys Gly Ala Glu Arg Lys Cys Tyr Arg Pro Leu Arg Pro Cys His Cys
            595                 600                 605

His Pro Val Leu Ser Glu Arg Glu Ala Val Ile Pro Tyr Ser His Arg
            610                 615                 620

Val Phe Asn Thr Ala Asn Pro Leu Lys Gln Gly Glu Cys Gly Leu Arg
625                 630                 635                 640

Ala Ala Ile Ser Asp Met Gly Arg Arg Ile Phe Gln Gln Glu Gln Gln
                    645                 650                 655

His His His Arg Ala Tyr Pro Ala Phe Ala Arg Lys Asn Glu Arg His
            660                 665                 670

His Ser Glu Ile Tyr Lys Asn Gly Met Gly Gly Trp Leu Asn Lys Ile

-continued

```
                675                 680                 685
Lys Lys Thr Thr Ile Pro Asn Glu Asn Phe Thr Cys Ile Ser Leu
    690                 695                 700
Gln Leu Leu Trp Gln Leu Tyr Ser Cys Cys Ile Phe Val Gln Ser Glu
705                 710                 715                 720
Gly Asn Leu Gly Ile Gly Ser Val Phe Trp Lys Thr Asn Met Thr Ile
                725                 730                 735
Thr Trp Thr Arg Asn Tyr Ile Asn Ile Pro Tyr Gly Thr Ile Ile Ser
                740                 745                 750
Leu Phe Met Trp Arg Leu Ser Leu Val Phe Leu Phe Tyr Val Ala Ser
                755                 760                 765
Cys Phe Gln Asn Ser Gln Asn Thr Leu Thr Arg Ile Pro Ala Leu Met
770                 775                 780
Tyr Leu Phe Arg Thr Lys Ile Asn Lys Leu Ser Phe Leu Arg Lys Trp
785                 790                 795                 800
Met Leu Trp Asn Lys Ser Ser Thr His Asn Gly Leu Trp Lys Ser Glu
                805                 810                 815
Ser Arg Met Gln Ser Trp Pro Asn Lys Glu Lys Met Thr Leu Leu Cys
                820                 825                 830
Thr Trp Arg Thr Ile Leu Lys Arg Pro Leu His Pro Leu Ser Val Ile
                835                 840                 845
Ala Cys Leu Thr Arg Leu Gln Thr Cys Arg Ile Lys Arg Gln Ser Met
850                 855                 860
Cys Ile Ser Arg Trp Thr Lys Arg Ile Asp Ser Asn Ser Ser Thr Ser
865                 870                 875                 880
Phe Leu Arg Leu His Gly Ile Thr Tyr Lys Arg Arg Gln Lys Arg Thr
                885                 890                 895
Thr Tyr Thr Ile Cys Trp Cys Arg Pro Met Asn Phe Ile Leu Ser Phe
                900                 905                 910
Pro His Met Glu Asn Arg Arg Leu Phe Thr Pro Pro Arg Ile Pro Cys
                915                 920                 925
Pro Ala Thr Leu Ile Asn Ser Arg Glu Ser Leu Thr Thr Phe Lys Thr
                930                 935                 940
Pro Leu His Thr Val Arg Ile Thr Ala Ser Leu Thr Leu Pro Arg Ala
945                 950                 955                 960
Ser Pro Gly Met Trp Cys Gln Ser Asn Ser Arg Thr Leu Glu Ala Ser
                965                 970                 975
Gln Lys Ile Ser Leu Pro Tyr Leu Lys Ser Ser Ile Gly Trp Thr Ile
                980                 985                 990
Leu Val Leu Pro Ile Arg Val Ala Arg Asp Leu Asp Trp Arg Leu Gln
                995                 1000                1005
Lys Lys Leu Leu Phe Ser Met Glu Gly Arg Phe Thr Arg Lys Ala Met
    1010                1015                1020
Ile Thr Ile Arg Arg Leu Gly Ser Phe Gln Arg Cys Gln Thr Trp Leu
1025                1030                1035                1040
Ile Lys Gly Gly Pro Lys Arg Cys Ile Phe Phe Arg Lys Ile Ser Arg
                1045                1050                1055
Leu Ser Leu Leu Phe Leu Arg Lys Leu Thr Ile Tyr Glu Thr Ala Arg
                1060                1065                1070
Ser Tyr Thr Val Asp Leu Ile Pro Glu Arg Ala Val Phe Val Leu Gln
                1075                1080                1085
Arg Lys Ile Gln Asp Tyr His Trp His Pro Arg Phe Ile Trp Cys Leu
                1090                1095                1100
```

-continued

Ser Gln Lys Gly Leu Val Leu Ile Met Asn Asn Ile Gly Ile Thr Val
1105                1110                1115                1120

Tyr Gly Cys Glu Gln Asp Glu Ala Asp Ala Phe His Ala Leu Ser Pro
            1125                1130                1135

Arg Phe Gly Val Met Ala Thr Ile Ile Asn Ala Asn Val Ser Glu Ser
                1140                1145                1150

Asn Ala Lys Ser Ala Pro Phe Asn Gln Cys Ile Ser Val Gly His Lys
            1155                1160                1165

Ser Glu Ile Ser Ala Ser Ile Leu Leu Ala Leu Lys Arg Ala Gly Val
    1170                1175                1180

Lys Tyr Ile Ser Thr Arg Ser Ile Gly Cys Asn His Ile Asp Thr Thr
1185                1190                1195                1200

Ala Ala Lys Arg Met Gly Ile Thr Val Asp Asn Val Ala Tyr Ser Pro
                1205                1210                1215

Asp Ser Val Ala Asp Tyr Thr Met Met Leu Ile Leu Met Ala Val Arg
    1220                1225                1230

Asn Val Lys Ser Ile Val Arg Ser Val Glu Lys His Asp Phe Arg Leu
            1235                1240                1245

Asp Ser Asp Arg Gly Lys Val Leu Ser Asp Met Thr Val Gly Val Val
    1250                1255                1260

Gly Thr Gly Gln Ile Gly Lys Ala Val Ile Glu Arg Leu Arg Gly Phe
1265                1270                1275                1280

Gly Cys Lys Val Leu Ala Tyr Ser Arg Ser Arg Ser Ile Glu Val Asn
            1285                1290                1295

Tyr Val Pro Phe Asp Glu Leu Leu Gln Asn Ser Asp Ile Val Thr Leu
                1300                1305                1310

His Val Pro Leu Asn Thr Asp Thr His Tyr Ile Ile Ser His Glu Gln
    1315                1320                1325

Ile Gln Arg Met Lys Gln Gly Ala Phe Leu Ile Asn Thr Gly Arg Gly
    1330                1335                1340

Pro Leu Val Asp Thr Tyr Glu Leu Val Lys Ala Leu Glu Asn Gly Lys
1345                1350                1355                1360

Leu Gly Gly Ala Ala Leu Asp Val Leu Glu Gly Glu Glu Phe Phe
            1365                1370                1375

Tyr Ser Asp Cys Thr Gln Lys Pro Ile Asp Asn Gln Phe Leu Leu Lys
            1380                1385                1390

Leu Gln Arg Met Pro Asn Val Ile Ile Thr Pro His Thr Ala Tyr Tyr
    1395                1400                1405

Thr Glu Gln Ala Leu Arg Asp Thr Val Glu Lys Thr Ile Lys Asn Cys
1410                1415                1420

Leu Asp Phe Glu Arg Arg Gln Glu His Glu Asn Lys Ser Cys Asn Thr
1425                1430                1435                1440

Val Trp Gly Leu Leu Arg Gly Ala Arg Ile Gly Lys Ile Cys Asn Arg
                1445                1450                1455

Asp Ser Arg His Arg Lys Ile Arg Ala Val Ile His Trp Asn Tyr Glu
            1460                1465                1470

Ile Trp Cys Met Glu Asn Val Arg Lys Thr Leu Arg Gly Met Gly Lys
            1475                1480                1485

Arg Gln Leu Leu Phe Ser Cys Thr Leu Ala Gly Lys Asn Ala Arg Ile
    1490                1495                1500

Thr Cys Lys Glu Pro Ile Asn Gln Pro Cys Cys Ser Ile Phe Ser Phe
1505                1510                1515                1520

Ala Trp Gln Val Arg Arg Trp Ile His Thr Arg Ser Val Ile Val Arg
                1525                1530                1535

```
Tyr Pro Phe Cys Arg Leu Arg Tyr Ser Lys Leu Ser Asn Leu Tyr Gly
                1540                1545                1550

Gln Ile Val Asp Ile His Arg Cys Glu Lys Cys Trp Asp Ser Tyr Ser
            1555                1560                1565

Arg Leu Leu Gly Tyr Arg Ala Gly Gly Ser Tyr Val Tyr Leu Ser Cys
        1570                1575                1580

Phe Cys Ala Gly Ala Phe Arg Leu Ile Leu Arg Cys Glu Lys Ser Gln
1585                1590                1595                1600

Arg Gly Arg Ile Gly Leu Arg Asn Ile Gly Lys Thr Ile Gln Gln Asn
                1605                1610                1615

Leu Asn Ala Gly Cys Phe Gly Leu Gly Arg Leu Cys Gly Ile Gly Lys
            1620                1625                1630

Gln Cys Arg Val Ser Cys Trp Arg Gly Gly Pro Asn Gln Ala Ala Val
        1635                1640                1645

Arg Asn Leu Ser Tyr Ser Ser Gly Ser Arg Ala Gly Lys Arg Leu Lys
1650                1655                1660

Arg Ser Tyr Asn Arg Ser Arg Arg Pro Phe Ser Arg Gly Ala Arg Thr
                1665                1670                1675                1680

Asp Thr Gly Asn Gly Lys Lys Asn Ile Ser Ala Arg Leu Arg Ser Ser
            1685                1690                1695

Pro Cys Gly Tyr Val Phe Thr Arg Arg Pro His Cys Thr Glu Arg Ser
        1700                1705                1710

Gln Tyr Ser Ala Arg Phe His Val Ile Gln Ser Leu Ser Pro Tyr Asp
    1715                1720                1725

Gly Arg Cys Arg Tyr Cys Thr Ser Arg Thr Asp Pro Leu Asp Arg Ile
            1730                1735                1740

Ser Val Lys Gly Val Ile Ser Met Glu Ile Gly Phe Thr Phe Leu Asp
1745                1750                1755                1760

Glu Ile Val His Gly Val Arg Trp Asp Ala Lys Tyr Ala Thr Trp Asp
                1765                1770                1775

Asn Phe Thr Gly Lys Pro Val Asp Gly Tyr Glu Val Asn Arg Ile Val
            1780                1785                1790

Gly Thr Tyr Glu Leu Ala Glu Ser Leu Leu Lys Ala Lys Glu Leu Ala
        1795                1800                1805

Ala Thr Gln Gly Tyr Gly Leu Leu Leu Trp Asp Gly Tyr Arg Pro Lys
    1810                1815                1820

Arg Ala Val Asn Cys Phe Met Gln Trp Ala Ala Gln Pro Glu Asn Asn
1825                1830                1835                1840

Leu Thr Lys Glu Ser Tyr Tyr Pro Asn Ile Asp Arg Thr Glu Met Ile
                1845                1850                1855

Ser Lys Gly Tyr Val Ala Ser Lys Ser Ser His Ser Arg Gly Ser Ala
            1860                1865                1870

Ile Asp Leu Thr Leu Tyr Arg Leu Asp Thr Gly Glu Leu Val Pro Met
        1875                1880                1885

Gly Ser Arg Phe Asp Phe Met Asp Glu Arg Ser His His Ala Ala Asn
    1890                1895                1900

Gly Ile Ser Cys Asn Glu Ala Gln Asn Arg Arg Arg Leu Arg Ser Ile
1905                1910                1915                1920

Met Glu Asn Ser Gly Phe Glu Ala Tyr Ser Leu Glu Trp Trp His Tyr
                1925                1930                1935

Val Leu Arg Asp Glu Pro Tyr Pro Asn Ser Tyr Phe Asp Phe Pro Val
            1940                1945                1950

Lys Thr Phe Asn Arg Cys Thr Asp Lys Leu Tyr Lys Leu Thr Leu Ser
```

```
                    1955                1960                1965
Ala Gly Asn Pro Thr Tyr Val Thr Gly Ser Gly Ile Tyr Ile Ile Val
    1970                1975                1980
Leu Lys Met Gly Arg Ala Ile Leu Arg Ser Leu Ser Ala Cys Ala Ala
1985                1990                1995                2000
Ala Arg Pro Asp Asn Lys Thr Asp Arg Ile Glu Gly Trp Tyr Phe Thr
                2005                2010                2015
Pro Pro Ile Val Asn Arg Gln Phe Ser Leu Val Lys Phe Ser Met Gly
            2020                2025                2030
Ile Thr Tyr Glu Asn Ser Ser Thr Leu Val Ile Ile Val Asn Pro Val
            2035                2040                2045
Gly Arg Asn Asn Leu Phe Thr Gly Gln Asn Gly Thr Ile Ser Asn Glu
        2050                2055                2060
Ile Val Pro Phe Lys Gly Lys Ile Leu Glu Ile Phe His Thr Ser Asn
2065                2070                2075                2080
Tyr Ile Val Lys Glu Glu Thr Glu Asn Glu Glu Val Val Phe Phe Ile
                2085                2090                2095
Val Ile Val Ile Leu Asn Ile Leu Arg Leu Leu Arg Ser Thr Val Phe
            2100                2105                2110
Ser Gly Lys Ser Arg Ile Ser Lys Leu Ser Lys Ser Gln Arg Thr Phe
        2115                2120                2125
Arg Lys Trp Asp Phe Lys Tyr Pro Arg Glu Asn Asn Tyr Arg Arg Thr
    2130                2135                2140
Gly Leu Ser Arg Lys Ser Ala Ile Asn Gln Ile Ser Cys Ser Pro Arg
2145                2150                2155                2160
Ser Val Lys Ser Asp Ile Val Asn Leu Ser Lys His Asp Glu Leu Ile
                2165                2170                2175
Asn Gly Tyr Gly Leu Leu Asp Ser Asn Ile Tyr Met Ser Lys Glu Ile
            2180                2185                2190
Ala Gln Lys Phe Ser Glu Met Val Asn Asp Ala Val Lys Gly Gly Val
        2195                2200                2205
Ser His Phe Ile Ile Asn Ser Gly Tyr Arg Asp Phe Asp Glu Gln Ser
    2210                2215                2220
Val Leu Tyr Gln Glu Met Gly Ala Glu Tyr Ala Leu Pro Ala Gly Tyr
2225                2230                2235                2240
Ser Glu His Asn Ser Gly Leu Ser Leu Asp Val Gly Ser Ser Leu Thr
                2245                2250                2255
Lys Met Glu Arg Ala Pro Glu Gly Lys Trp Ile Glu Asn Ala Trp
            2260                2265                2270
Lys Tyr Gly Phe Ile Leu Arg Tyr Pro Glu Asp Lys Thr Glu Leu Thr
        2275                2280                2285
Gly Ile Gln
    2290

(2) INFORMATION FOR SEQ ID NO:30:

(i) SEQUENCE CHARACTERISTICS:
        (A) LENGTH: 3190 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:30:

CAAAATATCA CCTCATTTTT GAGACAAGTC TTATGAGACG CTCTTAACTA TGATTTTATC      60
```

-continued

| | |
|---|---|
| AGTCTACTAC ATTTGTATCA ATAGAGTACA CTCTATTGAT ATATAATTGA ACTAATAAAT | 120 |
| TGAAAATACA GAAATGGAAT GATACTGAAA TGAAAATTGC GAGAGGTAGA GAATTGCTTA | 180 |
| CACCGGAACA GAGACAGGCT TTTATGCAAA TCCCTGAAGA TGAATGGATA CTGGGGACCT | 240 |
| ACTTCACTTT TTCCAAACGG GATTTAGAAA TAGTTAATAA GCGAAGGAGG GAAGAAAACC | 300 |
| GTTTAGGATT TGCTGTTCAA TTAGCTGTTC TTCGGTATCC CGGTTGGCCA TACACTCATA | 360 |
| TCAAAAGCAT CCCAGATTCG GTCATACAAT ATATATCGAA ACAGATTGGT GTTAGTCCAT | 420 |
| CCTCGCTTGA TCATTATCCT CAAAGGGAAA ATACACTTTG GGATCATTTG AAAGAAATTC | 480 |
| GAAGTGAATA CGACTTTGTA ACTTTTACCC TGAGTGAATA TCGAATGACA TTTAAGTACC | 540 |
| TTCATCAATT AGCTTTGGAA AATGGTGATG CCATTCATCT ACTGCATGAA TGCATAGATT | 600 |
| TTCTAAGAAA AAACAAAATT ATACTGCCTG CTATCACTAC ACTTGAAAGA ATGGTGTGGG | 660 |
| AAGCAAGGGC AATGGCTGAA AAGAAGCTAT TTAATACGGT TAGTAAATCT CTAACAAATG | 720 |
| AGCAAAAAGA AAAGCTTGAA GGGATTATTA CCTCGCAGCA TCCATCCGAA TCCAATAAAA | 780 |
| CGATATTGGG TTGGTTAAAA GAGCCACCGG GTCATCCTTC ACCCGAAACT TTTCTAAAAA | 840 |
| TAATAGAACG ACTCGAATAC ATACGAGGAA TGGATTTAGA AACAGTGCAA ATTAGTCATT | 900 |
| TGCACCGTAA CCGCCTGTTG CAGCTGTCTC GCTTAGGCTC AAGATACGAG CCGTATGCAT | 960 |
| TCCGTGACTT TCAAGAAAAT AAACGTTATT CGATATTAAC CATCTATTTA TTACAACTTA | 1020 |
| CTCAGGAGCT AACGGATAAA GCGTTTGAAA TTCATGATAG GCAAATACTT AGTTTGTTAT | 1080 |
| CAAAAGGTCG TAAGGCTCAA GAGGAAATCC AGAAACAAAA CGGTAAAAAG CTAAATGAGA | 1140 |
| AAGTTATACA CTTTACGAAC ATCGGACAAG CATTAATTAA AGCAAGAGAG GAAAAATTAG | 1200 |
| ACGTTTTTAA GGTTTTAGAA TCGGTTATTG AATGGAATAC CTTTGTCTCT TCAGTAGAAG | 1260 |
| AGGCTCAGGA ACTTGCACGT CCTGCCGACT ATGATTATTT AGACTTACTG CAAAAACGGT | 1320 |
| TTTATTCACT AAGAAAATAT ACGCCAACGC TATTAAGAGT ATTGGAATTT CATTCTACAA | 1380 |
| AGGCAAATGA GCCACTTTTA CAAGCTGTTG AGATTATCCG AGGAATGAAC GAATCTGGAA | 1440 |
| AGCGAAAAGT GCCTGATGAC TCACCTGTGG ATTTTATTTC AAAACGATGG AAAAGACATT | 1500 |
| TATACGAGGA TGATGGTACA ACAATTAATC GTCATTACTA TGAAATGGCT GTTTTAACAG | 1560 |
| AACTTCGGGA GCATGTTCGG GCAGGAGATG TTTCCATTGT TGGCAGCAGA CAATATAGGG | 1620 |
| ATTTTGAGGA ATATTTGTTT TCGGAAGATA CATGGAATCA ATCGAAGGGG AATACGAGAT | 1680 |
| TATCAGTTAG TTTATCATTC GAAGATTATA TAACGGAGAG AACCAGCAGC TTTAATGAAA | 1740 |
| GGTTAAAGTG GTTAGCTGCC AATTCCAATA AGTTAGATGG GGTTTCTCTT GAAAAAGGAA | 1800 |
| AGCTATCACT TGCACGCTTA GAAAAAGATG TTCCAGAAGA AGCAAAAAAA TTTAGTGCAA | 1860 |
| GCCTTTATCA GATGCTACCA AGAATAAAAT TAACTGATTT ACTCATGGAT GTGGCCCATA | 1920 |
| TAACAGGATT TCATGAGCAA TTCACTCATG CTTCCAATAA TCGAAAACCA GATAAGGAAG | 1980 |
| AAACAATCAT TATCATGGCT GCCCTTTTAG GAATGGGAAT GAATATTGGC TTGAGCAAGA | 2040 |
| TGGCCGAAGC CACACCCGGA CTTACATATA AGCAACTAGC CAATGTATCT CAATGGCGCA | 2100 |
| TGTATGAAGA TGCCATGAAT AAAGCCCAAG CCATATTAGT AAACTTTCAT CATAAATTAC | 2160 |
| AATTGCCTTT CTATTGGGGC GACGGTACAA CATCTTCGTC AGATGGTATG AGAATGCAGC | 2220 |
| TAGGTGTTTC ATCACTACAT GCAGATGCAA ATCCACATTA TGGAACTGGA AAAGGAGCCA | 2280 |
| CCATCTACCG ATTTACAAGT GATCAATTCT CTTCTTACTA CACAAAGATT ATTCATACTA | 2340 |
| ATTCAAGAGA TGCGATTCAT GTTTTGGATG GTTTGTTACA TCATGAGACG GATCTAAACA | 2400 |
| TAGAGGAACA TTATACAGAC ACTGCCGGTT ACACTGACCA AATATTCGGA CTGACTCATT | 2460 |

```
TATTAGGATT TAAATTTGCC CCAAGAATAA GGGATTTATC GGACTCAAAA TTATTTACGA      2520

TAGATAAAGC AAGTGAGTAT CCAAAACTAG AAGCCATTTT ACGTGGACAA ATAAATACAA      2580

AGGTCATTAA AGAAAATTAT GAGGATGTTT TGCGATTAGC TCATTCTATA AGGGAGGGAA      2640

CAGTTTCAGC ATCCCTTATT ATGGGAAGC TAGGTTCCTA TTCAAGACAA AACAGCTTAG       2700

CTACAGCCTT ACGTGAGATG GGCCGAATAG AAAAAACGAT CTTTATTTTG AATTATATAT      2760

CGGATGAATC ATTAAGAAGA AAAATACAAA GAGGATTGAA TAAAGGAGAA GCCATGAATG      2820

GATTGGCAAG AGCTATTTTC TTCGGAAAAC AAGGTGAGCT TAGAGAACGC ACCATACAGC      2880

ATCAATTGCA AAGAGCCAGT GCTTTAAACA TAATTATCAA TGCTATAAGT ATTTGGAATA      2940

CTCTCCACCT AACAACAGCA GTTGAATATA AAAAACGGAC AGGTAGCTTT AATGAAGATT      3000

TGTTACACCA TATGTCGCCC TTAGGTTGGG AACATATTAA TTTACTAGGA GAATACCATT      3060

TTAACTCAGA GAAAGTAGTC TCATTAAATT CTTTAAGACC ACTAAAACTT TCTTAACGTT      3120

GTTAAAAACG AGGGATTCGT CAGGAAAATA GGCTTAGCGT TGTAAATCCG CATTTTCCTG      3180

ACGCTACCCC                                                            3190
```

(2) INFORMATION FOR SEQ ID NO:31:

(i) SEQUENCE CHARACTERISTICS:
        (A) LENGTH: 1347 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:31:

```
GAGCTCTTCC TTCAACGCAC TTCTGTACCA AGAGTTGTTG TCCATTTGAT CACTAACAAT        60

AGCTTCCCCT GCTTTCTTCA AGCCCTTTGT CATAAAATCG TTAGATTTTC ATCATAAAAA       120

TACGAGAAAG ACAACAGGAA GACCGCAAAT TTTCTTTTCT TTTCCTAGGT ACACTGAATG       180

TAACCTTAAA AGAAAAAAGG AAAGGAAGAA ATGATGAAA AAAATTGCCG TTTTATTTGG        240

AGGGAATTCT CCAGAATACT CAGTGTCACT AACCTCAGCA GCAAGTGTGA TCCAAGCTAT       300

TGACCCGCTG AAATATGAAG TAATGACCAT TGGCATCGCA CCAACAATGG ATTGGTATTG       360

GTATCAAGGA AACCTCGCGA ATGTTCGCAA TGATACTTGG CTAGAAGATC ACAAAAACTG       420

TCACCAGCTG ACTTTTTCTA GCCAAGGATT TATATTAGGA GAAAAACGAA TCGTCCCTGA       480

TGTCCTCTTT CCAGTCTTGC ATGGGAAGTA TGGCGAGGAT GGCTGTATCC AAGGACTGCT       540

TGAACTAATG AACCTGCCTT ATGTTGGTTG CCATGTCGCT GCCTCCGCAT TATGTATGAA       600

CAAATGGCTC TTGCATCAAC TTGCTGATAC CATGGGAATC GCTAGTGCTC CCACTTTGCT       660

TTTATCCCGC TATGAAAACG ATCCTGCCAC AATCGATCGT TTTATTCAAG ACCATGGATT       720

CCCGATCTTT ATCAAGCCGA ATGAAGCCGG TTCTTCAAAA GGGATCACAA AAGTAACTGA       780

CAAAACAGCG CTCCAATCTG CATTAACGAC TGCTTTTGCT TACGGTTCTA CTGTGTTGAT       840

CCAAAAGGCG ATAGCGGGTA TTGAAATTGG CTGCGGCATC TTAGGAAATG AGCAATTGAC       900

GATTGGTGCT TGTGATGCGA TTTCTCTTGT CGACGGTTTT TTTGATTTTG AAGAGAAATA       960

CCAATTAATC AGCGCCACGA TCACTGTCCC AGCACCATTG CCTCTCGCGC TTGAATCACA      1020

GATCAAGGAG CAGGCACAGC TGCTTTATCG AAACTTGGGA TTGACGGGTC TGGCTCGAAT      1080

CGATTTTTTC GTCACCAATC AAGGAGCGAT TTATTTAAAC GAAATCAACA CCATGCCGGG      1140

ATTTACTGGG CACTCCCGCT ACCCAGCTAT GATGGCGGAA GTCGGGTTAT CCTACGAAAT      1200

ATTAGTAGAG CAATTGATTG CACTGGCAGA GGAGGACAAA CGATGAACAC ATTACAATTG      1260
```

```
ATCAATAAAA ACCATCCATT GAAAAAAAAT CAAGAGCCCC CGCACTTAGT GCTAGCTCCT      1320

TTTAGCGATC ACGATGTTTA CCTGCAG                                          1347
```

(2) INFORMATION FOR SEQ ID NO:32:

(i) SEQUENCE CHARACTERISTICS:
        (A) LENGTH: 364 amino acids
        (B) TYPE: amino acid
        (D) TOPOLOGY: linear (ii) MOLECULE TYPE: protein (xi) SEQUENCE DESCRIPTION: SEQ ID NO:32:

```
Met Glu Lys Leu Arg Val Gly Ile Val Gly Gly Lys Ser Ala Glu
1               5                   10                  15

His Glu Val Ser Leu Gln Ser Ala Lys Asn Ile Val Asp Ala Ile Asp
                20                  25                  30

Lys Ser Arg Phe Asp Val Val Leu Gly Ile Asp Lys Gln Gly Gln
        35                  40                  45

Trp His Val Ser Asp Ala Ser Asn Tyr Leu Leu Asn Ala Asp Asp Pro
    50                  55                  60

Ala His Ile Ala Leu Arg Pro Ser Ala Thr Ser Leu Ala Gln Val Pro
65                  70                  75                  80

Gly Lys His Glu His Gln Leu Ile Asp Ala Gln Asn Gly Gln Pro Leu
                85                  90                  95

Pro Thr Val Asp Val Ile Phe Pro Ile Val His Gly Thr Leu Gly Glu
            100                 105                 110

Asp Gly Ser Leu Gln Gly Met Leu Arg Val Ala Asn Leu Pro Phe Val
        115                 120                 125

Gly Ser Asp Val Leu Ala Ser Ala Ala Cys Met Asp Lys Asp Val Thr
    130                 135                 140

Lys Arg Leu Leu Arg Asp Ala Gly Leu Asn Ile Ala Pro Phe Ile Thr
145                 150                 155                 160

Leu Thr Arg Ala Asn Arg His Asn Ile Ser Phe Ala Glu Val Glu Ser
                165                 170                 175

Lys Leu Gly Leu Pro Leu Phe Val Lys Pro Ala Asn Gln Gly Ser Ser
            180                 185                 190

Val Gly Val Ser Lys Val Thr Ser Glu Glu Gln Tyr Ala Thr Ala Val
        195                 200                 205

Ala Leu Ala Phe Glu Phe Asp His Lys Val Ile Val Glu Gln Gly Ile
    210                 215                 220

Lys Gly Arg Glu Ile Glu Cys Ala Val Leu Gly Asn Asp Asn Pro Gln
225                 230                 235                 240

Ala Ser Thr Cys Gly Glu Ile Val Leu Thr Ser Asp Phe Tyr Ala Tyr
                245                 250                 255

Asp Thr Lys Tyr Ile Asp Glu Asp Gly Ala Lys Val Val Pro Ala
            260                 265                 270

Ala Ile Ala Pro Glu Ile Asn Asp Lys Ile Arg Ala Ile Ala Val Gln
        275                 280                 285

Ala Tyr Gln Thr Leu Gly Cys Ala Gly Met Ala Arg Val Asp Val Phe
    290                 295                 300

Leu Thr Pro Glu Asn Glu Val Val Ile Asn Glu Ile Asn Thr Leu Pro
305                 310                 315                 320

Gly Phe Thr Asn Ile Ser Met Tyr Pro Lys Leu Trp Gln Ala Ser Gly
                325                 330                 335
```

-continued

```
Leu Gly Tyr Thr Asp Leu Ile Thr Arg Leu Ile Glu Leu Ala Leu Glu
            340                 345                 350
Arg His Ala Ala Asn Asn Ala Leu Lys Thr Thr Met
            355                 360
```

(2) INFORMATION FOR SEQ ID NO:33:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:33:

```
Met Thr Asp Lys Ile Ala Val Leu Leu Gly Gly Thr Ser Ala Glu Arg
1               5                   10                  15
Glu Val Ser Leu Asn Ser Gly Ala Ala Val Leu Ala Gly Leu Arg Glu
            20                  25                  30
Gly Gly Ile Asp Ala Tyr Pro Val Asp Pro Lys Glu Val Asp Val Thr
            35                  40                  45
Gln Leu Lys Ser Met Gly Phe Gln Lys Val Phe Ile Ala Leu His Gly
        50                  55                  60
Arg Gly Gly Glu Asp Gly Thr Leu Gln Gly Met Leu Glu Leu Met Gly
65                  70                  75                  80
Leu Pro Tyr Thr Gly Ser Gly Val Met Ala Ser Ala Leu Ser Met Asp
                85                  90                  95
Lys Leu Arg Ser Lys Leu Leu Trp Gln Gly Ala Gly Leu Pro Val Ala
            100                 105                 110
Pro Trp Val Ala Leu Thr Arg Ala Glu Phe Glu Lys Gly Leu Ser Asp
            115                 120                 125
Lys Gln Leu Ala Glu Ile Ser Ala Leu Gly Leu Pro Val Ile Val Lys
        130                 135                 140
Pro Ser Arg Glu Gly Ser Ser Val Gly Met Ser Lys Val Val Ala Glu
145                 150                 155                 160
Asn Ala Leu Gln Asp Ala Leu Arg Leu Ala Phe Gln His Asp Glu Glu
                165                 170                 175
Val Leu Ile Glu Lys Trp Leu Ser Gly Pro Glu Phe Thr Val Ala Ile
            180                 185                 190
Leu Gly Glu Glu Ile Leu Pro Ser Ile Arg Ile Gln Pro Ser Gly Thr
            195                 200                 205
Phe Tyr Asp Tyr Glu Ala Lys Tyr Leu Ser Asp Glu Thr Gln Tyr Phe
        210                 215                 220
Cys Pro Ala Gly Leu Glu Ala Ser Gln Glu Ala Asn Leu Gln Ala Leu
225                 230                 235                 240
Val Leu Lys Ala Trp Thr Thr Leu Gly Cys Lys Gly Trp Gly Arg Ile
                245                 250                 255
Asp Val Met Leu Asp Ser Asp Gly Gln Phe Tyr Leu Leu Glu Ala Asn
            260                 265                 270
Thr Ser Pro Gly Met Thr Ser His Ser Leu Val Pro Met Ala Ala Arg
            275                 280                 285
Gln Ala Gly Met Ser Phe Ser Gln Leu Val Val Arg Ile Leu Glu Leu
        290                 295                 300
Ala Asp
305
```

(2) INFORMATION FOR SEQ ID NO:34:

```
        (i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:34:

Leu Phe Pro Met Val Ile
1               5

(2) INFORMATION FOR SEQ ID NO:35:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:35:

Ser Thr Gln Asn Cys
1               5

(2) INFORMATION FOR SEQ ID NO:36:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:36:

Gly Glu Asp Gly Ser Ile Gln Gly
1               5

(2) INFORMATION FOR SEQ ID NO:37:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:37:

Asn Thr Leu Pro Gly Phe Thr
1               5

(2) INFORMATION FOR SEQ ID NO:38:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:38:

Gly Glu Asp Gly Thr Leu Gln Gly
1               5

(2) INFORMATION FOR SEQ ID NO:39:

(i) SEQUENCE CHARACTERISTICS:
            (A) LENGTH: 7 amino acids
            (B) TYPE: amino acid
            (D) TOPOLOGY: linear
```

(ii) MOLECULE TYPE: peptide (xi) SEQUENCE DESCRIPTION: SEQ ID NO:39:

Asn Thr Ser Pro Gly Met Thr
1               5

(2) INFORMATION FOR SEQ ID NO:40:

(i) SEQUENCE CHARACTERISTICS:
        (A) LENGTH: 259 amino acids
        (B) TYPE: amino acid
        (D) TOPOLOGY: linear (ii) MOLECULE TYPE: protein (v) FRAGMENT TYPE: internal (vi) ORIGINAL SOURCE:
        (A) ORGANISM: E. faecium
        (B) STRAIN: BM4147

(xi) SEQUENCE DESCRIPTION: SEQ ID NO:40:

Glu Met Asp Val Met Glu Gln Lys Leu Asn Thr Leu Lys Arg Thr Leu
1               5                   10                  15

Glu Lys Arg Glu Gln Asp Ala Lys Leu Ala Glu Gln Arg Lys Asn Asp
                20                  25                  30

Val Val Met Tyr Leu Ala His Asp Ile Lys Thr Pro Leu Thr Ser Ile
            35                  40                  45

Ile Gly Tyr Leu Ser Leu Leu Asp Glu Ala Pro Asp Met Pro Val Asp
        50                  55                  60

Gln Lys Ala Lys Tyr Val His Ile Thr Leu Asp Lys Ala Tyr Arg Leu
65                  70                  75                  80

Glu Gln Leu Ile Asp Glu Phe Phe Glu Ile Thr Arg Tyr Asn Leu Gln
                85                  90                  95

Thr Ile Thr Leu Thr Lys Thr His Ile Asp Leu Tyr Tyr Met Leu Val
                100                 105                 110

Gln Met Thr Asp Glu Phe Tyr Pro Gln Leu Ser Ala His Gly Lys Gln
                115                 120                 125

Ala Val Ile His Ala Pro Glu Asp Leu Thr Val Ser Gly Asp Pro Asp
130                 135                 140

Lys Leu Ala Arg Val Phe Asn Asn Ile Leu Lys Asn Ala Ala Ala Tyr
145                 150                 155                 160

Ser Glu Asp Asn Ser Ile Ile Asp Ile Thr Ala Gly Leu Ser Gly Asp
                165                 170                 175

Val Val Ser Ile Glu Phe Lys Asn Thr Gly Ser Ile Pro Lys Asp Lys
                180                 185                 190

Leu Ala Ala Ile Phe Glu Lys Phe Tyr Arg Leu Asp Asn Ala Arg Ser
                195                 200                 205

Ser Asp Thr Gly Gly Ala Gly Leu Gly Leu Ala Ile Ala Lys Glu Ile
210                 215                 220

Ile Val Gln His Gly Gly Gln Ile Tyr Ala Glu Ser Asn Asp Asn Tyr
225                 230                 235                 240

Thr Thr Phe Arg Val Glu Leu Pro Ala Met Pro Asp Leu Val Asp Lys
                245                 250                 255

Arg Arg Ser (2) INFORMATION FOR SEQ ID NO:41:

(i) SEQUENCE CHARACTERISTICS:

(A) LENGTH: 256 amino acids
            (B) TYPE: amino acid
            (D) TOPOLOGY: linear (ii) MOLECULE TYPE: protein (v) FRAGMENT TYPE: internal (vi) ORIGINAL SOURCE:
            (A) ORGANISM: Escherichia coli (xi) SEQUENCE DESCRIPTION: SEQ ID NO:41:

Glu Ile Arg Val Met Pro Tyr Thr His Lys Gln Leu Leu Met Val Ala
1               5                  10                  15

Arg Asp Val Thr Gln Met His Gln Leu Glu Gly Ala Arg Arg Asn Phe
            20                  25                  30

Phe Ala Asn Val Ser His Glu Leu Arg Thr Pro Leu Thr Val Leu Gln
        35                  40                  45

Gly Tyr Leu Glu Met Met Asn Glu Gln Pro Leu Glu Gly Ala Val Arg
    50                  55                  60

Glu Lys Ala Leu His Thr Met Arg Glu Gln Thr Gln Arg Met Glu Gly
65                  70                  75                  80

Leu Val Lys Gln Leu Leu Thr Leu Ser Lys Ile Glu Ala Ala Pro Thr
                85                  90                  95

His Leu Leu Asn Glu Lys Val Asp Val Pro Met Met Leu Arg Val Val
            100                 105                 110

Glu Arg Glu Ala Gln Thr Leu Ser Gln Lys Lys Gln Thr Phe Thr Phe
        115                 120                 125

Glu Ile Asp Asn Gly Leu Lys Val Ser Gly Asn Glu Asp Gln Leu Arg
    130                 135                 140

Ser Ala Ile Ser Asn Leu Val Tyr Asn Ala Val Asn His Thr Pro Glu
145                 150                 155                 160

Gly Thr His Ile Thr Val Arg Trp Gln Arg Val Pro His Gly Ala Glu
                165                 170                 175

Phe Ser Val Glu Asp Asn Gly Pro Gly Ile Ala Pro Glu His Ile Pro
            180                 185                 190

Arg Leu Thr Glu Arg Phe Tyr Arg Val Asp Lys Ala Arg Ser Arg Gln
        195                 200                 205

Thr Gly Gly Ser Gly Leu Gly Leu Ala Ile Val Lys His Ala Val Asn
    210                 215                 220

His His Glu Ser Arg Leu Asn Ile Glu Ser Thr Val Gly Lys Gly Thr
225                 230                 235                 240

Arg Phe Ser Phe Val Ile Pro Glu Arg Leu Ile Ala Lys Asn Ser Asp
                245                 250                 255

(2) INFORMATION FOR SEQ ID NO:42:

(i) SEQUENCE CHARACTERISTICS:
            (A) LENGTH: 241 amino acids
            (B) TYPE: amino acid
            (D) TOPOLOGY: linear (ii) MOLECULE TYPE: protein (v) FRAGMENT TYPE: internal (vi) ORIGINAL SOURCE:
            (A) ORGANISM: Escherichia coli (xi) SEQUENCE DESCRIPTION: SEQ ID NO:42:

Ala Ser Glu Val Arg Ser Val Thr Arg Ala Phe Asn His Met Ala Ala
1               5                  10                  15

```
Gly Val Lys Gln Leu Ala Asp Asp Arg Thr Leu Leu Met Ala Gly Val
            20                  25                  30

Ser His Asp Leu Arg Thr Pro Leu Thr Arg Ile Arg Leu Ala Thr Glu
            35                  40                  45

Met Met Ser Glu Gln Asp Gly Tyr Leu Ala Glu Ser Ile Asn Lys Asp
 50                  55                  60

Ile Glu Glu Cys Asn Ala Ile Ile Glu Gln Phe Ile Asp Tyr Leu Arg
 65                  70                  75                  80

Thr Gly Gln Glu Met Pro Met Glu Met Ala Asp Leu Asn Ala Val Leu
                 85                  90                  95

Gly Glu Val Ile Ala Ala Glu Ser Gly Tyr Glu Arg Glu Ile Glu Thr
            100                 105                 110

Ala Leu Tyr Pro Gly Ser Ile Glu Val Lys Met His Pro Leu Ser Ile
            115                 120                 125

Lys Arg Ala Val Ala Asn Met Val Val Asn Ala Ala Arg Tyr Gly Asn
130                 135                 140

Gly Trp Ile Lys Val Ser Ser Gly Thr Glu Pro Asn Arg Ala Trp Phe
145                 150                 155                 160

Gln Val Glu Asp Asp Gly Pro Gly Ile Ala Pro Glu Gln Arg Lys His
                165                 170                 175

Leu Phe Gln Pro Phe Val Arg Gly Asp Ser Ala Arg Thr Ile Ser Gly
            180                 185                 190

Thr Gly Leu Gly Leu Ala Ile Val Gln Arg Ile Val Asp Asn His Asn
            195                 200                 205

Gly Met Leu Glu Leu Gly Thr Ser Glu Arg Gly Gly Leu Ser Ile Arg
            210                 215                 220

Ala Trp Leu Pro Val Pro Val Thr Arg Ala Gln Gly Thr Thr Lys Glu
225                 230                 235                 240

Gly (2) INFORMATION FOR SEQ ID NO:43:

(i) SEQUENCE CHARACTERISTICS:
        (A) LENGTH: 231 amino acids
        (B) TYPE: amino acid
        (D) TOPOLOGY: linear (ii) MOLECULE TYPE: protein (vi) ORIGINAL SOURCE:
        (A) ORGANISM: E. faecium
        (B) STRAIN: BM4147

(xi) SEQUENCE DESCRIPTION: SEQ ID NO:43:

Met Ser Asp Lys Ile Leu Ile Val Asp Asp Glu His Glu Ile Ala Asp
 1               5                  10                  15

Leu Val Glu Leu Tyr Leu Lys Asn Glu Asn Tyr Thr Val Phe Lys Tyr
            20                  25                  30

Tyr Thr Ala Lys Glu Ala Leu Glu Cys Ile Asp Lys Ser Glu Ile Asp
            35                  40                  45

Leu Ala Ile Leu Asp Ile Met Leu Pro Gly Thr Ser Gly Leu Thr Ile
 50                  55                  60

Cys Gln Lys Ile Arg Asp Lys His Thr Tyr Pro Ile Ile Met Leu Thr
 65                  70                  75                  80

Gly Lys Asp Thr Glu Val Asp Lys Ile Thr Gly Leu Thr Ile Gly Ala
                 85                  90                  95

Asp Asp Tyr Ile Thr Lys Pro Phe Arg Pro Leu Glu Leu Ile Ala Arg
```

```
                100            105              110
    Val Lys Ala Gln Leu Arg Arg Tyr Lys Lys Phe Ser Gly Val Lys Glu
                115                120                125

Gln Asn Glu Asn Val Ile Val His Ser Gly Leu Val Ile Asn Val Asn
    130                    135                140

Thr His Glu Cys Tyr Leu Asn Glu Lys Gln Leu Ser Leu Thr Pro Thr
    145                150                155                160

Glu Phe Ser Ile Leu Arg Ile Leu Cys Glu Asn Lys Gly Asn Val Val
                    165                170                175

Ser Ser Glu Leu Leu Phe His Glu Ile Trp Gly Asp Glu Tyr Phe Ser
                180                185                190

Lys Ser Asn Asn Thr Ile Thr Val His Ile Arg His Leu Arg Glu Lys
                195                200                205

Met Asn Asp Thr Ile Asp Asn Pro Lys Tyr Ile Lys Thr Val Trp Gly
    210                    215                220

Val Gly Tyr Lys Ile Glu Lys
    225                230
```

(2) INFORMATION FOR SEQ ID NO:44:

(i) SEQUENCE CHARACTERISTICS:
        (A) LENGTH: 239 amino acids
        (B) TYPE: amino acid
        (D) TOPOLOGY: linear (ii) MOLECULE TYPE: protein (vi) ORIGINAL SOURCE:
        (A) ORGANISM: Escherichia coli (xi) SEQUENCE DESCRIPTION: SEQ ID NO:44:

```
Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
                20                  25                  30

Ser Val Ala Asn Ala Glu Gln Met Asp Arg Leu Leu Thr Arg Glu Ser
            35                  40                  45

Phe His Leu Met Val Leu Asp Leu Met Leu Pro Gly Glu Asp Gly Leu
50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
            115                 120                 125

Gly Ala Pro Ser Gln Glu Glu Ala Val Ile Ala Phe Gly Lys Phe Lys
130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
                165                 170                 175

Arg Glu Pro Ile Ser Arg Asp Lys Leu Met Asn Leu Ala Arg Gly Arg
            180                 185                 190

Glu Tyr Ser Ala Met Glu Arg Ser Ile Asp Val Gln Ile Ser Arg Leu
            195                 200                 205
```

Arg Arg Met Val Glu Glu Asp Pro Ala His Pro Arg Tyr Ile Gln Thr
    210                 215                 220

Val Trp Gly Leu Gly Tyr Val Phe Val Pro Asp Gly Ser Lys Ala
225                 230                 235

(2) INFORMATION FOR SEQ ID NO:45:

(i) SEQUENCE CHARACTERISTICS:
        (A) LENGTH: 229 amino acids
        (B) TYPE: amino acid
        (D) TOPOLOGY: linear (ii) MOLECULE TYPE: protein (vi) ORIGINAL SOURCE:
        (A) ORGANISM: Escherichia coli (xi) SEQUENCE DESCRIPTION: SEQ ID NO:45:

Met Ala Arg Arg Ile Leu Val Val Glu Asp Glu Ala Pro Ile Arg Glu
1               5                   10                  15

Met Val Cys Phe Val Leu Glu Gln Asn Gly Phe Gln Pro Val Glu Ala
                20                  25                  30

Glu Asp Tyr Asp Ser Ala Val Asn Gln Leu Asn Glu Pro Trp Pro Asp
            35                  40                  45

Leu Ile Leu Leu Asp Trp Met Leu Pro Gly Gly Ser Gly Ile Gln Phe
        50                  55                  60

Ile Lys His Leu Lys Arg Glu Ser Met Thr Arg Asp Ile Pro Val Val
65                  70                  75                  80

Met Leu Thr Ala Arg Gly Glu Glu Asp Arg Val Arg Gly Leu Glu
                85                  90                  95

Thr Gly Ala Asp Asp Tyr Ile Thr Lys Pro Phe Ser Pro Lys Glu Leu
                100                 105                 110

Val Ala Arg Ile Lys Ala Val Met Arg Arg Ile Ser Pro Met Ala Val
            115                 120                 125

Glu Glu Val Ile Glu Met Gln Gly Leu Ser Leu Asp Pro Thr Ser His
        130                 135                 140

Arg Val Met Ala Gly Glu Glu Pro Leu Glu Met Gly Pro Thr Glu Phe
145                 150                 155                 160

Lys Leu Leu His Phe Phe Met Thr His Pro Glu Arg Val Tyr Ser Arg
                165                 170                 175

Glu Gln Leu Leu Asn His Val Trp Gly Thr Asn Val Tyr Val Glu Asp
            180                 185                 190

Arg Thr Val Asp Val His Ile Arg Arg Leu Arg Lys Ala Leu Glu Pro
        195                 200                 205

Gly Gly His Asp Arg Met Val Gln Thr Val Arg Gly Thr Gly Tyr Arg
        210                 215                 220

Phe Ser Thr Arg Phe
225

(2) INFORMATION FOR SEQ ID NO:46:

(i) SEQUENCE CHARACTERISTICS:
        (A) LENGTH: 129 amino acids
        (B) TYPE: amino acid
        (D) TOPOLOGY: linear (ii) MOLECULE TYPE: protein (vi) ORIGINAL SOURCE:
        (A) ORGANISM: Escherichia coli (xi) SEQUENCE DESCRIPTION: SEQ ID NO:46:

Met Ala Asp Lys Glu Leu Lys Phe Leu Val Val Asp Asp Phe Ser Thr
1               5                   10                  15

Met Arg Arg Ile Val Arg Asn Leu Leu Lys Glu Leu Cys Phe Asn Asn
                20                  25                  30

Val Glu Glu Ala Glu Asp Gly Val Asp Ala Leu Asn Lys Leu Gln Ala
                35                  40                  45

Gly Gly Phe Gly Phe Ile Ile Ser Asp Trp Asn Met Pro Asn Met Asp
50                      55                  60

Gly Leu Glu Leu Leu Lys Thr Ile Arg Ala Asp Ser Ala Met Ser Ala
65                  70                  75                  80

Leu Pro Val Leu Met Val Thr Ala Glu Ala Lys Lys Glu Asn Ile Ile
                85                  90                  95

Ala Ala Ala Gln Ala Gly Ala Ser Gly Tyr Val Val Lys Pro Phe Thr
                100                 105                 110

Ala Ala Thr Leu Glu Glu Lys Leu Asn Lys Ile Phe Glu Lys Leu Gly
                115                 120                 125

Met (2) INFORMATION FOR SEQ ID NO:47:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: E. faecium
        (B) STRAIN: BM4147

(xi) SEQUENCE DESCRIPTION: SEQ ID NO:47:

Met Asn Arg Ile Lys Val Ala Ile Leu
1               5

(2) INFORMATION FOR SEQ ID NO:48:

(i) SEQUENCE CHARACTERISTICS:
        (A) LENGTH: 10 base pairs
        (B) TYPE: nucleic acid
        (C) STRANDEDNESS: unknown
        (D) TOPOLOGY: linear (ii) MOLECULE TYPE: DNA (genomic)

(ix) FEATURE:
        (A) NAME/KEY: RBS
        (B) LOCATION: 1..10

(xi) SEQUENCE DESCRIPTION: SEQ ID NO:48:

TGAAAGGAGA                                                    10

(2) INFORMATION FOR SEQ ID NO:49:

(i) SEQUENCE CHARACTERISTICS:
        (A) LENGTH: 10 base pairs
        (B) TYPE: nucleic acid
        (C) STRANDEDNESS: unknown
        (D) TOPOLOGY: linear (ii) MOLECULE TYPE: RNA (genomic)

(xi) SEQUENCE DESCRIPTION: SEQ ID NO:49:

-continued

UCUUUCCUCC                                                          10

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:50:

GCTGCAGATA AAAATTTAGG AGG                                           23

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:51:

CGCATGCTAT TATAAAGCC AGTC                                           24

(2) INFORMATION FOR SEQ ID NO:52:

(i) SEQUENCE CHARACTERISTICS:
        (A) LENGTH: 10 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:52:

TGAAAGGGTG                                                          10

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: unknown
        (D) TOPOLOGY: linear (ii) MOLECULE TYPE: rRNA (vi) ORIGINAL SOURCE:
        (A) ORGANISM: B. subtilis (xi) SEQUENCE DESCRIPTION: SEQ ID NO:53:

GGGGGGTTGG NNNNNNNNTT G                                             21

(2) INFORMATION FOR SEQ ID NO:54:

(i) SEQUENCE CHARACTERISTICS:
        (A) LENGTH: 19 base pairs
        (B) TYPE: nucleic acid
        (C) STRANDEDNESS: unknown
        (D) TOPOLOGY: linear (ii) MOLECULE TYPE: rRNA

```
    (vi) ORIGINAL SOURCE:
         (A) ORGANISM: B. subtilis (xi) SEQUENCE DESCRIPTION: SEQ ID NO:54:

AGAACGAAAA NNNNNNATG                                                      19
```

We claim:

1. An isolated polynucleotide, wherein said polynucleotide consists of a nucleotide sequence which codes for the protein of SEQ ID NO:2 (VanH), SEQ ID NO:6 (Vanx, SEQ ID NO:8 (VanC), SEQ ID NO:12 (VanR), SEQ ID NO:14 (VanS), SEQ ID NO:19 (transposase), SEQ ID NO:21 (resolvase), SEQ ID NO:23 (VanY) or SEQ ID NO:25 (VanZ).

2. The isolated polynucleotide according to claim 1 which is SEQ ID NO:1 (vanH), SEQ ID NO:5 (vanX), SEQ ID NO:7 (vanC), SEQ ID NO:11 (vanR), SEQ ID NO:13 (vanS), SEQ ID NO:18 (encoding transposase), SEQ ID NO:20 (encoding resolvase), SEQ ID NO:22 (vanY) or SEQ ID NO:24 (vanZ).

3. A composition consisting of an isolated polynucleotide or mixture of polynucleotides encoding proteins consisting of SEQ ID NOS:2, 4, and 6.

4. An isolated complementary DNA or an isolated RNA corresponding to the polynucleotide of claim 1.

5. An isolated complementary DNA or an isolated RNA corresonding to the polynucleotide of claim 2.

6. An isolated polynucleotide from the plasmid pIP816, selected from the group consisting of a HindIII-EcoRI restriction fragment of about 7.3 kb in length, an EcoRI-XbaI restriction fragment of about 3.4 kb in length, an EcoRV-SacII restriction fragment of about 1.7 kb in length and a HindIII-EcoRI restriction fragment of about 3.3 kb in length.

7. The isolated polynucleotide of claim 6, containing from 5' to 3' the restriction sites HindIII, BglII, BglII, EcoRI, BamHI, XbaI and EcoRI.

8. An isolated polynucleotide of having a sequence selected from the group consisting of SEQ ID NO:15, SEQ ID NO:16, SEQ ID NO:17, DNA complementary thereto and RNA corresponding thereto.

9. An isolated recombinant polynucleotide which confers resistance to vancomycin or teicoplaninin in a host transformed with said isolated recombinant polynucleotide, containing the polynucleotide of claim 1, under the control of regulatory elements which enable expression of said polynucleotide of claim 1.

10. A recombinant vector which includes the isolated recombinant polynucleotide of claim 9, at a site non-essential for replication of said vector.

11. A recombinant vector, which is the plasmid pAT214.

12. A bacterium transformed with the isolated recombinant vector of claim 10.

13. The bacterium of claim 12, said bacterium being a gram-positive coccus.

14. An isolated polynucleotide, wherein said polynucleotide:
  (i) consists of a nucleotide sequence encoding a protein for resistance to vancomycin, teicoplanin, or both vancomycin and teicoplanin, and
  (ii) hybridizes under the following conditions:
    a reaction temperature of 65° C. overnight in a solution containing 0.1% SDS, 0.7% skimmed milk powder and 6× SSC followed by washing at 65° C. in 2× SSC and 0.1% SDS; or
    a reaction temperature of 60° C. overnight in a solution containing 0.1% SDS, 0.7% skimmed milk powder, 6× SSC followed by washing at 45° C. in 2× SSC and 0.1% SDA; with a nucleotide sequence SEQ ID NOS:1, 5, 7, 11, 13, 18, 20, 22 or 24.

* * * * *